US012331288B2

(12) United States Patent
Shalitin et al.

(10) Patent No.: US 12,331,288 B2
(45) Date of Patent: Jun. 17, 2025

(54) METHODS FOR IMPROVING TRAITS IN PLANTS

(71) Applicant: PLANTARCBIO LTD., Raanana (IL)

(72) Inventors: Dror Shalitin, Raanana (IL); Noam Grimberg, Raanana (IL); Arava Shatil Cohen, Raanana (IL)

(73) Assignee: PLANTARCBIO LTD., Raanana (IL)

( * ) Notice: Subject to any disclaimer, the term of this patent is extended or adjusted under 35 U.S.C. 154(b) by 0 days.

(21) Appl. No.: 18/407,975

(22) Filed: Jan. 9, 2024

(65) Prior Publication Data

US 2024/0141329 A1    May 2, 2024

Related U.S. Application Data

(63) Continuation of application No. 17/388,310, filed on Jul. 29, 2021, now Pat. No. 11,905,512, which is a continuation of application No. 16/496,445, filed as application No. PCT/IL2018/050349 on Mar. 27, 2018, now Pat. No. 11,111,491.

(60) Provisional application No. 62/644,600, filed on Mar. 19, 2018, provisional application No. 62/477,517, filed on Mar. 28, 2017.

(51) Int. Cl.
*C12N 15/82* (2006.01)
*C12N 15/10* (2006.01)

(52) U.S. Cl.
CPC ..... *C12N 15/1075* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 6,030,779 A | 2/2000 | Short | |
| 6,368,798 B1 | 4/2002 | Short | |
| 6,972,183 B1 | 12/2005 | Lafferty et al. | |
| 2002/0150949 A1 | 10/2002 | Short et al. | |
| 2010/0012051 A1 | 1/2010 | Born | |
| 2011/0088126 A1 | 4/2011 | Chang et al. | |
| 2011/0252501 A1 | 10/2011 | Abad et al. | |
| 2012/0131696 A1 | 5/2012 | Sharon et al. | |
| 2014/0053298 A1* | 2/2014 | Sanz Molinero | C12N 15/8261 800/290 |
| 2015/0376640 A1 | 12/2015 | Shoresh et al. | |

FOREIGN PATENT DOCUMENTS

| | | |
|---|---|---|
| CN | 1314782 A | 9/2001 |
| CN | 103382476 A | 11/2013 |
| EP | 1025262 | 8/2000 |
| WO | 2008027591 | 3/2008 |
| WO | 2016095124 | 6/2016 |

OTHER PUBLICATIONS

Gabor et al (2004) Quantifying the acccessibility of the metagenome by random expression cloning techniques, Environ Microbiol 6, 879-886.
Culligan et al (2014) Metagenomics and novel gene discovery: promise and potential for novel therapeutics, Virulence 5, 399-412.
Venter et al (2004) Environmental genome shotgun sequencing of the Sargasso Sea, Science, 304, 66-74.
Farooq et al (2009) Plant drought stress: effects, mechanisms and management, Agron. Sustain. Dev. 29, 185-212.
Zhao et al (2016) Ubiquitin-specific protease 24 negatively regulates abscisic acid signalling in *Arabidopsis thaliana*, Plant, Cell and Environment, 39:427-440.
Nonami H. (1998) Plant water relations and control of cell elongation at low water potentials, J. Plant Res. 111, 373-382.
Parida et al (2005) Salt tolerance and salinity effects on plants: a review, Ecotoxicology and Environmental Safety, 60(3), 324-349.
Carillo et al (2011) Salinity stress and salt tolerance, abiotic stress in plants—mechanisms and adaptations. In: Arun Shanker, editor Tech, DOI: 10.5772/22331.
Yang T-T et al (1996) Optimized codon usage and chromophore mutations provide enhanced sensitivity with the green fluorescent protein. Nucleic Acids Res 24:4592-4593.
Hema et al (2014) Stable Expression of mtlD Gene Imparts Multiple Stress Tolerance in Finger Millet. PLoS One 9(6): e99110.
Karaba et al (2007) Improvement of water use efficiency in rice by expression of HARDY, an *Arabidopsis* drought and salt tolerance gene, Proc Natl Acad Sci USA, 104:5270-5275.
Cao et al (1997) The *Arabidopsis* NPR1 gene that controls systemic acquired resistance encodes a novel protein containing ankyrin repeats, Cell 88(1), 57-63.
Gaj et al (2013) ZFN, Talen and CRISPR/Cas-based methods for genome engineering, Trends in Biotechnology, 31(7), 397-405.
Lever et al (2015) A modular method for the extraction of DNA and RNA, and the separation of DN pools from diverse environmental sample types, Frontiers in Microbiology, 6, 476.
Wujuan et al (2001) Determination of nucleic acids with crystal violet by a resonance light-scattering technique, Analyst, 126(4), 513-517.

(Continued)

*Primary Examiner* — Matthew R Keogh
(74) *Attorney, Agent, or Firm* — FULLER IP LAW LLC; Rodney J. Fuller; Scott H. Blackman

(57) ABSTRACT

The present invention discloses a method for screening for and identifying a desirable plant improving trait, said method comprises steps of: (a) obtaining genetic material from a sampling of a predefined source and (b) constructing an expression library from said genetic material. The aforementioned method further comprises steps of: (c) producing plants transformed with said expression library at a transformation efficiency of at least 0.05%-30%, representing at least $10^2$-$10^{10}$ trangenes; (d) screening for transformed plants expressing said desirable trait; and (e) identifying said transgene of said transformed plants expressing said desirable trait.

4 Claims, 13 Drawing Sheets
Specification includes a Sequence Listing.

(56) References Cited

OTHER PUBLICATIONS

Jayakannan et al (2015) The NPR1-dependent salicylic acid signalling pathway is pivotal for enhanced salt and oxidative stress tolerance in *Arabidopsis*, Journal of Experimental Botany, 66(7), 1865-1875.

Christoph Weiste et al (2007) In planta ORFeome analysis by large-scale over-expression of Gateway—compatible cDNA clones: screening of ERF transcription factors involved in abiotic stress defense: Functional analysis of the *Arabidopsis* transcription factor ORFeome, The Plant Journal, vol. 52, No. 2 pp. 382-390.

Wan-Song et al (2017) Construction of a Plant Transformation-ready Expression cDNA Library for Thellungiella halophila Using Recombination Cloning, Journal of Integrative Plant Biology, pp. 1313-1319.

Im et al (2009) Expression of Pyrococcus furiosus Superoxide Reductase in *Arabidopsis* Enhances Heat Tolerance, Plant Physiology, vol. 151:893-904.

Janbon et al (2014) (Genbank AFR94946), Analysis of the Genome and Transcriptome of *Cryptococcus neoformans* var. grubii Reveals Complex RNA Expression and Microevolution Leading to Virulence Attenuation, PLoS Genet. 10(4) E1004261.

NCBI Accession No. XP-009268808, 60S ribosomal protein L17 [Wallemia icthyophaga EXF-994].

Grandaubert et al (2015) RNA-seq-Based Gene Annotation and Comparative Genomics of Four Fungal Grass Pathogens in the Genus *Zymoseptoria* Identify Novel Orphan Genes and Species-Specific Invasions of Transposable Elements, G3 Genes | Genomes | Genetics, 5:1323-1333.

Uniprot A0A017SJD1_ASPRC (2014) (7 pages).

\* cited by examiner

METHODS FOR IMPROVING TRAITS IN PLANTS

RELATED APPLICATIONS

This application is a Continuation of U.S. patent application Ser. No. 17/388,310, filed on Jul. 29, 2021, which is a Continuation of U.S. patent application Ser. No. 16/496,445 filed on Sep. 22, 2019 (issued as U.S. Pat. No. 11,111,491), which is the U.S. National Stage of International Patent Application No. PCT/IL2018/050349, filed on Mar. 27, 2018, which claims the benefit of priority of U.S. Provisional Application Nos. 62/477,517 and 62/644,600, filed on Mar. 28, 2017 and Mar. 19, 2018, respectively. The contents of the above applications are all incorporated by reference as if fully set forth herein in their entirety.

SEQUENCE LISTING

The official copy of the sequence listing is submitted electronically in ST.26 XML format having the file name "11184_033US-CON4_Seq_List.xml" created on Mar. 27, 2018, and having a size of 452,840 bytes, and is filed concurrently with the specification. The Sequence Listing ST.26 XML file is part of the specification and is herein incorporated by reference in its entirety.

FIELD OF THE INVENTION

The present invention generally relates to the field of improving traits in plants. More particularly, the present invention relates to improving traits in plants by transformation of expression libraries from predefined sources into plants and screening for desirable traits.

BACKGROUND OF THE INVENTION

The world population is estimated to be 9.2 billion in 2050. To sufficiently feed this population, the total food production will have to increase by 60%-70%. Climate models predict that warmer temperatures and increases in the frequency and duration of drought during the present century will have negative impact on agricultural productivity. For example, maize production in Africa could be at risk of significant yield losses as researchers predict that each degree-day that the crop spends above 30° C. reduces yields by 1% if the plants receive sufficient water. These predictions are similar to those reported for maize yield in the United States. It has been further shown that maize yields in Africa decreased by 1.7% for each degree-day the crop spent at temperatures of over 30° C. under drought. Wheat production in Russia decreased by almost one-third in 2010, largely due to the summer heat wave. Similarly, wheat production declined significantly in China and India in 2010, largely due to drought and sudden rise in temperature respectively, thereby causing forced maturity. These new global challenges require a more complex integrated agriculture.

In addition global warming leads to the concurrence of a number of abiotic and biotic stresses, thus affecting agricultural productivity. Occurrence of abiotic stresses can alter plant-pest interactions by enhancing host plant susceptibility to pathogenic organisms, insects, and by reducing competitive ability with weeds. On the contrary, some pests may alter plant response to abiotic stress factors.

Biotic stress factors are caused by pathogens, insects, pests, weeds, or intraspecific competition for resources. The ability of biotic stress factors to cause yield or quality loss depends on the environment and thus may vary from region to region or from one agroecology to another. For example, in Australia, barley foliar diseases are some of the major biotic stress factors causing substantial yield and quality losses. Although it is known that some plant species have resistance to various diseases, they are hard or even impossible to breed in conventional methods.

The challenge is to create crops that are resistance to biotic stress factors and are flexible and adaptable to diverse environments and populations. There are currently two major acceptable ways to adapt crops to new environments: developing new crops through conventional breeding (long-term endeavor starting with domestication) and introducing target traits into existing crops through plant breeding, which includes genetic engineering. To maintain productivity in the face of increased climatic variability, both the population and the plant cultivars will need to be continually developed to withstand "new" climate extremes and other stresses such as diseases, pathogens, insects, pests etc. In addition there is a constant need to find new herbicide tolerance or resistant genes for new chemicals and new herbicides mode of action.

Genetic engineering has the potential to address some of the most challenging biotic and abiotic constraints faced by farmers, which are not easily addressed through conventional plant breeding alone.

Advantageous outcomes of these genetic modifications include increased food production, reliability, and yields; enhanced taste and nutritional value; and decreased losses due to various biotic and abiotic stresses, such as fungal and bacterial pathogens. These objectives continue to motivate modern breeders and food scientists, who are seeking for newer genetic modification methods for identifying, selecting, and analyzing individual organisms that possess genetically enhanced features.

The option to transform plants with foreign genes and/or genes from the same specie or genus, that are hard or impossible to breed, overcomes species barriers, making it possible to exploit powerful 'super-traits' that are not attainable through traditional methods. However, the molecular interactions and outcomes of introduced trans-genes and endogenous genes are not predictable.

When genes coding for certain traits are transferred, typically from one plant species to another, the desired traits are not always expressed unless the environment interacts with the genes in the anticipated way triggering the desired response, which depends on the regulating sequences inserted with the gene. This means that new transgenic cultivars, developed under laboratory conditions in a controlled climate, have to be tested under field conditions, as in more traditional breeding methods, so currently there is little difference in the speed with which either method will result in the release of new cultivars.

The knowledge gained from basic plant research will underpin future crop improvements, but effective mechanisms for the rapid and effective translation of research discoveries into public good agriculture remain to be developed.

U.S. Pat. Nos. 6,030,779 and 6,368,798 disclose a process for identifying clones having a specified enzyme activity by selectively isolating target nucleic acid from genomic DNA population, by use of polynucleotide probe identifying the nucleic acid sequence encoding an enzyme having the specified enzyme activity; and transforming a host with the isolated target nucleic acid to produce a library of clones which are screened for the specified enzyme activity.

U.S. Pat. No. 6,972,183 discloses a process for screening an expression library to identify clones expressing enzymes having a desired activity. The process involves generating from genomic DNA samples of one or more microorganisms an expression library comprising a plurality of recombinant cell clones, and then introducing into capillaries in a capillary array a substrate and a subset of the clones. Interaction of the substrate and a clone expressing an enzyme having the desired activity produces an optically detectable signal, which can then be spatially detected to identify capillaries containing clones producing such a signal. The signal-producing clones can then be recovered from the identified capillaries.

EP patent application 1025262 and US patent application 20020150949 teach a process for identifying clones having a specified activity of interest, by (i) generating expression libraries derived from nucleic acid directly isolated from the environment; (ii) exposing said libraries to a particular substrate or substrates of interest; and (iii) screening said exposed libraries utilizing a fluorescence activated cell sorter to identify clones which react with the substrate or substrates.

US patent application 20100152051 relates to a method for the identification and/or characterization of clones conferring a desired biological property from an expression library. The method comprises the step of screening for the expression of at least one (poly)peptide, such as a tag expressed as a fusion protein, together with a recombinant insert of a clone of said expression library. Said (poly)peptide may be fused N-terminally or C-terminally to said insert. The method further comprises the steps of contacting a ligand specifically interacting with the (poly)peptide expressed by the insert of a clone conferring said desired biological property.

All the above methods are based upon screening a DNA library (produced from microorganisms or environmental sample) for a specific sequence or biochemical activity via interaction with a predetermined probe. In addition, the screening and selection for a clone having the predetermined sequence or activity is performed prior to transformation into plant cells and could be expressed in plant cells (tissue cultures) but not in whole plants. Thus by the up-to-date used methods, only the preselected clone is expressed in plants and the expression and effect of the selected sequence in plants is unpredictable. In addition, in the methods described above, one can screen only for known activities based on prior knowledge. Thus, these methods are limited under the scope of known enzyme activities and enzyme families and prior known function.

In view of the above, there is a long felt need for efficient methods for screening and identifying unknown sequences conferring desirable plant improving traits.

SUMMARY OF THE INVENTION

It is therefore one object of the present invention to disclose a method for screening for and identifying a desirable plant improving trait, the method comprises steps of: (a) obtaining genetic material from a sampling of a predefined source; (b) constructing an expression library from said genetic material; wherein said method further comprises steps of: (c) producing plants transformed with said expression library at a transformation efficiency of at least 0.05%-30%, representing at least 102-1010 transgenes; (d) screening for transformed plants expressing said desirable trait; and (e) identifying said transgene of said transformed plants expressing said desirable trait.

It is a further object of the present invention to disclose the method as defined above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (a) further comprises steps of enriching said genetic material by growth on rich media or on selective media.

It is a further object of the present invention to disclose the method as defined in any of the above, wherein said step (a) further comprises steps of enhancing expression of said desirable trait by culturing said genetic material on selective media for said desirable trait.

It is a further object of the present invention to disclose the method as defined in any of the above, wherein said step (b) comprises steps of producing prokaryotic cDNA library or eukaryotic cDNA library or both.

It is a further object of the present invention to disclose the method as defined in any of the above, wherein said step (b) further comprises steps of cloning said cDNA library into at least one binary vector.

It is a further object of the present invention to disclose the method as defined in any of the above, wherein said binary vector comprises a constitutive promoter or a stress induced promoter.

It is a further object of the present invention to disclose the method as defined in any of the above, wherein said binary vector comprises bacterial selection marker and plant transformation selection marker.

It is a further object of the present invention to disclose the method as defined in any of the above, further comprises steps of transforming said cloned binary vectors into host cells.

It is a further object of the present invention to disclose the method as defined in any of the above further comprises steps of transforming said cloned binary vectors into *Agrobacterium tumefaciens*.

It is a further object of the present invention to disclose the method as defined in any of the above further comprises steps of introducing said transformed *Agrobacterium tumefaciens* into at least one of: whole plant, plant tissue and plant cell.

It is a further object of the present invention to disclose the method as defined in any of the above, comprises steps of introducing said transformed *Agrobacterium tumefaciens* by spraying said plants with an inoculum comprising transformed *Agrobacterium*.

It is a further object of the present invention to disclose the method as defined in any of the above, wherein said step (d) comprises growing said transformed plants under conditions selective for said desirable trait.

It is a further object of the present invention to disclose the method as defined in any of the above, further comprises steps of: (f) collecting T1 seeds from said transformed plants of step (d); (g) determining seed library transformation efficiency of said T1 seeds; (h) sowing said T1 seeds of step (e) under selective conditions allowing screening and selection of transformed plants expressing said desirable trait; (i) testing said selected plants expressing said desirable trait of step (g) for presence of said transgene; and (j) isolating and sequencing said transgene of said selected transformed plants positively tested for said transgene of step (h).

It is a further object of the present invention to disclose the method as defined in any of the above, further comprises steps of (k) collecting T2 seeds from said plants of (h), which are found positive for presence of said transgene; (l) growing plants of said T2 seeds under selective conditions allowing screening and selection of transformed plants expressing said desirable trait as compared to control plants transformed with known genes conferring said desirable trait; and (m) optionally, isolating and sequencing said transgene of said selected plants of step (j).

It is a further object of the present invention to disclose the method as defined in any of the above, comprises steps of (a) recloning and sequencing said isolated transgene of step (i) and/or (l); (b) transforming said recloned transgene into plants; (c) screening said transformed plants of step (b) for selection of transformed plants expressing said desirable trait; (d) isolating said transgene from said selected plants of step (c); and (e) optionally, repeating steps (a) to (d).

It is a further object of the present invention to disclose the method as defined in any of the above, wherein said environmental niche comprises ecological niche, populations, habitats, gene pools, prokaryotic culture, eukaryotic culture and any combination thereof.

It is a further object of the present invention to disclose the method as defined in any of the above, wherein said environmental niche comprises microbiome, microbiota, microbial culture, plant, yeast, algae, nematode or any other organism or combinations thereof.

It is a further object of the present invention to disclose the method as defined in any of the above, wherein said environmental niche comprises predefined biotic factors, abiotic factors and a combination thereof.

It is a further object of the present invention to disclose the method as defined in any of the above, wherein said sampling comprises soil sample, water sample, organic matter sample and any combination thereof.

It is a further object of the present invention to disclose the method as defined in any of the above, wherein said desirable trait is selected from the group consisting of resistance or tolerance to at least one biotic stress, resistance or tolerance to at least one abiotic stress, improved yield, improved biomass, improved food qualities and values, improved grain yield, herbicide or chemical resistance or tolerance and any combination thereof.

It is a further object of the present invention to disclose the method as defined in any of the above, wherein said abiotic stress is selected from the group consisting of: drought, salinity, heat, cold, fertilizer uptake, fertilizer usage efficiency and any combination thereof.

It is a further object of the present invention to disclose the method as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose the method as defined in any of the above, wherein said step (a) comprises steps of extracting RNA from said sampling of said predefined environmental niche.

It is a further object of the present invention to disclose the method as defined in any of the above, wherein said RNA extraction is performed according to standard commercial kits or according to any other protocol for extraction of RNA from environmental sampling.

It is a further object of the present invention to disclose the method as defined in any of the above, wherein said protocol for extraction of RNA from environmental sampling comprises steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (0 and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 µl water to 2 gr of soil of step (a).

It is a further object of the present invention to disclose a plant comprising said transgene identified by the method as defined in any of the above.

It is a further object of the present invention to disclose the plant as defined above, wherein said plant has at least one plant improving trait as compared to a plant of the same genus lacking said transgene.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs:1-148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above, wherein said polypeptide comprises an amino acid sequence corresponding to the sequence as set forth in a polypeptide sequence selected from the group consisting of SEQ ID NOs: 149-321 and any combination thereof.

It is a further object of the present invention to disclose a polypeptide sequence having at least 60% sequence similarity to the polypeptide sequence as defined in any of the above.

It is a further object of the present invention to disclose the use of the method as defined in any of the above for identifying genes conferring plant improving traits selected from the group consisting of resistance or tolerance to abiotic stress, resistance or tolerance to biotic stress, improved yield, improved biomass, improved food qualities and values, improved grain yield, herbicide or chemical resistance or tolerance and any combination thereof.

It is a further object of the present invention to disclose the use as defined in any of the above, wherein said abiotic stress is selected from the group consisting of: drought, salinity, heat, cold, fertilize utilization and any combination thereof.

It is a further object of the present invention to disclose the use as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose a method for screening for and identifying a drought or salinity resistance or tolerance improving trait in plants, said method comprises steps of: (a) obtaining genetic material derived from a low moisture or a high salinity source sample; (b) constructing expression library from said genetic material; wherein said method further comprises steps of: (c) producing plants transformed with said expression library at a transformation efficiency of at least 0.5%-30% representing at least $10^2$-$10^{10}$ transgenes; (d) screening for transformed plants resistant or tolerant to predetermined drought or salinity conditions; and (e) identifying said transgene of said drought or salinity resistant or tolerant transformed plants of step (d).

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (b) further comprises steps of cloning said expression library into at least one binary vector.

It is a further object of the present invention to disclose the method as defined in any of the above, further comprises steps of: (f) collecting T1 seeds from said transformed plants of step (c); (g) sowing said T1 seeds in soil selective for transformed plants, with water content of about 100% capacity; (h) growing plants of said T1 seeds in drought or salinity conditions and/or without irrigation until most of the plants die, to produce transformed plants surviving said drought or salinity conditions; (i) growing said drought or salinity surviving transformed plants to produce T2 seeds; (j) screening said drought or salinity surviving transformed plants of step (i) for presence of a transgene; and (k) isolating and sequencing said transgene from positively screened plants of step (j).

It is a further object of the present invention to disclose the method as defined in any of the above, further comprises steps of (l) collecting T2 seeds from each of said transgene-containing positively screened drought or salinity surviving transformed plants of step (j); (m) growing T2 plants from each of said transgene-containing T2 seeds of step (l) under predetermined drought or salinity conditions as compared to control plants of the same genus and lacking said transgene or transformed with known genes conferring drought or salinity tolerance or drought or salinity resistance; (n) performing drought tolerance or resistance screening measurements for each of said transgene-containing T2 plants as compared to said control plants, said measurements are selected from the group consisting of: turgor pressure measurements, plant death, leaf area, fresh weight, leaf number, branch fresh weight, main branch length, flowers and pods production, Chlorosis and damage to leaves, state or performance of plants and any combination thereof; (o) isolating the transgene from said screened dough or salinity resistance performing T2 plants of step (n); (p) optionally, recloning said transgene into a binary vector; (q) optionally, transforming said cloned binary vector into plants and growing said transformed plants under predetermined drought or salinity conditions; and (r) optionally, repeating steps (l) to (q).

It is a further object of the present invention to disclose the method as defined in any of the above, wherein said step of growing T2 plants comprises steps of: (a) sowing said T2 seeds in soil selective for transformed plants, with water content of about 100% capacity; and (b) irrigating said plants when water content in the soil reaches about 5-10%.

It is a further object of the present invention to disclose the method as defined in any of the above, wherein said predetermined drought or salinity conditions are selected from the group consisting of low moisture, high salinity, dry soil and heat.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs:1 to SEQ ID NO:148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above comprises an amino acid sequence corresponding to the sequence as set forth as set forth in polypeptide sequence selected from the group consisting of SEQ. ID Nos: 149-321 and any combination thereof.

It is a further object of the present invention to disclose a polypeptide sequence having at least 60% sequence similarity with the polypeptide sequence as defined in any of the above.

It is a further object of the present invention to disclose a method for extracting RNA from a soil sample comprising steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (0 and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 µl water to 2 gr of soil of step (a).

It is a further object of the present invention to disclose a method for screening for and identifying a desirable plant improving trait, said method comprises steps of: (a) obtaining a sampling of a predefined source; (b) extracting RNA from said sampling according to the method disclosed herein; (c) constructing an expression library from said RNA of step (b); wherein said method further comprises steps of: (d) producing plants transformed with said expression library at an efficiency of at least 0.05%-30% representing at least $10^2$-$10^{10}$ transgenes; (e) screening for transformed plants expressing said desirable trait; and (f) identifying said transgene of said transformed plants expressing said desirable trait.

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose an isolated polynucleotide having at least 80% sequence similarity to a nucleotide sequence selected from the group consisting of SEQ ID NOs:1 to SEQ ID NO:148 and any combination thereof.

It is a further object of the present invention to disclose an isolated polypeptide having at least 60% sequence similarity to an amino acid sequence selected from the group consisting of SEQ. ID Nos: 149-321 and any combination thereof.

BRIEF DESCRIPTION OF THE DRAWINGS

In order to understand the invention and to see how it may be implemented in practice, several embodiments will now be described, by way of non-limiting example only, with reference to the accompanying drawing, in which:

FIG. 1A illustrates the pPA-35H vector, which has a constitutive CaMV 35S promoter. FIGS. 1B-D present vectors containing stress induced promoters of *Arabidopsis thaliana*: pPA-CH with CBF3 promoter (FIG. 1B), pPA-EH with Erd10 promoter (FIG. 1C) and pPA-KH with Kin1 promoter (FIG. 1D);

DETAILED DESCRIPTION OF THE PREFERRED EMBODIMENTS

Figure 1A:
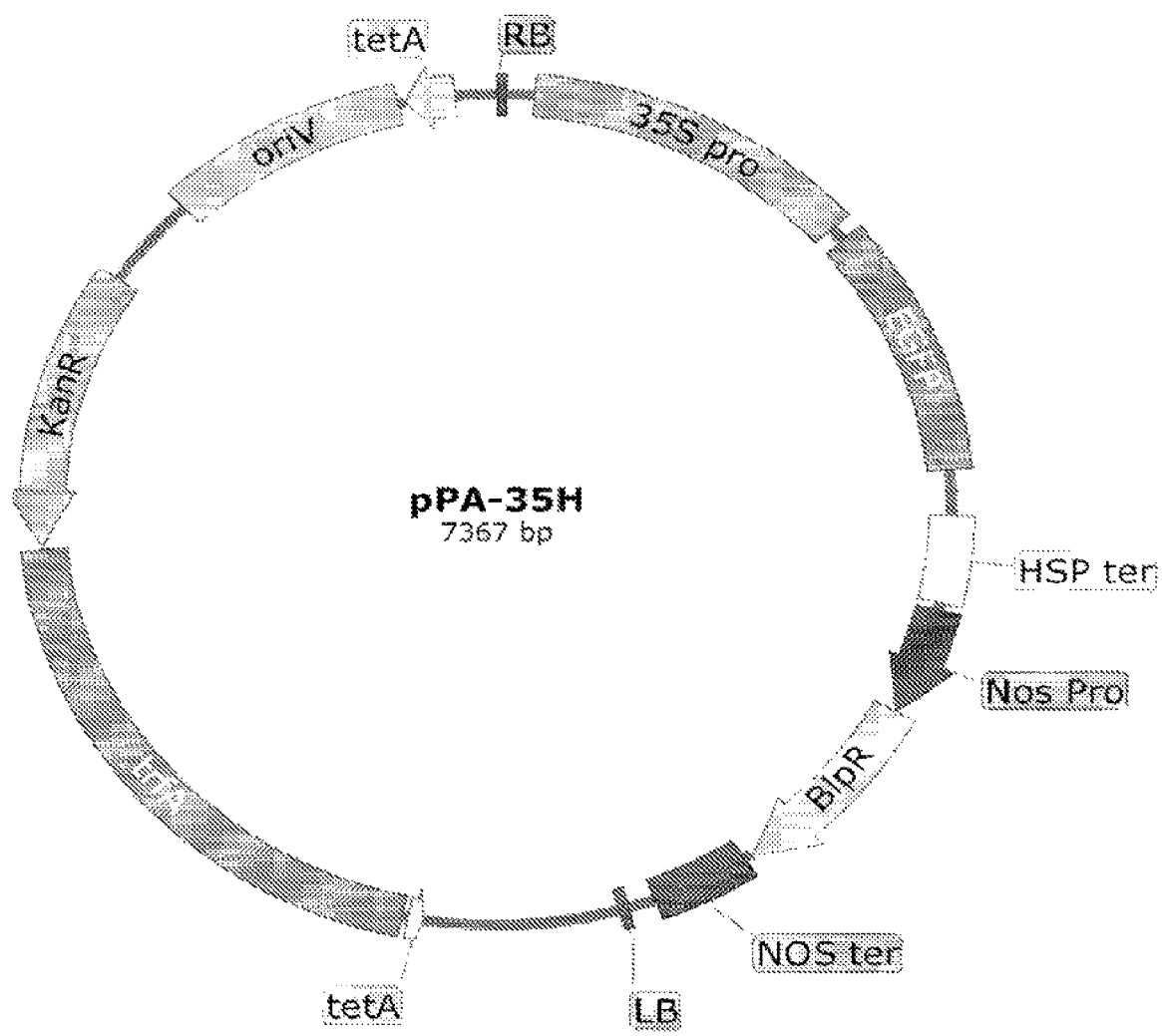
FIGS. 1A-D present schematic illustrations of binary vectors used for insertion of amplified cDNA clones between the promoter(s) (35S, CBF3, Erd10 and Kin1) and the HSP terminator.

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for screening and identifying a desirable plant improving trait.

It is known that some plant species have resistance to various diseases. However, such species are usually hard or impossible to breed in conventional techniques and methods.

The present invention provides a method and platform to discover and identify genes from plants that have unique and valuable features, such as disease resistance, abiotic stress resistance or tolerance, food improving qualities (e.g. improved oils, protein content, amino acids, vitamins etc.) and then to insert or express them in desired crops through gene editing, or other transformation technique.

It is therefore within the scope of the present invention to introduce target traits into existing crops through plant breeding, which includes genetic engineering and gene (genome) editing.

The present invention provides a novel method for screening and identifying a desirable plant improving trait. The method comprises steps of: (a) obtaining genetic material from a sampling of a predefined environmental niche or genetic material extracted from other sources such as plants from the same or other genus; and (b) constructing an expression library from said genetic material. According to core aspects, the present invention further comprises steps of: (c) producing plants transformed with said expression library at an efficiency of at least 0.05%-30% representing at least $10^2$-$10^{10}$ transgenes; (d) screening for transformed plants expressing said desirable trait; and (e) identifying said transgene of said transformed plants expressing said desirable trait.

The present invention provides for the first time a method for screening for and selecting unknown sequences derived from predefined sources (e.g. ecological niches and/or plants) which confer improved traits in valuable crop plants. The current method is effective and advantageous upon common and conventional screening methods by the following aspects:

1. An expression library is prepared from genetic material or genetic pool (i.e. RNA) originating from predefined sources, such as extreme environment, plant material and other. In this way, only genes which are expressed in the preselected environmental conditions are used for the screening procedure in plants.
2. The entire expression library is transformed into plants at an efficiency of 0.05% 30% and representation of at least $10^2$-$10^{10}$ unique transgenes.
3. In the method of the present invention, the screening of the expressed library for the desirable phenotype is performed at the target organism, which is the plant. In this way there is no preselection and new and unique genes for the desired phenotype, which are expressible in plants, are revealed.

In the conventional methods, the first step is selecting genes for a predefined trait in a source genetic material, e.g. by probing a DNA library with known sequences in prokaryotic- or eukaryotic cells, and only then the preselected gene is expressed in plants. The outcome of such a conventional method is limited and has the following drawbacks:

1. The screening is performed in a host cell/organism which is not the target organism (usually in prokaryotic or unicellular organism).
2. The screening is limited since it is performed with known sequences or probes or activity. It was shown that functional screening methods require detectable levels of enzyme activity that cannot be always achieved, for example, only about 40% of the enzymatic activities are likely to be detected in *E. coli*-based expression systems (Gabor et al., 2004). In addition, it is herein pointed out that despite the advanced sequencing techniques available, ~35-60% of the total protein-coding genes display high similarities to "hypothetical proteins", "predicted proteins" or "protein of unknown function" (Culligan, et al., 2014; Venter, et al., 2004).
3. Only the preselected clone is transformed into plants.
4. The expression and effect of a preselected clone in the target plant is unpredictable.

For the aforementioned reasons the novel method of the present invention of screening plants transformed with an expression library for a desirable phenotype is advantageous.

It is herein acknowledged that drought and salinity are considered as two abiotic stresses that have major effects on plant growth and development.

With respect to drought, it is considered the most devastating environmental stress, which decreases crop growth and productivity. Drought severely affects plant growth and development with substantial reductions in growth rate and biomass accumulation. The main consequences of drought in plants are reduced rate of cell division and expansion, leaf size, stem elongation and root proliferation, and disturbed stomatal oscillations, and water use efficiency (WUE) (Farooq et al. 2009). This phenomenon involves genetic, physiological, and environmental events and their complex interactions. The rate and amount of plant growth depend on these events, which are affected by water deficit. Cell growth is one of the most drought-sensitive physiological processes due to the reduction in turgor pressure and water availability (Taiz and Zeiger, 2006). Under water deficiencies, cell elongation of higher plants can be inhibited by interruption of water flow from the xylem to the surrounding elongating cells. Impaired mitosis, reduced cell elongation and expansion result in reduced plant height, leaf area and crop growth (Nonami, 1998).

Salinity is also considered one of the major severe abiotic factors affecting crop growth and productivity. During salt stress, all major processes such as photosynthesis, protein synthesis and energy and lipid metabolism are affected (Panda & Das, 2005). During initial exposure to salinity, plants experience water stress, which in turn reduces leaf expansion. The osmotic effects of salinity stress can be observed immediately after salt application and are believed to continue for the duration of exposure, resulting in inhibited cell expansion and cell division, as well as stomatal closure. During long-term exposure to salinity, plants experience ionic stress, which can lead to premature senescence of adult leaves, and thus a reduction in the photosynthetic area available to support continued growth. In fact, excess sodium and more importantly chloride has the potential to negatively affect plant enzymes, resulting in reduced energy production and other physiological changes. It is further acknowledged that ionic stress results in premature senescence of older leaves and in toxicity symptoms (chlorosis, necrosis) in mature leaves. Without wishing to be bound by theory, the high sodium ions affect plants by disrupting protein synthesis and interfering with enzyme activity (Carillo et al., 2011).

The present invention provides a method for efficiently screening for novel genes conferring resistance or improved tolerance to drought and/or salinity in plants and especially in valuable crops.

The method of the present invention overcomes the above drawbacks by using expressed genetic material (such as RNA or mRNA) that represent the genes that are being expressed in selected organisms, e.g. as a result of environmental conditions (such as drought or high salt), and producing a cDNA library that represents the 'Meta-Expression' or metatranscriptome status of a certain biological niche or other genetic source. The entire cDNA library is then transformed into plants and expressed and screened for the desirable phenotype in the plants.

A core aspect of the present invention is that an expression library is produced from various sources (including plants) and environments. The expression library is transformed into plants, which is the target organism in order to improve its traits or functions. The plant expression library is then screened for the desirable trait, such as salt or drought resistance or tolerance, improved biomass and yield production, biotic stresses (diseases and pathogens) resistance or tolerance, improved nutritional value or improved fertilizers utilization.

It is herein acknowledged that the environments (such as soils) in which plants grow are inhabited by microbial communities, e.g. one gram of soil contains about $10^7$-$10^9$ microbial cells (estimates of the number of species of bacteria per gram of soil vary between 2000 and 8.3 million, https://www.ncbi.nlm.nih.gov/pmearticles/PMC2970868/) which comprise about one gigabase of sequence information, or more. The microbial communities which inhabit environments in which plants grow (such as soils) are complex and remain poorly understood despite their economic importance. Such microbial consortia provide the ecosystem necessary for plant growth, including fixing atmospheric nitrogen, nutrient cycling, disease suppression, and sequester iron and other metals.

It is within the scope of the present invention to use functional metagenomics and metatranscriptomics approaches to explore new genes which confer improved traits to plants.

Reference is now made to metagenomics approaches, employed by the present invention according to some aspects. Metagenomics is the study of genetic material derived from environmental samples. It generally refers to as environmental genomics, eco-genomics or community genomics. While traditional microbiology and microbial genome sequencing and genomics rely upon cultivated clonal cultures, environmental gene sequencing cloned specific genes to produce a profile of diversity in a natural sample. In some aspects, metagenomics uses the study of the genomes in a microbial community to constitute the first step to studying the microbiome. Its main purpose is to infer the taxonomic profile of a microbial community. The whole-metagenome sequencing (WMS) provides data on the functional profile of a microbial community. Such work revealed that the vast majority of microbial biodiversity had been missed by cultivation-based methods. In fact it is estimated that over 99% of all microorganisms in almost every environment on earth cannot be cultivated in the laboratory.

Metagenomics is herein also refers to metatranscriptomics, which studies and correlates the transcriptomes of a group of interacting organisms or species. Metatranscriptomics involves sequencing the complete (meta)transcriptome of the microbial community. In some aspects, metatranscriptomics informs the genes that are expressed by the community as a whole. With the use of functional annotations of expressed genes, it is possible to infer the functional profile of a community under specific conditions, which are usually dependent on the status of the host. While metagenomics provides data on the composition of a microbial community under different conditions, metatrascriptomics provides data on the genes that are collectively expressed under different conditions. Metatranscriptomics involves profiling of community-wide gene expression (RNA-seq). In specific aspects, metatranscriptomics describes the genes that are expressed in a specific microbial environment. Thus, metatranscriptomics is the study of the function and activity of the complete set of transcripts (RNA-seq) from environmental samples.

It is noted that gene expression is log-like distributed, for example, top 100 genes of highest expression can cover up to 30% of all transcripts. Even a single gene can cover up to 10%. Thus, a very high sequencing depth is required to see also lower expressed genes.

By using methods such as "shotgun" or PCR directed sequencing, largely unbiased samples of the genes from the members of sampled communities can be obtained. It is herein acknowledged that metagenomics approaches provide a powerful tool for utilizing microbial ecology to improve traits in plants, for example, biological mechanisms that can be harnessed for agriculture and improved plant traits.

As used herein, the term "about" denotes ±25% of the defined amount or measure or value.

As used herein the term "similar" denotes a correspondence or resemblance range of about ±20%, particularly ±15%, more particularly about ±10% and even more particularly about ±5%.

As used herein the term "average" refers to the mean value as obtained by measuring a predetermined parameter in each plant of a certain plant population and calculating the mean value according to the number of plants in said population.

As used in this specification and the appended claims, the singular forms "a", "an", and "the" include plural referents unless the context clearly dictates otherwise. Thus, for example, reference to "a plant" includes one or more plants, reference to "a trait" includes one or more traits and reference to "a cell" includes mixtures of cells, tissues, and the like.

A "plant" as used herein refers to any plant at any stage of development, including a plant seed.

The term "plant" includes the whole plant or any parts or derivatives thereof, such as plant cells, plant protoplasts, plant cell tissue culture from which plants can be regenerated, plant callus or calli, meristematic cells, microspores, embryos, immature embryos, pollen, ovules, anthers, fruit, flowers, leaves, cotyledons, pistil, seeds, seed coat, roots, root tips and the like.

The term "plant cell" used herein refers to a structural and physiological unit of a plant, comprising a protoplast and a cell wall. The plant cell may be in a form of an isolated single cell or a cultured cell, or as a part of higher organized unit such as, for example, plant tissue, a plant organ, or a whole plant.

The term "plant cell culture" or "tissue culture" as used herein means cultures of plant units such as, for example, protoplasts, regenerable cells, cell culture, cells, cells in plant tissues, pollen, pollen tubes, ovules, embryo sacs, zygotes and embryos at various stages of development, leaves, roots, root tips, anthers, meristematic cells, microspores, flowers, cotyledons, pistil, fruit, seeds, seed coat or any combination thereof.

The term "plant material" or "plant part" used herein refers to leaves, stems, roots, root tips, flowers or flower parts, fruits, pollen, egg cells, zygotes, seeds, seed coat, cuttings, cell or tissue cultures, or any other part or product of a plant or any combination thereof.

A "plant organ" as used herein means a distinct and visibly structured and differentiated part of a plant such as a root, stem, leaf, flower, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture, protoplasts, meristematic cells, calli and any group of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "trait" refers to a characteristic or phenotype, particularly, to a plant improving characteristic or phenotype. A phenotypic trait may refer to the appearance or other detectable characteristic of an individual, resulting from the interaction of its genome, proteome and/or metabolome with the environment. For example, in the context of the present invention a plant improving trait or a desirable plant improving trait relates to resistance or tolerance to at least one biotic stress, resistance or tolerance to at least one abiotic stress, improved yield or biomass, improved grain yield, improved fertilizer uptake and usage efficiency and any combination thereof.

A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; conventionally, a recessive trait manifests itself only when present at homozygous state.

The term "phenotype" is understood within the scope of the present invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

It is within the scope of the current invention that "stress" may be defined as any external factor that has a negative influence on plant growth, function and/or reproduction The term "abiotic stress" is herein generally defined as the negative impact of non-living factors on the plant in a specific environment. The non-living variable must influence the environment beyond its normal range of variation to adversely affect the plant or plant population performance or physiology in a significant way. Non limiting examples of abiotic stress factors, or stressors, or environmental factors may encompass factors such as sunlight, wind, temperature (cold, heat), salinity, over watering (flooding), drought and factors such as fertilizer uptake and fertilizer usage efficiency and any combination thereof. Abiotic stress resistance or tolerance may enhance the growth and productivity of plants and specifically crops. It has been shown that abiotic stressors are most harmful and may result in synergistic effects when they occur together, in combinations of abiotic stress factors.

The term "drought" refers hereinafter to a physical phenomenon generally caused by an extended period of below average precipitation or irrigation. For example, not enough or low moisture (at the soil or at the air), water supply shortages, dry soil, moisture regimes, high salinity, heat and any combination thereof. Dry conditions may develop for different reasons. It can have a substantial impact on the ecosystem and agriculture, e.g. reduction in yield and crop damage.

Many organisms have drought tolerance physiological and genetic adaptations.

"Biotic stress" is herein defined as stress that occurs as a result of damage done to plants by other living organisms, such as bacteria, viruses, fungi, whitefly, *thrips*, spidermites, nematodes, parasites, beneficial and harmful insects, weeds, and cultivated or native plants. The types of biotic stresses imposed on a plant may be depended on both geography and climate and on the host plant and its ability to resist particular stresses.

As used herein, the phrase "resistance" refers to the ability of a plant to restrict the growth and development of a specified pathogen and/or the damage caused to the plant when compared to susceptible plants under similar environmental conditions. Resistant plants may exhibit some disease symptoms or damage under pathogen or pest pressure or under abiotic stress condition.

It is further within the scope of the present invention that resistance means that a plant completely immunizes itself from a particular stress, for example to a biotrophic pathogen infection. According to specific embodiments of the invention, by transformation of an expression library to a host plant, the transformed host acquires a resistance gene which prevents the proliferation of the pathogen and/or confers resistance to a particular abiotic stress (e.g. drought).

According to some aspects, resistance is an absolute term where the plant completely immunizes itself to a particular stress. It should be noted that this does not mean that tolerance cannot be obtained in case of biotic or abiotic stress.

The term "tolerance" refers hereinafter to the characteristic of a plant that allows a plant to avoid, tolerate or recover from biotic or abiotic stressors, under conditions that would typically cause a greater amount of injury to other plants of the same species. These inheritable characteristics influence the degree of damage caused to the plant. In terms of agricultural production tolerance means that the plant can be under stress (diseased/infected/or physiologically challenged) but the extent of loss does not exceed the economic threshold level (an extent of loss which do not hamper the economic potential of the produce). According to further aspects of the present invention, tolerance is a relative term. Examples of tolerance can be found in case of plant pathogens and all abiotic stresses, especially in the case of complex traits that are governed by multiple factors.

In general, 'resistance' and 'tolerance' are the terms used to denote the ability of the plant to manage the stress, be it biotic or abiotic.

The term "transformation" used herein refers to genetic alteration or modification induced by the introduction of exogenous DNA into a cell. This includes both integration of the exogenous DNA into the host genome, and/or introduction of plasmid DNA containing the exogenous DNA into the plant cell. Such a transformation process results in the uptake, incorporation and expression of exogenous genetic material (exogenous DNA, for examples expression library prepared from ecological niche sampling). Plant transformation may refer to the introduction of exogenous genes into plant cells, tissues or organs, employing direct or indirect means developed by molecular and cellular biology.

The term "environmental niche" or "ecological niche" generally refers to the behavior of a species living under specific environmental conditions. It includes the microbes, fungi, plants or other organisms that inhabit a given environmental location (extremophiles). The ecological niche describes how an organism or population responds to the distribution of resources and competitors and how it in turn alters those same factors. The type and number of variables comprising the dimensions of an environmental niche vary from one species to another and the relative importance of particular environmental variables for a species may vary according to the geographic abiotic and biotic contexts.

According to other aspects, the term "environmental niche" or "ecological niche" describes the relational position of a species or population in an ecosystem. More specifically, it describes how a population responds to the abundance of its resources and competitors and how it affects those same factors. The abiotic or physical environment is also part of the niche because it influences how populations affect, and are affected by, resources and competition. The description of a niche may include descriptions of the organism's life history, habitat, and place in the food chain. In context of the present invention "environmental niche" or "ecological niche" can be defined according to biotic factors or abiotic factors such as high salinity, drought conditions, elevated heat, cold conditions, pH or any other extreme environmental conditions.

It is within the scope of the current invention that the genetic material is derived from a sampling of a predefined environmental niche, including from soil, water, plant biomass, microorganisms, yeast, algae, nematode, etc.

The term "microbiome" or "microbiota" as used herein refers to an ecological community of commensal, symbiotic and pathogenic microorganisms found in and on all multi-cellular organisms from plants to animals. A microbiota includes bacteria, archaea, protists, fungi and viruses. Microbiota has been found to be crucial for immunologic, hormonal and metabolic homeostasis of their host. The synonymous term microbiome describes either the collective genomes of the microorganisms that reside in an environmental niche or the microorganisms themselves. The microbiome and host emerged during evolution as a synergistic unit from epigenetics and genomic characteristics, sometimes collectively referred to as a holobiont.

The term "genetic material" or "genetic pool" refers hereinafter to sum of a population's genetic material at a given time. It includes all genes and combinations of genes (sum of the alleles) in the population.

The term "isolated" as used hereinafter means that material is removed from its original environment (e.g., the natural environment if it is naturally occurring). For example, a naturally-occurring polynucleotide or polypeptide which is separated from some or all of the coexisting materials in the natural system is isolated.

The nucleic acid isolated or derived from microorganisms or any organism can preferably be inserted into a vector or a plasmid. Such vectors or plasmids are preferably those containing expression regulatory sequences, including promoters, enhancers and the like suitable for expression in plants. Particularly preferred plasmids and methods for introduction and transformation into them are described in detail in the protocol set forth herein.

The term "expression library" as used hereinafter refers to a collection of vectors or viruses (such as plant viruses used as virus-vectors) or plasmids or phages containing a representative sample of cDNA or genomic fragments that are constructed in such a way that they will be transcribed and or translated by the host organism (in the context of the present invention, plants). The technique uses expression vectors to generate a library of clones, with each clone transcribing one RNA and or expressing one protein. This expression library is then screened for the property of interest and clones of interest recovered for further analysis. One and non-limiting example would be using an expression library to isolate genes that could confer resistance or tolerance to drought.

It is within the scope of the present invention that the expression library (usually derived from microbial genetic material) can be constructed in a binary vector (or transfer DNA (T-DNA) binary system or a shuttle vector) able to replicate in multiple hosts (e.g. *E. coli* and *Agrobacterium tumefaciens*) to produce genetically modified plants. These are artificial vectors that have been created from the naturally occurring Ti plasmid found in *Agrobacterium tumefaciens*. In some aspects, the expression libraries are transferred from *Agrobacterium tumefaciens* to plants.

The term "editing" or "gene editing" or "genome editing" refers hereinafter to any conventional or known genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof. In the context of the present invention, the aforementioned gene editing techniques are used to edit a target gene in a desirable crop according to the information obtained from the transgene identified by the method of the present invention.

The term "corresponding to the sequence" refers hereinafter to sequence homology or sequence similarity. These terms relate to two or more nucleic acid or protein sequences, that are the same or have a specified percentage of amino acid residues or nucleotides that are the same, when compared and aligned for maximum correspondence, as measured using one of the available sequence comparison algorithms or by visual inspection.

According to further aspects of the invention, the term "corresponding to the nucleotide sequence" refers to variants, homologues and fragments of the indicated nucleotide sequence which possess or perform the same biological function or correlates with the same phenotypic characteristic of the indicated nucleotide sequence.

Another indication that two nucleic acid sequences are substantially similar or that a sequence is "corresponding to the nucleotide sequence" is that the two molecules hybridize to each other under stringent conditions. High stringency conditions, such as high hybridization temperature and low salt in hybridization buffers, permits only hybridization between nucleic acid sequences that are highly similar, whereas low stringency conditions, such as lower temperature and high salt, allows hybridization when the sequences are less similar.

The term "similarity" or "sequence similarity" refers hereinafter to the degree of resemblance between two sequences when they are compared. This is dependent on their identity and it shows the extent to which residues are aligned. Sequence similarity refers to an optimal matching problem (i.e. for sequence alignments). The optimal matching algorithm finds the minimal number of edit operations (inserts, deletes, and substitutions) in order to align one sequence to another sequence. Sequence similarity searches can identify "homologous" proteins or genes by detecting excess similarity, meaning, statistically significant similarity that reflects common ancestry.

It is within the scope of the current invention that similarity searching is an effective and reliable strategy or tool for identifying homologs (i.e. sequences that share a common evolutionary ancestor). Non limiting examples of similarity searching programs, include BLAST (e.g. Altschul et al. 1997); units 3.3 and 3.4), PSI-BLAST (e.g. Altschul et al., 1997), SSEARCH (e.g. Smith and Waterman, 1981); Pearson, 1991, unit 3.10), FASTA (e.g. Pearson and Lipman, 1988, unit 3.9) and the HMMER3 (e.g. Johnson et al., 2010). Such programs produce accurate statistical estimates, and can ensure that protein or nucleic acid sequences that share significant similarity also may have similar structures. Similarity searching is effective and reliable because sequences that share significant similarity can be inferred to be homologous; namely sharing a common ancestor.

Similarity is understood within the scope of the present invention to refer to a sequence similarity of at least 60%, particularly a similarity of at least 70%, preferably more than 80% and still more preferably more than 90%. The term "substantially similar" refers to a nucleic acid, which is at least 50% identical in sequence to the reference when the entire ORF (open reading frame) is compared, where the sequence similarity is preferably at least 70%, more preferably at least 80%, still more preferably at least 85%, especially more than about 90%, most preferably 95% or greater, particularly 98% or greater.

In some embodiments of the invention, such substantially similar sequences refer to polynucleotide or amino acid sequences that share at least about 60% similarity, preferably at least about 80% similarity, alternatively, about 90%, 95%, 96%, 97%, 98% or 99% similarity to the indicated polynucleotide or amino acid sequence/s.

The present invention encompasses nucleotide sequences having at least 60% similarity, preferably 70%, more preferably 80%, even more preferable 90% and especially more preferable 95% similarity to polynucleotide sequences identified by the method of the present invention or to a reference sequence.

The present invention further encompasses amino acid sequences having at least 60% similarity, preferably 70%, more preferably 80%, even more preferable 90% and especially more preferable 95% similarity to polypeptide sequences identified by the method of the present invention or to a reference sequence.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene or protein sequence.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

The term "identity" or "sequence identity" further refers hereinafter to the amount of characters which match exactly between two different sequences. Hereby, gaps are not counted and the measurement is relational to the shorter of the two sequences.

In other words, if two sequences, which are to be compared with each other, differ in length, sequence identity preferably relates to the percentage of the nucleotide residues of the shorter sequence, which are identical with the nucleotide residues of the longer sequence. As used herein, the percent of identity between two sequences is a function of the number of identical positions shared by the sequences, taking into account the number of gaps, and the length of each gap, which needs to be introduced for optimal alignment of the two sequences. The comparison of sequences and determination of identity percent between two sequences can be accomplished using a mathematical algorithm as known in the relevant art.

It is further within the scope that the terms "similarity" and "identity" additionally refer to local homology, identifying domains that are homologous or similar (in nucleotide and/or amino acid sequence). It is acknowledged that bioinformatics tools such as BLAST, SSEARCH, FASTA, and HMMER calculate local sequence alignments which identify the most similar region between two sequences. For domains that are found in different sequence contexts in different proteins, the alignment should be limited to the homologous domain, since the domain homology is providing the sequence similarity captured in the score. According to some aspects the term similarity or identity further includes a sequence motif, which is a nucleotide or amino-acid sequence pattern that is widespread and has, or is conjectured to have, a biological significance. Proteins may have a sequence motif and/or a structural motif, a motif formed by the three-dimensional arrangement of amino acids which may not be adjacent.

According to further embodiments, protein or polynucleotide sequences with specific location or domain sequence similarity are identified by the method of the present invention. When comparing residues with no conservation the low similarity is meaningless thus lower overall similarity sequences with high conservation in conserved region will be still considered as similar in a given range, for example of >60% (i.e. sequences showing low similarity of ~37% to the nearest homolog but possess all the conserved substrate binding residues of a specific protein family) that can be found in hmm-based search algorithms such as HMMER3.

The term "Conserved Domain Database (CDD)" refers to a collection of sequence alignments and profiles representing protein domains. It also includes alignments of the domains to known 3-dimensional protein structures in the database (i.e. Molecular Modeling Database (MMDB).

In some embodiments of the invention, such substantially identical sequences refer to polynucleotide or amino acid sequences that share at least about 60% identity, preferably at least about 80% identity, alternatively, about 90%, 95%, 96%, 97%, 98% or 99% identity to the indicated polynucleotide or amino acid sequence/s.

Polypeptides within the scope of the present invention are at least 50% identical to the protein identified by the method of the present invention; or at least 55% identical, or at least 60% identical, or at least 65% identical, or at least 70% identical, or at least 75% identical, or at least 80% identical, or at least 85% identical or at least 90% identical or at least 95% identical to the protein identified by the method of the present invention or to a reference sequence.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

The term "homolog" as used herein, refers to a DNA or amino acid sequence having a degree of sequence similarity in terms of shared amino acid or nucleotide sequences. There may be partial similarity or complete similarity (i.e., identity). For protein sequences, amino acid similarity matrices may be used as are known in different bioinformatics programs (e.g. BLAST, FASTA, Bestfit program—Wisconsin Sequence Analysis Package, Version 8 for Unix, Genetics Computer Group, University Research Park, 575 Science Drive Madison, WI 53711, Smith Waterman). Different results may be obtained when performing a particular search with a different matrix. Degrees of similarity for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402). Guidance in determining which amino acid residues may be substituted, inserted, or deleted without abolishing biological or activity may be found using computer programs well known in the art, for example, DNASTAR software.

The term "polymorphism" is understood within the scope of the invention to refer to the presence in a population of two or more different forms of a gene, genetic marker, or inherited trait or a gene product obtainable, for example, through alternative splicing, DNA methylation, etc.

The present invention encompasses "High-throughput screening" or "HTS" technique, which herein refers to a method to rapidly identify genes that modulate a particular biomolecular pathway or function. It includes metatranscriptomic and metagenomic gene expression.

The present invention outlines a procedure for producing expression libraries from genetic material isolated from ecological niches, which expression libraries can be transformed into the target plant for screening for a desirable trait such as tolerance or resistance to biotic or abiotic stress and improving yield or biomass production.

According to one embodiment, the present invention provides a method for screening for and identifying a desirable plant improving trait, the method comprises steps of: (a) obtaining genetic material from a sampling of a predefined environmental niche; and (b) constructing an expression library from the genetic material. According to core embodiments, the present invention further comprises steps of: (c) producing plants transformed with the expression library at an efficiency of at least 0.05%-30%, representing at least $10^2$-$10^{10}$ transgenes, thus creating the expressed library within the plants or seeds; (d) screening for transformed plants expressing the desirable trait; and (e) identifying the transgene of the transformed plants expressing the desirable trait.

It is further within the scope to disclose the method as defined in any of the above, wherein the step (a) further comprises steps of enriching the genetic material by growth on rich media or on selective media.

It is further within the scope to disclose the method as defined in any of the above, wherein the step (a) further comprises steps of enhancing expression of the desirable trait by culturing the genetic material on selective media for the desirable trait.

It is further within the scope to disclose the method as defined in any of the above, wherein the step (b) comprises steps of producing prokaryotic cDNA library or eukaryotic cDNA library or both.

It is further within the scope to disclose the method as defined in any of the above, wherein the step (b) further comprises steps of cloning the cDNA library into at least one binary vector.

It is further within the scope to disclose the method as defined in any of the above, wherein the binary vector comprises a constitutive promoter or a stress induced promoter.

It is further within the scope to disclose the method as defined in any of the above, wherein the binary vector comprises bacterial selection marker and plant transformation selection marker.

It is further within the scope to disclose the method as defined in any of the above, wherein the bacterial selection marker is Kanamycin resistance, or any other antibiotic resistance conferring gene, and the plant transformation selection marker is bar gene, conferring resistance to phosphinothricin containing herbicide (e.g. Basta herbicide).

Reference is now made to Glufosinate (also known as phosphinothricin and often an ammonium salt) is a naturally occurring broad-spectrum systemic herbicide produced by several species of Streptomyces soil bacteria. Glufosinate is a broad-spectrum herbicide that is used to control weeds. It is sold in formulations under brands including Basta, Rely, Finale, Challenge and Liberty. The bar gene confers resistance to the herbicide Basta (containing phosphinothricin).

It is further within the scope to disclose the method as defined in any of the above, further comprises steps of transforming the cloned binary vectors into host cells.

It is further within the scope to disclose the method as defined in any of the above, further comprises steps of transforming the cloned binary vectors into *Agrobacterium tumefaciens*.

It is further within the scope to disclose the method as defined in any of the above further comprises steps of introducing the transformed *Agrobacterium tumefaciens* into at least one of: whole plant, plant tissue and plant cell.

It is further within the scope to disclose the method as defined in any of the above, comprises steps of introducing the transformed *Agrobacterium tumefaciens* by spraying the plants with an inoculum comprising transformed *Agrobacterium*.

It is further within the scope to disclose the method as defined in any of the above, wherein the step (d) comprises growing the transformed plants under conditions selective for the desirable trait.

It is further within the scope to disclose the method as defined in any of the above, further comprises steps of:
f. collecting T1 seeds from the transformed plants of step (d);
g. determining seed library efficiency of the T1 seeds by calculating ratio of phosphinothricin resistant plants to total number of plants;
h. sowing the T1 seeds of step (e) under selective conditions allowing screening and selection of transformed plants expressing the desirable trait;
i. testing the selected plants expressing the desirable trait of step (g) for presence of the transgene; and
j. isolating and sequencing the transgene of the selected transformed plants positively tested for the transgene of step (h).

It is further within the scope to disclose the method as defined in any of the above, further comprises steps of
k. collecting T2 seeds from the plants of (h), which are found positive for presence of the transgene;
l. growing plants of the T2 seeds under selective conditions allowing screening and selection of transformed plants expressing the desirable trait as compared to control plants transformed with known genes conferring the desirable trait; and
m. optionally, isolating and sequencing the transgene of the selected plants of step (j).

It is further within the scope to disclose the method as defined in any of the above, comprises steps of
a. recloning and sequencing the isolated transgene of step (i) and/or (l);
b. transforming the recloned transgene into plants;
c. screening the transformed plants of step (b) for selection of transformed plants expressing the desirable trait;
d. isolating the transgene from the selected plants of step (c); and
e. optionally, repeating steps (a) to (d).

It is further within the scope to disclose the method as defined in any of the above, wherein the environmental niche comprises samples derived from ecological niches, sources, populations, habitats, gene pools, prokaryotic culture, eukaryotic culture and any combination thereof.

It is further within the scope to disclose the method as defined in any of the above, wherein the environmental niche sampling comprises microbiome, microbiota or microbial culture, plant, yeast, algae, nematode or any other organism or combinations thereof.

It is further within the scope to disclose the method as defined in any of the above, wherein the environmental niche is defined according to biotic factors, abiotic factors and a combination thereof.

It is further within the scope to disclose the method as defined in any of the above, wherein the environmental niche sampling comprises soil sample, water sample, organic matter sample, any living organisms (such as plant, yeast, bacteria, microorganism, algae, nematode) and any combination thereof.

It is further within the scope to disclose the method as defined in any of the above, wherein the desirable trait is selected from the group consisting of resistance or tolerance to at least one biotic stress, resistance or tolerance to at least one abiotic stress, improved yield or biomass, improved grain yield, improved fertilizer uptake and improved usage efficiency and a combination thereof.

It is further within the scope to disclose the method as defined in any of the above, wherein the abiotic stress is selected from the group consisting of: drought, salinity, heat, cold, fertilizer uptake, fertilizer utilization efficiency and any combination thereof.

It is further within the scope to disclose the method as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose the method as defined in any of the above, wherein the method comprises steps of extracting RNA from the sampling of the predefined environmental niche.

It is further within the scope to disclose the method as defined in any of the above, wherein the RNA extraction is performed according to standard commercial kits or according to any other protocol for extraction of RNA from environmental sampling.

It is further within the scope to disclose the method as defined in any of the above, wherein the protocol for extraction of RNA from environmental sampling comprises steps of:
a. obtaining a soil sample;
b. mixing the soil sample with an extraction buffer comprising 500 mM phosphate buffer pH 8 and 5% w/v cetyltrimethylammonium bromide (CTAB) with phenol (pH 8)/chloroform/IAA ratio of 25:24:1;
c. subjecting the mixture of step (b) to 15 min shaking at 37° C. or to a bead beater for 1 min;
d. centrifuging the mixture of step (c) at 2,500 g for about 10 minutes at room temperature to obtain an aqueous phase;
e. transferring the aqueous phase into a new tube;
f. adding to the aqueous phase within the tube of step (e) an equal amount of iso-propanol supplemented with 20 mg/ml crystal violet solution to obtain violate stained solution;
g. mixing the solution by inverting said tube of step (0 and then incubating the tube for about 30 minutes at room temperature;
h. centrifuging the tube of step (g) at 2,500 g for about 30 minutes at room temperature to obtain a violet stained layer;
i. transferring the violate stained layer into a new tube and centrifuging the tube for about 5 min at maximal speed to obtain pellet and supernatant;
j. washing the pellet with 80% v/v ice cold ethanol and centrifuging for additional 5 min to obtain pellet and supernatant;
k. removing the supernatant of step (j) and allowing the pellet to dry; and
l. suspending the dried pellet in water in a ratio of 100 µl water to 2 gr of soil of step (a).

It is further within the scope to disclose polynucleotide sequences obtainable by the method as defined above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs:1-148 and any combination thereof.

It is further within the scope to disclose a polynucleotide sequence having at least 80%, 85%, 90% or 95% sequence similarity to a polynucleotide sequence obtainable by the method as defined above.

It is further within the scope to disclose a polypeptide sequence obtainable by the method as defined above.

It is further within the scope to disclose the polypeptide sequence as defined above, wherein the polypeptide comprises an amino acid sequence corresponding to the sequence as set forth in a polypeptide sequence selected from the group consisting of SEQ ID NOs: 149-321 and any combination thereof.

It is further within the scope to disclose an amino acid sequence having at least 60%, 70%, 80% or 90% sequence similarity to an amino acid sequence obtainable by the method as defined above.

It is further within the scope to disclose the use of the method as defined above for identifying genes conferring resistance or tolerance to abiotic or biotic stress.

It is further within the scope to disclose the use of the method as defined above for identifying genes conferring improved yield and biomass, i.e. improved grain yield, in plants, for example by enhancing growth, with or without exposure to stress conditions.

It is further within the scope to disclose the use of the method as defined above for identifying genes conferring improved yield.

It is further within the scope to disclose the use as defined in any of the above, wherein the abiotic stress is selected from the group consisting of: drought, salinity, heat, cold, fertilizer utilization, fertilizer uptake and any combination thereof.

It is further within the scope to disclose the use as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose a method for screening for and identifying a drought resistance or tolerance improving trait in plants, the method comprises steps of: (a) obtaining genetic material derived from a low moisture or a high salinity environmental niche sample; and (b) constructing expression library from the genetic material. According to core embodiments, the method further comprises steps of: (c) producing plants transformed with the expression library at an efficiency of at least 0.05%-30%, representing at least $10^2$-$10^{10}$ transgenes; (d) screening for transformed plants surviving predetermined drought conditions; and (e) identifying the transgene of the drought surviving transformed plants of step (d).

It is further within the scope to disclose the method as defined above, wherein the step (b) further comprises steps of cloning the expression library into at least one binary vector.

It is further within the scope to disclose the method as defined in any of the above, further comprises steps of:
f. collecting T1 seeds from the transformed plants of step (c);
g. sowing the T1 seeds in soil selective for transformed plants, with water content of about 100% capacity;
h. growing plants of the T1 seeds in drought condition and/or without irrigation until most of the plants die, to produce transformed plants surviving the drought conditions;
i. growing the drought surviving transformed plants to produce T2 seeds;
j. screening the drought surviving transformed plants of step (i) for presence of a transgene;
k. isolating and sequencing the transgene from positively screened plants of step (l);

It is further within the scope to disclose the method as defined in any of the above, further comprises steps of
l. collecting T2 seeds from each of the transgene-containing positively screened drought surviving transformed plants of step (j);
m. growing T2 plants from each of the transgene-containing T2 seeds of step (l) under predetermined drought conditions as compared to control plants transformed with known genes conferring drought tolerance or drought resistance;
n. performing drought tolerance or resistance screen measurements for each of the transgene-containing T2 plants as compared to the control plants selected from the group consisting of: turgor measurements, number of plants death, state of plants and any combination thereof;
o. isolating the transgene from the screened drought resistance performing T2 plants of step (n);
p. optionally, recloning the transgene into a binary vector;
q. optionally, transforming the cloned binary vector into plants and growing the transformed plants under predetermined drought conditions; and
r. optionally, repeating steps (l) to (q).

It is further within the scope to disclose the method as defined in any of the above, wherein the step of growing T2 plants comprises steps of: (a) sowing the T2 seeds in soil selective for transformed plants, with water content of about 100% capacity; and (b) irrigating the plants when water content in the soil reaches about 5-10%.

It is further within the scope to disclose the method as defined in any of the above, wherein the predetermined drought conditions are selected from the group consisting of low moisture, high salinity, dry soil and heat.

It is further within the scope to disclose polynucleotide sequences obtainable by the method as defined in any of the above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs:1 to SEQ ID NO:148 and any combination thereof.

It is further within the scope to disclose polynucleotide sequences having at least 80%, 85%, 90% or 95% sequence similarity to polynucleotide sequences obtainable by the method as defined in any of the above.

It is further within the scope to disclose a polypeptide sequence obtainable by the method as defined in any of the above.

It is further within the scope to disclose the polypeptide sequence as defined above, wherein the polypeptide sequence comprises an amino acid sequence corresponding to the sequence as set forth as set forth in polypeptide sequence selected from the group consisting of SEQ. ID Nos: 149-321 and any combination thereof.

It is further within the scope to disclose polypeptide sequences having at least 60%, 70%, 80% or 90% sequence similarity to amino acid sequences obtainable by the method as defined in any of the above.

It is further within the scope of the present invention to disclose a method for extracting RNA from a soil sample comprising steps of:
  m. obtaining a soil sample;
  n. mixing said soil sample with an extraction buffer comprising 500 mM phosphate buffer pH 8 and 5% w/v cetyltrimethylammonium bromide (CTAB) with phenol (pH 8)/chloroform/IAA ratios of 25:24:1;
  o. subjecting said mixture of step (b) to about 15 min shake at 37° C. or to a bead beater for 1 min;
  p. centrifuging said mixture of step (c) at 2,500 g for about 10 minutes at room temperature to obtain an aqueous phase;
  q. transferring said aqueous phase into a new tube;
  r. adding to said aqueous phase within said tube of step (e) an equal amount of iso-propanol supplemented with 20 mg/ml crystal violet solution to obtain violate stained solution;
  s. mixing said solution by inverting said tube of step (f) and then incubating said tube for about 30 minutes at room temperature;
  t. centrifuging said tube of step (g) at 2,500 g for about 30 minutes at room temperature to obtain a violet stained layer;
  u. transferring said violate stained layer of step (h) into a new tube and centrifuging said tube for about 5 min at maximal speed to obtain pellet and supernatant;
  v. washing said pellet with 80% v/v ice cold ethanol and centrifuging for about additional 5 min to obtain pellet and supernatant;
  w. removing said supernatant of step (j) and the pellet is left to dry; and
  x. suspending said dried pellet in water in a ratio of 100 μl water to 2 gr of soil of step (a).

It is further within the scope of the present invention to disclose a method for screening for and identifying a desirable plant improving trait, said method comprises steps of:
  y. obtaining a sampling of a predefined environmental niche;
  z. extracting RNA from the sampling according to the method for extracting RNA from a soil sample as defined above;
  aa. constructing an expression library from the RNA of step (b);

The method further comprises steps of:
  bb. producing plants transformed with the expression library at an efficiency of at least 0.05%-30% representing at least $10^2$-$10^{10}$ transgenes;
  cc. screening for transformed plants expressing the desirable trait; and
  dd. identifying the transgene of the transformed plants expressing the desirable trait.

It is further within the scope of the present invention to disclose an isolated polynucleotide having a nucleotide sequence corresponding to the sequence as set forth in a polynucleotide sequence selected from the group consisting of SEQ ID NOs:1 to SEQ ID NO:148 and any combination thereof.

It is further within the scope of the present invention to disclose an isolated polypeptide having an amino acid sequence corresponding to the sequence as set forth in polypeptide sequence selected from the group consisting of SEQ. ID Nos: 149-321 and any combination thereof.

In order to understand the invention and to see how it may be implemented in practice, a plurality of preferred embodiments will now be described, by way of non-limiting example only, with reference to the following examples.

Example 1

A Process for Improving Traits in Plants by Transformation of Expression Libraries from Ecological Niches into Plants and Screening for Desired Traits 1. Sample Collection and Processing In the first step, genetic pools of a varied environmental samples and sources such as soil, water or organic matter from different habitats have been isolated. The source is selected according to the specific desired target traits. For example, when screening for drought or salinity resistant gene, a dry land such as desert land or a high salinity land or other enforcement will be used, but not necessarily.

The microbiome found in each sample may optionally be enriched by growth on rich media or selectively grown with antibiotics. To enhance expression of potentially desired genes, the culture is grown in stress conditions or media resembling, associated with or affecting the target trait, such as salt or PEG rich media for drought or salinity resistance trait.

Sample enrichment is carried on rich growth media (e.g. YPD) for several days at 28° C.-37° C. in shaker incubator. If eukaryotic libraries are prepared, anti-bacterial antibiotics such as Penicillin-Streptomycin and Spectinomycin are added.

To induce stress resistant genes, the sample is grown under any desired environmental stress conditions. For example, to induce drought resistance genes, the sample is grown under high osmotic stress by adding PEG to the growth media (10%-30% w/v). High salt concentration media such as NaCl (5%-10% w/v) was used to induce high salinity stress. In addition, the samples are exposed to different nitrogen concentration (from 0-100 mM $KNO_3$ in water supplemented with 6 mM $KH_2PO_4$ and micro elements, see Table 1, http://www.gatfertilizers.com/properties-of-solid-and-liquid-fertilizers/ as recommended by the manufacturer), extreme temperatures (50-60° C.) and any environmental stress desired.

TABLE 1

| Element | Percentage | gr/Lt |
|---|---|---|
| Iron | 1.09 | 12.20 |
| Manganese | 0.48 | 5.47 |
| Zinc | 0.15 | 1.75 |
| Copper | 0.05 | 0.55 |
| Molybdenum | 0.02 | 0.16 |
| Boron | 0.20 | 2.00 |

2. RNA Extraction

Total RNA extraction has been performed according to standard commercial kits such as RNeasy PowerSoil Total RNA Kit (Qiagen) and Quick-RNA (Zymo research). In addition, a unique protocol is used for extraction of RNA from soil samples, as follows:

In a 7 ml tube, 2 g of soil is disrupted with extraction buffer (500 mM Phosphate buffer pH 8 and 5% w/v CTAB with Phenol (pH 8), chloroform, IAA (25:24:1)). The tube is subjected to 15 min shaking at 37° C. or to a bead beater for 1 min. The tube is then centrifuged at 2,500 g for 10 minutes at room temperature. The aqueous phase is transferred into a new tube and an equal amount of iso-propanol supplemented with 5 ul of crystal violate solution (20 mg/ml) is added. The tubes are mixed by inverting and left to stand for 30 minutes at room temperature, then centrifuged at 2,500 g for 30 minutes at room temperature. The violate stained layer is transferred into a new 1.5 ml tube and centrifuged for 5 min at maximal speed. The pellet is washed with 500 μl of 80% v/v ice cold ethanol and centrifuged for additional 5 min. After centrifugation, the liquid is removed, and the pellet is left to dry. The dry pellet is suspended in 100 μl water.

3. Construction of cDNA Libraries 3.1. Eukaryotic cDNA Libraries

Figure 1B:
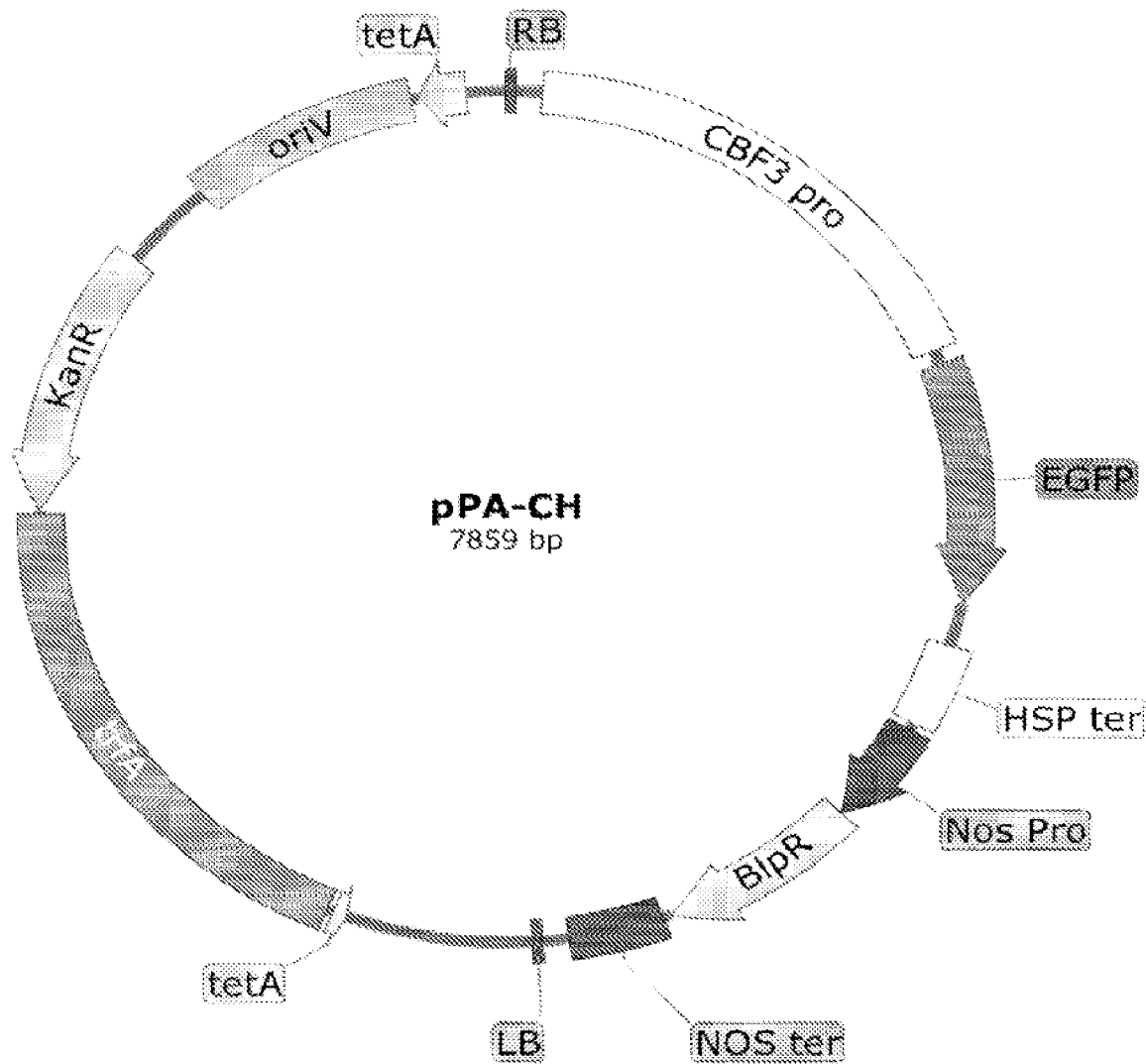
Figure 1C:
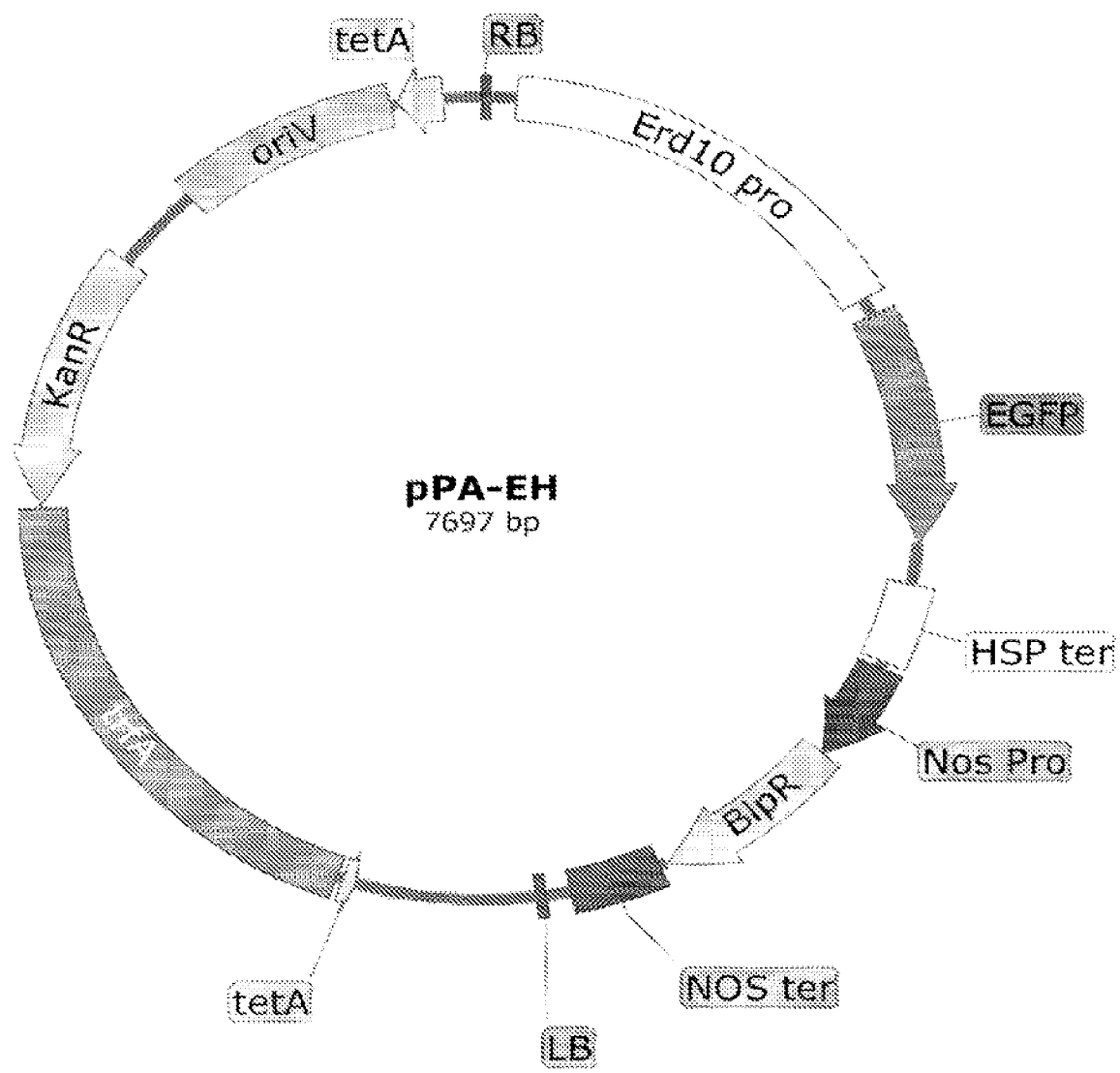
Figure 1D:
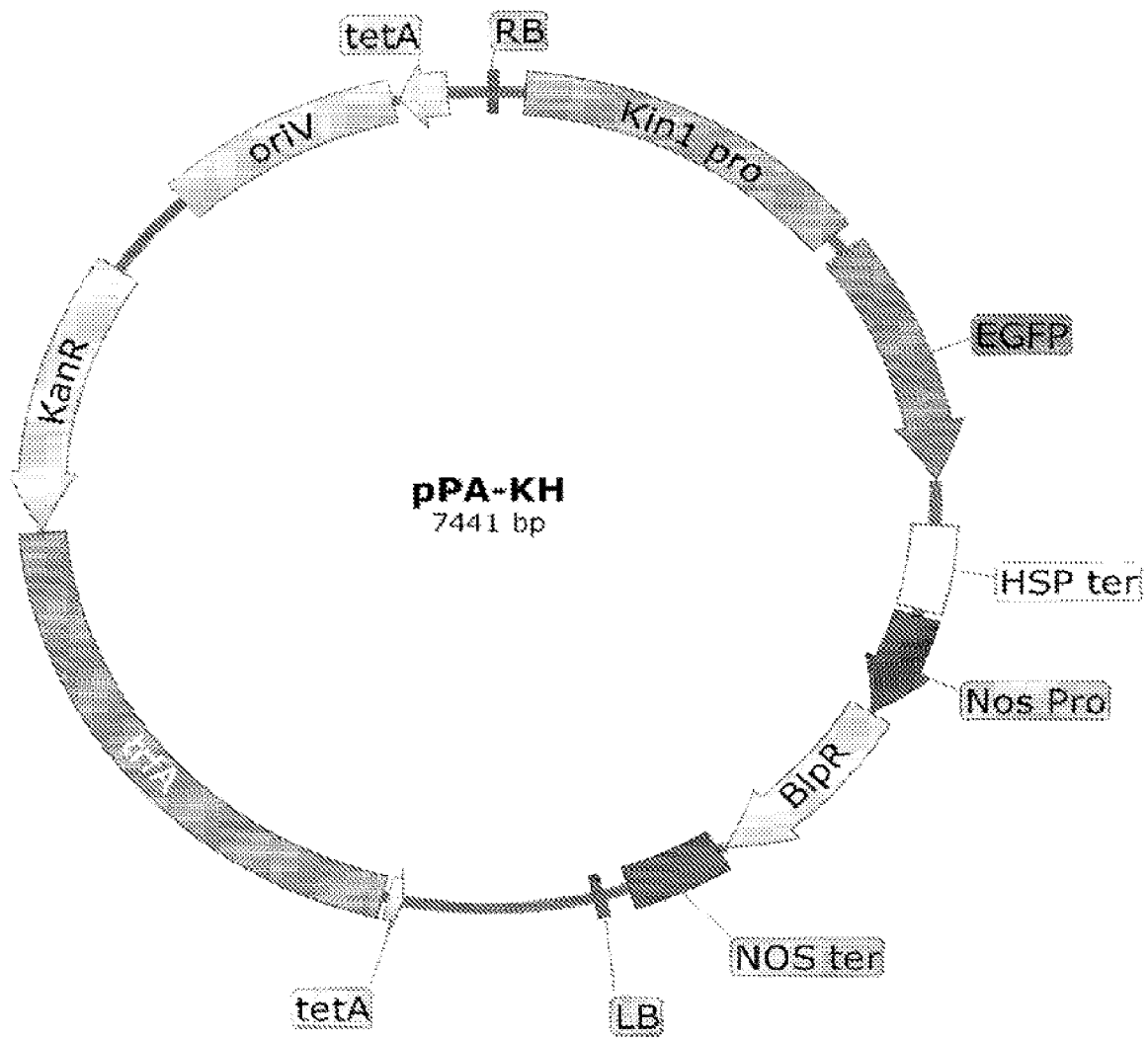
Figure 2:
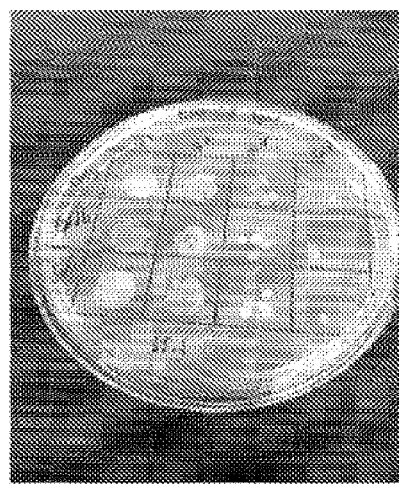
FIG. 2 presents a photographic illustration of *agrobacterium* library counting for 3 different libraries on LB petri dishes.

Eukaryotic cDNA libraries from total-RNA and mRNA are constructed based on template switching—reverse transcription of poly-A mRNA (SMART) or oligo-capping rapid amplification of cDNA ends (5'-RACE) methods. The reverse transcription of poly-A mRNA primers used are 5'-ATTCTAGAGCGATCGCA-CATGTTTTTTTTTTTTTTTTTTTTTTTTTTTTTVN-3' (referred to as SEQ. ID NO:321) and 5'-AAGCAGTGGTATCAACGCAGAGTGGCGCGCCr-GrGG-3' (referred to as SEQ. ID NO:322). The oligo-capping rapid amplification of cDNA ends primers used are 5'-ATTCTAGAGCGATCGCA-CATGTTTTTTTTTTTTTTTTTTTTTTTTTTTTTVN-3' (referred to as SEQ. ID NO:321) and 5'-InvddT (5' Inverted Dideoxy-T)-r (AAGCAGUGGUAU-CAACGCAGAGUGGCGCGCCG)-3' (referred to as SEQ. ID NO: 323). The amplified cDNA is inserted into binary vectors (see FIGS. 1-4) between the promoter(s) (35S, KIN1, erd10 and/or CBF3) and the HSP or NOS terminator. FIG. 1A illustrates the pPA-35H vector, which has a constitutive CaMV 35S promoter with the GFP gene cloned between the promoter and terminator as an example. FIGS. 1B-D present vectors containing stress induced promoters from *Arabidopsis thaliana*: pPA-CH vector with CBF3 promoter having a nucleotide sequence as set forth in SEQ. ID NO: 330 (FIG. 1B), pPA-EH with Erd10 promoter having a nucleotide sequence as set forth in SEQ. ID NO: 331 (FIG. 1C) and pPA-KH with Kin1 promoter having a nucleotide sequence as set forth in SEQ. ID NO: 332 (FIG. 1D) with the GFP gene cloned between the promoter and terminator as an example (Plant Physiol. 1997 October; 115(2): 327-334, Plant Journal (2004) 38, 982-993 incorporated herein by reference).

Figure 5:
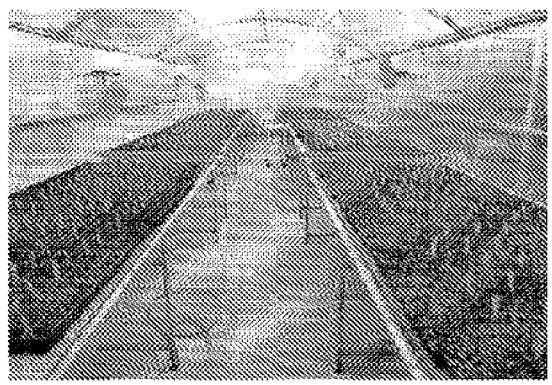
FIG. 5 presents a photographic illustration of T2 and T3 controlled experiments in the greenhouse.

These vectors contain Kanamycin as a bacterial selection and the bar gene as a transgenic plant selection conferring resistance to the phosphinothricin herbicide. At least one of the non-limiting examples of Gibson assembly, Restriction-ligation, Restriction free or In-Fusion methods is used and then ligation products are transformed to *E. coli* competent cells to grow under kanamycin selection. The library size is estimated by live count of transformed bacteria sown on LB petri dishes (usually 10^5-10^7) (FIG. 5). Vectors of the cDNA library are purified from *E. coli* bacteria with standard mini-prep kits and transformed to electrocompetent *Agrobacterium tumefaciens* GV3101 cells. The transformed *Agrobacterium* are grown on LB media under kanamycin and rifampicin selection (50 μg/ml each) over night at 28° C., (250 ml per 1 m² of target plant growth area). The growth arrested on ice for at list 30 min and then centrifuged for 10 min at 8000 rpm at 4° C. The pelleted *Agrobacterium* are suspended in suspension buffer (5% sucrose and 0.03% L-77 Silwet, Momentive, US).

3.2. Prokaryotes cDNA Libraries

Prokaryotes cDNA libraries from total RNA are constructed based on standard 5' and 3' RNA modifications with ScriptSeg™ Complete Kit (epicenter). Primers used are 5'-ATTCTAGAGCGATCGCA-CATGTTTTTTTTTTTTTTTTTTTTTTTTTTTTTVN-3' (referred to as SEQ. ID NO:321) and 5'-InvddT (5' Inverted Dideoxy-T)-r(AAGCAGUGGUAU-CAACGCAGAGUGGCGCGCCG)-3' (referred to as SEQ. ID NO:324). The amplified cDNA inserted into carrier vectors barring Kanamycin and phosphinothricin resistance and then transformed to *E. coli* competent cells to grow under kanamycin selection (50 μg/ml). The library size is estimated by live count of transformed hosts (usually 10^5-10^7). Vectors of the cDNA library are purified from host cells with standard mini-prep kit (50 μl) and transformed to electrocompetent *Agrobacterium* GV3103 cells (100 μl). The transformed *Agrobacterium* are grown on LB media under kanamycin and rifampicin selection (50 μg/ml) over night at 28° C. (100 ml per 1 m 2 of target plant growth area). The growth is arrested on ice for at list 30 min and then centrifuged for 5 min at 8000 rpm at 4° C. The pelleted *Agrobacterium* are suspended in suspension buffer (5% sucrose and 0.03% L-77 Silwet).

4. Growing and Transformation of Plants 4.1. *Arabidopsis* Plants

Plants are grown in controlled greenhouses as a preparation for transformation. Plants are grown in soil composed of 75% peat, 25% perlite and are being irrigated routinely with water supplemented with fertilizer (e.g. Shefer 5.3.8, ICL Israel) according to manufacturer instructions, as needed. Plants start flowering after 3-4 weeks and then they are ready for transformation. Transformed *Agrobacterium* with expression libraries are grown as mentioned above and suspended in suspension buffer (5% sucrose and 0.03% L-77 Silwet) and are sprayed by 2 liter sprayers (e.g. Solo, Germany) on the flowers. After 5-6 weeks of continued growth when plants become dry, seeds are collected and kept in a cool dry place for 2 weeks or until used.

4.2. Tobacco Plants

Figure 3A:
FIGS. 3A-3C presents a photographic illustration of tobacco tissue culture transformed with a library, 7 days after transformation (FIG. 3A), 40 days after transformation (FIG. 3B) and 6-8 weeks after transformation (FIG. 3C)
Figure 3B:
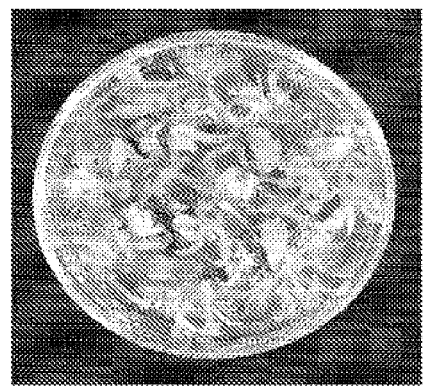
Figure 3C:

Tobacco leaves are cut into 1-2 cm 2 pieces and sterilized by 70% ethanol followed by 0.3% bleach treatments for 5 minutes. Leaf pieces are mixed with libraries transformed Agrobacterium (or with a any identified gene of SEQ ID 1-148 from Table 4), suspended in liquid Regeneration Medium (RM) supplemented with MS including Gamborg B5 vitamins, 3% sucrose, 2 mg/L BAP (6-Benzylaminopurine) and 0.2 mg/L NAA (Naphthalene acetic acid) (e.g. Duchefa, Netherland) for 30 minutes. Bacteria are than washed and leaf pieces are placed on RM plant-agar plates for one day in the dark. Leaf pieces are transferred to new selection RM plant-agar plates supplemented with 300 µg/ml of timentin antibiotic to kill the Agrobacterium and 1.5 µg/ml phosphoinotricin (e.g. Duchefa, Netherland) for selection of transgenic plants. FIG. 3A-B present a photographic illustration of tobacco tissue culture transformed with a library, 7 days after transformation (FIG. 3A) and 40 days after transformation (FIG. 3B). After 6-8 weeks, plantlets start to appear and are transferred to new vessels containing the same selection RM plant-agar, but BAP is excluded (see FIG. 3C). After rooting, plants are transferred to soil in the greenhouse.

Example 2

Figure 4:
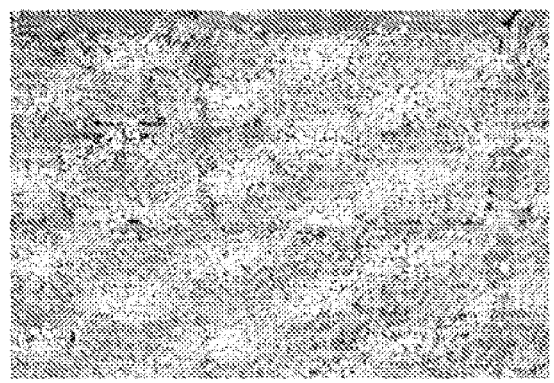
FIG. 4 presents a photographic illustration demonstrating selection for phosphinothricin resistance of 10 days old *Arabidopsis* expressing library seedlings. The green plants are resistant to phosphinothricin while small yellow plants are absent of the transgene and therefore susceptible.

A Process for Identifying Drought Resistance Traits in Plants
A. Screening for Drought and/or Salinity Resistant Plants/Genes Arabidopsis T1 seeds harboring the desired expression library are being used for the screen. At the first stage, the transformation efficiency is defined for a specific seed library. 1 ml of seeds (~50,000 seeds) is being sowed on soil irrigated with water supplemented with Basta (e.g. Bayer, Germany) according to manufacturer instructions. Seven days post sowing, the number of phosphinothricin resistant plants is counted and compared with phosphinothricin susceptible plants (FIG. 4). As demonstrated in FIG. 4, the bigger plants are resistant to phosphinothricin while small plants are absent of the transgene and therefore susceptible and will die. The seed library efficiency is represented by the ratio of the number of resistant plants to the number of total plants.

The library is then sowed according to the desired number of plants intended to be represented in the specific experiment and which represents best the library size. For example, if an expression library consists of $5\times10^4$ genes, and the transformation efficiency is 1%, >5 million seeds should be sowed. In this case, in ~20 m² of soil, 50,000 Basta resistant plants will be grown for the experiment.

Soil is irrigated once, when seeds are sown, with water supplemented with phosphinothricin and fertilizer (e.g. Shefer 5.3.8, ICL Israel) according to manufacturer instructions, and soil water content reaches 100% capacity. Plants are grown in air-conditioned controlled greenhouses, and soil is not irrigated until most of the plants die from lack of water. Surviving plants, ~0.1% of initial phosphinothricin resistant plants, are being rescued by irrigation until they produce seeds which are being collected for T2 experiments. During their growth, the surviving plants are tested for their transgene, by gDNA extraction from one of their leaves and PCR using primers for the gene specific promoters (CaMV 35S, CBF3, Erd10 and Kin1) and terminators (NOS, HSP) (see Table 2). PCR products are being sequenced and the resulted sequence is blasted versus sequence databases such as NCBI, both for DNA comparisons (i.e. BLASTn) and for amino acid sequence comparisons (i.e. BLASTx).

Reference is now made to Table 2 presenting SEQ ID NOs of primer and promoter sequences used in the present invention:

TABLE 2

SEQ ID NOs of primer sequences

| SEQ ID NO. | Description |
|---|---|
| SEQ ID NO: 321 | Reverse primer for transcription of poly-A mRNA |
| SEQ ID NO: 322 | Forward primer for transcription of poly-A mRNA |
| SEQ ID NO: 323 | Forward primer for oligo-capping amplification of cDNA ends |
| SEQ ID NO: 324 | Forward primer for amplification of prokaryote cDNA library (e.g. derived from total RNA) |
| SEQ ID NO: 325 | Forward primer for CaMV 35S promoter |
| SEQ ID NO: 326 | Forward primer for CBF3 promoter |
| SEQ ID NO: 327 | Forward primer for Erd10 promoter |
| SEQ ID NO: 328 | Forward primer for Kin1 promoter |
| SEQ ID NO: 329 | Reverse primer for NOS/HSP terminator |
| SEQ ID NO: 330 | CBF3 promoter |
| SEQ ID NO: 331 | Erd10 promoter |
| SEQ ID NO: 332 | Kin1 promoter |

B. Subsequent Generations (T2, T3) Experiments

Seeds collected from drought surviving plants are being tested again in further experiments including repeats and controls to test their resistance/tolerance to drought (see FIG. 5).

Several genes were chosen to serve as controls in the drought experiments:
1) EGFP—jellyfish green fluorescent protein, cloned under the control of the various used promoters and HSP terminator (see vector maps of FIGS. 1A-D), is being served as a negative control for drought, since it was not been shown to be associated with improving plants resistance to drought (Yang T-T, et al., 1996).
2) mtlD—mannitol-1-phosphate dehydrogenase from Escherichia coli, cloned under the control of the various used promoters and HSP terminator (see vector maps of FIGS. 1A-D), is being served as a positive control since it was shown to be associated with improving plants resistance to drought and salt (Hema R. et al., 2014).
3) HRD—The HARDY gene from Arabidopsis thaliana cloned under the control of the various used promoters and HSP terminator (see vector maps of FIGS. 1A-D), is being served as a positive control since was shown to be associated with improving plants resistance to drought and salt (Kaaba A. et al., 2007).

Plants identified as expressing unique genes in the screen experiments, including all controls, are sown in trays 38×28 cm with 16 plastic inserts in each tray (e.g. Desch Plantpak, Netherland), filled with soil supplemented with fertilizer and phosphinothricin as above. In each insert several seeds are sown and after 10 days a single phosphinothricin resistant plant is being kept for further experiments. Each experiment contains 20-40 repeats of each plant, representing the expressed unique genes, which are spread in random on the greenhouse tables. Irrigation of the soil is similar to the screen experiment; it is done when the seeds are sown, except when soil is completely dry and reaches weight lower then initial weight of soil before irrigation (~5%-10% of water content), then plants are irrigated again to check revival performance.

Figure 6:
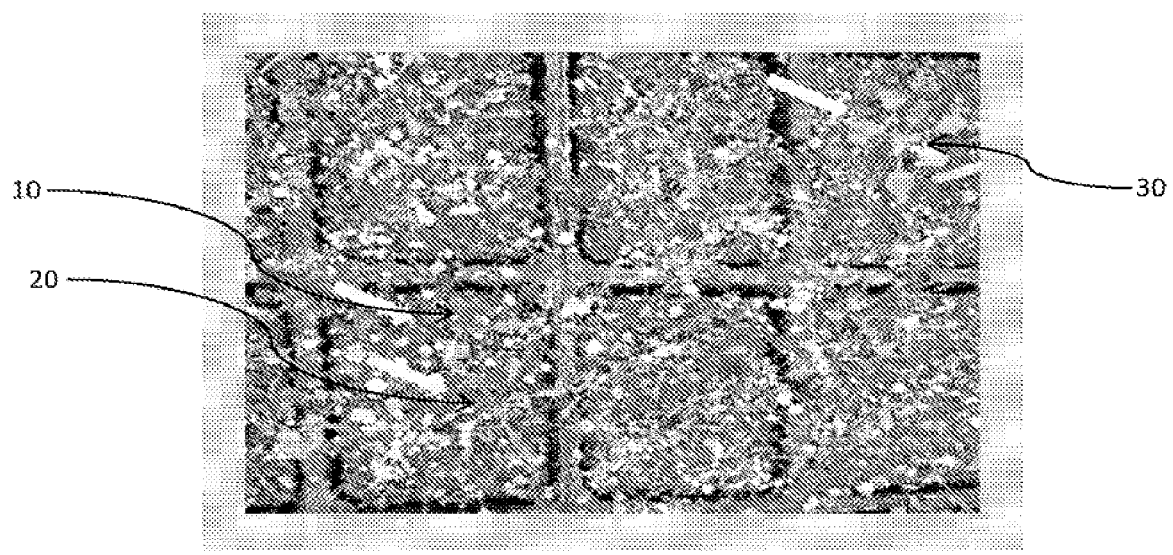
FIG. 6 presents photographic results of screening for transgenic plants resistance to drought.

Reference is now made to FIG. 6 showing photographic results of screening for transgenic plants resistance to drought grown under the conditions as described above. This figure shows that transgenic plants carrying drought resistance genes 10, 20 and 30 survive in severe drought conditions, while other transgenic plants that do not harbor drought resistant conferring genes do not survive the stress conditions. It is noted that within the small area shown in this figure (~15×25 cm), about 300 plants were screened while 3 survived the drought conditions.

When drought conditions start to develop, various measurements are taken, as shown in Table 3:
1) turgor observation, measured by scale of 1-10, when 1 is high turgor and 10 is total loss of turgor (see FIG. 7).
2) Weight of plant and pot, by scale in grams.
3) Death of plants observation, 10=dead and 1=alive (see FIG. 8)
4) State of plants observation in a scale of 1-10, when 1 is good state and 10 is poor.

TABLE 3

Measurements taken in drought experiments

| measurement | units | time of measurement |
| --- | --- | --- |
| Weight of pot | Grams | Start till end of experiment |
| Turgor | Observation units 1-10, where 1 is 0 turgor loss and 10 is 100% turgor loss | From beginning of turgor loss (~15-27 days from last irrigation) |
| Death | Observation units 1-10 | From first death observed |
| State of plants | Observation units 1-10 | During first 2 weeks and one day after revival |

Figure 7:
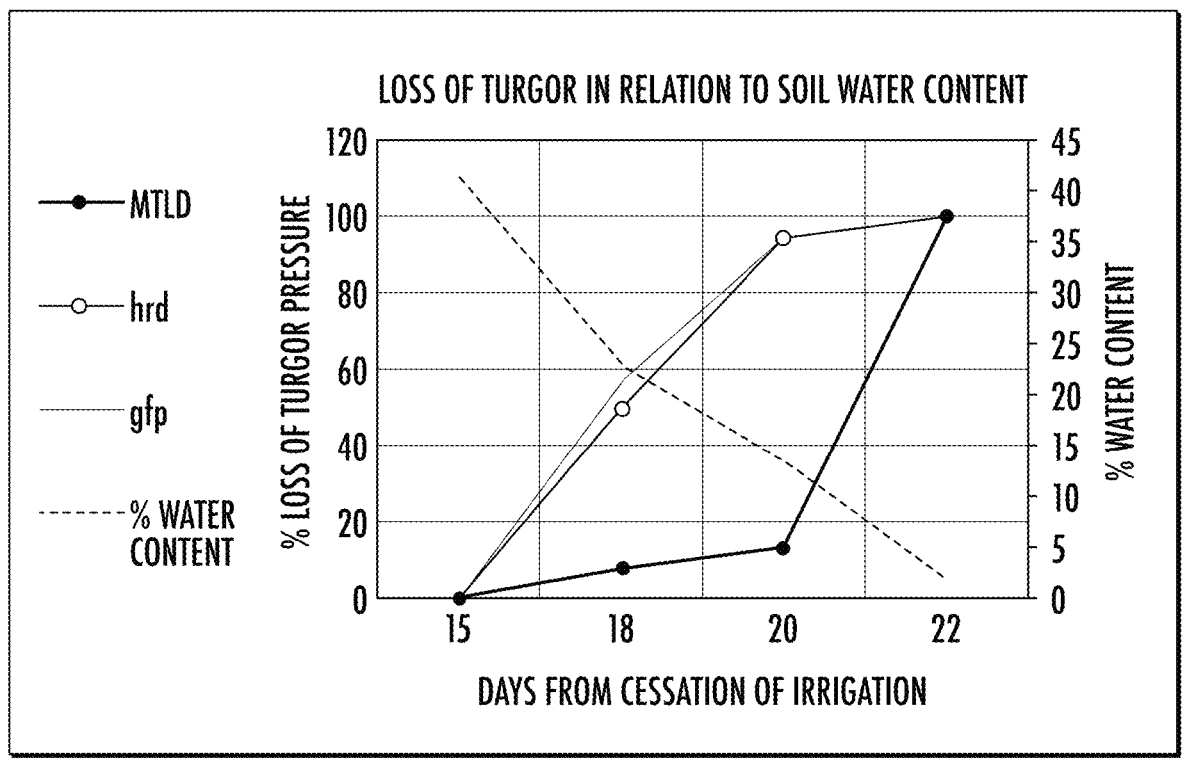
FIG. 7 presents a graphic illustration demonstrating loss of turgor pressure in plants expressing genes used as control relative to soil water content (dark gray), days after cessation of irrigation.

Reference is now made to FIG. 7, showing loss of turgor pressure in plants expressing genes used as control relative to soil water content (dark gray), days after cessation of irrigation. This figure shows curves of *Arabidopsis* plants, expressing different genes (indicated), as a response to growth under drought conditions. Dark line indicates soil water content from 40% in day 15 after water irrigation ceased, to close to 0% at day 22 after water irrigation ceased. The negative control GFP plant's loss of turgor pressure response is similar to that of HRD expressing plants, while mtlD expressing plants turgor pressure, seem to be less effected by drought until day 20 after water irrigation ceased.

It is demonstrated in this figure that plants expressing the positive control genes mtlD and HRD showed improved resistance to drought by showing significantly reduced loss of turgor pressure effects, while transgenic plants expressing the negative control GFP gene showed elevated loss of turgor pressure effect when exposed to the same water content loss.

Figure 8:
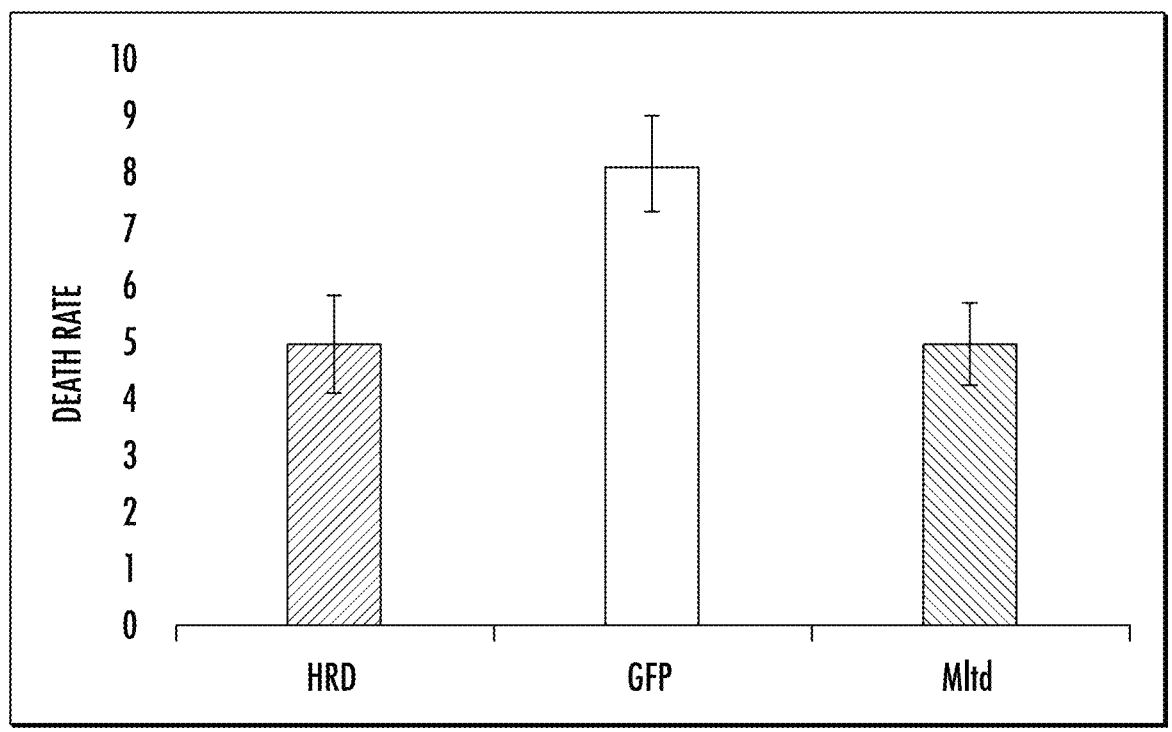
FIG. 8 presents a graphic illustration showing normalized death scale of positive control expressing transgenic plants as compared to GFP expressing plants.

Reference is now made to FIG. 8 showing normalized death scale of positive control expressing transgenic plants as compared to GFP expressing plants. As can be seen plants expressing the drought resistance positive control genes HRD and mtlD showed significantly reduced death rate as compared to the negative control GFP expressing plants.

Figure 9:
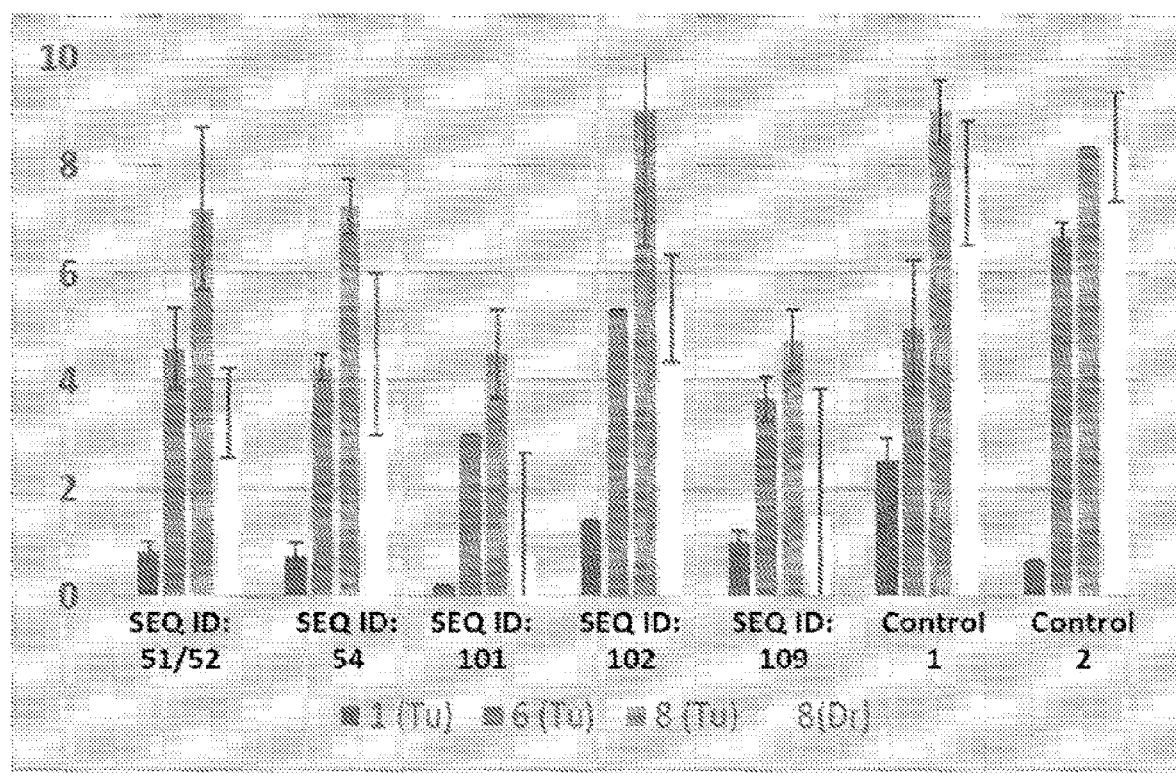
FIG. 9 graphically shows results of several drought resistance genes identified by the method of the present invention.

Reference is now made to FIG. 9 graphically showing phenotypic results of several drought resistance genes identified by the method of the present invention.

The graph shows average results of turgor pressure (Tu) and death rate (Dr) for several identified genes (see Table 4) under severe drought conditions. Scale for death and turgor loss is 1-10 when 10 is considered dry-brown and dead plants, or total loss of turgor, respectively. The results in the graph represent day 23 (1), day 28 (6) and day 30 (8) from sowing. Each column for each of the different expressed genes represents average of 5 repeats with 4 plants in each repeat. GFP expressing plants served as negative control and HRD as positive control. As can be seen, all tested genes identified by the method of the present invention showed significantly reduced turgor loss (by at least two fold after about 23 days from sowing) and reduced death rate (in the range of 9 to 2 fold after 30 days from sowing) as compared to plants expressing the negative control GFP gene. Moreover, plants expressing the newly discovered genes (see Table 4) demonstrated a significantly reduced death rated as compared to the positive control HRD expressing plants. These results indicate that by the method of the present invention, newly drought resistance genes are identified, which confer improved tolerance to drought in plants.

Another method used for evaluating plants performance in drought conditions is measuring their leaf area during the growth phase when drought conditions become prominent. About 10-14 days from sowing the plants, plant images were taken every 2-3 days together with a 50 mm 2 white surface. Image analysis was performed on pictures taken from the drought experiments and leaf area was calculated. The leaf area of several plant lines expressing novel genes identified as conferring drought resistance after re-cloning was compared to positive and negative controls (see Table 5 and FIG. 10).

Figure 10:
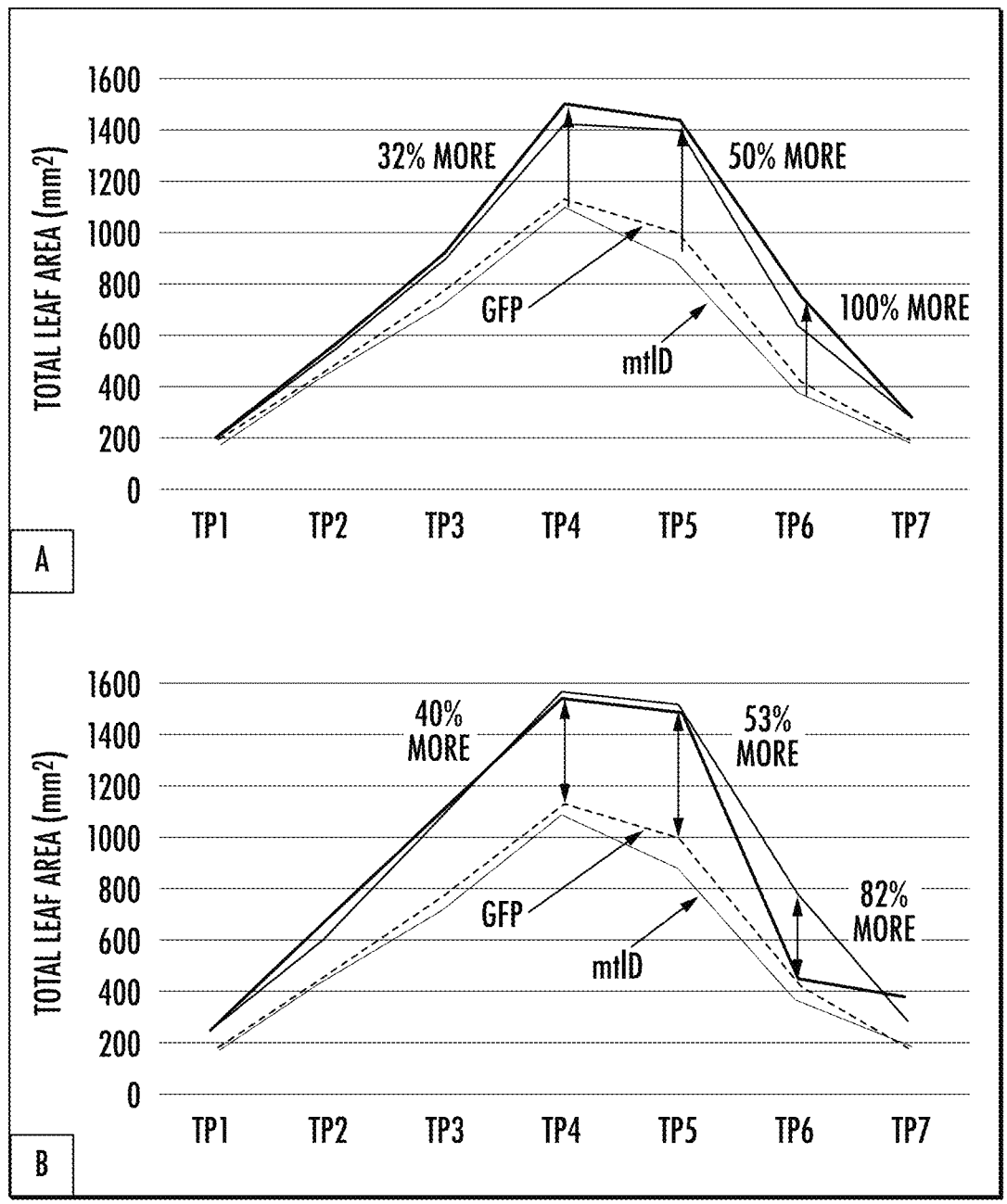
FIG. 10 graphically shows leaf area analysis of several transgenic plant lines expressing identified novel genes conferring drought resistance after re-cloning as compared to positive and negative controls.

The graph of FIG. 10 shows image analysis of leaf area of transformed plant lines. Two independent transformation events of the identified gene having SEQ ID NO:16 (FIG. 10A) and two independent transformation events of the identified gene having SEQ ID NO:25 (FIG. 10B) are shown in darker lines on top of each of the FIGS. 10A and 10B. These transgenic plants are compared to negative control plants expressing GFP, and positive control plants expressing mtlD, shown in lighter gray lines on the bottom of each of the FIGS. 10A and 10B. Improved performance under drought is shown as percentage from control plants at the indicated measured timepoint (TP) (arrows and percentages shown in the figure).

As can be seen in this figure, the total leaf area of plants expressing the newly identified tested genes was increased by between about 10% and about 82% (e.g. by about 45%) relative to plants expressing negative control genes.

To conclude, the present invention provides newly identified genes demonstrated to confer tolerance to drought conditions in plants.

C. Re-Cloning and Retransformation of Selected Genes into Plants

Selected genes from section B are re-cloned into the binary vectors as described above (i.e. FIG. 1A-D) and sequenced to confirm that it has the same sequence as the original gene from T1 and T2 experiments. Plants are transformed with the re-cloned gene and seeds are collected. Experiments are repeated as in B except for each gene 3-5 individual transgenic plants with different unrelated transformation events are tested. Each individual transgenic plant/event is subjected to 5-10 times of repeats in experiments, hence for each event for every gene 20-40 plants are tested, and for every different gene 60-200 plants are tested.

Example 3

Polynucleotide Sequences Identified as Improving Drought and/or Salinity Resistance in Plants The process described above of screening of T1 transgenic seeds revealed about 1000 transgenes as candidate polynucleotide sequences for improving drought resistance in plants. Of these candidates, the screening of T2 seeds revealed about 140 best performing transgenes potentially improving drought resistance or tolerance in plants. These transgene sequences are subjected to further validation tests.

Reference is now made to Table 4, presenting examples of novel and unique polynucleotide sequences and polypeptides encoded by these sequences, found by the method of the present invention. These sequences are metatranscriptomes purified from environmentally challenged niches, SEQ ID NO:1 to SEQ ID NO:148 represent polynucleotide sequences found by the method of the present invention as candidates for improving drought resistance in plants (Table 4).

SEQ ID NO:149 to SEQ ID NO:321 represent polypeptide sequences encoded by the corresponding polynucleotide sequence found by the method of the present invention as candidates for improving drought resistance in plants (see Table 4).

Note that DNA sequences SEQ ID NO:9, SEQ ID NO:11, SEQ ID NO:20, SEQ ID NO:21, SEQ ID NO:28, SEQ ID NO:36, SEQ ID NO:43, SEQ ID NO:47, SEQ ID NO:51, SEQ ID NO:54, SEQ ID NO:55, SEQ ID NO:60, SEQ ID NO:75, SEQ ID NO:78, SEQ ID NO:80, SEQ ID NO:81, SEQ ID NO:85, SEQ ID NO:87, SEQ ID NO:97, SEQ ID NO:98, SEQ ID NO:105, SEQ ID NO:106, SEQ ID NO:107, SEQ ID NO:109, SEQ ID NO:111, SEQ ID NO:112, SEQ ID NO:120, SEQ ID NO:132, SEQ ID NO:134, SEQ ID NO:135, SEQ ID NO:140, SEQ ID NO:141 encode more than one open reading frame (ORF) (referred to as SEQ. ID NO X.1p and X.2p etc.) depending on different start codons.

TABLE 4

SEQ ID Nos of polynucleotide and polypeptide sequences

| Polynucleotide SEQ ID NO. | Polynucleotide name |
|---|---|
| SEQ ID NO: 1 | A454 |
| SEQ ID NO: 2 | A456 |
| SEQ ID NO: 3 | A458.1 |
| SEQ ID NO: 4 | A458.2 |
| SEQ ID NO: 5 | A460 |
| SEQ ID NO: 6 | A462 |
| SEQ ID NO: 7 | A463 |
| SEQ ID NO: 8 | A466 |
| SEQ ID NO: 9 | A468 |
| SEQ ID NO: 10 | A470 |
| SEQ ID NO: 11 | A475 |
| SEQ ID NO: 12 | A477 |
| SEQ ID NO: 13 | A480 |
| SEQ ID NO: 14 | A481 |
| SEQ ID NO: 15 | A483 |
| SEQ ID NO: 16 | A484 |
| SEQ ID NO: 17 | A485a |
| SEQ ID NO: 18 | A485b |
| SEQ ID NO: 19 | A486 |
| SEQ ID NO: 20 | A498 |
| SEQ ID NO: 21 | A499 |
| SEQ ID NO: 22 | A501 |
| SEQ ID NO: 23 | A504.1 |
| SEQ ID NO: 24 | A504 |
| SEQ ID NO: 25 | A506 |
| SEQ ID NO: 26 | A507.1 |
| SEQ ID NO: 27 | A507.2 |
| SEQ ID NO: 28 | A510a |
| SEQ ID NO: 29 | A510b |
| SEQ ID NO: 30 | A512 |
| SEQ ID NO: 31 | A513a |
| SEQ ID NO: 32 | A513b |
| SEQ ID NO: 33 | A518 |
| SEQ ID NO: 34 | A520a |
| SEQ ID NO: 35 | AC2510 |
| SEQ ID NO: 36 | AD2607.1 |
| SEQ ID NO: 37 | AD2607.3 |
| SEQ ID NO: 38 | D860a |

TABLE 4-continued

SEQ ID Nos of polynucleotide and polypeptide sequences

| Polynucleotide SEQ ID NO. | Polynucleotide name |
|---|---|
| SEQ ID NO: 39 | D860b |
| SEQ ID NO: 40 | D862 |
| SEQ ID NO: 41 | D863 |
| SEQ ID NO: 42 | D881 |
| SEQ ID NO: 43 | D890 |
| SEQ ID NO: 44 | De203 |
| SEQ ID NO: 45 | De214a |
| SEQ ID NO: 46 | De215a |
| SEQ ID NO: 47 | De215b.1 |
| SEQ ID NO: 48 | De215b.4 |
| SEQ ID NO: 49 | De215c |
| SEQ ID NO: 50 | De217 |
| SEQ ID NO: 51 | De223a |
| SEQ ID NO: 52 | De223b |
| SEQ ID NO: 53 | De227 |
| SEQ ID NO: 54 | De239a |
| SEQ ID NO: 55 | De245 |
| SEQ ID NO: 56 | De250.1 |
| SEQ ID NO: 57 | De250.2 |
| SEQ ID NO: 58 | De251 |
| SEQ ID NO: 59 | De313 |
| SEQ ID NO: 60 | F1022a |
| SEQ ID NO: 61 | F1022b |
| SEQ ID NO: 62 | G1085a |
| SEQ ID NO: 63 | G1181 |
| SEQ ID NO: 64 | G1190 |
| SEQ ID NO: 65 | H1301.1 |
| SEQ ID NO: 66 | H1301.2 |
| SEQ ID NO: 67 | K1464 |
| SEQ ID NO: 68 | K1475 |
| SEQ ID NO: 69 | M603 |
| SEQ ID NO: 70 | M606.1 |
| SEQ ID NO: 71 | M606.2 |
| SEQ ID NO: 72 | M607.1 |
| SEQ ID NO: 73 | M607.2 |
| SEQ ID NO: 74 | M609a.1 |
| SEQ ID NO: 75 | M609a.2 |
| SEQ ID NO: 76 | M609b |
| SEQ ID NO: 77 | M619a |
| SEQ ID NO: 78 | M619b |
| SEQ ID NO: 79 | M622a |
| SEQ ID NO: 80 | M622b |
| SEQ ID NO: 81 | M623a |
| SEQ ID NO: 82 | M623b.1 |
| SEQ ID NO: 83 | M623b.3 |
| SEQ ID NO: 84 | M623c |
| SEQ ID NO: 85 | M624 |
| SEQ ID NO: 86 | M625a.3 |
| SEQ ID NO: 87 | M625a |
| SEQ ID NO: 88 | M625b |
| SEQ ID NO: 89 | M631 |
| SEQ ID NO: 90 | M632a |
| SEQ ID NO: 91 | M635.1 |
| SEQ ID NO: 92 | M635.2 |
| SEQ ID NO: 93 | M638 |
| SEQ ID NO: 94 | M643 |
| SEQ ID NO: 95 | M649 |
| SEQ ID NO: 96 | M650a.3 |
| SEQ ID NO: 97 | M650a |
| SEQ ID NO: 98 | M650b |
| SEQ ID NO: 99 | M657 |
| SEQ ID NO: 100 | M659a |
| SEQ ID NO: 101 | M661 |
| SEQ ID NO: 102 | M663 |
| SEQ ID NO: 103 | M664.1 |
| SEQ ID NO: 104 | M664.2 |
| SEQ ID NO: 105 | M666 |
| SEQ ID NO: 106 | M671 |
| SEQ ID NO: 107 | M673 |
| SEQ ID NO: 108 | M676.3 |
| SEQ ID NO: 109 | M676 |
| SEQ ID NO: 110 | M677a |
| SEQ ID NO: 111 | M677b.1 |
| SEQ ID NO: 112 | M677b.3 |
| SEQ ID NO: 113 | M680 |
| SEQ ID NO: 114 | M691a.1 |

TABLE 4-continued

SEQ ID Nos of polynucleotide and polypeptide sequences

| Polynucleotide SEQ ID NO. | Polynucleotide name |
|---|---|
| SEQ ID NO: 115 | M691a.2 |
| SEQ ID NO: 116 | M691b |
| SEQ ID NO: 117 | M693 |
| SEQ ID NO: 118 | M697 |
| SEQ ID NO: 119 | M698 |
| SEQ ID NO: 120 | M705 |
| SEQ ID NO: 121 | M706 |
| SEQ ID NO: 122 | M715a |
| SEQ ID NO: 123 | M715b |
| SEQ ID NO: 124 | M719 |
| SEQ ID NO: 125 | M724 |
| SEQ ID NO: 126 | N1503a |
| SEQ ID NO: 127 | N1527.1 |
| SEQ ID NO: 128 | N1527.2 |
| SEQ ID NO: 129 | N1529 |
| SEQ ID NO: 130 | N1530 |
| SEQ ID NO: 131 | P1611 |
| SEQ ID NO: 132 | P1620.1 |
| SEQ ID NO: 133 | P1620.3 |
| SEQ ID NO: 134 | P1623a |
| SEQ ID NO: 135 | P1623b |
| SEQ ID NO: 136 | P1625a |
| SEQ ID NO: 137 | P1625b |
| SEQ ID NO: 138 | P1731 |
| SEQ ID NO: 139 | P1744 |
| SEQ ID NO: 140 | P1747.1 |
| SEQ ID NO: 141 | P1747.3 |
| SEQ ID NO: 142 | SN8 |
| SEQ ID NO: 143 | V1906b |
| SEQ ID NO: 144 | V1906c |
| SEQ ID NO: 145 | V1907a |
| SEQ ID NO: 146 | V1907b |
| SEQ ID NO: 147 | X2005 |
| SEQ ID NO: 148 | X2026 |
| SEQ ID NO: 149 | A454p |
| SEQ ID NO: 150 | A456p |
| SEQ ID NO: 151 | A458.1p |
| SEQ ID NO: 152 | A458.2p |
| SEQ ID NO: 153 | A460p |
| SEQ ID NO: 154 | A462p |
| SEQ ID NO: 155 | A463p |
| SEQ ID NO: 156 | A466p |
| SEQ ID NO: 157 | A468.1p |
| SEQ ID NO: 158 | A468.2p |
| SEQ ID NO: 159 | A470p |
| SEQ ID NO: 160 | A475.1p |
| SEQ ID NO: 161 | A475.2p |
| SEQ ID NO: 162 | A477p |
| SEQ ID NO: 163 | A480p |
| SEQ ID NO: 164 | A481p |
| SEQ ID NO: 165 | A483p |
| SEQ ID NO: 166 | A484p |
| SEQ ID NO: 167 | A485ap |
| SEQ ID NO: 168 | A485bp |
| SEQ ID NO: 169 | A486p |
| SEQ ID NO: 170 | A498.1p |
| SEQ ID NO: 171 | A498.2p |
| SEQ ID NO: 172 | A499.1p |
| SEQ ID NO: 173 | A499.2p |
| SEQ ID NO: 174 | A501p |
| SEQ ID NO: 175 | A504.1p |
| SEQ ID NO: 176 | A504.2p |
| SEQ ID NO: 177 | A506p |
| No ORF identified | No ORF identified |
| SEQ ID NO: 178 | A507.2p |
| SEQ ID NO: 179 | A510a.1p |
| SEQ ID NO: 180 | A510a.2p |
| No ORF identified | No ORF identified |
| SEQ ID NO: 181 | A512p |
| SEQ ID NO: 182 | A513ap |
| SEQ ID NO: 183 | A513bp |
| SEQ ID NO: 184 | A518p |
| SEQ ID NO: 185 | A520ap |
| SEQ ID NO: 186 | AC2510ap |
| SEQ ID NO: 187 | AD2607.1p |
| SEQ ID NO: 188 | AD2607.2p |
| SEQ ID NO: 189 | AD2607.3p |
| SEQ ID NO: 190 | D860ap |
| SEQ ID NO: 191 | D860bp |
| SEQ ID NO: 192 | D862p |
| SEQ ID NO: 193 | D863p |
| SEQ ID NO: 194 | D881p |
| SEQ ID NO: 195 | D890.1p |
| SEQ ID NO: 196 | D890.2p |
| SEQ ID NO: 197 | De203p |
| SEQ ID NO: 198 | De214ap |
| SEQ ID NO: 199 | De215ap |
| SEQ ID NO: 200 | De215b.1p |
| SEQ ID NO: 201 | De215b.2p |
| SEQ ID NO: 202 | De215b.3p |
| SEQ ID NO: 203 | De215b.4p |
| SEQ ID NO: 204 | De215cp |
| No ORF identified | No ORF identified |
| SEQ ID NO: 205 | De223a.1p |
| SEQ ID NO: 206 | De223a.2p |
| SEQ ID NO: 207 | De223bp |
| SEQ ID NO: 208 | De227p |
| SEQ ID NO: 209 | De239a.1p |
| SEQ ID NO: 210 | De239a.2p |
| SEQ ID NO: 211 | De245.1p |
| SEQ ID NO: 212 | De245.2p |
| SEQ ID NO: 213 | De250p |
| SEQ ID NO: 214 | De250.2p |
| SEQ ID NO: 215 | De251p |
| SEQ ID NO: 216 | De313p |
| SEQ ID NO: 217 | F1022a.1p |
| SEQ ID NO: 218 | F1022a.2p |
| SEQ ID NO: 219 | F1022bp |
| SEQ ID NO: 220 | G1085ap |
| SEQ ID NO: 221 | G1181p |
| SEQ ID NO: 222 | G1190p |
| SEQ ID NO: 223 | H1301.1p |
| SEQ ID NO: 224 | H1301.2p |
| No ORF identified | No ORF identified |
| SEQ ID NO: 225 | K1475p |
| SEQ ID NO: 226 | M603p |
| SEQ ID NO: 227 | M606.1p |
| SEQ ID NO: 228 | M606.2p |
| SEQ ID NO: 229 | M607.1p |
| SEQ ID NO: 230 | M607.2p |
| SEQ ID NO: 231 | M609a.1p |
| SEQ ID NO: 233 | M609a.3p |
| SEQ ID NO: 232 | M609a.2p |
| SEQ ID NO: 234 | M609bp |
| SEQ ID NO: 235 | M619ap |
| SEQ ID NO: 236 | M619b.1p |
| SEQ ID NO: 237 | M619b.2p |
| SEQ ID NO: 238 | M622ap |
| SEQ ID NO: 239 | M622b.1p |
| SEQ ID NO: 240 | M622b.2p |
| SEQ ID NO: 241 | M623a.1p |
| SEQ ID NO: 242 | M623a.2p |
| No ORF identified | No ORF identified |
| SEQ ID NO: 243 | M623b.3p |
| SEQ ID NO: 244 | M623cp |
| SEQ ID NO: 245 | M624.1p |
| SEQ ID NO: 246 | M624.2p |
| SEQ ID NO: 249 | M625a.3p |
| SEQ ID NO: 247 | M625a.1p |
| SEQ ID NO: 248 | M625a.2p |
| SEQ ID NO: 250 | M625bp |
| SEQ ID NO: 251 | M631p |
| SEQ ID NO: 252 | M632ap |
| SEQ ID NO: 253 | M635.1p |
| SEQ ID NO: 254 | M635.2p |
| SEQ ID NO: 255 | M638p |
| SEQ ID NO: 256 | M643p |
| SEQ ID NO: 257 | M649p |
| SEQ ID NO: 260 | M650a.3p |
| SEQ ID NO: 258 | M650a.1p |
| SEQ ID NO: 259 | M650a.2p |
| SEQ ID NO: 261 | M650b.1p |

TABLE 4-continued

SEQ ID Nos of polynucleotide and polypeptide sequences

| Polynucleotide SEQ ID NO. | Polynucleotide name |
|---|---|
| SEQ ID NO: 262 | M650b.2p |
| SEQ ID NO: 263 | M657p |
| SEQ ID NO: 264 | M659ap |
| SEQ ID NO: 265 | M661p |
| SEQ ID NO: 266 | M663p |
| SEQ ID NO: 267 | M664.1p |
| SEQ ID NO: 268 | M664.2p |
| SEQ ID NO: 269 | M666.1p |
| SEQ ID NO: 270 | M666.2p |
| SEQ ID NO: 271 | M671.1p |
| SEQ ID NO: 272 | M671.2p |
| SEQ ID NO: 273 | M673.1p |
| SEQ ID NO: 274 | M673.2p |
| SEQ ID NO: 277 | M676.3p |
| SEQ ID NO: 275 | M676.1p |
| SEQ ID NO: 276 | M676.2p |
| SEQ ID NO: 278 | M677ap |
| SEQ ID NO: 279 | M677b.1p |
| SEQ ID NO: 280 | M677b.2p |
| SEQ ID NO: 281 | M677b.3p |
| SEQ ID NO: 282 | M677b.4p |
| SEQ ID NO: 283 | M680p |
| SEQ ID NO: 284 | M691a.1p |
| SEQ ID NO: 285 | M691a.2p |
| SEQ ID NO: 286 | M691bp |
| SEQ ID NO: 287 | M693p |
| SEQ ID NO: 288 | M697p |
| SEQ ID NO: 289 | M698p |
| SEQ ID NO: 290 | M705.1p |
| SEQ ID NO: 291 | M705.2p |
| SEQ ID NO: 292 | M706p |
| SEQ ID NO: 293 | M715ap |
| SEQ ID NO: 294 | M715bp |
| SEQ ID NO: 295 | M719p |
| SEQ ID NO: 296 | M724p |
| SEQ ID NO: 297 | N1503ap |
| SEQ ID NO: 298 | N1527.1p |
| SEQ ID NO: 299 | N1527.2p |
| SEQ ID NO: 300 | N1529p |
| SEQ ID NO: 301 | N1530p |
| SEQ ID NO: 302 | P1611p |
| SEQ ID NO: 303 | P1620.1p |
| SEQ ID NO: 304 | P1620.2p |
| SEQ ID NO: 305 | P1620.3p |
| SEQ ID NO: 306 | P1623a.1p |
| SEQ ID NO: 307 | P1623a.2p |
| SEQ ID NO: 308 | P1623b.1p |
| SEQ ID NO: 309 | P1623b.2p |
| SEQ ID NO: 310 | P1625ap |
| SEQ ID NO: 311 | P1625bp |
| SEQ ID NO: 312 | P1731p |
| SEQ ID NO: 313 | P1744p |
| SEQ ID NO: 314 | P1747.1p |
| SEQ ID NO: 315 | P1747.2p |
| SEQ ID NO: 316 | P1747.3p |
| SEQ ID NO: 317 | P1747.4p |
| No ORF identified | No ORF identified |
| SEQ ID NO: 318 | V1906bp |
| No ORF identified | No ORF identified |
| SEQ ID NO: 319 | V1907ap |
| No ORF identified | No ORF identified |
| SEQ ID NO: 320 | X2005p |
| SEQ ID NO: 321 | X2026p |

Reference is now made to Table 5 presenting phenotypic results of several of the identified genes in the drought tolerance experiments. Plants were grown in soil in controlled greenhouses and tested for drought tolerance under the conditions mentioned above. During their growth, measurements and images were taken (see Table 3) and image analysis was applied converting the images to leaf area per plant. Results are shown as percentage of GFP expressing plants measurements that served as a negative control during the drought phase.

TABLE 5

Results of drought experiments conducted with T2 Arabidopsis plants

| Seq ID | DR | ±SD | Seq ID | DR | ±SD | Seq ID | DR | ±SD | Seq ID | DR | ±SD | Seq ID | DR | ±SD |
|---|---|---|---|---|---|---|---|---|---|---|---|---|---|---|
| SEQ ID NO: 1 | 116.00 | 3.13 | SEQ ID NO: 25 | 137.14 | 7.05 | SEQ ID NO: 55 | 144.00 | 5.56 | SEQ ID NO: 91/92 | 143.23 | 7.26 | SEQ ID NO: 122 | 120.00 | 10.25 |
| SEQ ID NO: 2 | 132.86 | 6.68 | SEQ ID NO: 26/27 | 135.00 | 7.64 | SEQ ID NO: 56/57 | 134.00 | 3.28 | SEQ ID NO: 93 | 133.33 | 6.84 | SEQ ID NO: 124 | 130.73 | 5.93 |
| SEQ ID NO: 17/18 | 151.43 | 10.52 | SEQ ID NO: 28 | 187.64 | 11.00 | SEQ ID NO: 58 | 151.6 | 20.7 | SEQ ID NO: 94 | 102.50 | 7.08 | SEQ ID NO: 125 | 139.10 | 9.76 |
| SEQ ID NO: 5 | 146.9 | 20.6 | SEQ ID NO: 30 | 118.57 | 1.88 | SEQ ID NO: 60 | 134.08 | 4.45 | SEQ ID NO: 97 | 133.41 | 7.61 | SEQ ID NO: 127/128 | 119.09 | 4.03 |
| SEQ ID NO: 6 | 118.57 | 5.26 | SEQ ID NO: 31 | 112.56 | 4.97 | SEQ ID NO: 62 | 99.72 | 4.71 | SEQ ID NO: 99 | 137.50 | 8.80 | SEQ ID NO: 129 | 135.01 | 7.89 |
| SEQ ID NO: 7 | 156.7 | 23.4 | SEQ ID NO: 33 | 167.57 | 7.20 | SEQ ID NO: 63 | 277.71 | 16.80 | SEQ ID NO: 100 | 160.11 | 20.12 | SEQ ID NO: 130 | 196.80 | 9.06 |
| SEQ ID NO: 8 | 162.1 | 17.1 | SEQ ID NO: 34 | 118.92 | 5.31 | SEQ ID NO: 64 | 136.83 | 6.62 | SEQ ID NO: 101 | 182.50 | 10.00 | SEQ ID NO: 131 | 113.98 | 7.65 |
| SEQ ID NO: 9 | 138.24 | 20.36 | SEQ ID NO: 35 | 115.20 | 6.60 | SEQ ID NO: 65/66 | 107.77 | 10.82 | SEQ ID NO: 102 | 136.67 | 8.72 | SEQ ID NO: 132/133 | 110.33 | 6.64 |
| SEQ ID NO: 10 | 116.00 | 3.19 | SEQ ID NO: 36/37 | 109.71 | 7.79 | SEQ ID NO: 67 | 131.25 | 7.04 | SEQ ID NO: 103/104 | 121.79 | 7.45 | SEQ ID NO: 134 | 107.54 | 9.76 |
| SEQ ID NO: 11 | 107.14 | 2.93 | SEQ ID NO: 38 | 124.59 | 6.74 | SEQ ID NO: 68 | 186.67 | 9.85 | SEQ ID NO: 105 | 126.73 | 6.48 | SEQ ID NO: 137 | 114.17 | 5.84 |
| SEQ ID NO: 12 | 122.86 | 4.53 | SEQ ID NO: 40 | 154.29 | 10.83 | SEQ ID NO: 69 | 132.64 | 8.96 | SEQ ID NO: 106 | 125.00 | 5.94 | SEQ ID NO: 138 | 139.80 | 9.87 |
| SEQ ID NO: 13 | 160.00 | 12.32 | SEQ ID NO: 41 | 117.14 | 5.71 | SEQ ID NO: 70/71 | 145.00 | 7.07 | SEQ ID NO: 107 | 130.00 | 6.64 | SEQ ID NO: 139 | 115.04 | 6.38 |
| SEQ ID NO: 14 | 142.86 | 8.37 | SEQ ID NO: 42 | 118.27 | 3.56 | SEQ ID NO: 72/73 | 134.08 | 7.08 | SEQ ID NO: 109 | 175.00 | 7.38 | SEQ ID NO: 140/ | 105.73 | 8.08 |
| SEQ ID NO: 15 | 145.71 | 7.24 | SEQ ID NO: 43 | 141.69 | 8.03 | SEQ ID NO: | 187.50 | 10.00 | SEQ ID NO: | 118.92 | 5.89 | | | |

TABLE 5-continued

Results of drought experiments conducted with T2 *Arabidopsis* plants

| Seq ID | DR | ±SD | Seq ID | DR | ±SD | Seq ID | DR | ±SD | Seq ID | DR | ±SD | Seq ID | DR | ±SD |
|---|---|---|---|---|---|---|---|---|---|---|---|---|---|---|
| SEQ ID NO: 16 | 136.13 | 8.55 | SEQ ID NO: 44 | 144.00 | 6.36 | SEQ ID NO: 74/75/76 | | | SEQ ID NO: 110 | | | SEQ ID NO: 141 | 141.43 | 3.65 |
| SEQ ID NO: 17 | 108.33 | 2.73 | SEQ ID NO: 45 | 142.70 | 9.33 | SEQ ID NO: 77 | 125.00 | 8.29 | SEQ ID NO: 113 | 113.14 | 8.47 | SEQ ID NO: 142 | 115.50 | 7.96 |
| SEQ ID NO: 19 | 121.67 | 5.66 | SEQ ID NO: 46 | 119.36 | 9.40 | SEQ ID NO: 79 | 123.73 | 6.78 | SEQ ID NO: 114/115/116 | 108.04 | 5.44 | SEQ ID NO: 143 | 112.59 | 7.32 |
| SEQ ID NO: 20 | 118.68 | 2.48 | SEQ ID NO: 50 | 110.51 | 7.81 | SEQ ID NO: 81 | 159.79 | 8.45 | SEQ ID NO: 117 | 167.50 | 9.13 | SEQ ID NO: 145 | 121.66 | 8.81 |
| SEQ ID NO: 21 | 116.67 | 4.01 | SEQ ID NO: 51 | 158.00 | 13.73 | SEQ ID NO: 85 | 180.00 | 7.07 | SEQ ID NO: 118 | 131.68 | 8.77 | SEQ ID NO: 147 | 121.07 | 5.86 |
| SEQ ID NO: 22 | 131.67 | 8.00 | SEQ ID NO: 53 | 119.42 | 8.70 | SEQ ID NO: 87 | 267.03 | 16.40 | SEQ ID NO: 119 | 121.04 | 6.30 | SEQ ID NO: 148 | | |
| SEQ ID NO: 23/24 | 124.29 | 6.45 | SEQ ID NO: 54 | 145.00 | 11.92 | SEQ ID NO: 89 | 173.33 | 4.58 | SEQ ID NO: 120 | 104.85 | 7.51 | GFP | 100.00 | 6.55 |
| | | | | | | SEQ ID NO: 90 | 135.00 | 9.29 | SEQ ID NO: 121 | 113.85 | 6.36 | | | |

DR - performance (leaf area) under Drought shown in % of GFP expressing plants
SD - value shown ± standard deviation As shown in Table 5, all plants expressing the tested genes identified by the method of the present invention revealed increased leaf area by about 15% to about 90% under drought conditions as compared to plants expressing the negative control gene (GFP). These results demonstrate that the method of the present invention provides novel genes conferring improved drought tolerance in plants.

Reference is now made to Table 6 presenting results of drought experiments conducted with T2 *Arabidopsis* plants re-cloned with the relevant Seq. IDs. Different Seq. IDs were re-cloned and re-transformed into *Arabidopsis* plants generating several independent events (represented by E1-3 in Table 6). Plants were grown in soil in controlled greenhouses and tested for drought tolerance under the conditions mentioned above. During their growth, images were taken and image analysis was applied, converting the images into leaf area per plant. Results are shown in Table 6 as percentage of GFP expressing plants that served as a negative control during the drought phase.

TABLE 6

Results of drought experiments conducted with T2 *Arabidopsis* plants re-cloned with the relevant Seq. IDs

| Seq ID | DR RC E1 | E1 ± SD | DR RC E2 | E2 ± SD | DR RC E3 | E3 ± SD |
|---|---|---|---|---|---|---|
| SEQ ID NO: 2 | 114.05 | 12.00 | 126.33 | 6.27 | 94.42 | 14.75 |
| SEQ ID NO: 7 | 125.74 | 7.50 | 118.43 | 12.40 | 82.39 | 17.20 |
| SEQ ID NO: 8 | 126.96 | 10.73 | 110.07 | 13.09 | 132.74 | 5.34 |
| SEQ ID NO: 9 | 159.34 | 19.75 | 151.99 | 27.05 | 113.97 | 18.65 |
| SEQ ID NO: 10 | 185.23 | 19.29 | 165.97 | 30.99 | 90.04 | 9.27 |
| SEQ ID NO: 11 | 116.91 | 9.54 | 106.90 | 10.41 | 106.32 | 10.87 |
| SEQ ID NO: 12 | 178.80 | 24.09 | 107.57 | 14.72 | 157.66 | 15.22 |
| SEQ ID NO: 14 | 162.78 | 14.10 | 151.93 | 9.90 | 123.68 | 10.10 |
| SEQ ID NO: 16 | 144.23 | 8.42 | 141.32 | 7.03 | 127.03 | 8.31 |
| SEQ ID NO: 18 | 176.30 | 26.57 | 126.24 | 11.63 | 138.53 | 23.03 |
| SEQ ID NO: 22 | 113.00 | 12.14 | 109.38 | 9.14 | 105.16 | 12.38 |
| SEQ ID NO: 25 | 150.56 | 7.57 | 153.02 | 9.91 | 120.25 | 13.63 |
| SEQ ID NO: 28 | 193.32 | 28.79 | | | | |
| SEQ ID NO: 30 | 123.33 | 11.83 | 113.97 | 8.18 | 112.53 | 16.34 |
| SEQ ID NO: 33 | 141.20 | 10.90 | 127.98 | 13.30 | 112.63 | 11.50 |
| SEQ ID NO: 34 | 167.25 | 12.60 | 150.19 | 13.30 | 138.48 | 10.20 |
| SEQ ID NO: 41 | 160.43 | 11.60 | 153.92 | 14.10 | 112.83 | 10.80 |
| SEQ ID NO: 43 | 229.50 | 18.12 | 136.33 | 32.37 | 106.83 | 26.53 |
| SEQ ID NO: 51 | 178.07 | 13.10 | 170.57 | 14.60 | 146.17 | 11.20 |
| SEQ ID NO: 54 | 169.39 | 15.50 | 131.72 | 11.30 | 120.10 | 16.70 |
| SEQ ID NO: 55 | 126.72 | 16.39 | 122.48 | 18.62 | 111.94 | 17.92 |
| SEQ ID NO: 56/57 | 138.08 | 8.64 | 134.76 | 9.21 | 127.74 | 10.65 |
| SEQ ID NO: 58 | 115.36 | 11.52 | 117.79 | 13.24 | 93.16 | 11.94 |
| SEQ ID NO: 60 | 151.90 | 12.80 | 137.24 | 11.90 | 93.80 | 5.60 |
| SEQ ID NO: 61 | 140.14 | 12.10 | 116.31 | 14.70 | 114.09 | 10.30 |
| SEQ ID NO: 74/75/76 | 175.07 | 13.50 | 160.92 | 12.30 | 105.95 | 11.30 |
| SEQ ID NO: 77 | 210.21 | 18.03 | 174.80 | 18.44 | 160.93 | 29.97 |
| SEQ ID NO: 78 | 182.00 | 15.30 | 175.52 | 16.80 | 115.61 | 11.10 |
| SEQ ID NO: 85 | 132.73 | 10.80 | 119.86 | 11.50 | 114.46 | 9.90 |
| SEQ ID NO: 89 | 167.95 | 21.26 | 154.64 | 21.46 | 142.21 | 29.65 |
| SEQ ID NO: 90 | 141.50 | 24.45 | 137.53 | 17.22 | 110.29 | 32.15 |
| SEQ ID NO: 91/92 | 219.30 | 29.16 | 192.51 | 22.47 | 92.77 | 20.90 |
| SEQ ID NO: 93 | 127.73 | 16.50 | 122.99 | 11.32 | 119.54 | 17.08 |
| SEQ ID NO: 94 | 123.64 | 13.85 | 120.32 | 9.86 | 107.77 | 15.59 |
| SEQ ID NO: 95 | 129.53 | 9.05 | 108.36 | 9.42 | 98.43 | 14.09 |

TABLE 6-continued

Results of drought experiments conducted with T2 *Arabidopsis* plants re-cloned with the relevant Seq. IDs

| Seq ID | DR RC E1 | E1 ± SD | DR RC E2 | E2 ± SD | DR RC E3 | E3 ± SD |
|---|---|---|---|---|---|---|
| SEQ ID NO: 101 | 161.68 | 14.10 | 141.20 | 11.30 | 134.68 | 13.60 |
| SEQ ID NO: 105 | 204.51 | 27.93 | 188.14 | 5.31 | 156.19 | 17.89 |
| SEQ ID NO: 106 | 153.33 | 12.60 | 143.91 | 10.80 | 130.47 | 11.50 |
| SEQ ID NO: 109 | 141.18 | 14.20 | 134.15 | 11.60 | 124.80 | 10.30 |
| SEQ ID NO: 110 | 118.66 | 10.30 | 113.58 | 8.40 | 104.01 | 7.60 |
| SEQ ID NO: 111/112 | 228.16 | 35.62 | 202.43 | 18.73 | 132.98 | 18.32 |
| SEQ ID NO: 113 | 158.59 | 24.54 | 155.03 | 21.36 | 135.44 | 17.44 |
| SEQ ID NO: 126 | 185.07 | 13.40 | 147.37 | 16.20 | 131.05 | 10.80 |

DR - performance (leaf area) under drought shown as % of GFP expressing plants
RC E1-3 - performance with re-cloned relevant Seq. ID event 1-3
SD - value shown ± standard deviation As shown in Table 6, plants expressing the re-cloned genes identified by the method of the present invention presented enhanced leaf area as compared to plats expressing the negative control gene, in *Arabidopsis* plants subjected to drought conditions.

Reference is now made to Table 7 presenting results of drought experiments conducted with T2 tobacco plants. Different genes identified by the present invention were re-cloned and transformed into tobacco plants generating several independent events (represented by E1-3 in Table 7). Plants were grown in soil in controlled greenhouses and tested for drought tolerance under the conditions mentioned above. At the end of the experiment plant shoots fresh weight, leaves number, length of main branch and weight of main branch were evaluated. Results are shown in Table 7 as percentage of wild type (WT) plants that served as a negative control.

The results presented in Table 7 show that most of the genes identified by the present invention confer improved tolerance to drought conditions in Tobacco plants, as shown by the tested parameters (e.g. fresh weight, leaf number, branch fresh weight, branch length) as compared to negative control plants.

Reference is now made to Table 8 presenting results of salinity experiments of transgenic tobacco plants as compared to control WT plants. Different tobacco lines expressing various genes identified by the method of the present invention (see Table 4), were germinated in soil. Seven days post germination; plants were irrigated with fertilized water containing 400 mM NaCl. Leaf images were taken 14 days after irrigation with salt and analyzed for leaf area for the different independent events. Results are shown in Table 8 as percentage leaf area difference from WT plants.

TABLE 7

Results of drought experiments conducted with T2 Tobacco plants

| Seq ID | FW | FW ± SD | LN | LN ± SD | BFW | BFW ± SD | BL | BL ± SD |
|---|---|---|---|---|---|---|---|---|
| SEQ ID NO: 1 E1 | 104.71 | 11.18 | 73.58 | 11.63 | 106.78 | 14.75 | 122.73 | 9.25 |
| SEQ ID NO: 1 E2 | 97.28 | 2.18 | 67.92 | 4.76 | 86.18 | 5.10 | 97.27 | 8.86 |
| SEQ ID NO: 1 E3 | 99.22 | 11.21 | 64.15 | 7.70 | 116.72 | 6.30 | 118.18 | 8.90 |
| SEQ ID NO: 2 E1 | 122.23 | 2.70 | 116.76 | 4.84 | 115.42 | 3.47 | 97.33 | 4.87 |
| SEQ ID NO: 2 E2 | 119.11 | 5.62 | 101.62 | 3.97 | 122.99 | 2.70 | 114.84 | 2.98 |
| SEQ ID NO: 2 E3 | 116.69 | 9.00 | 111.35 | 4.58 | 117.50 | 14.45 | 102.67 | 9.91 |
| SEQ ID NO: 15 E1 | 111.60 | 4.18 | 98.38 | 7.58 | 113.65 | 4.39 | 102.08 | 4.89 |
| SEQ ID NO: 15 E2 | 121.87 | 2.88 | 118.92 | 2.53 | 122.25 | 3.70 | 100.59 | 3.71 |
| SEQ ID NO: 15 E3 | 113.93 | 5.39 | 116.76 | 6.42 | 103.32 | 7.79 | 95.25 | 9.41 |
| SEQ ID NO: 44 E1 | 124.04 | 4.23 | 118.92 | 6.69 | 130.31 | 5.23 | 94.66 | 6.12 |
| SEQ ID NO: 44 E2 | 121.17 | 8.34 | 108.11 | 3.54 | 128.45 | 14.00 | 112.02 | 8.14 |
| SEQ ID NO: 44 E3 | 113.80 | 10.36 | 117.84 | 7.28 | 118.83 | 9.15 | 90.80 | 8.89 |
| SEQ ID NO: 55 E1 | 120.52 | 3.43 | 123.24 | 5.53 | 122.56 | 5.65 | 102.08 | 5.33 |
| SEQ ID NO: 55 E2 | 117.85 | 8.35 | 113.51 | 3.42 | 121.35 | 11.26 | 95.55 | 7.40 |
| SEQ ID NO: 55 E3 | 123.13 | 5.02 | 111.35 | 9.31 | 127.92 | 8.75 | 110.09 | 7.81 |
| SEQ ID NO: 56/57 E1 | 101.58 | 5.17 | 75.47 | 8.92 | 80.26 | 23.40 | 109.55 | 6.45 |
| SEQ ID NO: 56/57 E2 | 106.93 | 9.10 | 79.25 | 8.50 | 101.30 | 10.14 | 103.64 | 7.22 |
| SEQ ID NO: 56/57 E3 | 98.16 | 10.90 | 75.47 | 8.92 | 81.97 | 10.54 | 100.91 | 15.84 |
| SEQ ID NO: 142 E1 | 110.50 | 5.07 | 94.34 | 15.46 | 109.37 | 7.31 | 116.82 | 16.89 |
| SEQ ID NO: 142 E2 | 119.83 | 5.07 | 94.34 | 1.98 | 105.75 | 5.15 | 118.64 | 19.00 |
| SEQ ID NO: 142 E3 | 114.89 | 2.74 | 98.11 | 6.86 | 101.90 | 5.94 | 95.45 | 19.44 |
| WT | 100.00 | 2.43 | 100.00 | 1.67 | 100.00 | 9.84 | 100.00 | 11.65 |

FW - fresh weight measured in grams
LN - leaf number
BFW - branch fresh weight measured in grams
BL - main branch length measured in cm
SD - value shown +/- standard deviation as % of measured trait
E1-3 - different independent events

TABLE 8

Results of salinity experiments on tobacco plants

| Seq ID | HST | ± SD |
|---|---|---|
| SEQ ID NO: 1 | 225.12 | 12.65 |
| SEQ ID NO: 2 | 240.63 | 28.91 |
| SEQ ID NO: 15 | 505.52 | 17.57 |
| SEQ ID NO: 44 | 767.46 | 7.48 |
| SEQ ID NO: 55 | 206.71 | 26.27 |
| SEQ ID NO: 56/57 | 286.19 | 4.86 |
| SEQ ID NO: 70/71 | 1366.07 | 4.70 |
| SEQ ID NO: 142 | 318.54 | 29.75 |
| WT | 100.00 | 13.22 |

HST - high salinity tolerance shown as % difference of leaf area as compared to WT
SD - value shown +/− standard deviation between 4 independent events The results of Table 8 clearly show that plants expressing the novel salinity tolerance genes identified by the present invention revealed significantly higher leaf area as compared to WT control plants.

Reference is now made to Table 9 presenting salinity experiments conducted on *Arabidopsis* plants expressing novel genes having Seq. IDs as indicated. Ten plants per event per pot were grown in soil in controlled greenhouse. After germination, all pots with plants were irrigated by submerging them with 100 mM NaCl. The results of Table 9 represent average data of 4 different events per Seq. ID and wild type plants (WT).

TABLE 9

Results of salinity experiments conducted on *Arabidopsis* plants expressing novel identified genes

| Seq ID | Flower & Pod production | FP ± SD | Chlorosis | Chlor ± SD |
|---|---|---|---|---|
| SEQ ID NO: 1 | 2.50 | 0.50 | 4.17 | 0.00 |
| SEQ ID NO: 2 | 3.75 | 0.48 | 4.58 | 0.00 |
| SEQ ID NO: 5 | 1.00 | 0.41 | 2.33 | 1.00 |
| SEQ ID NO: 6 | 3.25 | 0.25 | 4.42 | 0.00 |
| SEQ ID NO: 7 | 3.50 | 0.50 | 4.42 | 0.25 |
| SEQ ID NO: 8 | 4.00 | 0.41 | 4.67 | 0.00 |
| SEQ ID NO: 9 | 3.25 | 0.25 | 4.33 | 0.25 |
| SEQ ID NO: 10 | 2.25 | 0.48 | 3.42 | 0.41 |
| SEQ ID NO: 11 | 1.50 | 0.50 | 3.00 | 0.50 |
| SEQ ID NO: 12 | 2.75 | 0.63 | 3.83 | 0.63 |
| SEQ ID NO: 13 | 2.75 | 0.25 | 3.58 | 0.00 |
| SEQ ID NO: 16 | 2.75 | 0.63 | 4.08 | 0.00 |
| SEQ ID NO: 18 | 1.50 | 0.29 | 2.92 | 0.25 |
| SEQ ID NO: 22 | 2.50 | 0.87 | 3.33 | 0.41 |
| SEQ ID NO: 23/24 | 3.50 | 0.29 | 4.50 | 0.00 |
| SEQ ID NO: 25 | 2.25 | 0.75 | 3.08 | 0.29 |
| SEQ ID NO: 26/27 | 1.75 | 0.48 | 3.00 | 0.25 |
| SEQ ID NO: 29 | 2.50 | 0.29 | 3.83 | 0.25 |
| SEQ ID NO: 30 | 3.25 | 0.48 | 4.25 | 0.29 |
| SEQ ID NO: 30 | 3.00 | 0.71 | 4.33 | 0.00 |
| SEQ ID NO: 33 | 2.50 | 0.87 | 3.42 | 0.25 |
| SEQ ID NO: 94 | 2.50 | 0.29 | 3.67 | 0.29 |
| SEQ ID NO: 40 | 1.25 | 0.48 | 2.33 | 1.25 |
| SEQ ID NO: 43 | 2.00 | 0.41 | 3.75 | 0.25 |
| SEQ ID NO: 44 | 3.50 | 0.29 | 4.42 | 0.25 |
| SEQ ID NO: 55 | 2.00 | 0.41 | 3.67 | 0.00 |
| SEQ ID NO: 56/57 | 2.50 | 0.29 | 3.58 | 0.25 |
| SEQ ID NO: 58 | 1.75 | 0.85 | 2.67 | 1.04 |
| SEQ ID NO: 59 | 3.00 | 0.41 | 3.75 | 0.48 |
| SEQ ID NO: 70/71 | 1.75 | 0.63 | 2.67 | 1.00 |
| SEQ ID NO: 77 | 2.00 | 0.00 | 3.50 | 0.29 |
| SEQ ID NO: 89 | 1.75 | 0.63 | 2.50 | 1.11 |
| SEQ ID NO: 90 | 3.00 | 0.71 | 3.83 | 0.25 |
| SEQ ID NO: 91/92 | 1.00 | 0.00 | 3.17 | 0.58 |
| SEQ ID NO: 93 | 2.75 | 0.25 | 4.17 | 0.25 |
| SEQ ID NO: 95 | 3.75 | 0.25 | 4.50 | 0.25 |
| SEQ ID NO: 99 | 2.00 | 0.41 | 3.00 | 0.25 |
| SEQ ID NO: 103/104 | 2.00 | 0.00 | 3.67 | 0.29 |
| SEQ ID NO: 106 | 1.00 | 0.00 | 2.25 | 0.29 |

TABLE 9-continued

Results of salinity experiments conducted on *Arabidopsis* plants expressing novel identified genes

| Seq ID | Flower & Pod production | FP ± SD | Chlorosis | Chlor ± SD |
|---|---|---|---|---|
| SEQ ID NO: 107 | 1.75 | 0.25 | 3.00 | 0.25 |
| SEQ ID NO: 110 | 1.75 | 0.25 | 2.83 | 0.25 |
| SEQ ID NO: 111/112 | 1.00 | 0.00 | 3.08 | 0.25 |
| SEQ ID NO: 113 | 1.25 | 0.75 | 1.83 | 1.44 |
| SEQ ID NO: 118 | 2.50 | 0.29 | 3.25 | 0.50 |
| SEQ ID NO: 119 | 2.25 | 1.03 | 2.75 | 1.19 |
| SEQ ID NO: 120 | 2.00 | 0.41 | 3.08 | 0.29 |
| SEQ ID NO: 124 | 1.75 | 0.25 | 3.00 | 0.00 |
| HRD | 1.25 | 0.25 | 2.83 | 0.48 |
| WT | 1.00 | 0.00 | 1.83 | 0.55 |

FP - Flowers and pods production
1-No Flowers
2-Few flowers formation with short flowering stems
3-Some flower formation almost no pods
4-Flowers and pods forming
Chlorosis - Chlorosis and damage to leaves
1-Completely dry leaves
2-Dry leaf edges
3-Yellow
4-Some Yellow
5-Green
± SD-standard deviation As shown in Table 9, plants expressing genes identified by the method of the present invention as conferring salinity tolerance, demonstrated significantly higher flowers and pods yield and significantly reduced chlorosis and damage effects to the leaves as compared to WT control plants subjected to the same salinity stress conditions.

To conclude, the experimental results presented above clearly demonstrate that by the unique method of the present invention, highly valuable stress tolerance (e.g. drought, salinity) genes in plants can be identified. The newly identified genes confer improved tolerance or resistance to the preselected stress in plants in various important parameters such as leaf area, turgor pressure, aerial yield and quality, flowers and fruits yield etc. These results show that the present invention provides a novel screening method that identifies stress tolerance plant genes that can be expressed in desirable and important crops to enable their growth and enhance their yield under various abiotic and biotic stress conditions.

REFERENCES

Gabor, E. M., Alkema, W. B. & Janssen, D. B. (2004) Quantifying the accessibility of the metagenome by random expression cloning techniques. Environ Microbiol 6, 879-886.

Culligan, E. P., Sleator, R. D., Marchesi, J. R. & Hill, C. (2014) Metagenomics and novel gene discovery: promise and potential for novel therapeutics. Virulence 5, 399-412

Venter, J. C. et al. Environmental genome shotgun sequencing of the Sargasso Sea. Science 304, 66-74.

Farooq, M., Wahid, A., Kobayashi, N., Fujita, D. & Basra, S. M. A. (2009) Plant drought stress: effects, mechanisms and management. Agron. Sustain. Dev. 29, 185-212.

Taiz L. & Zeiger E. (2006) Plant Physiology, 4th Ed Sinauer Associates Inc. Publishers, Massachusetts.

Nonami H. (1998) Plant water relations and control of cell elongation at low water potentials, J. Plant Res. 111, 373-382.

Panda, A. K. & Das, A. B. (2005) Salt tolerance and salinity effects on plants: A review. Ecotoxicology and Environmental Safety, 60(3), 324-349.

Carillo P, Annunziata M G, Pontecorvo G, Fuggi A, & Woodrow P. 2011. Salinity stress and salt tolerance, abiotic stress in plants—mechanisms and adaptations. In: Arun Shanker, editor Tech, DOI: 10.5772/22331.

Yang T-T, Cheng L & Kain S R (1996) Optimized codon usage and chromophore mutations provide enhanced sensitivity with the green fluorescent protein. Nucleic Acids Res 24:4592-4593 Hema R, Vemanna R S, Sreeramulu S, Reddy C P, Senthil-Kumar M, & Udayakumar M (2014) Stable Expression of mtlD Gene Imparts Multiple Stress Tolerance in Finger Millet. PLoS ONE 9(6): e99110.

Karaba A. Dixit S, Greco R. Aharoni A, Trijatmiko K R, Marsch-Martinez N, Krishnan A, Nataraja K N, Udayakumar M, Pereira A (2007) Improvement of water use efficiency in rice by expression of HARDY, an *Arabidopsis* drought and salt tolerance gene. Proc Natl Acad Sci USA 104:5270-15275

---

What is claimed is:

1. A plant comprising a transgene encoding a polypeptide sequence having at least 95% identity to the polypeptide sequences set forth in SEQ ID NO: 197 and wherein the transgene confers to the plant one or more of the following improved/increased characteristics: improved drought resistance; increased biomass under conditions of drought or increased salinity; increased salinity tolerance; and increased yield under conditions of drought or increased salinity; wherein said improved/increased characteristic is in comparison to a WT version of the plant or to a GFP expressing version of the plant devoid of the transgene.

2. The plant according to claim 1, wherein the transgene has a polynucleotide sequence having at least 80% identity to the polynucleotide sequences set forth in SEQ ID NO: 44.

3. The plant according to claim 1, wherein said transgene is expressed under a constitutive promoter or a stress induced promoter.

4. The plant according to claim 1, wherein the plant is an agricultural crop.

* * * * *

SEQUENCE LISTING

```
Sequence total quantity: 333
SEQ ID NO: 1              moltype = DNA  length = 1019
FEATURE                   Location/Qualifiers
source                    1..1019
                          mol_type = genomic DNA
                          organism = unidentified
SEQUENCE: 1
ggactttctc attttcagaa ttattttcta tactctgaca agagcaagca ataccaaaca   60
tcttccacat cgaagcttta accattttgc ccttaacatt tgaacaagac gaaatggcct  120
tcttcccaca ctacaccact aatctgtcgc ctctgctcta cttgttggac gacgactatg  180
ctgtctaccg ctcaacttgt ccaaagtcca actaccacca caagcaacac cacagccgcc  240
gtcagccttc gccagttcgt tactttagtc cgaattttga tatgcgagag gggaatgact  300
cctactacct tgacggagag ctccctggtg tcaaccagaa tgatgtcgat attgaattct  360
ctgaccctca gacactggtg atcaagggtc gagtgggacg gaattacaac aatctcgacg  420
gcatgaacga ggaaaaccag caagatgaag aacaattctc tgaaactctc tctagcaagt  480
cgtaccaacc cactgtcgag gacgaggacg aggcgaacca ttcaccaccc gtggcgacac  540
caacctactc tgagaagtct gttactgaga aaactcagaa gcctgcgtac aaataccgaa  600
attctgaacg tgctattggc gaattccacc gagccttcaa tctccctaca agagtcgatc  660
aagatgcggt cagggctaca ttgaggaatg gaatcctctc gctggagctc ccgaaggagc  720
cggcaccgaa gatgaagaag attcggattg aatagaggat ttcgaataaa atttttgatt  780
tgatgagtag ttggtgttta ttgttatgtc taattatatg gggctatgtc atgattggga  840
aatgggacac cgcatttgtt tccttttcc ccatttcttc agacgccatc tatattacat  900
gtatgttgca tgaactatgg tttttgctag gagcggttgc ttctgctctg cattttcatg  960
aactatttc tttttattaa attaataact agcatatcaa ttaatgatct gtcatatgg  1019

SEQ ID NO: 2              moltype = DNA  length = 712
FEATURE                   Location/Qualifiers
source                    1..712
                          mol_type = genomic DNA
                          organism = unidentified
SEQUENCE: 2
gatcatcaat caattaatca atctactcta ctttccaaaa cataactacc aaataaccag   60
aatgcagctc ctcagcaccc tcacccccct tgccctccta gtcaccgtcg cttccgccac  120
cggcaaagcc gtcaataatg ccgttggcaa cgccgtcgtc acaaaccact gtaaagaccc  180
aatctatctc tggtccgtcg gctcctccgt ctccccgaca cacccatcc cctccggctc  240
caactatacc gagcccttcc gccacgacga cgcatctggc ggcatcgcgc tgaagatcac  300
ccgtaacgac aacgggctgt atgacgggag tgcgcagtta gtttactcct acgctttgga  360
tggggaacag gtgtggtatg atttgtcgag tgtgtttggg gatgcgtttg caggggaggc  420
tgttgctgtg aagccgaga atgaggggtg tgggagtatt tgttggccta agggtaccac  480
gcctggtgga agccaggtta aggtctgtga tgcggagggg gatgttggat tggttgtttg  540
tgcgaagggg tgttagggg tctgagtgaa ggttggtggt ggtaatgagc aatttgggtat  600
gagagggggaa aggatatgtt aatcgtttat gttatttact tgatcaaaat atttgtattg  660
acgtcggttg ttttgttatt gttgtttaa atgcaaatgt atatgaactt tc           712

SEQ ID NO: 3              moltype = DNA  length = 580
FEATURE                   Location/Qualifiers
source                    1..580
                          mol_type = genomic DNA
                          organism = unidentified
SEQUENCE: 3
ggttcgtcaa cgcgacgatc cgcggggtc caagctagga cgtggcagtt gtgacacaac   60
aagagcatgc tatggcaaat gccattcgcg agctcgccac taccctgtga actgtggcct  120
tactcctata cccgccagag tctgacttat tcctgtcact ggaatctggc ttactgctgg  180
tgctggagtc tggtcccagt attttagtat agtacaattg ctagctgaag ccataaggcg  240
tggattgttg gggtggcgca gggctgaagc caaatgcag cggtgttgct gctggttgag  300
caccgggcat agcgccagaa agtgcacccg cgaacattcc ctggtattgc atgaacggct  360
gtccaggaat cgcgccaggc attggcaagg cgttgttcg ctttgcctcc gctgccagca  420
gcctctctgc ttccgtaccg tgtctttcgc ccttaccgtc cttcttgaat gcataatcaa  480
ccgtcagagg cttgttcatc aagtactggc cattcatagc cgtgattgcc tggtccgagc  540
tgtcaaagtc gttgtactgg atgaatccat atccttcaa                        580

SEQ ID NO: 4              moltype = DNA  length = 580
FEATURE                   Location/Qualifiers
source                    1..580
                          mol_type = genomic DNA
                          organism = unidentified
```

```
SEQUENCE: 4
ttgaaaggat atggattcat ccagtacaac gactttgaca gctcggacca ggcaatcacg  60
gctatgaatg ccagtactt gatgaacaag cctctgacgg ttgattatgc attcaagaag  120
gacggtaagg gcgaaagaca cggtacggaa gcagagaggc tgctggcagc ggaggcaaag  180
cgcaacaacg ccttgccaat gcctggcgcg attcctgaca agccgttcat gcaataccag  240
ggaatgttcg cgggtgcact ttctggcgct atgcccggtg ctcaaccagc agcaacaccg  300
ctgccatttg gcttcagccc tgcgccaccc caacaatcca cgcctatgg cttcagctag  360
caattgtact atactaaaat actgggacca gactccagca ccagcagtaa gccagattcc  420
agtgacagga ataagtcaga ctctggcggg tataggagta aggccacagt tcacagggta  480
gtggcgagct cgcggaatgg atttgccata gcatgctctt gttgtgtcac aactgccacg  540
tcctagcttg gaccccgcg gatcgtcgcg ttgacgaacc                         580

SEQ ID NO: 5          moltype = DNA  length = 781
FEATURE               Location/Qualifiers
source                1..781
                      mol_type = genomic DNA
                      organism = unidentified
SEQUENCE: 5
gaaaaaaact ttagaataca gtttaatcaa tcttcacagc tacaaggcta tatcatttga  60
tatagcatat caaagtggct ttgatttctg taaatttata tctaataata atagtgttta  120
tatcagctaa atacatattt ctatcctatc tatatatcac cgacagacca tatttgaaac  180
tgctgttgac actattttc atatgttcgg atttaattt aatacgacaa aattgttaaa  240
aacaattctc gttgtttgtt atttgcaggc aacagtgtta gctgatcctt atacaagagt  300
atcttgggaa gcgtatatga atcatgtcaa tggatccgac gactatcgta ctcaaggga  360
tgataccaga gctacacgct ttccagagac taaacctcca aaacaaggaa aagatttcct  420
gtggtcgagt aaaccagtcc cagttcaga tctatttctg tggttcttta tgtatgaggg  480
agaaccagat gaattcagca ggacgactga atcgtatcaa tcacttccga gcaacgcgtt  540
aactgctagg caaaatgccc ttacttgtca ggacatagag tcatgttcgt atcctccaca  600
ggtgaacaac tttcaagctt tattcgacga cctggggcca tcaacttgta atctcataaa  660
agacgaaact cgtgactgga tattgcagca gtggcccggg ttagctgtag agccgttat  720
atcgtttgcg gtagccgttg cgggaagctc ctgtgatata ttatattaat cagctttggc  780
a                                                                  781

SEQ ID NO: 6          moltype = DNA  length = 661
FEATURE               Location/Qualifiers
source                1..661
                      mol_type = genomic DNA
                      organism = unidentified
SEQUENCE: 6
ggtcgagcta ctttcaaggt caagcaagat ggtccgttac gcacacaatg ctgagaaccc  60
agagaagacc gccaaggctc gtggtcagca cttgcgtacg cacttcaaga cacccgtga  120
agtcgctgct gctctgaccg gcttgaagct ttcaaaggct tacaagtacc tcggcgatgt  180
ccaagacgcac aaggatgtca tcccattccg tcgcttcaac ggtggtgttg gcagagccgc  240
tcaggctaag aaccacggta cgacccaagg tcgttggcca gtcaagtcga ttggcttctt  300
gctcagactt tgaagaacg ctgaggccaa cgctgacgcc aagtcactcg acacgggaaga  360
cctcttgatc aagcacattg ttgtccaaca agctccaaaa accgtcgtc gtacttaccg  420
tgctcacggt cgtatcaacc cttaccaagg acacccatgc cacattgaga tcactctggc  480
tgtcccagac gagcaagtcg ctcgcaacaa ggacgttgag gtgaaccaac caaagaagat  540
ccaaggcaac aagcgtcaag tcgctgctca acgtcgcttg acctctgcat aaactggcta  600
ctcggttgtg taccactcta tacaaattat tcagtaaaat gctatccatc ttggcttcga  660
a                                                                  661

SEQ ID NO: 7          moltype = DNA  length = 713
FEATURE               Location/Qualifiers
source                1..713
                      mol_type = genomic DNA
                      organism = unidentified
SEQUENCE: 7
agccacaacc acatcaatcc tccaccactt tcagctttcg acttcatcaa acaactcctt  60
ctaccactac tacctcaaca accttcatca aaatgactgg acgcggcaag ggcggcaagg  120
gtctcggaaa gggcggcgcc aagcgtcacc gcaagatctt gcgcgacaac atccagggca  180
tcaccaagcc cgccatccgc cgtctggcgc gtcgtggcgg tgtcaagcgt atctccgcca  240
tgatctacga ggagacccgc ggtgtcctca agaccttcct cgagggtgtc atccgcgacg  300
ccgtcaccta caccgagcac gccaagcgca gaccgtcac ctccctcgac gtcgtctacg  360
ccctcaagag gcaaggccgc accctctacg gtttcggtgg ttaagcagct cgctcttctc  420
tcttcgactg ctttgctttc ttcaaacaca ataacaatca cgacaacaac aacttcatca  480
gatatccacc cacaatgcga gagttgggct tgcgggtatg cgcgaatggg caatgggct  540
atccgggttt tttcatttt ggggttttt tctcttttcc tgtttcgatg ctgcgaggtg  600
agcacactgg gctgcggctc atgaggcttt gagtgtagaa taggctcaac atcatcaaag  660
aagcattcca cgagacgtgg cgctttcttc atcaaccaaa tgaatattgc agc          713

SEQ ID NO: 8          moltype = DNA  length = 1021
FEATURE               Location/Qualifiers
source                1..1021
                      mol_type = genomic DNA
                      organism = unidentified
SEQUENCE: 8
ggacttgcga ccacacacat ctttatacct caaaatgtcg ctcgatgtcg gagatgtaga  60
cgcctggatc gacacgctat cgcagtgcaa gcagctatct gaatctgacg tgaagctcct  120
```

```
ctgcgacaag gccagagaaa ttcttataga ggagtccaac gtacagccag tcagatgccc   180
cgtcaccgtc tgcggcgata ttcacggtca attccacgac ttgattgagc tctttagaat   240
aggcggcaac tccccatcca ccaattacct cttcatgggc gattacgtag acaggggta    300
ctactcggtc gaaactgtca ccctcctcgt cgccttgaag ctccgctaca gggaaagaat   360
caccatcttg cgcggtaacc acgagtcgag acagatccag caggtctacg gtttctacga   420
cgagtgcttg agaaagtatg gaaacgccaa cgtctggaag ttcttcaccg atctctttga   480
ctacctccca ctgacggcgc ttattgacaa tcaaatcttc tgtcttcacg gtggtttgtc   540
tccttccatc gacacgctcg accacatccg ctctatcgac cgtatccaag aggtgcctca   600
cgaaggtcct atgtgcgatc tcctctggtc cgatccagac gaccgctgcg gctgggcatt   660
atcccctcgt ggtgccggtt acaccttcgg tcaggacatt tcagaggctt tcaaccactc   720
aaacggcttg acgctcgtag cccgtgctca ccaacttgtc atggaaggtt acaactggtc   780
ccaggacagg aatgtcgtca ctctcttctc tgcgccaaat tactgctaca gatgcggtaa   840
ccaagctgcg atcatggaga ttgacagaaa tctcaagtac actttcctcc aattcgatcc   900
agcaccaaga gctggcgaac cgatggtgtc tcgaagagtt ccggactact tcttatagcc   960
tcttactcac tgtatttatg tttgcactgg gtattgttta cttgtacaat gtgtaactac  1020
g                                                                 1021

SEQ ID NO: 9              moltype = DNA   length = 715
FEATURE                   Location/Qualifiers
source                    1..715
                          mol_type = genomic DNA
                          organism = unidentified
SEQUENCE: 9
ggagccacaa ccacatcaat cctccaccac tttcagcttt cgacttcatc aaacaactcc    60
ttctaccact actacctcaa caaccttcat caaaatgact ggacgcggca agggcggcaa   120
gggtctcgga aagggcggcg ccaagcgtca ccgcaagatc ttgcgcgaca acatccaggg   180
catcaccaag cccgccatcc gccgtctggc gcgtcgtggc ggtgtcaagc gtatctccgc   240
catgatctac gaggagaccc gcggtgtcct caagaccttc ctcgagggtg tcatccgcga   300
cgccgtcacc tacaccgagc acgccaagcg caagaccgtc acctccctcg acgtcgtcta   360
cgccctcaag aggcaaggcc gcacccctca cggtttcggt ggtaagcag ctcgctcttc    420
tctcttcgac tgctttgctt tcttcaaaca caataacaat cacgacaaca caacttcat    480
cagatatcca cccacaatgc gagagttggg cttgcgggta tggcgcgaat gggcaatggg   540
ctatccgggt tttttcattt ttggggtttt tttctctttt cctgtttcga tgctgcgagg   600
tgagcacact gggctgcggc tcatgaggct ttgagtgtag aataggctca acatcatcaa   660
agaagcattc cacgagacgt ggcgctttct tcatcaacca aatgaatatt gcagc        715

SEQ ID NO: 10             moltype = DNA   length = 503
FEATURE                   Location/Qualifiers
source                    1..503
                          mol_type = genomic DNA
                          organism = unidentified
SEQUENCE: 10
aatcacccaa atgttctcta aactcatcgc catcgcctct cttgccctcg ctgccaacgc    60
tgcagtcatc gacccaagtg accacactgt ccaatacgaa gctgcaccag gaaaggttgt   120
gactgagcac tacgaggttc tcagccacgc cgaagcatcg cgcataatcg aagccaatcc   180
acacatcagc gactatcgct acagatgcaa ctaccaatgc aacgatagca gcggcaacta   240
catgagaaac ctgcagcagg gagttccaaa ccaagcatgc atcttctcta gctgctacga   300
ctgtgactgg aaattccaaa actgtagcta ctgtcgcttg tcgactggcc acaactaccg   360
tgatatcggt ggactcgaga gctggtgcta caacaacggc ggtactacag tgacgcacaa   420
ctgtgtggtt at actgatggcg accaatgcta agagcggcct tgtaaagtaa aacttgtact   480
ctgaatttgc ctttatctttt ccc                                          503

SEQ ID NO: 11             moltype = DNA   length = 580
FEATURE                   Location/Qualifiers
source                    1..580
                          mol_type = genomic DNA
                          organism = unidentified
SEQUENCE: 11
atcatctcaa acccaattat cttgaacacc tagtttctca agaacatcct caaaatgcac    60
ttcaaatctc tctttattgc tggcgccctc ttcatggtcg gtgccagtgc cgttgattgt   120
gccactcctg agattcactg cgagactagt gatggcagcc cctggtacga cgatgccgtc   180
caagccactg aatactggaa agaaatccag gacgccggca agacagctg cggtgatgct   240
ggttgcgcac agccccatgg ctctggatgc cacagcgacg tggtagcta tggtaccgcc   300
gagatcgttc tgtgccagga tgactcgtcc tcttcaactc cccaatgtga cgactgccgg   360
tgtgtctaca gctacctgaa gcctcttctc gaccaatgca aagggtgcca acaacaagatt   420
ggtggatatg ctcatgttga catgggaggc aactacatca actatgaatt tgttaagaaa   480
tgagcggatc tcacgtgtgt gagaccatca tatagggttt tgaagtctgt ttcctttgta   540
tttaacgtcg aaagacaatt atgagccagg tttatactcc                         580

SEQ ID NO: 12             moltype = DNA   length = 607
FEATURE                   Location/Qualifiers
source                    1..607
                          mol_type = genomic DNA
                          organism = unidentified
SEQUENCE: 12
cgcgccgggg gaaattggac catgatagac gacctcacca ctggctcaga ggacagcttc    60
tccaacagct ggatatcgtg gttcttatct accaaaggga acgagtactt ctgtgaggtg   120
gatgaggagt acatactgga cagattcaac ctcactggcc tcaacaacga cgtgcagaac   180
tactcgcagg cgctggagct catcacagac agcctcgacg acgaggacct cgatgatgag   240
```

```
cagagagacg ctatcgagaa cagtgccagg tatctctatg gcttgatcca cgccagatac    300
atcattacct cccgcggact ggcaaagatg ctcttcttgg tgtacccgca gcagctgccg    360
tcaaagacga cgaactcagt gccgagcacg aagccggcaa cttcagcaga cgcagcggtc    420
ggggtggaca ggtacctgcc caagatattc gggttccgg tgcacgagat gtccaagcac     480
gcgaggtggc aggaggcgca gagggatctg cagatttcga ggctgcagca aagtgcgagt    540
gacccgtcgt acgtgtagag cgttcaaaca tgtattacta ttggtataat aatttaactt    600
tactgcc                                                              607

SEQ ID NO: 13           moltype = DNA   length = 1406
FEATURE                 Location/Qualifiers
source                  1..1406
                        mol_type = genomic DNA
                        organism = unidentified
SEQUENCE: 13
aagttacccg gcttattagt cctagattcc gagatgtcgc tcactcccga acaaaccgaa     60
atcatcaagg ccaccgtgcc tgtcgttaaa gaacatggca agaccatcac caccgttttc    120
tacaagaaca tgctcgaagc gcatcctgag ctgaacgcca ttttcaacac taccaatcag    180
gtcaatggtc accagcccaa cgcactcgcg ggagccctct tcgcctacgc ctccaacatt    240
gacaaccttg gcgccttggg ccctgccgtc gaactcatct gcaacaagca tgcttcgctg    300
tatatccaac ctgagcacta cggcatcgtc ggcaagttcc ttctcgaagc gatgggacag    360
gttttggggt acgccttgac tccgcagatc ctcgacgcct gggcagctgc ctactggcag    420
ctcgccaacc tctttattgg tcgcgaaagt gctatctaca agcagagtga gggatggaca    480
cagtggcgca agttccgggt tgcacagaag gtccctgagt ccgcggagat cacatcgttc    540
tacctcaagc ctgtcgacga aagcctttg ccccgcttcc gccccggaca gtacatttcc     600
gtccaagtgc acgttcctca gcttgaatgc cccaagctc gccaatactc cctcagcgac     660
aagccccgcg acgattacta ccgcatcagc gtgaagaagg aacgggtct caacacagca    720
aagccggagg ccaaggtcaa cccgggttac gtctcgaata ttctgcacga gaacgtcaac    780
gagggcgacg tgatcaaggt gtcgcaccct tgccggcgatt tcttcttgac cgagcaggaa    840
ccgtcgcacc ctgtcgtcct catcgcagcc ggtgtgggtc tgacgccact tacctcgatg    900
ctcaacacat tggactccac ccccgcggac tctcagcgca agattcactt catccacggt    960
gcgcgcacca cttccgtccg cgcttttcaag gaccagatta gtctcgcgc tgagcgactc   1020
ccgaatctcc aggccacctt cttcaccagc tccccgtcgg cagatgaaaa gcaaggcgtc   1080
gactatgacg tccagggccg tatcgatgtg tccaagatgg atgccagcaa ggatcttttc   1140
ctcgacagtc cgcagaccga gttctacatt tgtggtccca cttccttcat gaatgatatc   1200
gcgaacagct tgaaagctcg gggggctacc tcggagcgta tccacatgga attgttcggc   1260
actggcggcg tgcctgttta gatgatggct cagttagccg tgattgggtt ttatttctt    1320
acgacgatat gactcaggtt tctaagttag tatacataat catgataaat tcttatatag   1380
atatatcaat aatacatctc ctctcg                                        1406

SEQ ID NO: 14           moltype = DNA   length = 750
FEATURE                 Location/Qualifiers
source                  1..750
                        mol_type = genomic DNA
                        organism = unidentified
SEQUENCE: 14
gggtctcttc catttgaatt tttcaaccca cagcatggcc ttcatgaatc tcccatggcc     60
cactgaatgc ctgcatgccg ctctcaagaa cggatcctta cctttctggg gatttgtaat    120
ctatcgaacg acctacaccg ctcagtcaga tgccgcctgg ccgcagatta tcgagctat    180
tgcctcctat atgaaagcct tactctacca cgagtataac gacaagaaaa aagatggaga    240
tgagcctaca gtctacgacg aaatctgggc aaggcatcag ttgacgatta tggatgatag    300
acaattcaac ggagcgtctg tgtttgatat ccaacttcac ttcgaaaagt gggttgaggc    360
gcagggaaag cgagatgaat ctactatgta tcgcatgtgt atggtcattg atgatgaatc    420
aatccagacg ttattggagg cgccaccgg ggaaaatagg aaactcggac gacgtatagg     480
gggccctgta cgctttgtca aagtcgtgga ggctttcccc gagctagaca gccttgacga    540
attccaggga tggatgaaat gtgagatcaa cgcgttatgg ccgctgtgga agatgatgc    600
tgacggagat gaaatgagga tgtcatatga tgagatgaag gggaatgaga agcaggtcta    660
tggcgcaatt taatcggttt ttcttcatgt tatcctgatg gaaaaaatgg cagaacatat    720
gtctgtacat gcagaaaata aggtgattgg                                    750

SEQ ID NO: 15           moltype = DNA   length = 811
FEATURE                 Location/Qualifiers
source                  1..811
                        mol_type = genomic DNA
                        organism = unidentified
SEQUENCE: 15
gacaccacct cttttcgac aaccacaccc cgtttcgcag gaagtccatt tccagcagtc      60
aaaatggccc gtcgtcccgc gagatgttac cgctactgca agaacaagcc ttaccctaag    120
tcccggttca accgtggtgt tcccgacccc aagatccgta tcttcgactt gggtcgtaag    180
aaggcttccg tggacgactt ccccctgtgc gtccacatgg tctccacaga atacgaacag    240
ctttcctccg aagctctcga agctgcccgt atctgtgcca acaagtacct cgtcaagatc    300
gccggtaagg aaggtttcca cctgcgtgtc gcgcccacc ccttccacgt cgtccgtatc     360
aacaagatgt tgtcgtgcgc tggtgccgat cgtctccaga ccggtatgcg tggtgccttc    420
ggtaagccca acggtgttgt cgcccgtgtg aacatcggc agatcctcct gtccatcgc     480
acccgtgact ccaaccgcgc cgccgccgtt gaggccgtgc gccgctccac ctacaagttc    540
cctggtcgca aaaagatcat tatctccaag aactggggct tcaccccgt ccgtcgtgag     600
gagtacgtca agctccgccg gagggcaag ctcaagcagg acggtgccta cgtccagttc    660
ctgcgtggcc acgtttggt cgaggagaac atgaagcgct ccccccaggc ctacgagggc    720
gttgctcagt agattgggat gaattaggtg gttttatgtg ctggtcgtat ttatcgtttt    780
tactagggcc aaatgagaac aaaaaaaggc t                                   811
```

```
SEQ ID NO: 16              moltype = DNA   length = 923
FEATURE                    Location/Qualifiers
source                     1..923
                           mol_type = genomic DNA
                           organism = unidentified
SEQUENCE: 16
gtctttagtt ggccattgaa cactgacaga tttgcattgc ttatatttgc atctacctca    60
catctactca actcctcctc tccgtttgtc atgtccttct accagtctcg tccagacact   120
atcaagggtc ctgatccttt gaccgacaat tggacttatg atagtgccat tgatctcttc   180
tcttggaatc ccatgatgcc cgatcctttt acctttgacc tgcccgacga tcttatgaaa   240
tttgaatcta aggatatgtc tgctggcatg gtcgctcctt cggacattag tggttttgcc   300
attggtaacc atttgggcga ggatgctgcc tcgatatctg atcccgagag tgatgaccac   360
ccatggtccc cctccgctca tgctgccttc ccggagctct ctcccatcac atcgacagag   420
caagtccatc aagaaactgc tcgatactca actaccccg atgccacctc acctcaagaa    480
caaccctcct caccaccaac acgatctact cgccgccgat catccgctga cggtcccgtt   540
cgcaacgctg ccaaacgagc agcccacaac gtcattgaaa agcgctacag aacaaacatg   600
aatgccaaat tcgtggcact cgagaaagca atgaatggcg gtaatggcgt gcaaacatca   660
tcaagaggcg gagggtccgc gtcgcttaag aaatccgaaa tcctctctaa tgctattgcc   720
tacatgcatg gactgcaaga ggaaaatcgc tatttacaaa aggagcttgc tatcgttaaa   780
cagaatcttg taccggcagg gatatggcga ggggctccta gttgtaaacg ggagacgagt   840
tatcgttaac ttgttgattt ccctgtggtt gtttagattt tttttacgat gttacgtgta   900
taataatact ctcccctcgg gtc                                           923

SEQ ID NO: 17              moltype = DNA   length = 1046
FEATURE                    Location/Qualifiers
source                     1..1046
                           mol_type = genomic DNA
                           organism = unidentified
SEQUENCE: 17
ggacaagccc atcttcaatt cgagacagtc gccatgggtc gcgttatccg caaccagagg    60
aagggccgtg gctccatttt cacggctcac accgtctga acaaggctcc cgcccagttc    120
cgtaccctcg acttcgctga gcgtcacgga tacacccgtg tgttgtcaa ggagatcatc    180
cacgatgccg gccgtggtgc tcccctcgcc aaggtccagt tccgccaccc ctacaagttc   240
aagatggtga ccgagacctt catcgccaac gagggcatgt acaccggtca gttcatctac   300
gccggtaaga acgctcagct caccgtcggc aacgttctgc ccctcgcctc catgcccgag   360
ggtaccgtca tctccaacgt tgaggagaag tccggtgacc gtggtgcgct tggccgtacc   420
tccggtaact acgttaccgt cattggccac aaccccgagg acggcaagac ccgtgtcaag   480
cttcccctcc ggtgccaaaaa ggtcatcaag aacaccgccc gtggtatggt tggtatcgtc   540
gccggtggtg gtcgtaccga caagcccctg ctcaaggctt cccgcgccaa gcacaagttc   600
gccgtcaagc gcaactcttg gcccaagact cgtggtgttg ccatgaaccc cgttgatcac   660
cctcacggtg gtggtaacca ccagcatatc ggtaaggcct ctaccatctc ccgctacgcc   720
gcccaggggtc aaaaggccgg tctcattgct gcccggagaa ccggtctgcc ccgtggtacc   780
cagaagacca aggattaagc gtgatattac gtggagtttt ctttgtgacg ggttgaaaat   840
ggacttctgc tatgagacat atgtacttag gcgagtgcgg ataagcgtcc catgcgccct   900
tagcgaatta aggttgtggt caccatcctt ttcttttat taaatcaaaa agggtgatg    960
gaatgggggtc cgaggctggc ctcaagtcaa ggcagaacgg aaaagtcaaa aatgccccctt  1020
ggggttttgg aaatgataca cctttg                                        1046

SEQ ID NO: 18              moltype = DNA   length = 780
FEATURE                    Location/Qualifiers
source                     1..780
                           mol_type = genomic DNA
                           organism = unidentified
SEQUENCE: 18
ggcgcagagg cctattactc cccagtatca tcgctaatag gcatgtccac gggtctaagg    60
ttcagcactt tgccagctgc ttccaatcca cagtcgtcgt cattgatacc cagccctagt   120
gctcccatat caacttttcc atatactttta acactcacgc taactccctt gacgggatcc   180
ctctcaacct catactcatt acgcgcctct cccaatctgt catttagctc tcggttcggt   240
ttcaatgttt acagttggga agcgagatg gtagcgggat ttgaactatg gcgacaatcg   300
aaaaagccca agttggccgc gggaagcgat ggcgacgatc ttgaatgggc ccgcaggaag   360
gtccgtgtct gggatccctc agcttttccc ctggcacccc ctgaacctga atcccacaa    420
ccaaaccatg aagatgagtc tcaagagtca gtacttaagc tacgagtcga ccaatcctgg   480
aatgttcgtc ttctctggga aggtcgggtg aaggagcttt tggtcagcgc tggtgtccgg   540
ctcggcccga gttccttctc accatcgtca tatgcaaatc ccccgggtac agccgggcct   600
caaggcagcg gtgggggctc accggcctca tactggaggg gcgtgggggg tttcggtatc   660
atattcttca tgagggattt cttcggatct atgtacttga atgagcactg tctagatgta   720
tatagtttat cagatttttat gagacaatag acaccatgaa tctgcgttat tgcgagacgg   780

SEQ ID NO: 19              moltype = DNA   length = 896
FEATURE                    Location/Qualifiers
source                     1..896
                           mol_type = genomic DNA
                           organism = unidentified
SEQUENCE: 19
ggccctggcg tgctttctgg ctttcaacct cccgacctcc ctctaattac ctcaattgaa    60
ctcgatttag acgtggtgct gccacctccc gcctgccgca caatgtttct tcgcaccgtt   120
tctcgcgctg tccctcgcag caccgcggcc atccgtgctg caccgactgc ctctgtgaac   180
gccctgcaga cccgcgctgc ctcggaccat gctatcccca accctaccct cgccaacatt   240
```

```
gagaagcgct gggaggtcat gcccctcag gagcaggccg agctctggat gcagctccgt  300
gaccgcatga aggttgactg gcaccagatg accctgcagg agaagaaggc cgcttactac  360
attgccttcg cgcccacgg ccccgcgcc cagcccccca agggtgaggg catgcgcgtg  420
ttcgccaagg tgctccagct cactgccgcc tccgttgctg tcttctacgc catccacgcc  480
ttcgccggca agcagcccgc caccatgtcc aaggagtgga aggaggcctc caacgaatat  540
gccctgaaag agaagatcaa ccccatccac ggcatcagca agagggtta cgaaggcaag  600
ggcttcgtcc agagccccc tgccgagaag tcataggtgt accagttgcc cgaccgggaa  660
tgagttgata tctacgccgg acggacggcg gcacccatcg cacgatctat atgtcgatct  720
tattacaagc tactctttcc atagccatgt tcgacatgtc tttgtgtcgg aggatgggcc  780
tccgcccgtg cgcgcggccg tcgattgttc cattctatct tttttggcaa gcattggaaa  840
atgcgtgtat cccgtactgt gctataatca atgtatctct tttttagcca tagagc       896

SEQ ID NO: 20            moltype = DNA  length = 641
FEATURE                  Location/Qualifiers
source                   1..641
                         mol_type = genomic DNA
                         organism = unidentified
SEQUENCE: 20
gtggcgcgcc ggggggcat ctacctcgac ggcaacaacg acctggtcac tatgaagggt  60
aactacatct accacaccag cggccgctct cctaaggttc agggtaacac cttgctgcac  120
gctgtcaaca actactggca cgacaactcc ggccacgcct cgagatcgg tgagggtggt  180
tacgttctgg ccgagggtaa cgtcttccag gatgttacta ccccgttga cgaccccgtt  240
gacggccagc tcttcacttc ccctgacccc agcaccaacg ctcagtgctc gtcatacctt  300
ggccgggcct cgcgaaatcaa cggcttcggt aactctggta ccttcaacca ggctgacact  360
agcctgctgt ctaaatttaa gggtcagaac attgcttctg ctgatgctta ctctaaggtt  420
gcctcgacgg ttgccagcaa cgccggtcag ggacacctgt aaaatggaaa gaggaggttc  480
agagcttaat ttgctcatgt cggacgacat agccctagcg gcttgctggt gaatttggca  540
taatagcgtt tctcttctca tacctacttt attactccgt ttggatcctt attaggtaaa  600
tattagccca ttgtatggtt caattcgatt gactttgagg c                      641

SEQ ID NO: 21            moltype = DNA  length = 591
FEATURE                  Location/Qualifiers
source                   1..591
                         mol_type = genomic DNA
                         organism = unidentified
SEQUENCE: 21
gtggcgcgcc gggattctca tcatcagata aaatcaagat taatcttact ggacatcaca  60
acgatccaac acaaagttcc ttcatacttc aaacaaatct ctacaattga atcaaaatgc  120
catccaaaac cgaagcagcc cgtctacaaa acgacttcgg tcagactac tgggttagaa  180
atacccaaga acgccgccac tcaaccgctg gccgcggact attcgccggt ctccaggatg  240
tcaagcacta taacgtcgac catggctggg cccgtcgcaa gtctagcgat aaccccggac  300
tccttgcttc tttcttcagt cgattcaccg ggggatcata ccatccgccc tcggaataga  360
attccttttc ttaatgtgcg atattgggag gagtgtgatt tgaattgggga ataagggaaa  420
agagtgcttg gaatatttga gtctcagact taactcgagt caagtttcat ttatgagtat  480
actgaggttt ttgtgttagt agcttggagt ttgggtggtt tattagtatt acctattgca  540
ttaccatgtt tatacatcgt gaatcatcga atgaatacca tgtcttcaat t            591

SEQ ID NO: 22            moltype = DNA  length = 639
FEATURE                  Location/Qualifiers
source                   1..639
                         mol_type = genomic DNA
                         organism = unidentified
SEQUENCE: 22
gtggtatcaa cgcagagtga cgagcccacc atccccggag gcgccgctgt caccatccac  60
tcccgtaacg agaagaaggc ccgtaaggcc atttggcagt tcggtctcaa gcacgtcccc  120
ggcatcaccc cgtgttactct ccgccgtcct aagaacatcc ttttcgttgt taaccagccc  180
gatgtctaca agtcgccttc cagcaacacc tggatcatct tcggtgaggc caagatcgag  240
gacctgaact cccaggccca ggcttccgct gctcagcagc ttgccgccgc cgaggctgcc  300
gccggaggtg agcacgctgg tcacgaccac gagcacgaca tcctcggcaa gggcaaggcc  360
cccgagaccg agggcaagaa ggaagaagag gaggacgacg gcgaggaggt tgacgaggcc  420
ggcctcgagg ccaaggacat cgaccttgtc atgcccagg ccaacgtctc ccgcaagaag  480
gccgtcaagg ccctccggga aacgacaat gatatcgtga actcgatcat ggctctcagc  540
atatgatttg gctgcctgcc ggcaggatga atgagtgagc tttgggcgcg aggtcacgtt  600
gatatccctg ttctgggccc tctcccttaa gtgtatagc                          639

SEQ ID NO: 23            moltype = DNA  length = 832
FEATURE                  Location/Qualifiers
source                   1..832
                         mol_type = genomic DNA
                         organism = unidentified
SEQUENCE: 23
gctcccaacg tcaacacccc ctccgccttc ccctcgaccg ttactcctgc ccgtccgatt  60
acaacaagga gaatgttcct tcagcgtacg gtatctaccc tcgcgaggcg cacccccgtg  120
cggggccttg ctgccgcgcg cccgtttttct tcgtccgtta gccgattcaa caagtacgag  180
gttaaggagg ccaagctccg ttctcttgac gagatccaaa ctgaagaaga cctcatcccc  240
cctggtgcta agcccggtac cgtccctagc gatatcgaac acgccactgg tctcgagcgt  300
ctcgaactcg tcgtaaaat gcagggaatt gacatcttcg acttgaggcc tctggatgct  360
tcccgcaagg gaaccctcga aaaccccatt gttgtcaacg tgctggtga cgagcagtac  420
gctggttgca ctggttaccc cgtcgactct caccaggtta actggttgac tgtctctcgt  480
```

```
gagcgcccca tcgagcgctg caacgaatgc ggtaacgttg tcaagctgaa ctatgtcgga   540
cctgaggagg accctcacgc tcacgaccac ggccacggcc accaccctgc ccccgaggag   600
cccaagacct tcgccgacta cgtcaagccc gagtactggt accggtaaat accccagcag   660
tacgacgcga gagttttcaa aaagagaat aagaaacaag caagggacg gatcaagacg     720
ggctagtgcg ggaatgtcaa acgcaacata tttaagcatt gggtctacta tatacgggtt   780
cattcgtcca ttgattcctc ggtctagtgt tttcttgaac gtctttagct gg            832
```

```
SEQ ID NO: 24           moltype = DNA   length = 832
FEATURE                 Location/Qualifiers
source                  1..832
                        mol_type = genomic DNA
                        organism = unidentified
SEQUENCE: 24
ccagctaaag acgttcaaga aaacactaga ccgaggaatc aatggacgaa tgaacccgta    60
tatagtagac ccaatgctta aatatgttgc gtttgacatt cccgcactag cccgtcttga   120
tccgtccctt tgcttgtttc ttattctctt ttttgaaaac tctcgcgtcg tactgctggg   180
gtatttaccg gtaccagtac tcgggcttga cgtagtcggc gaaggtcttg ggctcctcgg   240
gggcagggtg gtggccgtgg ccgtggtcgt gagcgtgagg gtcctcctca ggtccgacat   300
agttcagctt gacaacgtta ccgcattcgt tgcagcgctc gatggggcgc tcacgagaga   360
cagtcaacca gttaacctgg tgagagtcga cggggtaacc agtgcaacca gcgtactgct   420
cgtcaccagc accgttgaca caatggggt tttcgagggt tcccttgcgg gaagcatcca    480
gaggcctcaa gtcgaagatg tcaattccct gcatttacc gacgagttcg agacgctcga    540
gaccagtggc gtgttcgata tcgctaggga cggtaccggg cttagcacca gggggatga    600
ggtcttcttc agtttggatc tcgtcaagag aacggagctt ggcctcctta acctcgtact   660
tgttgaatcg gctaacggac gaagaaaacg ggcgcgcggc agcaaggccc cgcacggggg   720
tgcgcctcgc gagggtagat accgtacgct gaaggaacat tctccttgtt gtaatcggac   780
gggcaggagt aacggtcgag gggaaggcgg aggggggtgtt gacgttggga gc            832
```

```
SEQ ID NO: 25           moltype = DNA   length = 1263
FEATURE                 Location/Qualifiers
source                  1..1263
                        mol_type = genomic DNA
                        organism = unidentified
SEQUENCE: 25
acccaaaccc tgcgaagcaa aacgcgttac tcgatttggt catttcctcc aaagcatcat    60
tcctctttgg gcactgcctg tttcgtccat taatcaactg tgcttgaatc tctaactatc   120
ttttgatata ccctctttat ctctctcccc tttaatcttt tttctctct ctctcttttc    180
ctttcttttt cggttactca ctatcatggc cgacatcact gccgtcggtg aggagaaccc   240
ttctctacc caggatgagc tgcagcaggc cgcggccgt aacggcgctc gctgataaccg    300
cactcccaag cgtcgcatga gtgacgatga agaggacgag gagaagcagg gtcgcgagcg   360
cagaaagatt gagatcaagt tcattcagga taagtcgcgt cgccacatca ccttctccaa   420
gcggaaggcg gtatcatga agaaggcata cgaattgtcc gtcctcacag gcacccaggt    480
gctgttgctg gtcgtgtccg agaccggcct ggtctatacc tttaccaccc ctaagctcca   540
accattggtc accaaggcgg agggcaagaa cctgattcag gcttgcctca acgccccga    600
ccctaccacc agcgagaatg gcgtcgatgc ccccgaggtc ccagcggaga cccccgagga   660
tgtcaaccac gccaacgtca acgctgccgc agccagcagca accaacatcc ctcgtcccac   720
cggaatgcat cccggctaca tgaccaacga acaacagcag cagatggcct actaccaaaa   780
ccacctccag cagcaacagc aggccggtgg gcagtaccct ggcatgtctg tcggtggtcg   840
catgcctacg cagcaccagc ctaccgcata atcttattta ctcttatcta cgctcccacg   900
cacctcctct ttctgatttc cctgcatatg gtcttgtttt tagtagctga ggagtccaga   960
gttcagttgt ttttgccttc tttccgcatc tacccttcat tttccccctct ttcgttatta  1020
tctctctccc ctgacatttg ataccccgaca atcctgttgt tcaatccatc gtcgcatgaa  1080
aacgggtcct ataaatataa tgcatcccc tgtttacttt cgactgcgaa cgagagcatg   1140
caaatctgaa gaacagcatg gtcaattgtc tcagtaacct cgttaaggcg ccgatgagtt   1200
tggcgtttac atactctgct ttggaacgtg tgatgccttt ttaccgttca atgaaagcga   1260
ctc                                                                 1263
```

```
SEQ ID NO: 26           moltype = DNA   length = 1066
FEATURE                 Location/Qualifiers
source                  1..1066
                        mol_type = genomic DNA
                        organism = unidentified
SEQUENCE: 26
aggctttgat ggcctcttca aaggggaaca ttgttcactc gaccagagtt gagtagagcc    60
aagaccattc cataatctcc aggggcatat cgccatgccg tcttgtcaag acgatctcct   120
tctcacacat attgatgata ggtaccgtta gattggactc ggttgaaccg agtccaattt   180
ggaactacga ctcctcccgg gcctgatttt gcaacgagga ttccactccc gtacactaca   240
gaactatatc gacaccgtcg ctgagattca atgtattcgt tcattcgact ggcttcttcc   300
tccgggtgag acgagctgat atttgggaga aatattggac atcccagata atctcgcgca   360
aagtctagtt tggtctggtt gatatccgaa atgatcactt gtttggctcc aaacgctgtg   420
gccgtcgctg cacagaacag accgatagtc cccgacgctt gtaccaggac agtatgaccg   480
ggagtgatac ctgccacccg agctccatga attgcaacac tcaacggctc gaccaaaaca   540
gtttcttcaa gtgagaaatt tcgggaatc ggataccaca aatcctcggg tgcgcggaat    600
agatgggtca gagtcccatg gttattgggg ggaggattcc cggcaaagct catctctgga   660
aaaatatcat atctccctgc tttacattgt ttacatcgtc gacgagagaa actagctcga   720
tggcaaagcg gtcgccagga atcacttttg tcactgccgg tccaattgag tgcacgatac   780
ctgatgcctc atgacccatg accagtggtt gctcgtcaga gaccattcga agtaccccgc   840
cgtgtttcca gaaatgggcc tatggaattg gaaattagca aaagaccccc tggtgaaagg   900
aagagggatt tgtgggact catatcgctc ccatacacac ccacatacgc gatgcgaact   960
```

```
aatatatcat agggatcact gagggtaggg acatcgcggt actcaagtcg agctttccca   1020
ggcccgtaga gtaggcagga caaattattc tgaaattatg atcaac                  1066

SEQ ID NO: 27           moltype = DNA   length = 1066
FEATURE                 Location/Qualifiers
source                  1..1066
                        mol_type = genomic DNA
                        organism = unidentified
SEQUENCE: 27
gttgatcata atttcagaat aatttgtcct gcctactcta cgggcctggg aaagctcgac   60
ttgagtaccg cgatgtccct accctcagtg atccctatga tatattagtt cgcatcgcgt   120
atgtgggtgt gtatgggagc gatatgagtc cccacaaatc cctcttcctt tcaccagggt   180
ctcttttgct aatttccaat tccataggcc catttctgga aacacggcgg ggtacttcga   240
atggtctctg acgagcaacc actggtcatg ggtcatgagg catcaggtat cgtgcactca   300
attggaccgg cagtgacaaa agtgattcct ggcgaccgct tgccatcga gctagtttct   360
ctcgtcgacg atgtaaacaa tgtaaagcag ggagatatga tatttttcca gagatgagct   420
ttgccgcgga tcctcccccc aataaccatg ggactctgac ccatctattc cgcgcacccg   480
aggatttggt gtatccgatt cccgaaaatt tctcacttga agaaactgtt ttggtcgagc   540
cgttgagtgt tgcaattcat ggagctcggg tggcaggtat cactcccggt catactgtcc   600
tggtacaagc gtcggggact atcggtctgt tctgtgcagc gacggccaca gcgttttgga   660
ccaaacaagt gatcatttcc gatatcaacc agaccaaact agactttgcg cgagattatc   720
tgggatgtcc aatatttctc ccaaatatca gctcgtctca cccggaggaa gaagccagtc   780
gaataaaga atacattgaa tctcagcgac ggtgtcgata tagttctgta gtgtacggga   840
gtggaatcct cgttgcaaaa tcaggcccgg gaggagtcgt agttccaaat ggactcggt   900
tcaaccgagt ccaatctaac ggtacctatc atcaatatg tgagaagga gatcgtcttg   960
acaagacggc atgcgatat gccctggag attatgaat ggtcttggct ctactcaact   1020
ctggtcgagt gaacaatgtt cccctttgaa gaggccatca aagcct              1066

SEQ ID NO: 28           moltype = DNA   length = 564
FEATURE                 Location/Qualifiers
source                  1..564
                        mol_type = genomic DNA
                        organism = unidentified
SEQUENCE: 28
agactcaacg ataattcaat acccagttgc aacactattt gttttctaaa catatcctca   60
agaccaattc taccttaatc tccccaacac aactcaattg aaaacataca ccatgcctcg   120
cggagccgaa tacgccaacg gtcctctcca gagcgacaat gccatcgaag ctggcgaaaa   180
taaggcccac ggaacctccg gtaacaccgg cctcaaccgc gtcaacaagg tcgccgaatt   240
ccccgaaggc gccagaggaa ccggtaccgc tgctaaccg gtcagtggcc agggtagcgc   300
cggccatcag gatggaaagg gtggccatga cccgaagacc cttggagaga acaagggact   360
gggtactcaa tgatcttatg attcagaaga catgagttat ttgcatgagc tgggctcgct   420
gcgattctgt gggattctgt gatttgtaat atgatttgca tgggtcaggt cagacttaat   480
taagcatgcg ctattgtttc cgttatgctt atgatatgga tgggtccatg gttggagttg   540
ataatctaat atgaattga agtg                                           564

SEQ ID NO: 29           moltype = DNA   length = 39
FEATURE                 Location/Qualifiers
source                  1..39
                        mol_type = genomic DNA
                        organism = unidentified
SEQUENCE: 29
attccatcta aagctaaata ttggcctgag accgatagc                           39

SEQ ID NO: 30           moltype = DNA   length = 577
FEATURE                 Location/Qualifiers
source                  1..577
                        mol_type = genomic DNA
                        organism = unidentified
SEQUENCE: 30
gagactatga cgacgatcac agagttcccg ccattctaca cgcagcagcc gaatgcgagc   60
gcgctgacgc agcagctggg gctgtggcag aagcatatac tgagcacgtg caagcagcgg   120
cggcagttca agctgagcgt gagtgatgat atctgggcca acgagaggat aaagcgagct   180
gcttctcgtg aatttatttc tgtgattatc tcctcgctgg tgacagaagg gctagcgagc   240
tatacagacg ccaccaagga ggctgtgtgg gtgtactggc ggctctatc tgattgggcg   300
caggcggcgt acgcgtacgc ggaaagcaca gcgcagctga acacgccgtt gacgtactat   360
gagctagtac aagggagta cagccatcta tctgagctgc atgagatgcc agtagagctg   420
ctcaagcttg ctgtgtcgct gctggtgaag cagaacaaag cggtgataat caaaacgagt   480
caagggggaag gtgtcaaatt cgtctagtat agaataactt aggttacatt ggaatctggt   540
aatcaattcc cttgtcattc agcttctgct gctttcc                            577

SEQ ID NO: 31           moltype = DNA   length = 606
FEATURE                 Location/Qualifiers
source                  1..606
                        mol_type = genomic DNA
                        organism = unidentified
SEQUENCE: 31
gggaacaaac tctcattcta actaaatact ttttactctc tgctcccta tcgcattctt   60
tttaggacat tcagaaggtg atcgcttgac caaatgtcta tcccaaaagc ggcagctcat   120
accgacaagg cgcctcagcc tttcaaggac ctctattcgc aagcagttat tgctggtggc   180
```

```
gtggtctatt gctctggaat tgttgccatt gaccctgaaa ccggtagcct gattgaagga    240
gatgtcaagg ctcatacgga acgaatttta caaagccttt ctagtactct acaggccgcc    300
ggtaccagtc ttgatcgagc tgtaaagatc aatgtttacc tagcaaacat ggaagacttc    360
acatccatga actcagttta cgaaaagtat tttgtggatg gagtgaaacc ctgcagaacc    420
tgtgtggctg ttaagtctct accttttggc actgatgttg agatggaatg cattgcagta    480
ctgtaaatgt ttagttttat gcgcaactga gaaagacgga aggatcatcc tattactttt    540
tcgaatgtgc tctttggatt tctctgttgg atacacaaca atgccacaca ttgggtacaa    600
ccagat                                                               606

SEQ ID NO: 32          moltype = DNA   length = 411
FEATURE                Location/Qualifiers
source                 1..411
                       mol_type = genomic DNA
                       organism = unidentified
SEQUENCE: 32
ggaaccaatt acatccatca accaaaccaa caaaatgctg agatctcaat tcggtgtaat    60
ttcaaacgca gcaaagacag ccgcattcct caagcctgtt caaaccagat tgtacgctag    120
tggcgctctc tcgaagggcg acatccaaac tcgcattttt gatgtcctca agtcgtttga    180
taaggtgaag gctgataacc tcactgaatc ggcttctttc accaacgacc tcggcttgga    240
tagcttggac gccgttgaag tcgttatgcc cattgaggag gagtttgcca tcgaaattcc    300
agacgctgaa gctgacgcaa tccaaaacgt gaaccaggct atcgaataca tcgccaaaac    360
ccctgaagca cactaaacac gctaaataat tttatcaatt catttcaaac g             411

SEQ ID NO: 33          moltype = DNA   length = 619
FEATURE                Location/Qualifiers
source                 1..619
                       mol_type = genomic DNA
                       organism = unidentified
SEQUENCE: 33
gtggtatcaa cgcagagtgg cgcgccggga acgaagaaag tttcttcgac ctacctatca    60
aagatatgta aggagcaaca taaatcaata ttctttatc tgattgacct tcactctagt    120
gcctcgctac gatcagttac aaccttgccc gcgcgaatgg aacgtatacg actttccgaa    180
caggccgcga cgatttgcaa ccaaattcgt gaaatgatac cagagactgc cactttgccc    240
aatcaacctg gcaaggatca agctgaactc atgcatgaaa atgaaaacgg gaataagata    300
tacggcggga aacttttaac ggagagagct gctcgactga aagagcacat gaagattgac    360
caagtgagtg ccagatttat ctcacagtac tttactaatg gcattcagga ctggacagag    420
cgcttggtat attggacaaa gccgacgaaa ctattgaacc aacggaaaca aggatatatc    480
ataccgttat ctaaagacat cgttctacaa cctggggac ctttagaagc aaataacggc    540
tttcgggtca caaacgagcg gattctgagt tcaggagctg ccctttcat tatgccccaa    600
tgatattatt ttgaaaccc                                                619

SEQ ID NO: 34          moltype = DNA   length = 1647
FEATURE                Location/Qualifiers
source                 1..1647
                       mol_type = genomic DNA
                       organism = unidentified
SEQUENCE: 34
accgctaccg tcatcactac aaatgctggc tcgcagctta cagcaaatca gacgctcaag    60
caggctgagc ttacaattgc gcgcctacgc cagcagtcca gaccgcagcg caagcttctc    120
taagctctca gagcaagatc tcccatcact cgcctccatc ttctcatccc ccgacacctc    180
cctcctcacc acgctcggcg acaagccaac agccaccagc gacgatctcg agccattcaa    240
cgtcgactgg atgggcaagt acaagggcca ctcttccata attgtgaaac caaagacgac    300
gcaagaagtc agcaaggtgc tgcagtggtg caacgagcgc aacgtagctg ttgttccaca    360
aggtggcaac accggtctcg ttggtggatc cgtgcctttg cacgacgagg tcgtcttatc    420
tctctcctca atgaacagca tcagacactt cgaccctctt tccggttacg tttctgtcga    480
ttccggtatc gtgctcgaaa atttggataa ctacctcgca caacaaggac acattgtccc    540
tctcgatctg ggtgctaaag gctcctgtca gattggtggc aacgtcgcaa ccaacgctgg    600
tggtctgcgc atgttgagat acggtagttt gcacggcaac gtgctcggcc tcgaagtcgt    660
tctgccagat ggtagagtaa tcaatggtat gaagggactc aagaaggaca acactggtat    720
cgatctcaag cagctcttca tcggctcgga gggtgttctc ggtgttatca ctggtgtcac    780
tctcgccaca cccgtcagac catccgcaac taacgtcgct gtcttcgctt tgcctgacta    840
tgagtcagtg cagactgcct tctcatcagc tagacgcgat ctcggtgaga tcttgtcggc    900
gtttgagttc ttcgatgctg cctcatacaa gctcgtgcgc agccatggac acgcagctga    960
gcgcaaaacc ttcgaagatg gggaagacgc accattttc tgcttggtcg agactctgg    1020
ctcgaacaaa gaccacgacg atgagaaact gggtgctttc ctagagcagc tcatggagtc    1080
aggtatcgtc aatgacggtg tattggcaca agacgagacg caaattggcc agctgtggtc    1140
gctgcgtgag ggcattccag aagctgcagg caaagctggt cgcgtgtaca agtacgactt    1200
gagtttacca gtcgagaaga tgtactcgct ggtgccagag ctgcgccaaa agcttgctga    1260
gaagggtctg cttgccgctg agtcagaggg tggtaatgga gatgggccag tcaagacagt    1320
cttcggattt ggtcaccttg gcgatgcgca acctgcacatc aacattgttg ccgatgctta    1380
cagaaaggag gtgaggaag tcgtcgagcc atacatttac gagttggtag ccaagtacaa    1440
tggatctatc tcagcagagc atggtctcgg tctgatgaag gcacctatg tcgcatacag    1500
tcaagacgcg ccatcgcttg acctcatgcg cactctcaag aagacactcg atccaaaggg    1560
cattctcaac ccatacaagt gcgtcaccgc ggaatagatt ggagttatag atttacgtta    1620
tatgcatgcg atcctgttac attatcc                                       1647

SEQ ID NO: 35          moltype = DNA   length = 669
FEATURE                Location/Qualifiers
source                 1..669
```

```
                        mol_type = genomic DNA
                        organism = unidentified
SEQUENCE: 35
gtcatcaact tcattcagca aaatggctct ctattacggc atcgtatttg gtatcttaac    60
atttgagatt attctctttt tcttattctt gttgcctatc ccaactcgtt ggcaaaaacc   120
agtgttccgt tggttagcta cctcacctac cattgcacat gctcaatata tcatgaaaat   180
tgtatttgta ttcatctttg tgctcttcct tgattccgtc aacactctcc gcgctttcta   240
cgaagtagtg aacactgaag atgagaatgg tggtattcca gctgccggta actctgattt   300
cagagctcaa gttggtcaag ctgcaaagaa gttttatgct caaagaaatt tgtatctcac   360
tggattcacc attctgttat tactcatttt gaacaagatc aagaacatgg ctatggacta   420
tattagattg gaagatcaat tcattgagct tgaaggatcc gtttccaaag atcccgccat   480
cagaaaggca agcaaagaaa tcgacactac tcccatcgaa gaccatgtta caagactcga   540
gcctgttgaa caagaacagg aaaacaaaaa ggatatctaa ttcacacctg taactaatat   600
gtaaacatct ccctcgctaa aagcgcaata aactaaaatc agcatcattg cgtatctctt   660
tcttctcac                                                           669

SEQ ID NO: 36          moltype = DNA  length = 873
FEATURE                Location/Qualifiers
source                 1..873
                        mol_type = genomic DNA
                        organism = unidentified
SEQUENCE: 36
gtggcgcgcc gggaggcgcc taacggtcat gaattgcctc ctcgcggtta tgatcccgga    60
gaaaacactt accaagcacc acctgatgaa cgtagtcaag tagatgttgc gattgaccct   120
aaatccaacc gtcttcagct gttgaagcct ttccagaagt gggacggcaa ggacatcacc   180
aatgttccta tcttgattaa ggtgcaaggc aaatgcacta cagatcatat ttccatggcc   240
ggcccttggc tcaagtatcg tggtcatttg acaatatca gtaacaattt cctcattggc   300
gccaagagta gcgaaggcaa agtcaacagc atcaagaatg cttttactgg tgaatacaag   360
ggtgtccaga aacagctcgt gattacaaga aggaaggtgt tcgttgggtc gtggtaggt    420
atgagaacta tggcgaaggc tcctctcgtg agcatgccgc tctagaacct cgattcctca   480
atggagctgc catcattacc aaatcatttg ctcgtatcca tgaaaccaat ctcaaaaagc   540
aaggaatgct tccctttaac ctttgctgatc ccaaggacta tgacaaggtg gacgcctcag   600
ataaagttga tattcttggc ttgactgatt tccaagaagg aaagccattg acccttcgct   660
tgcacaaaaa agatggatca actgtcgatg ttcctttga ccatacatt caacggtcagc   720
aaattgaatg gttcaagcat tggatctgcct tgaaccttat gaaggaaaat actgccaaga   780
acggaagctt gtaggtgcac cgttacgtta tcttcacaag catttgtatg tcaaatactc   840
tcgattagtt acttgcactt ttgttaagtt tat                                873

SEQ ID NO: 37          moltype = DNA  length = 874
FEATURE                Location/Qualifiers
source                 1..874
                        mol_type = genomic DNA
                        organism = unidentified
SEQUENCE: 37
gtggcgcgcc gggaggcgcc taacggtcat gaattgcctc ctcgcggtta tgatcccgga    60
gaaaacactt accaagcacc acctgatgaa cgtagtcaag tagatgttgc gattgaccct   120
aaatccaacc gtcttcagct gttgaagcct ttccagaagt gggacggcaa ggacatcacc   180
aatgttccta tcttgattaa ggtgcaaggc aaatgcacta cagatcatat ttccatggcc   240
ggcccttggc tcaagtatcg tggtcatttg acaatatca gtaacaattt cctcattggc   300
gccaagagta gcgaaggcaa agtcaacagc atcaagaatg cttttactgg tgaatacaag   360
ggtgtcccag aaacagctcg tgattacaag aaggaaggtg ttcgttgggt cgtggtaggt   420
gatgagaact atggcgaagg ctcctctcgt gagcatgccg ctctagaacc tcgattcctc   480
aatggagctg ccatcattac caaatcattt gctcgtatcc atgaaaccaa tctcaaaaag   540
caaggaatgc ttcctttaac ctttgctgat cccaaggact atgacaaggt ggacgcctca   600
gataaagttg atattcttgg cttgactgat tccaagaag gaaagccatt gacccttcgc   660
ttgcacaaaa aagatggatc aactgtcgat gttcctttga accatacatt caacggtcag   720
caaattgaat ggttcaagca tggatctgcc ttgaacctta tgaaggaaaa tactgccaag   780
aacggaagct tgtaggtgca ccgttacgtt atcttcacaa gcatttgtat gtcaaataaa   840
ctcgattagt tacttgcact tttgttaagt ttat                               874

SEQ ID NO: 38          moltype = DNA  length = 718
FEATURE                Location/Qualifiers
source                 1..718
                        mol_type = genomic DNA
                        organism = unidentified
SEQUENCE: 38
ggcgcgccct tgacacagga gcacgggttt cccgtgcgcg tcatcgttcc aggcgtggcg    60
ggcgcgaggg ccgtgaagtg gttggatcac atcacagtgc agcgggaaat gagcagcaat   120
cattatatgc atttcgacta caaggtccta ccaccaagca cggtcgatgc ggaaagggca   180
cgcaccttct ggcataaagt cccgccggtg atcgacatgc cagcgaattc tgccatcacg   240
tcgccacgaa atgaagacac ggtggaagtg gatcagagg gatttatcac ggtggatggg   300
tacgctttgc cgggggagaa gatgggccg gtgaaaagag tcgaggtctc cattgacaag   360
gagagatggg tcgacgcgga actgtttaca catcccatgg aaagcaagtg gacttggaaa   420
atcgtgaagg ccaaagtgca ggtcgagccg ggcgagcgaa gatgtctcta cagcagaacc   480
actgatgaag cggcaactc gcagccgcag cgttctcagt ggaacctgag aggcgtatgt   540
tacaacggct atgagaagt gaggaatttg aaggtggtga aaggataggc ccaatcgttc   600
attccatcat ccatcaagat gtgtctgtat gtgtatgaag gcctgaagcg accacggac   660
cccagggtgg tcactaaaca gtactcaaac ggactgtttg gttcgtttga cacttttcg    718
```

| SEQ ID NO: 39 | moltype = DNA length = 160 |
| --- | --- |
| FEATURE | Location/Qualifiers |
| source | 1..160 |
| | mol_type = genomic DNA |
| | organism = unidentified |

SEQUENCE: 39

| | | | | | |
| --- | --- | --- | --- | --- | --- |
| aatcaagttc | gactgtcaaa | atgccagcca | acacgatgtc | tgccactctc | agatccctcc | 60 |
| acgttcccgg | gaaaccagtc | atcttcgcca | atgtctggga | caccgtctcc | gccaaatcaa | 120 |
| tcgcacctct | ggattcatgc | aaagctctag | caacggccag | | | 160 |

| SEQ ID NO: 40 | moltype = DNA length = 1274 |
| --- | --- |
| FEATURE | Location/Qualifiers |
| source | 1..1274 |
| | mol_type = genomic DNA |
| | organism = unidentified |

SEQUENCE: 40

| | | | | | |
| --- | --- | --- | --- | --- | --- |
| gccttgccca | tgctactcat | caaccctcct | cgcaacctca | tcggccaaag | tcagtctggt | 60 |
| accggcaaga | cggctgcatt | caccctcaac | atgctctcac | gagtcgaccc | aaacatcatg | 120 |
| accccctcagg | ctatctgttt | ggcaccgtcg | cgagagcttg | ctcgacagat | tcaggaagta | 180 |
| gtcgacaaga | ttggccagtt | cacccagatc | aagagtttcc | tcgctgttcc | gggctcttgg | 240 |
| tcgcgtaatg | tcaagatcga | caagcacatt | cttgtcggta | cgcctggtac | actcgtcgac | 300 |
| atgctttcgc | gaggaggcag | gatcttcgac | ccgaagcaga | ttagagtctt | tgtgctggat | 360 |
| gaagcggacg | aaatgatcgc | tttgcaaggt | ctggggggacc | agacgaagcg | catcaagagg | 420 |
| atgctgccgc | ctggggtcca | gaacgtcctg | ttctccgcta | cttttcccga | caacgtccga | 480 |
| gactttgcag | gcgacttcgc | acccgaggcg | aaccagatct | tcctgaagaa | agaggagatc | 540 |
| actgtcgacg | ccatcaagca | gctctacctc | gagtgtgatg | gagaggagca | gaagtacaac | 600 |
| gcccttcctg | ccttgtacga | catcatgtcg | atcggtcaga | gtatcgtatt | ctgcaagcga | 660 |
| aaagacacgg | ccgaccgaat | tgcggcgaga | ctgacggatg | agggtcactc | tgtcgcttct | 720 |
| ctacacggtg | acaaacagac | tcgagaccgt | gatgacatcc | ttgacgcttt | ccgagatggc | 780 |
| aaaaccaagg | ttctgatcac | caccaacgtc | gttgctcgag | gtatcgatat | ccagcaagtg | 840 |
| aacatggtgg | tcaactatga | cgttcccgat | ctccggtccga | agggagattg | gaagcctgat | 900 |
| atcgagacct | atatccatcg | aataggtcga | accggtcgat | ttggtcgaaa | aggttgttcg | 960 |
| gtcatctttg | cccatgatca | gaggtcgatg | caggatgttc | agttcatcgc | cgatacgctc | 1020 |
| ggcaagaaaa | tgagcagaat | caacgctacc | aggcagactg | atctcgatca | gctcgaagcg | 1080 |
| gctttgaaag | ccgccatcaa | gggcaatcaa | ccgaaaagagt | gaagagtggc | accgaattcg | 1140 |
| aagagacggg | cgctggaaga | tatcctgaag | caacagggag | gagctcccct | tatagcatga | 1200 |
| tcattgacga | taaccatcta | gggcctgaag | tacattatga | tagatagcag | acatcaatgc | 1260 |
| aacgtcgcgt | cgcc | | | | | 1274 |

| SEQ ID NO: 41 | moltype = DNA length = 919 |
| --- | --- |
| FEATURE | Location/Qualifiers |
| source | 1..919 |
| | mol_type = genomic DNA |
| | organism = unidentified |

SEQUENCE: 41

| | | | | | |
| --- | --- | --- | --- | --- | --- |
| cacctccaac | ctctttctag | tttaccttca | aaacacatcg | gtgtaaggtc | ttgcccaaca | 60 |
| tggctacctt | ctcgacccgc | atcaacctcg | tccccaccc | ccgaacgtc | gctagcggcg | 120 |
| ttccattcgc | acccaggatc | gcccttgttc | atcctcccgc | gtctcacggt | cacgaaacga | 180 |
| gcggtcccag | gagtgatgtc | ccacccaggt | gggctggtgt | ccagggtgga | ttcgcctcga | 240 |
| actcgagggt | caatgtactc | cccaccggca | acttccagca | acgattcatg | tccaccacgc | 300 |
| cagcccgcaa | gatcgaggct | caaccccacg | tccgaggtgt | tcccgattgg | tcggcatatc | 360 |
| agtcttcggg | caagggcgag | aacacccgat | ccctttcgta | cttcatggtc | ggatctctcg | 420 |
| gtgtcctcgc | tgcttcaggt | gccaagtcga | ccgtcagcga | cattctgagc | aacatggccg | 480 |
| cttcggctga | tgttttggct | ttggccaaga | tcgaagttga | gatgggtgct | atccctgagg | 540 |
| gcaagaacct | gatcgtcaag | tggcgaggaa | agccgtcctt | cattcgacac | cgaacggaag | 600 |
| atgagattaa | cgaggcacgc | gcagtcgaca | tcaagtctct | gcgtgatccg | gagagcgacg | 660 |
| aggataggac | ccaaaggga | gagtggcttg | tcatgctggg | tgtctgcact | cacttgggtt | 720 |
| gtgttcccat | tggcgaggct | ggtgattacg | gaggatggtt | ctgcccctgt | cacggatctc | 780 |
| actacgatat | ctctggccga | atccgacgag | gtcccgcccc | tctcaacttg | gaggttcccg | 840 |
| agtacgcttt | caacgacgac | gaggagaagc | ttgtcattgg | ttaggtgtag | atggacatat | 900 |
| gcagtctatg | gccatagcg | | | | | 919 |

| SEQ ID NO: 42 | moltype = DNA length = 1459 |
| --- | --- |
| FEATURE | Location/Qualifiers |
| source | 1..1459 |
| | mol_type = genomic DNA |
| | organism = unidentified |

SEQUENCE: 42

| | | | | | |
| --- | --- | --- | --- | --- | --- |
| ggggagcatc | accatagtga | cagggactgt | agctcggtca | agcgcgtatt | cgcacttggg | 60 |
| cgcctggacg | ttactctggc | cgtggagtgc | gggagtgtca | ggacgatgtc | ccttcgtgac | 120 |
| ctcgcttgct | acactctcac | gctcaagcca | tctaccgaga | ataccctcct | gaccgagctc | 180 |
| acggctttga | agggaccgag | tgaggagcca | cgattcgcaa | gagtgcggga | gaaggtggaa | 240 |
| ggagaggtct | attcgtctgc | catatacgat | gcgttgacgg | gagccaagct | ggcctcggtg | 300 |
| ggtttcgctt | ccgaaaagca | gaagaacagg | aggctacagc | tacacaaccc | gatgagagt | 360 |
| gtgccttttg | acaatactag | caagctaggt | ttcgaatgga | cattcatctt | cgaaggcaac | 420 |
| aagtacaggt | ggacgagaga | gctatacgga | aaagattata | tctgctcact | agaccggaaa | 480 |
| cccgatccaa | gggtggagat | ctgcctagct | cgagacgcag | attcgaaagc | gcctggacga | 540 |
| ctgcagattc | tacactacaa | catcgaacga | ttcccgaacg | agatcaagga | tttgagggga | 600 |
| ctggaaacgc | tactcattgc | taccctcatg | tgcttcgtcg | acgcggccga | agatcggtcc | 660 |

```
aattccggtc cgacccgcac ttcgcccttg cctgctaagc cggttgccaa tgctgcagca   720
ggtcaaagcg gcaccagcgc aagtggatct tctgataccc gagcgaaagt tgcgccggtg   780
acagtgccag taatcactgc agaggacttt gaggatgatt gtgacccgaa tgagatactg   840
gtaggaacgg agactgatgt gggcgagcac attgcacgag ctatagcgct tttggaggac   900
ccgaccatgc tgttcattgt cattcgaacg cgaactgccg ccgcgagctc aagagcgtta   960
gaagtctcct tagggggttac aaggttccgg caccgtgagg gcatgagcga gctgcatcaa  1020
tacgtggtag aggaagatcc ggtccggaag ccgaaaccca ttatgcctgc tcagggcctc  1080
aagttgatca acctggatga tcgaccagcg gcacaatcac ccaccaaacc ggaatggtct  1140
gccccaccta acatcgctgt ttacctatca tcgatcgagt tgccagatct cacgcccaag  1200
cccaagcctg tccaggggca cacacgaccg ccaactcaag cacctcatgc tcggcctccg  1260
ccgccttctc aactaccaca aaagccgcag ccgcggccac gcccgcctcc atccgatggt  1320
tcaggtagta gtcagactac actcgcttca acgcgaccgc cccaggacga cgggaaggat  1380
tcgagaaagt ctagctttgg aagactcttt ggcaggtagt acgatacact tagcagggca  1440
tatgcaggtg tatcgacgg                                              1459

SEQ ID NO: 43           moltype = DNA  length = 623
FEATURE                 Location/Qualifiers
source                  1..623
                        mol_type = genomic DNA
                        organism = unidentified
SEQUENCE: 43
ggcgacgaca acaagaaaac aatacctcac ctgaacatat tcaataatgg cgtcccaatt    60
gatgcccctg gagctgatcg atcgttgcat cggatcaaga atgcgtgtga tcatgaaagg   120
cgacaaagag ttcagcggca cacttctcgg attcgacgac ttcgtcaata tggtgctcga   180
ggatgtcacc gagtacgact acaccggcgc aacgaccaag cttcccaaga tccttctgaa   240
cggcaacaac atctgcatgc tcatcccagg tggcatgccc ggaggcgagt catgaatcac   300
ggacatatga tatcccttct tacgtctctt gaaatggcaa agcgagtctg atttaagaac   360
cacacgtgtc atgagaaggc agactatacc gctgtccagt ccaagctgct tgaacaataa   420
ttatcccgac ggagccacga aaacgtgaca agcggaagct cgcattcgca aagcgccggc   480
gcaataaaac gccttgttca gctcgccgac tttgtgcatg catgcagctc gccacacccc   540
gcagatatca ggctgccttc ttgttatcag gtatgcgtgt ttatactcta gcttatttca   600
gctatgcaaa acctatatca tcc                                          623

SEQ ID NO: 44           moltype = DNA  length = 489
FEATURE                 Location/Qualifiers
source                  1..489
                        mol_type = genomic DNA
                        organism = unidentified
SEQUENCE: 44
gcaaaggagt tgtcgcctga cgtcaagcct gagccgacat ggtcttgtgg cgaggttgtc    60
aatgtcgtcg atgagcacgg caatgtcatc aaaccgtcag acctctgggt caagatgggg   120
atgcagcagc aggacaatgt ggacaaccta ttgatcgacg acctgtgtga tcagatgagg   180
gccaaggcca aatgcacaga gaaccgcgct caattgatcg tcgacgacct gaaccacatg   240
atgtcgtatg acaagtcata taagcagaaa agggtagacg acctcaaaga caagtacggc   300
tgggagcag tctttggccc gaaatgagcc gcctccgcgg gggcaaggtg gacggacgat   360
ggtagacatg aaatatgagag caaacagaca tagggtctga gtccagtagt gtgcttgtac   420
caccactgta aatatttgta cgatagccct acaccactta caattgatca tgtaactgtg   480
tgaaccgtg                                                          489

SEQ ID NO: 45           moltype = DNA  length = 480
FEATURE                 Location/Qualifiers
source                  1..480
                        mol_type = genomic DNA
                        organism = unidentified
SEQUENCE: 45
gggagcctga cccgccgtgc ttggttcatc caatccacct gcgccaccac tggtgatggt    60
ctctacgagg gtctggagtg gctcgccgac actctccgga aaacgaaccg cgattaaacg   120
cgtataatac gaaattgtga tggggaggat tgtgtacgta gcagagcaag agaaatacca   180
cgggaaatct gcaaatgatg gaatgatgat tatggcggga gtttcttcca atgttcttct   240
gcgaggccaa atatcccggc gatgaaaaag aattccctca ccggcatgcc atggccatcc   300
tcaggagcaa ggtgtttgtg tttggctcgc cagggctcta tttctcttcg ctatgctatt   360
agcctcattt gttcttttct ctctggcgcc acgtcaaaat tgctggttta tctccttttg   420
attgcatgtt cagtatcggt atgatctcag tataccagca cttgggttga gcattcttct   480

SEQ ID NO: 46           moltype = DNA  length = 1139
FEATURE                 Location/Qualifiers
source                  1..1139
                        mol_type = genomic DNA
                        organism = unidentified
SEQUENCE: 46
acctcacttt gtgcgaatta tcctcctaca gcatcagctc tcttcagaaa gaggctaaat    60
ctatagaccg tccggaacag gttgtcaaca cgcgcgataa gagaagaagg gaatctactg   120
gtagacaaca gatcgatcgc tcttcagcaa acgcaagatg gagaaccttc ttcgtcagat   180
gcaaggggga ggtggtagga tgggtgcacg gccaggccgg ggaggcgaaa ctatcctcgc   240
cgacaacggt gaaacagtcc atatttcatc tcttgctcta ttgaagatgc tcaagcatgg   300
acgagcgggt gtgccatgg aagtcatggg tctcatgctt ggcgaatttg ttgatgacta   360
cactatctcc tgtgtcgacg ttttttgcaat gcctcaatcc ggtacgacag tgacggtcga   420
atcagtggat cacgtctttc aaaccaagat gttggatatg ttaaaacaga cgggccgacc   480
cgagatggtc gtccggttggt accactcgca ccccggtttt ggttgttggc tgtccagtgt   540
```

```
cgatgtcaac actcagcagt cttccgaaca gctacatccg cgagcagtag ccgttgtcat    600
cgacccatatc cagtctgttc gtggtaaagt cgtcatcgac gctttccgat ccatcaaccc   660
tcaatcactt gtcgctggac aagagtcgag gcaaacaacg agtaacattg gtcatctgaa   720
caaaccgtcc attcaggctc tcatacacgg tctgaatagg cattactaca gtctggccat   780
cgattacagg aaaacagaag gggagcaggg tatgttgttg aacctgcaca acgcggggatg  840
gacagagggt ttgaagatgc gtgatcactc agagatgaag gagggtaatg agaaggcaat   900
caaggaaatg ctctctcttg cctcggccta cacgaaatct gttcaggaag agacgacaat   960
gacggccgaa cagcttaaaa cccgtcacgt aggaaagctt gatccaaaac gtcatttggg   1020
cgaggcggct gagaaagcga tgggtgatca agtgacgcaa agtctggcca tgggtgtcct   1080
ggctgagctg tagacgtaga agagggaaga aaggaaacga catgcattgt acatatcgc   1139

SEQ ID NO: 47         moltype = DNA    length = 674
FEATURE               Location/Qualifiers
source                1..674
                      mol_type = genomic DNA
                      organism = unidentified
SEQUENCE: 47
ggacacaccg gtgacgtctt gagcgtctcg ttctcggccg acaaccgaca aatcgtttct    60
gcttcccgag accgaactac caagctctgg aacactctcg gagagtgcaa gttcaacatt   120
gttgacgatg gtcactcgga gtgggtctct tgcgttcgat tctctcctaa ccccgtcatt   180
cccgtcatcg tctctgctgg ttgggacaag gtcgtcaagg tctgggaatt gtccaagtgc   240
aagctcaaga ccaaccacca cggtcacact ggttacatca acaccctcgc cgtttcgccc   300
gacggatcgc tcgccgcatc cggtggaaaa tatggcatca ccatgctttg ggatttgaac   360
gatggcaaac acctctactc tctagaggct ggagacattg tcaactcgct cgtcttctct   420
cctaaccgat actggctctg tgccgccact gcttcgtcaa tcaagatctt agacttggag   480
tccaagtcaa tcgttgacga cctcaagcca gacttctccg ccgagtaccc tgacaaggct   540
caaaagccac aatgtacttc cctcgcctgg tctgccgatg gtcagacccc ctttgccggt   600
ttctccgaca acctcgtccg agtctgggtt gtcactgctt agagtcgtga ggattgtatg   660
catggataac gtgg                                                     674

SEQ ID NO: 48         moltype = DNA    length = 674
FEATURE               Location/Qualifiers
source                1..674
                      mol_type = genomic DNA
                      organism = unidentified
SEQUENCE: 48
ccacgttatc catgcataca atcctcacga ctctaagcag tgacaaccca gactcggacg    60
aggttgtcgg agaaaccggc aaagagggtc tgaccatcgg cagaccaggc gagggaagta   120
cattgtggct tttgagcctt gtcagggtac tcggcggaga agtctggctt gaggtcgtca   180
acgattgact tggactccaa gtctaagatc ttgattgacg aagcagtggc ggcacagagc   240
cagtatcggt taggagagaa gacgagcgag ttgacaatgt ctccagcctc tagagagtag   300
aggtgtttgc catcgttcaa atcccaaagc atggtgatgc catactttcc accggatgcg   360
gcgagcgatc cgtcgggcga aacggcgagg gtgttgatgt aaccagtgtg accgtggtgg   420
ttggtcttga gcttgcactt ggacaattcc cagaccttga cgaccttgtc ccaaccagca   480
gagacgatga cggaatgac ggggttagga gagaatcgaa cgcaagagac ccactccgag   540
tgaccatcgt caacaatgtt gaacttgcac tctccgagag tgttccagag cttggtagtt   600
cggtctcggg aagcagaaac gatttgtcgg ttgtcggccg agaacgagac gctcaagacg   660
tcaccggtgt gtcc                                                     674

SEQ ID NO: 49         moltype = DNA    length = 480
FEATURE               Location/Qualifiers
source                1..480
                      mol_type = genomic DNA
                      organism = unidentified
SEQUENCE: 49
gggagcctga cccgccgtgc ttggttcatc caatccacct gcgccaccac tggtgatggt    60
ctctacgagg gtcgcgagtg gctcgccgac actctccgga aaacgaaccg cgattaaacg   120
cgtataatac gaaattgtga tggggaggat tgtgtacgta gcagagcaag agaaatacca   180
cgggaaatct gcaaatgatg aatgatgat tatggcggga gtttcttcca atgttcttct   240
gcgaggccaa atatcccggc gatgaaaaag aattccctca ccggcatgcc atggccatcc   300
tcaggagcaa ggtgttgtg tttggctcgc cagggctcta tttctcttcg ctatgctatt   360
agcctcattt gttcttttct ctctggcgcc acgtcaaaat tgctggttta tctccttttg   420
attgcatgtt cagtatcggt atgatctcag tataccagca cttgggttga gcattcttct   480

SEQ ID NO: 50         moltype = DNA    length = 1170
FEATURE               Location/Qualifiers
source                1..1170
                      mol_type = genomic DNA
                      organism = unidentified
SEQUENCE: 50
aaagttgatc gaccacattg ggtctgagaa aaacccaatg ctttttttgta cagcagtgag   60
gaatattggt caatggccga aaggctgaac cagtaacttg gaagaatgaa attgtatttg   120
tataaataca atagtggtta aaccacataa aattctaaat agattatata taatgacaaa   180
atctatttat aagtcttgac caaactacgt gccagcagtc gcggtaatac gtagaaggct   240
agtgttagtt atctttattg ggtttaaagg gtaagtagac ggtaaattaa actctaaaag   300
agtacttatt tactagagtt atatgagaga aggaagaatt cctggagtag agataaaatt   360
ttttgatacc aggaggactg tcaacggcga aggcgtcctt ctatgtaata actgacgttg   420
agagacgaag gcttgggtag caaacaggat tagatacccct aatagtccaa gcagacaatg   480
atgaatgtca tacattagat agattttaat gtataaacga aagtgtaagc attccacctc   540
```

```
aagagtacta tggcaacata taaactgaaa tcattagacc gtttctgaaa ccagtagtga    600
agtatgttat ttaattcgat gatccgcgaa aaaccttacc acagcttgta tagcagttat    660
gaaaaattgt tacaagcgct gcatggctgt cttagttaa tgtcgtgaga tttggttaac    720
tcctctaatt aacgaaaacc ctcactttat ttatatatat aaagtggttc gctattacat    780
tggttgataa tagggattaa gacaagtcat tatggcctaa atgctgtggg ctatagacgt    840
gccacatacg cctttacaaa gggatgcgat attgtgaaat ggagctaacc cccaaaaaag    900
gaaatactat ggatagtagt ctgtaactcg actgcttgaa taaggaatta ctagtaatcg    960
tgaatcacca tcgtcacggt gaattatttc tcagttaggt actaaccact cgtcaggcgc   1020
tgaaagaaga agatgcagta agtttgatgt tttctgtgta tgattataca taaagttgtt   1080
gtataactac gcagaaaagt tttcgtatgc aaaactttga ttggtgttaa gtcgaaataa   1140
ggttcgtgta atggaaattg cacggggagc                                    1170

SEQ ID NO: 51           moltype = DNA   length = 1231
FEATURE                 Location/Qualifiers
source                  1..1231
                        mol_type = genomic DNA
                        organism = unidentified
SEQUENCE: 51
ggacgatatg acttcaagca gcctcagcga attcgagacg cttctgtcac ggccacgcca     60
gaatggaacc tgcttgaaga gatcgagttt ggccgattgg gcaagctcaa cctttccgtc    120
gaagagcccg aagacctcga atcgcacggt accctccaag gttacgacaa gacgtttgac    180
cgcatcaaca ctcgtaccga aagacctctc gagatcattg atcgagcatg gtacaatcaa    240
accacttctg acgatcccgt tattgctcag ctcgctcaaa cgcagtctgc ccaaatcttc    300
gcgacagatg ccattcttgc ggttctgatg tgcaccactc gttccgtaaa ctcgtgggat    360
atcattctcg agcgacgagg taaccagctt ttcctcgaca aacgagattc tggtccattc    420
gactacgtca ctgttcacga aaacgccgcc gacccacctg ccgactctga cgatcccaac    480
aacgtaaact cggcttcttc cctttcgctc gaggccacct acattacccg aaatttctcg    540
tctcaagtca ttgatgccaa gtccaagcca tattcgccta gccccaatcc gttctattcg    600
gaggacgagc catcacccgt cgcttcctgc ttgtacaggt accgaaagtt cgacctgtct    660
gttggcgagg aagatacct ggacctcatt gtacgaacgc aagtcgacgc ctatcaaggc    720
aagaaggact ctctcgtcac tgtcaaggca ttgaacgagt ttgatcctcg agcttcaggt    780
ggtggcaaag ccctagactg gcgaaagtac ctcgacactc aaaagggtgc cattgtcgcc    840
tcggaaatga gaacaactc ggctaaactc gctcgatggg ctatccagtc tgtcttggcc    900
ggtgccgaag tcatgaagat gggatacatc tcgcgagctt cgcccaggga tacaactcat    960
cacgtcattg tcggtgtgca aaattacaag ccaaaagact ttgccgctca aatgaatgct   1020
tccctcaaca acggttgggg tatcgtccga acgattgccg atcttgtcct caagcagcca   1080
gagggcaagt atgtcctcgt caaggaccca aatgcaggca tcattcgtct ctacagtgtg   1140
ccagagaatg ctttcgaggc agaggaggag gaggagcaat agtcgaaaag tctagacagg   1200
ccgtgtcgga catgcatcat atacttcaag g                                  1231

SEQ ID NO: 52           moltype = DNA   length = 788
FEATURE                 Location/Qualifiers
source                  1..788
                        mol_type = genomic DNA
                        organism = unidentified
SEQUENCE: 52
gagcgctcaa ggtccttggc cccagaagcc gatcaaggtg tcgcgactca gtgtcacgaa     60
gtcagatcgt caggtagcta cgacacgttc gagatcggcc atcaccaacc tgacagcgat    120
acctcgggag tagctgactt gcgcacttcc agtcgtatgg acacctgcga cgcgcatctt    180
ctacggcggg tcaaaagctg ccctcttttc agctaccgcg aagacgaggt gtccgaaact    240
gtacaattgc ctacaggcga atggacgacg atcagagata tcactccgag tgcaccaaag    300
atcggctttg aagtgcgcga ctcgctctcc gcgttcccga cagccaagcc tgtcgaagcg    360
aagcacgagt ccgcctccag catatccaat gatttaccct ctcagccatc ctcaaggccg    420
ctgattgagt gtccgacact ggtcgccgat tcacgcacaa cgacgggtc caactctgtg    480
cgcagtttcg acgcccagac cgaacgcctg agcggcttga gcgacgtgca ccacagatac    540
atgcaggaca agccgtcaca gcgttctgat tcctggaccg acgtcaaatc ctccgctccg    600
tcctcccagt cgatggcagt ccccaacaaa gcggcttacc tggctccgat cccagctggc    660
ccaaatgaca gtaagacttc gagttccggt cgcgccccgt cagacgccgc gaccgaacac    720
gagtgttcgc tacaataagt cagacttgct gttgaacgtt tcctacctc atgcataccg    780
ggcatgct                                                             788

SEQ ID NO: 53           moltype = DNA   length = 706
FEATURE                 Location/Qualifiers
source                  1..706
                        mol_type = genomic DNA
                        organism = unidentified
SEQUENCE: 53
accctccaaa ctccaagctc ttttcaaccc tttcctacct tacacaacaa cttcaacaac     60
aactatggca cccaagtcca ctgacaagcc cgcatccacc gctggcaagg cccctctgc    120
tggaggcaag gctcctgcct ccaagactgt cggtgctaag aagaccgcag caaagaagtc    180
tgctaagtct actggcgagg gcggcgagaa gaagaagcgt gtcaagtcca gaaggagac    240
ctactctacc tacatctaca aggtcctcaa gcaggtccac cctgacactg gtatctccaa    300
caaggccatg cttatcctca actctttcgt gaacgacatt tcgagcgta ttgccggtga    360
agcctccaag tcgctcactt acaacaagaa gtctaccatc tcctcccgcg agatccagac    420
tgctgtccgc ctgatcctcc ccggtgaact gtccaagcca gctatttctg agggcaccaa    480
gggtgtcacc aagtactcca gctccaagta aacttgtctt ttgcttggct gagagtcttt    540
ccccttcct tcttcattgt ccctacccte ctgttcttcc cctctccctc acattcatca    600
tgttgtctat taggcgagct gcctgcagac ttgctcgctg tcaaggctga agcagtcgcg    660
tagttagtgt aatggagcca caaatgtaat tctgagcac atgcag                    706
```

| SEQ ID NO: 54 | moltype = DNA length = 1203 |
|---|---|
| FEATURE | Location/Qualifiers |
| source | 1..1203 |
| | mol_type = genomic DNA |
| | organism = unidentified |

SEQUENCE: 54

```
gatgtcaagc gattcaccaa ggatctgctg ttcaactcgg agggcaacct aaccttcaag    60
ccccacttgt ggaacgacat ccgtcacacc ctcctcccca cctttatccg acagatcgga   120
tacgttccca tcccacgagc cgagttctcc tcgcctgaca ttgaccttgt catcgagaat   180
ctggtcctgt ccggacccaa cctcttcccc aacgtcgtct cgctcgagag ccacaactcg   240
ttcaagttct cgccttacca gcagctcaac aagggtatgg acacgcatca ccacaagttc   300
aggctgggta tgagccagat ccaggccgat atccgagatg tccgattctc gttccgacga   360
aagactggat ggcccaagct caaggaccac ggtctcgccg atgtcatcct tgccggtaag   420
ggtatgtcga tcgacgtcga gctcgagtct gtcgagggac gacgagactc tgttgtgcga   480
gtcaaccacg tccacaccac catcgacacc ctcaccttct ccatccgaga ctccaagcac   540
gacttgctct acaagttcgt caagtcggtg gccacgggta cgatcaagaa ggcaatccag   600
gccgccgtcg acaatgccat ccgtacggct gtcggtcacc tcgacgacca gctcgtccag   660
gtccgaaaca ccgtcgatga cgccaagaag tctgacgaga ccacccgaac gcaagccctc   720
aaggacttgt actcgaagaa ggcggacacg gcacagaaga agcaggccga gtccaaggag   780
cagcctggta ctttccgaat cgtcgccaac cgagactctg ttctcaaccc cgacatgggc   840
ggtggcaagg gcgccatgac caacaagatg tggaagaccg aggaccttgc acactctggc   900
aaggaatggc actctcccgc tttcgacttg ctcgactcca agcacccagc acgtaccggt   960
cagacccacc ccgaggccaa ggagggtgct ggacacggaa acagcttgag ctcaaaggct  1020
cagcccggcg ccaacgcggc cgaccagctc aaggctactc acggtcagtc tgaggctgag  1080
gccatcgctg gtcagaagcg acagcaatag gtggaagaga gggagccgcg tattgagaag  1140
taggaaggac tagctgtata cccccttata cttttgtgtc tatagtaatg aatgcgtgaa  1200
acc                                                                 1203
```

| SEQ ID NO: 55 | moltype = DNA length = 962 |
|---|---|
| FEATURE | Location/Qualifiers |
| source | 1..962 |
| | mol_type = genomic DNA |
| | organism = unidentified |

SEQUENCE: 55

```
ggacctttca tccatcagcg tatcgcatat cagcttcctg acaaagtaag aggtaataac    60
aagacaccac actctttcag cacgtacctc ataccggacc gccatgtaca catccgccgt   120
gacactgctc tcttttggtct tgctcctggc gacttccgtt attgcacaag aacaagctgg   180
tcggcctggc actcagcgag gcggcgtctt ctttgggtgt tatgccgatc gacctacagg   240
caatgccaac cagcccatca ctcgagtcgc caactccgac acattctttg aatgcatgga   300
gaattgtgct gcgataacgt ctccttcgtt gctgggatac tatcaaccct cctccggtca   360
atgcttctgc ggcaaccttt tatttaaccc tcaagctcaa ttgaacgta acggttgtca   420
aggtagtgat tggtccttg gccggacttc gaccacctc aggaggttcg gtgacgcttg   480
tcgaccttc ggtggtgtcg gattttctgc gaatcaatac actacagtca ctggtccgt   540
agcttgtcat gttcaatgcg catcaaacag attcgcctat gtctggtccg atactggaag   600
caactcatgg caatgtgctt gcagcaacaa tgtccgtgtt caggaggact tccagtacac   660
ttgtcaaggt ggcggtgtat ttgtgtttga acattcgagg cttcttcgct   720
taacaggaag cggacggtgg aggaacaatg ggcgtgtccg aaagacgccc tctgtccatt   780
cggaatgtca gcgtgcaagg tatcaggtgt cgataatgct tacgaggtat gcttctttc   840
agaccgctag gcccctggtt ccctggccac gagttgaa acacgccatt gacctgtagt   900
gcctcgatac ctcagccgag ctagaatcgt gcggtggttg tctgcatggt caattgttct   960
ga                                                                  962
```

| SEQ ID NO: 56 | moltype = DNA length = 909 |
|---|---|
| FEATURE | Location/Qualifiers |
| source | 1..909 |
| | mol_type = genomic DNA |
| | organism = unidentified |

SEQUENCE: 56

```
gggggaggaa cggtcgttag caatgctttg ctggagaatg ccaagctctg caagacccag    60
ggcaaggaga gctctcttcg agtcatcgtg tgtggccgaa ataggttgga gaatgggtct   120
gcacctcatt gggccgaggc gtttgctacg catggcaaat tggtggaagt gaggatgccg   180
caaaacggca ttcgcatgga gggcatcaaa gctatcgccg acggactggc caagtgtccg   240
acattggaag tgcttgattt gcaggacaac acggctacca agacaggaac acggagtatt   300
gtccgacacc tctcaacttg gcctaaactt cgaatactca atctctcgga ctgtcttttg   360
ggttcggtcg gcggtatcgc tcttgcaacc gcattgtcca ctggctcgaa caagcacctc   420
gaacagctca aactgcaata tggcgagttt gacaagagga cggttgagat actgtcgacg   480
gcaattagcc agcatttgcc aaaattgacg acactcgaac tgaatggaaa ccgtttcgat   540
gccgaagacg aatgcgttga gaccctgaag aaggctacat gg agctacatg ggaacgaggat   600
gctttggacg aacttgacga tatggaggag gtggacgagg acgaagagga tgatgatgac   660
gaggacgagg aggacgaaga cgaggacaag gacactagcg ccgacgatgg gatcgatgca   720
ggagctgctg gagaagacgc tctaccacca gtcacgaaga aggacgagga cgtacttgcg   780
gatctcctgt ccaaggtcca cgttcagcct agctgagtcc aagcgctttc cggtcggcaa   840
gtagatagac tagacagcat aataccttga ccctcatgat gccacccgca tgtacacatt   900
tgttctccg                                                           909
```

| SEQ ID NO: 57 | moltype = DNA length = 909 |
|---|---|
| FEATURE | Location/Qualifiers |
| source | 1..909 |

```
                    mol_type = genomic DNA
                    organism = unidentified
SEQUENCE: 57
cggagaacaa atgtgtacat gcgggtggca tcatgagggt caaggtatta tgctgtctag    60
tctatctact tgccgaccgg aaagcgcttg gactcagcta ggctgaacgt ggaccttgga   120
caggagatcc gcaagtacgt cctcgtcctt cttcgtgact ggtggtagag cgtcttctcc   180
agcagctcct gcatcgatcc catcgtcggc gctagtgtcc ttgtcctcgt cttcgtcctc   240
ctcgtcctcg tcatcatcat cctcttcgtc ctcgtccacc tcctccatat cgtcaagttc   300
gtccaaagca tcctcgttcc catgtagctc aagtgccttc ttcagggtct caacgcattc   360
gtcttcggca tcgaaacggt ttccattcag ttcgagtgtc gtcaattttg gcaaatgctg   420
gctaattgcc gtcgacagta tctcaaccgt cctcttgtca aactcgccat attgcagttt   480
gagctgttcg aggtgcttgt tcgagccagt ggacaatgcg gttgcaagag cgataccgcc   540
gaccgaaccc aaaagacagt ccgagagatt gagtattcga agtttaggcc aagttgagag   600
gtgtcggaca atactccgtg ttcctgtctt ggtagccgta ttgtcctgca aatcaagcac   660
ttccaatgtc ggacacttgg ccagtccgtc ggcgatagct ttgatgccct ccatgcgaat   720
gccgttttgc ggcatcctca cttccaccaa tttgccatgc gtagcaaacg cctcggccca   780
atgaggtgca gacccattct ccaacctatt tcggccacac acgatgactc gaagagagct   840
ctccttgccc tgggtcttgc agagcttggc attctccagc aaagcattgc taacgaccgt   900
tcctccccc                                                           909

SEQ ID NO: 58       moltype = DNA length = 596
FEATURE             Location/Qualifiers
source              1..596
                    mol_type = genomic DNA
                    organism = unidentified
SEQUENCE: 58
ggatggtgaa gcttagtaac agtcttgtcc gtcgtcttaa atggcaacac gttcgcagtc    60
tcggcgtggt ggcgctgact gcccaattgc gaggaccaca acctcagagc gccgaggacg   120
aagattctga agcagctggc aagaagctca aactggctgg cgaccaagct acatctgcgg   180
tcattcccaa gtccgcagac aagcccgata cttttccctct actcgacaca ctacctgcta   240
ctatggctgc tggcaccagg tctatgacta ggcccttgca tgtcggtgat ctgaggttga   300
ctgatctgcg taaaatcatg caggcagctg gccacacggc tgagttccga ggtgagggaa   360
cactactcat tgcacaagtcc gtcgctgtca gaaaatcagg cacagggcag attgaaatcg   420
aggcatctgc tcaagcagct gcaaaccaag ctactcctgg ccgaggtgcg agtagcttcc   480
tcgctgtcaa aagaaagata tacgagggtc tcgctgttgt cacagaagtt taaatgaccg   540
tgtaccctat attcaatttt tgtataattt acgcaatacc aacgatattc tctcgt       596

SEQ ID NO: 59       moltype = DNA length = 418
FEATURE             Location/Qualifiers
source              1..418
                    mol_type = genomic DNA
                    organism = unidentified
SEQUENCE: 59
gaaaatgaaa attgatgtgg agaagctgaa taaagatatc agccttttcc cgcaggtgca    60
tccgattacg gaagatatga aaatcacgca caaaggtgtt tcgcgccttg taatgctgga   120
caggtattca tttaaagaca ctgaaaaaat tacgctatct gaaggcgatt ttgtagtgct   180
gacgatcaag gaagatccaa aatttcctgc aagagggcta ggctacatta aagaaattga   240
ttgggaaaat aaaaaggcaa aggttcaggt cgaagaagag tttcgtcata ctcttgaaaa   300
gcctgaagaa cgggagacgg gaatcatcgt tcgctctttta gatgtcatcg aaaaaccgct   360
tgaaattttt tatgaacaaa ttgccaaaag aaatgcaaca ggtcttgctg ctgttgaa     418

SEQ ID NO: 60       moltype = DNA length = 988
FEATURE             Location/Qualifiers
source              1..988
                    mol_type = genomic DNA
                    organism = unidentified
SEQUENCE: 60
ggggatgcaa cggtgactca actgcgcgaa atcatggacg acccagctgg ctatttcttg    60
ccaaatctca aacatggcgc cgataacatg ttctacgtcg gtccacgcgg acttgcacaa   120
gagctcgagg agcttttttac cttcccaagc acaatcctca gaaagcgcca ggataccagt   180
cagcatgacg aaaggcaggc aaagaaggcg cgcacgcaag aggacgaagc ggctggtgac   240
gcgttggagg agcccgagac tgggcgacgc gacagtgtgc ttccgactga acgggccgct   300
tttggtctcg agggtgatga ctcgggcttt tccttggcg accagacgat gggagacgac   360
atgctgccta tggacgacat gggagccatg gacaccggag acgcatgcga   420
acaccatcag tcgcaccgtc ggtcaccgaa tcgatcgcac gtcagattca gaatgaccga   480
agcgctggca cacacccact ggctatattc gagaaggagg caagggacga cacgcagtcg   540
caatcgcagg ctacgcccaa caaatcggtg gcctccgagt ctatcagcaa gacttcttcc   600
ggccaatcaa agaatctggg catggcatg ggtttgttgc gaagggagat tgaggcgatc   660
gaggaggaag acaagatggt cgggtttgat cacttggcag acaaggcgtc caagcgagca   720
gcgtctgcat tcttcttcga gctgttggtg cttggtacca aacatgcggt caagcttgaa   780
caagctcagg ctttcggcga catccacata cgcggcaaag acaagctgtt tgcagaggtt   840
gttgcataga caaacttgaa gagccacgat cttacgcgca acgagggagg atctaatgac   900
catcttgatg tcgactttaa tgttatttgg tacttgtaca tgagctgcta agagggtctt   960
gaatgagatg atgcatcgct tcatgagg                                      988

SEQ ID NO: 61       moltype = DNA length = 614
FEATURE             Location/Qualifiers
source              1..614
                    mol_type = genomic DNA
```

```
                          organism = unidentified
SEQUENCE: 61
gcagaccgtc tcttttaaat ctcctccttg acaccgtct cctttgcaca tttactacac      60
tccacatatc tccataacaa ccttatatct ttacacaatg ggtgaccacg ccactaccaa    120
cgaccctcc  aacgccacct tcgaggagaa gggcaagggc aaggacgtcc aggatcaaat    180
cgcggaggac tccagcgacg aggagagtga ccaggagcct gagatggttg acgaggaaga    240
ggatgacaac aacctcgagc ccatctccca agacaacatc atctcaggtg gtcgccgtac    300
acgcggcaag atcatcgatt atgccgccga agccgagaag aacaaggatg agatggagga    360
ctctgaggat gacgaggatt accaaggcgc taatgacgac gaggatgacc agagatcgcgca   420
ctaagcgcat ggtcttgatg acggatctca attaacatag gactttggag gattggcgct    480
atggtttctg aaggaggttc tctcgtgcgc ctttgtggtt agcatctcac ctatgaaatg    540
tcatggcctg agcctggcaa tggacatgac tatgaataaa tgaaatgaag cctgcttctg    600
tctttgtgta acag                                                      614

SEQ ID NO: 62         moltype = DNA   length = 418
FEATURE               Location/Qualifiers
source                1..418
                      mol_type = genomic DNA
                      organism = unidentified
SEQUENCE: 62
gaacttaagt attttaaagc agttgcacta tacaacctga gccggtactt ggatgcacgg     60
aaagcaatca atgacctcat tcagagctac ccggacttcc ggcaagctga ggccctcaag    120
tcagccattg atgacaaggt ggtgcgcgat gggctgattg gcgtgagtgt ggcaggagca    180
gtggtggctg gcgtcgtggg cttggctgtg gctcttgcac gtggcaacag aggatgatgc    240
tacaggaggc agcaggttgt tggacagttc agtgcaccgt gccaatgctt caacggtctg    300
gcacaggagg cagcaggttg tgaccctgca caagcttggg ccatgattct acagacacac    360
cttatggcaa tcaaatgtgt gtttgcatgt gcgttgaaga gtgtaaatgt gctcttcc      418

SEQ ID NO: 63         moltype = DNA   length = 94
FEATURE               Location/Qualifiers
source                1..94
                      mol_type = genomic DNA
                      organism = unidentified
SEQUENCE: 63
tatcccgagt agcatgggac acgtggaatc ccgtgtgaat cagcgaggac cacctcgtaa     60
ggctaaatac tcctgggtga ccgatagcga aaaa                                 94

SEQ ID NO: 64         moltype = DNA   length = 371
FEATURE               Location/Qualifiers
source                1..371
                      mol_type = genomic DNA
                      organism = unidentified
SEQUENCE: 64
cacgatttaa ataccggggg gacgttttgg attcgacagg gatagatcga gcttaagctg     60
cgagccggag ggatcgtctc cgtcatcaac gtcgcctaaa gataactggc aaacaaaaca    120
actacgcttt agctgcttaa tgctaaaggc tcctttcttc catcgcccat gtggaggaaa    180
aggggttcaa cttaagtggg ctacgcccga ttccgccgtg tggaagag ggaagagacg      240
aatcagacta gctgtccgga tgcctgccga caggctaagg aacagtgaaa tgttaaatat    300
gtcggatacg ctcgtagatg cttaagtggc gatatctctg acgtgggtt cgattcccac     360
cgtctccacc a                                                         371

SEQ ID NO: 65         moltype = DNA   length = 681
FEATURE               Location/Qualifiers
source                1..681
                      mol_type = genomic DNA
                      organism = unidentified
SEQUENCE: 65
gccatcagca ccgcaaagct acctcatcaa ccattgaaag cacgcaaata actcccaaa      60
gttaatgccc gtacgaccct acctggaaga aatggccgac atgccgtgc cctgtttcgc     120
gtacgacgca ccgcccaccc tggccgacca ccctcacgcc cgcgagcacc aacacacgag    180
cttcatgcaa taccttgcgc gcaagcagcc ggacccaaag aactacccca actaccctga    240
cgtggacatc cgcgacgcca tcaatcacta cctgatcgag ctcaatgcc cggggatcaa     300
agacgcagcc gacatccact gccagtgac gagctcgcgg cacctgaccg tcaccggcga    360
catcgcccgt cctgaggaaa gccagatcga agcgcaggc cagcaggcc cgtctacct      420
ggttctggga gagagacgca ttggctcttt ccgtcgcaac tttaccttcc ctgtggaggt    480
cgagcaggaa aatatgactg ccaagttgga ggccggattg ttgaagattg tcttgcccaa    540
gcacaagcac catactccga agggaacagg aaaggtcgac attgatgtca ttgagtgaac    600
gtcttttggg tctgcgatta tatgcgagga gttcttagat tgccggagtg ggtacctgta    660
tgggaattat gtatctgcaa c                                              681

SEQ ID NO: 66         moltype = DNA   length = 681
FEATURE               Location/Qualifiers
source                1..681
                      mol_type = genomic DNA
                      organism = unidentified
SEQUENCE: 66
gttgcagata cataattccc atacaggtac ccactccggc aatctaagaa ctcctcgcat     60
ataatcgcag acccaaaaga cgttcactca atgcatcaa tgtcgacctt tcctgttccc    120
ttcggagtat ggtgcttgtg cttgggcaag acaatcttca acaatccggc ctccaacttg    180
```

```
gcagtcatat tttcctgctc gacctccaca gggaaggtaa agttgcgacg gaaagagcca    240
atgcgtctct ctcccagaac caggtagacg ggcctgctct cgatctgcgc ttcgatctgg    300
cttttcctcag gacgggcgat gtcgccggtg acgtcaggt gccgcagct cgtccactgg     360
cagtggatgt cggctgcgtc tttgatcccc gggcattcga gctcgatcag gtagtgattg    420
atggcgtcgc ggatgtccac gtcagggtag ttggggtagt tctttgggtc cggctgcttg    480
cgcgcaaggt attgcatgaa ggtcgtgtgt tggtgctcgc gggcgtgagg gtggtcggcc    540
agggtgggcg gtgcgtcgta cgcgaacagg ggcacgggca tgtcggccat tcttccagg    600
tagggtcgta cgggcattaa ctttggggag ttatttgcgt gctttcaatg gttgatgagg    660
tagctttgcg gtgctgatgg c                                             681

SEQ ID NO: 67       moltype = DNA  length = 50
FEATURE             Location/Qualifiers
source              1..50
                    mol_type = genomic DNA
                    organism = unidentified
SEQUENCE: 67
gggatgatat gcatcatata gatcttgaga aatcaaggta agtatacaaa              50

SEQ ID NO: 68       moltype = DNA  length = 558
FEATURE             Location/Qualifiers
source              1..558
                    mol_type = genomic DNA
                    organism = unidentified
SEQUENCE: 68
gggaaaaaaa ctttagaata cagtttaatc aatcttcaca gctacaaggc tatatcatt    60
gatatagcat atcaaagtgg cttgatttc tgtaaattta tatctaataa taatagtgtt    120
tatatcagct aaatacatat ttctatccta tctatatatc accgacagac catatttgaa    180
actgctgttg acactattat tcatatgttc ggatttaatt ttaatacgac aaaattgtta    240
aaaacaattc tcgttgtttg ttatttgcag gcaacagtgt tagctgatcc ttatacaaga    300
gtatcttggg aagcgtatat gaatcatgtc aatggatccg acgactatcg tactcaaggg    360
gatgatacca gagctacacg cttttccagag actaaacctc caaacaagg aaaagatttc    420
ctgtggtcga gtaaaccagt ccccagttca gatctatttc tggagttctt tatgtatgag    480
ggagaaccag atgaattcag caggacgact gaatcgtatc aatcacttcc gagcaacgcg    540
ttaactgcta ggcaaaaa                                                 558

SEQ ID NO: 69       moltype = DNA  length = 1164
FEATURE             Location/Qualifiers
source              1..1164
                    mol_type = genomic DNA
                    organism = unidentified
SEQUENCE: 69
ggacacatca cacaacaaca atgtctccaa caccaacatc accacacaac aagctctcgc    60
tccccgcaag agcttcttcc cacgactcga cagacggcat ccgtaagcga gtatgcaagg    120
cttgcgacag gtgtcgattg aagaagagca aatgcgacgg atcaagtcca tgctctcgat    180
gcaaagcaga caacgccatc tgcgtgttcg gagagcgcaa acgatcacat gataaacact    240
atcccaaagg ctatgtcgag atgctcgaac aacagcaggg tcagctcgtc tcaggcctca    300
aagaaatgta ccacagactc cagaaagcct ccgcctggtg ttggacgaaa              360
gcaccggaca gcctctcact cacgacatcc tgtcagcatt agacctcctc gaaccaaagc    420
atgacgacag caacgagcca gaagtcttcg aagagaactg cgaaaagctg caatcaaaat    480
tgctcgcaga cggcgcgggc tttgcccacc gacgaggatc gatcagttcg gattctgaac    540
acagccatca cgatcgaccc aaaacatcct cacgccacga cacgcccgtg caacccaaac    600
cgtcgatctt caaggagaac ctgagcttcg ccagcgcggc ctcatcacca ctcacgcaaa    660
gccccatccc tcgatcgaaa cccttgaacg tcatgccata ccaaacgctg caaccgtcgt    720
caagaccatc cccactccag atgccctcag catacaacga cccgcaacta tacgcacccg    780
aatgggcaca agcactggca gacatgagcg gcgatcccaa ctaccgccaa agattctcca    840
tgcagcagca acaacaaaac gacttcgaca acctgctctg ggatccctca gcgcaagcgc    900
ccatggaatc gcccttcagc caaccagcct tcttcaacca ggcgcaactg atcggcagcg    960
gcaacgtctt tgggctgtct gacatcaacg atctgggccc caaccccgcg gatggcggga   1020
tggactttga cttcagcaag ttcgtgcagc agaccgaagt catgacatga acatgattct   1080
tgccttctgt caatacgcgc gagaattttg cttcagagtt ccagtccgtg taattcttgt   1140
gtatttatta cgatacgaac acgc                                         1164

SEQ ID NO: 70       moltype = DNA  length = 923
FEATURE             Location/Qualifiers
source              1..923
                    mol_type = genomic DNA
                    organism = unidentified
SEQUENCE: 70
agagctcttc gtactccaca ccaccatctt ccatccgacc acactttcat cccaaatcca    60
tcaacaaccc atctcaactc catctccacca cctcaccatc atcacaatgt cttccttccg   120
cgtcgccgcc cccaagatgg cctccatggc cgctcagtcc tccgtgaagg tcgcccgccc   180
ggccttccag gctgctcagc tccagaagtt caccgcgcc tactccgcgg tccccaagaa    240
caccgtcttc aacaccatga gcgcaccca gatgatggcc gcgcaggcct cccccatcgc    300
caagccgtgcc tactcctctg agatggccaa cgcccgtcgc caggtctccc agaacatgga    360
tatgggttcc gccgccatcg gtcttgccgg tgccggtgtc ggtatcggtc tcgtcttcgc    420
cgccctcatc caggccgtcg cccgcaaccc ctccctccgt ggcagctttt tctcttacgc    480
cattcttggt ttcgctttcg tcgaggccat cggtctcttc gacctcatgg ttgccatgat    540
ggccaagttc ttgtaaaaaa tgtgcattcca ttacctaccg agatggagat ggatgcgaag    600
gcgattgggg acgagacag tgcgttgctg cagcagcatt agtaccggtg ttggtcgtgt    660
```

```
accagtagtc tgatggagac ggatagatgg atagaaagct ggtgaatggg ggctacgaag   720
aaaacgtacc tctcgatcca tttgtaccca tactcatgaa gtatatccgt cttctttcct   780
tctatcattc gcgcgcactt ccttgctggt ggcttttgg ggttgcgctc tcaccgaaaa    840
gcaacgtcac tcttgtatat aacttattcg accacggcca tatcttggtt tggctgggga   900
aataacaatg tctcatttgt acc                                            923

SEQ ID NO: 71              moltype = DNA   length = 923
FEATURE                    Location/Qualifiers
source                     1..923
                           mol_type = genomic DNA
                           organism = unidentified
SEQUENCE: 71
ggtacaaatg agacattgtt atttccccag ccaaaccaag atatggccgt ggtcgaataa    60
gttatataca agagtgacgt tgcttttcgg tgagagcgca accccaaaaa gccaccagca    120
aggaagtgcg cgcgaatgat agaaggaaag aagacggata tacttcatga gtatgggtac    180
aaatggatcg agaggtacgt tttcttcgta gcccccattc accagctttc tatccatcta    240
tccgtctcca tcagactact ggtacacgac caacaccggt actaatgctg ctgcagcaac    300
gcactgtctc cgtccccaat cgcctccgca tccatctcca tctcggtagg taatgaatg    360
cacatttttta caagaacttg gccatcatgg caaccatgag gtcgaagaga ccgatggcct   420
cgacgaaagc gaaaccaaga atggcgtaag agaaaagctg gccacggagg gaggggttgc    480
gggcgacggc ctggatgagg gcggcgaaga cgagaccgat accgacacca gcaccggcaa   540
gaccgatggc ggcggaaccc ataccgatgt tctgggagac ctggacgagg gcgttggcca    600
tctcagagga gtaggcacgc ttggcgatgg gggaggcctg gcgggccatc atctgggtgc    660
gcttcatggt gttgaagacg tgttcttgg gaccgcgga gtaggcgcgg gtgaacttct     720
ggagctgagc agcctggaag gccgggcggg cgaccttcac ggaggactga gcggccatgg    780
aggccatctt gggggcggcg acgtggaagg aagacattgt gatgatggtg aggtggtgag    840
atggagttga gatgggttgt tgatggattt gggatgaaag tgtggtcgga tggaagatgg    900
tggtgtggag tacgaagagc tct                                            923

SEQ ID NO: 72              moltype = DNA   length = 1368
FEATURE                    Location/Qualifiers
source                     1..1368
                           mol_type = genomic DNA
                           organism = unidentified
SEQUENCE: 72
ggaggattct cggtcaagtt caggaccgca gaaggaaatt gggactttgt ggccaacaac    60
accccgtct tcttcctccg agacccggcc aagttccccc acttcatcca cccagaag     120
cgagatcccg ccacccactt gtctggtgac gatgactcga ccatgttctg ggactacctg   180
tcgcagaacc ccgagtcgat ccaccaagtc atgatcctca tgggtgatcg aggtatccgc    240
aagggctggc gattcatgca tggctactac ggccacaccc tcaagattgt caatgacaag   300
ggcgaatggg tctacgccca gttccacctc atctctgatc agggcaccca gaacttcacg    360
ggtgacgagg ctgctcagca atccaacgat tacgacagaa aggatctgta cgaagccatc    420
gagaagggag acttcccctc gtggaagatg aaggttcaga tcatgaccga gaagcaagcc    480
gaggaggcat gggagcaaaa gaggatcaac gtctttgatt tgacccacgt ctggcctcat    540
ggtgattacc cacttcgaac agtcggtaaa ttcacccctta acgagaatgc caagaactac   600
ttcgccgagg tggaacaagt cgcattcaac ccgtctcaca tgattcccgg tgtcgagccg    660
tccaacgacc cagtgttgca gtcgcgactg ttctcttacc ccgatgctca ccgacaccga    720
atcggagcca actatcagca actgcccgtt aaccagaatg tgcccctt cgccttgggc     780
aacttccagc gagacggcca gatggcattc tacaatcaag gtagtcgacc caactacctt    840
tcttcgattg agcaatctc attcaaggag agggcgtatg atctcaacaa ggtccacggc    900
aaattcgtcg gagaagccgt cgccttcttg tctgaaatca ggccagagga cttcaatgcg    960
ccaagggcac tgtggcagaa agtctttagc gaggaaagca agcagcgatt cgtcgacacc   1020
gtctctggtc acatgtcgac agtccgagac aaagccatca ccgctcgaat gatgactatc   1080
ttccgagaag tttcgcctga tcttggtgat cgacttgaga aggccactgg tgtcaagggc   1140
gaatccacca ttgccgggat gaagttcaac ggaacgcaca atgggtttga caaggccaac   1200
aagatcccgg ctaatgggat gaagaagggt ggagaagtca tctttgacaa tggtgcacct   1260
gctactgctg ccaggtaaat gagcggtcag gcgtacttga tatatgttgt tacgatatgt   1320
cggtctcgta gtcatgtagc caggataaat gaagcggatg tggcagtg                1368

SEQ ID NO: 73              moltype = DNA   length = 1368
FEATURE                    Location/Qualifiers
source                     1..1368
                           mol_type = genomic DNA
                           organism = unidentified
SEQUENCE: 73
cactgccaca tccgcttcat ttatcctggc tacatgacta cgagaccgac atatcgtaac    60
aacatatatc aagtacgcct gaccgctcat ttacctggca gcagtagcag gtgcaccatt    120
gtcaaagatg acttctccac ccttcttcat cccattagcc gggatcttgt tggccttgtc    180
aaaccattg tgcgttccgt tgaacttcat cccggcaatg ggtggattcgc ccttgacacc    240
agtggccttc tcaagtcgat caccaagatc aggcgaaact tctcggaaga tagtcatcat    300
tcgagcggtg atggctttgt ctcggactc cgacatgtga ccagacgg tgtcgacgaa       360
tcgctgcttt ctttcctcgc taaagacttt ctgccacagt gcccttgggg cattgaagtc    420
ctctggcctg atttcagaca agaaggcgac ggcttctccg acgaatttgc cgtggacctt    480
gttgagatca tacgccctct ccttgaatga gattggctca atcgaagaaa ggtagttgga    540
tcgactacct tgattgtaga atgccatctg gccgtctcgc tggaagttgc caaggcgaa     600
ggggcacaca ttctggttaa cgggcagttg ctgatagttg ctccgattc ggtgtcggtg     660
agcatcgggg taagagaaca gtcgcgactg caacactggg tcgttggacg gctcgacacc    720
gggaatcatg tgagacgggt tgaatgcgac ttgttccacc tcggcgaagt agttcttggc    780
attctcgtta agggtgaatt taccgactgt tcgaagtggg taatcaccat gaggccagac    840
```

```
gtgggtcaaa tcaaagacgt tgatcctctt ttgctcccat gcctcctcgg cttgcttctc   900
ggtcatgatc tgaaccttca tcgtccacga ggggaagtct cccttctcga tggcttcgta   960
cagatccttc tgtccgtaat cgttggattg ctgagcagcc tcgtcacccg tgaagttctg  1020
ggtgccctga tcagagatga ggtggaactg gcgtagacc cattcgccct tgtcattgac   1080
aatccttgag gtgtggccgt agtagccatg catgaatcgc cagcccttgg ggatacctcg  1140
atcacccatg aggatcatga cttggtggat cgactcgggg ttctgcgaca ggtagtccca  1200
gaacatggtc gagtcatcgt caccagacaa gtgggtggcg ggatctcgct tctgggtgtg  1260
gatgaagtgg gggaacttgg ccgggtctcg gaggaagaag acgggggtgt tgttggccac  1320
aaagtcccaa tttccttctg cggtcctgaa cttgaccgag aatcctcc                1368

SEQ ID NO: 74            moltype = DNA   length = 1377
FEATURE                  Location/Qualifiers
source                   1..1377
                         mol_type = genomic DNA
                         organism = unidentified
SEQUENCE: 74
ggacaccatt gacgcagagg tgctcgacag tttgggtgtc acccaagaga acttccagtt    60
tgcccttggc gtcagcaacc cctctgccct tcgcgaggtc gcagtggtcg aggttcccaa   120
cgtcagatgg gaggacattg gtgtctcga ggaggtcaag agggagctca tcgagagcgt    180
gcaataccc gtcgaccacc ccgagaagtt cctcaagttt ggcatgtccc catcaaaggg    240
tgtgcttttc tacggtcccc ctggtactgg taagactctt ctggccaagg ctgtcgccaa   300
cgagtcgcgc gccaacttta tttccgtcaa gggtcccgag cttctctcca tgtggttcgg   360
tgagtctgag agcaacattc gtgacatctt cgacaaggct cgtgctgccg cgccttgcgt   420
tgtcttcctc gacgagctgg actccatcgc caagtctcgt ggcggttctc agggcgatgc   480
tggcggtgct tccgaccgtg tggtcaacca gcttctcact gagatggacg gtatgaccag   540
caagaagaac gttttcgtca tcggtgccac caacaggccg gagcgctcg acaacgctct    600
ctgccgtcct ggtcgtctcg acactctcgt ctacgttccc ctgcctgacc aggagggccg   660
tgagagcatt ctcaaggccc agctccgcaa gactcctatc gccgacgaca tcgacctttc   720
ctacatggcc tccaagactc acggtttctc tggtgccgat cttggcttca tcacccagcg   780
tgccgtcaag ctggccatca gcagtctat tgacctggcc atccagaact aaaaggctag    840
agaggccgag ggtgacaccg ccatggacga ggacatccag gaggacgacc ccgtgcccga   900
gctgaccaag gctcactttg aggaggctat gagcatggct cgtcgctccg tcaccgacac   960
cgagatcagg cgctacgagg cttctgccca gagcatgaag agctccggtg gcggcagcgc  1020
tttcttccgc ttccctgaga gcggtgccga tggcaacgca gccgagcagc agcaaaatgg  1080
tgctggcgag gaggacctct acgactaaat tggttcacg aacctcacga cctaatcctt   1140
tgctgttatc ggagtaatat tccagatgga gagcaatc atgcattcag gcgcgtctat    1200
ggactgaagg ggaagatgga tagagtgttc cagtagccct tttctctttt tttctgggaa  1260
ctcttgctgt tggctggtc gcctcttatc gagtgtggtt gtgctagagt aggcagttca   1320
gagtttccct gttatgttat gcctttccgg gcagtatgag aataatttcc ttgcaaa      1377

SEQ ID NO: 75            moltype = DNA   length = 1377
FEATURE                  Location/Qualifiers
source                   1..1377
                         mol_type = genomic DNA
                         organism = unidentified
SEQUENCE: 75
tttgcaagga aattattctc atactgcccg gaaaggcata acataacagg gaaactctga    60
actgcctact ctagcacaac cacactcgat aagaggcgac cagccaaaca gcaagagttc   120
ccagaaaaaa agagaaaagg gctactggaa cactctatcc atcttcccct tcagtccata   180
gacgcgcctg aatgcatgat tgctctctcc atctggaata ttactccgat aacagcaaag   240
gattactcg tgaggttcgt gaaaccaatt tagtcgtaga ggtcctcctc gccagcacca   300
ttttgctgct gctcggctgc gttgccatcg gcaccgctct cagggaagcg gaagaaagcg   360
ctgccgccac cggagctctt catgctctgg gcgaaagcct cgtagcgcct gatctcggtg   420
tcggtgacgg agcgacgagc catgctcata gcctcctcaa agtgagcctt ggtcagctcg   480
ggcacggggt cgtcctcctc gatgtcctcg tccatgggtg tgtcacccct ggctctctcta  540
gcctttggt tctggatggc caggtcaata gactgcttga tggccagctt gacggcacgc   600
tgggtgatga agccaagatc ggcaccgag aaaccgtgag tcttggaggc catgtaggaa   660
aggtcgatgt cgtcggcgat aggagtcttg cggagctggg ccttgagaat gctctcacgg   720
ccctcctggt caggcaggg aacgtagacg agagtcgaca gacgaccagg acggcagaga   780
gcgttgtcga gctgctcagg cctgttggtg gcaccgatga cgaaaacgtt cttcttgctg   840
gtcataccgt ccatctcagt gagaagctgg ttgaccacac ggtcggaagc accgccagca   900
tcgccctgag aaccgccacg agacttggcg atggagtcca gctcgtcgag gaagacaacg   960
caaggcgcgg cagcacgagc cttgtcgaag atgtcacgaa tgttgctctc agactcaccg  1020
aaccacatgg agaaaagctc gggacccttg acggaaataa agttggccgc gcactcgttg  1080
gcgacagcct tggccagaag agtcttacca gtaccagggg gaccgtagaa agcacaccc   1140
tttgatgggg acatgccaaa cttgaggaac ttctcggggt ggtcgacggg gtattgcacg  1200
ctctcgatga gctccctctt gacctcctcg agaccaccaa tgtcctccca tctgacgttg  1260
ggaacctcga ccactgcgac ctcgcgaagg gcagagggt tgctgacgcc aagggcaaac  1320
tggaagttct cttgggtgac acccaaactg tcgagcacct ctgcgtcaat ggtgtcc      1377

SEQ ID NO: 76            moltype = DNA   length = 699
FEATURE                  Location/Qualifiers
source                   1..699
                         mol_type = genomic DNA
                         organism = unidentified
SEQUENCE: 76
gaaggtgacg acgagcagac tttgcgcccc acgacgatac taacgtaacg acccagcaca    60
cattaatcca caatgggtca ctccgccggt ctcaggaagg gcactcgcta tgccttctct   120
cgcgacttca agaagagggg catgatcccc ctctccacct accttaagca gtacaaggtc   180
```

```
ggcgacatcg tccacgtcgt ctgcaacggt gccgtccaga agggcatgcc ccacaaggac    240
ttccacggca agactggtgt cgtctacaac gtgaccaagt ccgccgtcgg cgtcatcctg    300
tacaagcagg ttggcaaccg ttacatcgag aagcgcgtca acctccgcat cgagcacgtc    360
cgcctctccc gctcgcgtga ggagttcatc gtccgcgtca agaccaacgc tgagaagaag    420
cgcaaggcca aggaggaggg caccaccgtc ttcctcaagg gccaggccga caagccccgc    480
gaggcccgca ccatcagcgc caaggacaac aagcccgaga gcatcgctcc tatcgcctac    540
gacacccaca tttaagcgtg cttgtttcga aagggagggc gtacgggctg tatgatggc     600
gaggctagga ggttggtatc ggcggatcgg attccaccgg atgggaaata cctgccggat    660
gagccagcta gcttcgcaag gtgcatgaat tctagcgcc                           699

SEQ ID NO: 77           moltype = DNA   length = 1664
FEATURE                 Location/Qualifiers
source                  1..1664
                        mol_type = genomic DNA
                        organism = unidentified
SEQUENCE: 77
ggggacatgg gcatcggtgg tcttgatacg gagttctcgg ctatcttccg acgagcattt     60
gccagtcgta tttccgcc gggactggtc gagaaattag gtatccagca cgtcaagggt    120
atcttactgt ttggcccgcc aggaacagga aaaaccttga tggcacggca gatcggaacg    180
atgctcaacg ccagagagcc taaggtggtc aacggtcccg aaatcctcaa caagttcgtc    240
ggtcagagtg aggagaatat cagaaagctg tttgccgatg ctgagaaaga gcaaaaggaa    300
aagggggatg aaagtggctc gcacatcatc atcttcgatg agctggacgc tatctgtaaa    360
cagcgaggat ctacaaacag cggtaccggc gttggagact cggttgtcaa tcagctgtta    420
tcgaagatgg acggtgtaga tcaactgaac aatgtcttga tcatcggtat gactaatcga    480
atggacatga tcgacgaagc gctcctccga cctggacgtc tggaagtcca cattgagatc    540
tcgttgcctg acgaagctgg ccgattccaa atcctcaaca ttcataccaa caagatgagg    600
acgaatggtg tcatggacag cgatgtggat ctgggcgaac tagcggccct gacgaagaac    660
ttctcggggtg ccgagattgg tggtctggtc aaatcagcga ccagtttcgc tttcaaccgt    720
cacgtcaagg ttggctccgt cgccgcgttt gatgatatcg acaatatgaa gatctcacga    780
gccgacttcc tccacgccct agacgaggtt acacctgtgt ttggtgtctc cgaagaagag    840
ctgcaacagg tcgtgcagaa cggtatcatt cactactcgc aacacgtcaa tgacacacta    900
aacgatggaa gtctgcttgt ggagcaagtg cgaaaatccg accgcacccc gcttgtctcg    960
gccctccttc acggtccatc tggcgcgggc aagacggctt tggcagccac gatcgccatg   1020
gcatccgagt tcccttttcat caagctcatc tgcctgaaa caatggttgg gttttctgag   1080
ccgcagaaga ttgctcaact caacaaggtg ttcacagaca gctacaagag tccgatgagc   1140
atcatcgttg tcgacagtct cgagagattg ctggactgga acccgatcgg acccaggttc   1200
tcgaatggtg tgcttcaggc tttggttgtc ctctttggca aacgtccgcc caagggtcgg   1260
cgtcttctca ttctggccac cacgtcaaat cgcaacatcc tcacggatat ggacgtcctt   1320
tcggctttcg acactgatat ccccattaac cccatctcat cgatcgatgc agtggtgcac   1380
gttctagatg aggtcaagtt attcccgaac tcgaaggaaa agcagagagc aacacagatg   1440
cttcgcgagg cgagactggg cgaaggtggt cgaccagact tgttggtcgg agtgaaaaag   1500
ctgttgagta tggcagagat ggcccggcag gatccggatc ccacgatgaa gatcgtgacg   1560
agcattctca gggaggcgag ttaggatgtg tgaagcgtga tcatgataga gtgtagtcca   1620
aacaatgtac tagtgcaaca gaagctatgc agataataa cgtt                     1664

SEQ ID NO: 78           moltype = DNA   length = 1368
FEATURE                 Location/Qualifiers
source                  1..1368
                        mol_type = genomic DNA
                        organism = unidentified
SEQUENCE: 78
ggaggattct cggtcaagtt caggaccgca gaaggaaatt gggactttgt ggccaacaac     60
accccgtct tcttcctccg agacccggcc aagttccccc acttcatcca cccagaag     120
cgagatcccg ccaccactt gtctggtgac gatgactcga ccatgttctg ggactacctg    180
tcgcagaacc ccgagtcgat ccaccaagtc atgatcctca tgggtgatcg aggtatccgc    240
aagggctggc gattcatgca tggctactac ggccacaccc tcaagattgt caatgacaag    300
ggcgaatggg tctacgccca gttccacctc atctctgatc agggcaccca gaacttcacg    360
ggtgacgagg ctgctcagca atccaacgat tacggacaga aggatctgta cgaagccatc    420
gagaagggag acttcccctc gtggacgagt aaggttcaga tcatgaccga gaagcaagcc    480
gaggaggcat gggagcaaaa gaggatcaac gtctttgatt tgacccacgt ctggcctcat    540
ggtgattacc cacttcgaac agtcggtaaa ttcacccta acgagaatgc caagaactac    600
ttcgccgagg tggaacaagt cgcattcaac ccgtctcaca tgattccggg tgtcgagccg    660
tccaacgacc cagtgttgca gtcgcgactg ttctcttacc ccgatgctca ccgacaccga    720
atcggagca actatcagca actgcccgtt aaccagaatg tgtgcccctt cgccttgggc    780
aacttccagc gagacggcca gatggcattc tacaatcaag gtagtcgacc caactacctt    840
tcttcgattg agccaatctc attcaaggag agggcgtatg atctcaacaa ggtccacggc    900
aaaattcgtcg gagaagccgt cgccttcttg tctgaaatca ggccagagga cttcaatgcc    960
ccaagggcac tgtggcagaa agtctttagc gaggaaagca agcagcgatt cgtcgacacc   1020
gtctctggtc acatgtcgac agtccgagac aaagccatca gctcgaat gatgactatc   1080
ttccagaaag tttcgcctga tcttggtgat cgacttgaga aggccactgg tgtcaagggc   1140
gaatccacca ttgccgggat gaagttcaac ggaacgcaca tgggtttga aaggccaac    1200
aagatcccgc ctaatgggat gaagaaggt ggagaagtca tctttgacaa tggtgcacct   1260
gctactgctg ccaggtaaat gagcggtcag gcgtacttga tatatgttgt tacgatatgt   1320
cggtctcgta gtcatgtagc caggataaat gaagcggatg tggcagtg              1368

SEQ ID NO: 79           moltype = DNA   length = 1280
FEATURE                 Location/Qualifiers
source                  1..1280
                        mol_type = genomic DNA
```

```
                        organism = unidentified
SEQUENCE: 79
gagcacatac acacaccacc gcaatcatgc ctccccgcca accagcaaca cggctctttg    60
ccctaccgcc tcgcttcctc tgcccttcgc tgcccaccac gcaaacgcgc accatccgct   120
ccatcgacaa acccgcccca aaacccagcc gattcaatgc ctcactcaat ctcccccgtgc   180
tgggctcctc gtccaccgcc gccttcgcgc gcaaagagca ctcgctcccc ctgcgcaccg   240
gcgcgctcgc catcaaaaag ggcatgacgg cactcttcga cccggtcaca gcgaagcgca   300
cgccctgcac cgtcctgcaa ctcgacagat gccaggtggt cagccacaag cgacgcgaca   360
tccacggcta ctgggcggtg caagtgggcg cgggcgcaca agaagcgagg aacgtcaccg   420
ggccggagag gggccacttc gccgcctaca acgtgcccct gagcaggcac ctggccgagt   480
tcagagtcaa gaacgccgag ggcctgcccc ccgttggctc ggctattacc gccgacccgt   540
tcatcgaggg ccagttcatc gatgccaaag ccgaccgcag aggcatgggt ttcgaggggtg   600
gtatgaagcg ctggaacttc ggcggacagc ccgcgtcgca cggtaactcg ctcgcgcaca   660
gattgatggg ttcgtccggt ggtggacagg gcagcggtca cagagtcttg cccggcaaga   720
agatgccggg tcgcatgggt ggcgagcagg cgaccgttgc gaacctgagg gtcatgcagg   780
tggacaagga gaacggtatc gtggttgtga gtggcgctgt gcctggcccg aagaactgca   840
tggtcaagct gcaggatgcg ctcaagaagc cttggcctga tgcgacttgg ccgccgtcta   900
ttgagggcgc gacggaggtt ctgagggagg ccactgagaa ggcgcctgct gcgtaagggg   960
gtcggtcgag gtcaagaaat atcgttgcaa tttgggagat gatgctgtcc gatgcctgtc  1020
gaaaagggt tcttgtgggg aggtctggag aatcatcgat gcaagcatta acatgagcgt  1080
gatctcacga gcaatcccag agaagcggtt acagctgctt gctcgaaatg tacactgctc  1140
aaagcttgcc ggagaagttg gccaaagtca tcactctcgg cacaggaata tactttgtaa  1200
ccatagggaa aagaggagag ggtctcgagc caggatcaaa aataggaaat gtacattata  1260
attgcatatc gtcatcatcc                                              1280

SEQ ID NO: 80              moltype = DNA   length = 677
FEATURE                    Location/Qualifiers
source                     1..677
                           mol_type = genomic DNA
                           organism = unidentified
SEQUENCE: 80
ggaatcgacg aacgacacct caatcgaaac caccactcgc cattgtgaat ctttccacct    60
gtcgcaatgg gtatctggga cgctttcacc gatattgtcg aggctgtgac gccatggagc   120
gtcgttgagg ccgaggctcc tgctgaggag ccccaggagg agaacgagtc caagaccgag   180
tccaaggacg agcccgagga ggaggaagag gatgaggaag aagaggagga tgaggatgat   240
gaggaggagc tcgtcgaccc caaggagact ctcgaggaag agtgcaagaa ctctcctcaa   300
tgtgcccccg ccaagcacca cttcgacgag tgtgttgagc gcgttcagca gcaggagagc   360
gagggtggtg ctaaggagga ctgtgtcgag gagttcttcc accttgccca ctgtgcgacc   420
gcttgcgccg ctcccaagct ttggtctcag ctcaagtaaa ctcacaacat cccggttatc   480
gttactacga cgacgcaatg gctacataca cgtcgaaaag atgcctggag ccggaacgag   540
gcaatgctgc ccactacgga aggctgttcc cttgtacgaa tgctcatctg ccgggtcatc   600
agtcggccag agattactct gatgtcgact ctctctgtac catacgctct tacgcctgaa   660
tagatttctt gcactttt                                                 677

SEQ ID NO: 81              moltype = DNA   length = 1019
FEATURE                    Location/Qualifiers
source                     1..1019
                           mol_type = genomic DNA
                           organism = unidentified
SEQUENCE: 81
gggagatact accgtgcgcc cgagatcatg ttgacatggc aaaaatacga tgtcgccgtc    60
gacatttgga gcacaggatg tatcttcgcc gagatgctcg agggaaaagcc cctgttcccg   120
ggcaaggacc acgttaatca gttctcgatc atcacagaat tgctcggcac acctcctgac   180
gatgtcatcc agaccatcgc atctgagaac accctccgat tcgtccagtc gctgcccaag   240
cgtgagaagg tcccattcac tacgaaattc gccaatgccg acccgctttc gcttgacttg   300
ttggagaaga tgcttgtctt cgatccacgt acccgtatct cggcatcaga agggctgtcg   360
cacgagtacc ttgcgccata ccatgacccg acggatgagc ccgtcgctgc cgaggtgttt   420
gactggagtt tcaacgatgc ggatctacca gtagacacct ggaaggtcat gatgtactcc   480
gagatcctgg acttccacaa cttgggtgat atccagcaag accaggccgc cgaaggaccc   540
gtcactggcg acctagcccc accttccgct acgacttcgg catagacagc ttgccttttag   600
gggtttttttt ctcgtttttc tcttctcgtc tcattacgtt cctagtcaac atgtgtccat   660
tagcatccca aattattggt ggtagaaagg agggaaggaa ttggtgcaac atgatctctc   720
ctagaaaatc gtttctcttc atctctcgtc catgatccac gctttcccaa gctttatctc   780
cccttcccc ttcctcacgc ctcaacttct cctgtaccaa caaatcttcg ctaccgcttt   840
ctcgaccgtc gaacgaacat cacaaagaat caagaaaggt agaagaggtg tgaatagacc   900
aggaaaggca ttcttggagc gaggggggag gaggaagtaa tctggaacga aagcccatca   960
cactgttttc tttgaaccta catacacgga cagagggaa tgcatgtgca tggtaatgt  1019

SEQ ID NO: 82              moltype = DNA   length = 391
FEATURE                    Location/Qualifiers
source                     1..391
                           mol_type = genomic DNA
                           organism = unidentified
SEQUENCE: 82
cgctaccggt cgccggcgcg ccggggttga cctcggatca ggtagggata cccgctgaac    60
ttaagcatat caataagcgg aggaaaagaa accaaccggg attgccctag taacggcgag   120
tgaagcggca agagctcaaa tttgaaagct ggccccctcg gggtccgcat tgtaatttgc   180
agaggatgct tcgggaacgg ccccatcta agtgccctgg aacgggccgt catagagggt   240
gagaatcccg tctgggatgg ggtggccgcg cccgtgtgaa gctccttcga cgagtcgagt   300
```

```
tgtttgggaa tgcagctcta attgggtggt aaatttcatc taaagctaaa tattggccgg    360
agaccgatag cgcacaagta gagtgatcga a                                   391

SEQ ID NO: 83         moltype = DNA  length = 391
FEATURE               Location/Qualifiers
source                1..391
                      mol_type = genomic DNA
                      organism = unidentified
SEQUENCE: 83
cgctaccggt cgccggcgcg ccggggttga cctcggatca ggtagggata cccgctgaac    60
ttaagcatat caataagcgg aggaaaagaa accaaccggg attgccctag taacggcgag   120
cgaagcggca agagctcaaa tttgaaagct ggcccctcg gggtccgcat tgtaatttgc    180
agaggatgct tcgggaacgg cccccatcta agtgccctgg aacgggccgt catagagggt   240
gagaatcccg tctgggatgg ggtggccgcg cccgtgtcaa gctccttcga cgagtcgagt   300
tgtttgggaa tgcagctcaa attgggtggt aaatttcatc taaagctaaa tattggccgg   360
agaccgatag cgcacaagta gagtgatcga a                                  391

SEQ ID NO: 84         moltype = DNA  length = 124
FEATURE               Location/Qualifiers
source                1..124
                      mol_type = genomic DNA
                      organism = unidentified
SEQUENCE: 84
gggtctggtg gcgatagcga gacgccaca cccgttccca tgccaaacac ggaagttaag     60
cgtctcagcg ccgaaagtag ttgggggatc tcccctgtg aggataggac gttgccaggc    120
aaaa                                                                124

SEQ ID NO: 85         moltype = DNA  length = 717
FEATURE               Location/Qualifiers
source                1..717
                      mol_type = genomic DNA
                      organism = unidentified
SEQUENCE: 85
agatggagcc tgaccaagaa gagtctgaag aggaagaaga ggaagaggat gacgagatgg     60
atgaagatga ggatgagggc cagcagcagg acgccagtgg catgcagaca ccctctgggc   120
tcgccacgcc ctcaggctat gcctctacta catctacaat gcctggtggc atggagacgc   180
ctgactttat ggacttgcgc aagcagcgac agacgcgcga cgagaccgct gatcaagagg   240
accagggtgc accgcgagac ctctatacgg tcgtgcccga gcgcagagcc accgcttctg   300
gcttcctcgg ttctgaccgc gcctatgact tgtccaatgc tccacagtct tccaacatcg   360
ctgtgttggg tcaagaagac tcgcgcaaga agaaaggcgg cagatctggt gcagacgacg   420
tcgacctggc cttggatcca gctgagctcg agggcatgtc tgagcaagag cttaggcaga   480
agtacgactc gcacaggcgc tcctcgtcca gtcaaggcgc cggcggacag caggacaaag   540
aagatttctc agatttcgtc gcgcaagagg tcgcaaagaa gaggcaggag gctcagcagc   600
gcggcggcag tggacgcgac cgcgaaagct ctcggagcaa ggaaaagttc aagttttaga   660
gtgtatgttt gtattgtatg aagatcgagc aaaaaatgcta tgggtggcgt tgctgct     717

SEQ ID NO: 86         moltype = DNA  length = 872
FEATURE               Location/Qualifiers
source                1..872
                      mol_type = genomic DNA
                      organism = unidentified
SEQUENCE: 86
cgtgtagcat aaagctagaa gtaatattca cagctaactc tacagtagaa caaagttctt     60
gtttcgttct ccagatccaa gtgatagcaa ctgcttcaca aggatggaag aaccaaattg   120
ttgaaagatt cggcacctaa taggcggcac ccatgttgaa atcgtcagtc atgttgaaac   180
tccgtaaacc cgcttttggt gccctctaat ccgcaaaacc ttgaaaccct atgttgaact   240
tttggtatca tcttcgtaat cgtcataaaa cagaactccc cgtgccagag gcggcaggtt   300
gagaataccg ccccttgaat taacacatta taggaagtgg aacaaaggaa aaatgagaaa   360
tgttaatgcg cacagaatta ctgagtgtac ttctggcggt agaacttagc agcctcgacc   420
agagaggtca gctggccgat agtctgctca gtggtacggg tcttcagacc cgagtcaggg   480
ttgatccaga gctgctcagg cttgaggtac tggagcatct gctcgatacg ctccttgatc   540
tcatccacgg agggaacacg aggagagtgg atatcgtaga caccaggtcc aatgtgggcg   600
gggaaactct gatcaacgaa gacctggagg agcttggcat cggacttgct gttctcgatg   660
gacaaaacat cggtatcaag ggcagcaata gcgtggaaga ttcactgtag                   720
cagaagtggg agtggacctg ggtgctgtcg gtgacaccag cagtagacag cttgaaagca   780
ttgacagccc acttaacata agcatcacgg gcagcgccag tacgcagagg aagaccctca   840
cgcagggcag gctcgtcgac ttggatgacc cc                                 872

SEQ ID NO: 87         moltype = DNA  length = 872
FEATURE               Location/Qualifiers
source                1..872
                      mol_type = genomic DNA
                      organism = unidentified
SEQUENCE: 87
ggggtcatcc aagtcgacga gcctgccctg cgtgagggtc ttcctctgcg tactggcgct     60
gcccgtgatg cttatgttaa gtgggctgtc aatgctttca gctgtctac tgctggtgtc    120
accgacagca cccaggtcca ctcccacttc tgctacagtg aattccagga cttcttccac   180
gctattgctg cccttgatac cgatgttttg tccatcgaga acagcaagtc cgatgccaag   240
ctcctccagg tcttcgttga tcagagtttc cccgcccaca ttgacctgg tgtctacgat    300
```

```
atccactctc ctcgtgttcc ctccgtggat gagatcaagg agcgtatcga gcagatgctc      360
cagtacctca agcctgagca gctctggatc aaccctgact gcggtctgaa gacccgtacc      420
actgagcaga ctatcggcca gctgacctct ctggtcgagg ctgctaagtt ctaccgccag      480
aagtacactc agtaattctg tgcgcattaa catttctcat ttttcctttg ttccacttcc      540
tataatgtgt taattcaagg ggcggtattc tcaacctgcc gcctctggca cggggagttc      600
tgttttatga cgattacgaa gatgatacca aaagttcaac ataggggttc aaggttttgc      660
ggattagagg gcaccaaaag cgggtttacg gagtttcaac atgactgacg atttcaacat      720
gggtgccgcc tattaggtgc cgaatctttc aacaatttgg ttcttccatc cttgtgaagc      780
agttgctatc acttggatct ggagaacgaa acaagaactt tgttctactg tagagttagc      840
tgtgaatatt acttctagct ttatgctaca cg                                    872

SEQ ID NO: 88          moltype = DNA   length = 362
FEATURE                Location/Qualifiers
source                 1..362
                       mol_type = genomic DNA
                       organism = unidentified
SEQUENCE: 88
gttgacctcg gatcaggtag ggatacccgc tgaacttaag catatcaata agcggaggaa      60
aagaaaccaa cagggattgc tctagtaacg gcgagtgaag cagcaatagc tcaaatttga      120
aatctggcgt cttcggcgtc cgagttgtaa tttgtagagg atgcttctgg gcagccaccg      180
acctaagttc cttggaacag gacgtcatag agggtgagaa tcccgtatgc ggtcggaaag      240
gcaccctaca cgtagctcct tcgacgagtc gagttgtttg ggaatgcagc tctaaatggg      300
aggtaaattt cttctaaagc taaatattgg ccagagaccg atagcgcaca agtagagtaa      360
cc                                                                     362

SEQ ID NO: 89          moltype = DNA   length = 663
FEATURE                Location/Qualifiers
source                 1..663
                       mol_type = genomic DNA
                       organism = unidentified
SEQUENCE: 89
gaccctcact ctctttctcc ctctcttaca tagcgagctg gtctccatcc ttgttgtttg      60
atttgatctt ctttgcattt ccctatccca gtgatgaagt tatccaattc cgctcattac      120
tcgcttttcc tcctatcctc catcctcggc ttctccagcg cgtcggccaa ctctcacctc      180
agtgatgatt ctccttgtgt ggccgctcg ccaacaagtg ggctctatta tgatctgaat      240
gctatctcat tagcaccgcc ggaatggaag aacgggaaga aagttgatca ggaagcgcga      300
gatgaaagct ggcatgccaa ggggcatgac taccccgcga acttcacaat caatgtctgc      360
gcgccggttc ttgagaatgt aaccaatgtt gtcgggtag atgcctctcg atgggcgaat      420
gtcagtgctt tctatgagca agctgggaag atatactcaa tgggagagca agcctccgag      480
cctttcttcc gcggccgcaa gctagtactc aactacacgg acggttcgcc atgtcccggt      540
gattcgaata ctgctagcgg caatagctct attcgaacca agtccactct gatgtccttc      600
ctctgcgatc gcgcggccga attccccggg ctcgagaagc ttggatccac cggatctaga      660
taa                                                                    663

SEQ ID NO: 90          moltype = DNA   length = 1243
FEATURE                Location/Qualifiers
source                 1..1243
                       mol_type = genomic DNA
                       organism = unidentified
SEQUENCE: 90
atgtccatcc gcaatgaatg gcttcaatga gaaaggcctc gacggggatg cctttggaga      60
gaagtccaat ctctccgggc taaagacatt tgacgctttc cccaaaacaa aaacatccta      120
cacaacccca acccgacgag gcggccaatg gaccgttctc atcctagcag tatgcacact      180
attcagcctc cacgaactcc gcacctggtg gcgcggcaca gaagcccacc acttcagcgt      240
ggaaaaaggc gtatcccacg atctccaatt aaacctcgat atggtcgttc acatgccctg      300
tgacactctc cgcataaaca ttcaagacgc ctccggagac cgcgtttag ctggcgaact       360
cctaacccgc gaagacacaa actgggaccc ttggatgaag aagcgcaatt cgaatcccca      420
cggcgaacac gaataccaaa cgctcaatca tgaagcggct gatcgattaa gtgcgcagga      480
tgaagacgcg cacgtacacc atgtcctggg tgaagtgcgc cgtaacccgc gccgcaagtt      540
ttctaagggt ccacgtctac gctggggcga taacaaggat tcttgtcgaa tttatgaag       600
tcttgaaggg aataaagtgc aaggggattt ccatattacg gcacgggac atggatatat       660
ggaattggcg ccgcatttgg atcacgaagt cttcaattc tcccacatga ttacagaact       720
gtccttcgga ccacactatc catcccttct aaaccctctt gacaagacca tcgccgaaag      780
cgaaacccac taccagaaat tccaatactt ccttccgtcc gtcccgaccc tctactcaaa      840
gggccacaat gcacttgacc tcgtgacaac aaatataagat aactccgtcc gctacggccg      900
taacacaatc ttcacaaacc aatacgcagc cacaagccag agtaccgcc tccctgaaat       960
ccccacccta atcccgggaa tcttttttcaa gtataatatc gagccgatct tgctacttgt      1020
cagcgaagag cggacgggat tcttggctct tgtcattcga gtcattaata ccgtttctgg      1080
ggtcttggtt acgggtggtt ggatcctacc gatttcggg tggattgttg agatccttgg       1140
gaaaaggaaa cggcagtctg agggtgtttt gactggggaag cattattcgg attgatttgt       1200
ttctagtagt ttcgtctcaa tataagtttg atttccttt tcc                         1243

SEQ ID NO: 91          moltype = DNA   length = 1007
FEATURE                Location/Qualifiers
source                 1..1007
                       mol_type = genomic DNA
                       organism = unidentified
SEQUENCE: 91
gaacggtgat agtagtagta ggctcgtcat ctatctacaa cccctctctc ctcactcccc      60
```

```
tctctcgacg ccatgttcac gcgtactctc cgaccggccg tggcggtcgc caggactcag    120
gctgtccagc agcaacaggc cggtatggcc acattgaagg aaatcgacca gcgtttgaaa    180
tccgtcaaga acattgggaa gatcaccaag tcgatgaagg tcgttgcctc gaccaagttg    240
acgcgagctg agaaggccat gcgtgaagcc aagaagtacg tgccgccaa caacgttctg     300
ttcgagcaga ccaaggctgg tgaggaggag cccaaggagc gcaagatcct ctacctcgcg    360
atgacatccg acggtggtct gtgcggtggt atccactcca acattacgcg atacatgaag    420
aaggctgtgg ccaaggaacc cggaatgctg gctgttgtcg gtgacaagcc caaggctcag    480
ctctctcgag cgatgcccaa ggctttgacc atgtctttca acggcgtcgg caaggatgtc    540
cccactttcg tcgaggccag cgctatcgcc gatgagatta tgaaatctgc cggtgacttt    600
gacgagatcc gaatcgtctc taacaagtac ctttccgcta tcgcctacga acctcacacc    660
aacgccgtca tctccgctga ggcactccga caagccgccg gtttcagca atacgagatg     720
gaggaggatg tctccaagga cttggccgag ttcgctcttg ccaacgccat ctacactgcc    780
ctggtcgagg acacgccgc cgagatctct gcaaggaggc aagctatgga gaacgcttcc     840
aacaacgcca acgacatgat caactctctc cagctgcagt acaaccgtgg tcgacaggct    900
gtcattacca ccgagctgat cgatatcatt accggtcgcct cggctctgta agcgggtgta    960
gactagatgc acaaaacaac aaaaatggca tgcagcgaat gacattg                  1007

SEQ ID NO: 92        moltype = DNA   length = 1007
FEATURE              Location/Qualifiers
source               1..1007
                     mol_type = genomic DNA
                     organism = unidentified
SEQUENCE: 92
caatgtcatt cgctgcatgc cattttgtt gttttgtcca tctagtctac acccgcttac     60
agagccgagg caccggtaat gatatcgatc agctcggtgg taatgacagc ctgtcgacca    120
cggttgtact gcagctggag agagttgatc atgtcgttgc cgttgttgga agcgttctcc    180
atagcttgcc tccttgcaga gatctcggcg gcgtgtccct cgaccagggc agtgtagatg    240
gcgttggcaa gagcgaactc ggccaagtcc ttggagacat cctcctccat ctcgtattgc    300
tggaaaccgg cggcttgtcg gagtgcctca gcggagatga cggcgttggt gtgaggttcg    360
taggcgatag cggaaaggta cttgttagag acgattcgga tctcgtcaaa gtcaccggca    420
gatttcataa tctcatcggc gatagcgctg gcctcgacga aagtggggac atccttgccg    480
acgccgttga agacatggt caaagccttg ggcatcgctc gagagagctg agccttgggc    540
ttgtcaccga caacagccag cattccgggt tccttggcca cagccttctt catgtatcgc    600
gtaatgttgg agtggatacc accgcacaga ccacctgcag atgtcatggc gaggtagagg    660
atcttgcgct ccttgggctc ctcctcacca gccttggtct gctcgaacag aacgttgttg    720
gcggcaccgt acttcttggc ttcacgcatg gccttctcag ctcgcgtcaa cttggtcgag    780
gcaacgacct tcatcgactt ggtgatcttc ccaatgttct tgacggattt caaacgctgg    840
tcgatttcct tcaatgtggc cataccggcc tgttgctgct ggacagcctg agtcctggcg    900
accgccacgg ccggtcggag agtacgcgtg aacatgcgt cgagagaggg gagtgaggag    960
agaggggttg tagatagatg acgagcctac tactactac accgttc                   1007

SEQ ID NO: 93        moltype = DNA   length = 1139
FEATURE              Location/Qualifiers
source               1..1139
                     mol_type = genomic DNA
                     organism = unidentified
SEQUENCE: 93
acctcactt tgtgcgaatta tcctcctaca gcatcagctc tcttcagaaa gaggctaaat    60
ctatagaccg tccggaacag gttgtcaaca cgcgcgataa gagaagaagg gaatctactg    120
gtagacaaca gatcgatcgc tcttcagcaa acgcaagatg gagaaccttc ttcgtcagat    180
gcaaggggga ggtggtagga tgggtgcacg gccaggccgt ggaggcgaaa ctatccgatc    240
cgacaacggt gaaacagtcc atatttcatc tcttgctcta ttgaagatgc tcaagcatgg    300
acgagcgggt gtgccgatgg aagtcatggg tctcatgctt ggcgaatttg ttgatgacta    360
cactatctcc tgtgtcgacg ttttttgcaat gcctcaatcc ggtacgacag tgacggtcga    420
atcagtggat cacgtctttc aaaccaagat gttggatatg ttaaaacaga cgggccgacc    480
cgagatgggtc gtcggttggt accactcgca ccccggtttt ggttgttggc tgtccagtgt    540
cgatgtcaac actcagcagt ctttcgaaca gctacatccg cgagcagtag ccgtttgtcat   600
cgacccctatc cagtctgttc gtggtaaagt cgtcatcgac gctttccgat ccatcaaccc    660
tcaatcactt gtcgctggac aagagtcgag gcaaacaacg agtaacattg gtcatctgaa    720
caaaccgtcc attcaggctc tcatacacgg tctgaatagg cattactaca gtctggccat    780
cgattacagg aaaacagaag gggagcaggg tatgttgttg aacctgcaca agcggggatg    840
gacagagggt ttgaagatgc gtgatcactc agagatgaag gagggtaatg agaaggcaat    900
caaggaaatg ctctctcttg cctcggccta cacgaaatct gttcaggaag acgacaat     960
gacggccgaa cagcttaaaa cccgtcacgt aggaaagctt gatccaaaac gtcatttggg   1020
cgaggcggct gagaaagcga tgggtgatca agtgacgcag agtctggcca tgggtgtcct   1080
ggctgagctg tagacgtaga agagggaaga aaggaaacga catgcattgt acatatcgc    1139

SEQ ID NO: 94        moltype = DNA   length = 526
FEATURE              Location/Qualifiers
source               1..526
                     mol_type = genomic DNA
                     organism = unidentified
SEQUENCE: 94
aacccacccc gccattctca attcttcgtc cgtgttcttc tcgagaagct acacttcgca     60
aaaatggggtg ccattccgga atatgatccc gaggagcccc tcgagaccaa gcccttcaag   120
ttcgtgactc ctggttacga cgctcgtttc ccccagcaga accagaccaa gcactgctgg   180
caaaactac tcgactacta caagtgtgtc gaggccaagg gtgaagactt ccgcccctgc    240
aagcagttcc accacgcttt ccgctccctc tgccccaagg cctggactga ccgctgggac    300
acccagcgcg agggtggtaa cttcccctgct atccttaaca aatagataac caatggctgc    360
```

```
tttgtgttgg tgaattgggt tatagcagat tctgtattga caaactttcc aatgtactct    420
acctggtcat gcggggatac atttcttttc tgtttggatg taattttccc actctgatga    480
agaaagtgtg tctataaact cgctgttttg aaactaaacg tcttcc                   526

SEQ ID NO: 95           moltype = DNA   length = 839
FEATURE                 Location/Qualifiers
source                  1..839
                        mol_type = genomic DNA
                        organism = unidentified
SEQUENCE: 95
gggccattgc tcgaggagct cgatgtcgag gcgtacgcca agaagtaccg ttacctgaga    60
ttcatgtgcc aggagacgct ggaccatctc gcctttctca aggacaaagt gaaggatgtc   120
gaagggttct gggcatccac cttgttgaag caccgcgatc tcaggggcta catcacttca   180
cgatccgaca aggacgcatt gaagtacttg actcacattg agctcgttca ggatcccaag   240
gatccccgtc cgttcgctct caaattctac ttcaaggaga acccatactt ctccgacttg   300
gtcttggaga agaagtacga tatgtccgag ggttccgaac ccgcacctgc cgatggtagc   360
attacgcgag gaatgcgcaa tttcaaagaa gacgagctgg tcaccaaggc taccacgatc   420
aactggaagt cggacgacaa gaatctagtc gccaagcagc ccagatccaa aattcccgac   480
aatgacgacg atgaagattt cgacgggac gtcggatcgt tcttcaacta ctttacagat    540
gacacagata ttttccagat tggggccctc ctgcagtcgg agctactgcc tgatgccatc    600
gactactttg ttggccgagg cgagcaggtg gactctgaag gagaggagct agacgagctg    660
gaagagagatg atgaagacga cgatgaggat gatgagggca gtatcgacct cgaagacgag    720
gaggagcagc cgagtaaaaa gaagcccaag agggcctaag aaacatttga tccgtcaaca    780
tgtacggacg aggtaatcgt gttcgaatgt taatgatcat gcatatgcta gtaaattcg     839

SEQ ID NO: 96           moltype = DNA   length = 804
FEATURE                 Location/Qualifiers
source                  1..804
                        mol_type = genomic DNA
                        organism = unidentified
SEQUENCE: 96
ggatctttcc tcacccctca acacactcac acaccattcg gacgcgctat gcacaatgcc    60
ttgacggttt cgaggctcaa cgacaagttc aagagccgc tcgttgttct tgtgagctt     120
ttgcgtgctc gtgttctgca cgaccgcaac ttctcgaaca gacaattctc aggtggtcct   180
tcattcggga cagacaatca gaagagaagc atgcttttga tcttccgtac tctgtccatt   240
attccgctcc aattcaaggc cgagcactgg tcaggaccat tgtcaagaga gctgcttgtc    300
ttcaactcat tccacaagac actgtcaaga tccctgagaa cgctggtcga atcaatcact    360
atgaacgcct tcctcaagaa caatgcgaga agagcacgtg acgactatct tgacattgca    420
ctttcactac cattccaaaa cgataccaac actggattcg gtatcttctt taagatttac    480
ttggatgcat tgactacatt tgcagaaggc aacatcactg aagagaacaa agacagcgag    540
tctgtgaaag aggccaagca gtcagcaatg gagatcctag gtgacgccat accgaacgtg    600
aaggacccag aggccgagct tttgcggggt ttcagattct gggatgctgt gctcgtgtgc    660
gtccgtacac tcaaagcaga cagggcaatc gatctcaagc tagctgagtc tttcgaggcg    720
gcaaacagct accttaatat gatgagacca aattgatacg gcgttttgta gcaatcttga   780
gctttatgca atctacttct gtcg                                           804

SEQ ID NO: 97           moltype = DNA   length = 848
FEATURE                 Location/Qualifiers
source                  1..848
                        mol_type = genomic DNA
                        organism = unidentified
SEQUENCE: 97
ggatctttcc tcacccctca acacactcac acaccattcg gacgcgctat gcacaatgcc    60
ttgacggttt cgaggctcaa cgacaagttc aagagccgc tcgttgttct tgtgagctt     120
ttgcgtgctc gtgttctgca cgaccgcaac ttctcgaaca gacaattctc aggtggtcct   180
tcattcggga cagacaatca gaagagaagc atgcttttga tcttccgtac tctgtccatt   240
attccgctcc aattcaaggc cgagcactgg tcaggaccat tgtcaagaga gctgcttgtc    300
ttcaactcat tccacaagac actgtcaaga tccctgagaa cgctggtcga atcaatcact    360
atgaacgcct tcctcaagaa caatgcgaga agagcacgtg acgactatct tgacattgca    420
ctttcactac cattccaaaa cgataccaac actggattcg gtatcttctt taaggttggt    480
ggccttgcag gagtctgaca tagcgctgac gcagacagat ttacttggat gcattgacta   540
catttgcaga aggcaacatc actgaagaga acaaagacag cgagtctgtg aaagaggcca   600
agcagtcagc aatggagatc ctaggtacgc ccataccgaa cgtgaaggac ccagaggccg   660
agcttttgcg gggtttcaga ttctgggatg ctgtgctccgt acactcaaag               720
cagacagggc aatcgatctc aagctagctg agtctttcga ggcggcaaac agctacctta   780
atatgatgag accaaattga tacggcgttt gtagcaatc ttgagcttta tgcaatctac    840
ttctgtcg                                                             848

SEQ ID NO: 98           moltype = DNA   length = 628
FEATURE                 Location/Qualifiers
source                  1..628
                        mol_type = genomic DNA
                        organism = unidentified
SEQUENCE: 98
ggggcatcta cctcgacggc aacaacgacc tggtcactat gaagggtaac tacatctacc    60
acaccagcgg ccgctctcct aaggttcagg gtaacacctt gctgcacgct gtcaacaact   120
actggcacga caactccggc cacgccttcg agatcggtga gggtggttac gttctggccg   180
agggtaacgt cttccaggat gttactaccc ccgttgagga ccccgttgac ggccagctcc   240
tcacttcccc tgaccccagc accaacgctc agtgctcgtc atacctggc cgggcctgcg    300
```

```
aaatcaacgg cttcggtaac tctggtacct tcaaccaggc tgacactagc ctgctgtcta  360
aatttaaggg tcagaacatt gcttctgctg atgcttactc taaggttgcc tcgagcgttg  420
ccagcaacgc cggtcaggga cacctgtaaa atggaaagag gaggttcaga gcttaatttg  480
ctcatgtcgg acgacatagc cctagcggct tgctggtgaa tttggcataa tagcgtttct  540
cttctcatac ctactttatt actccgtttg gatccttatt aggtaaatat tagcccattg  600
tatggttcaa ttcgattgac tttgaggc                                    628
```

SEQ ID NO: 99             moltype = DNA    length = 804
FEATURE                   Location/Qualifiers
source                    1..804
                          mol_type = genomic DNA
                          organism = unidentified
SEQUENCE: 99
```
agttggaaat ctgatcaatt actctccatc ttctcgttct actatctaat cctctcttcc   60
ttccaaaaca tatcatcatg tctgctcaac ctctccgcat tgtcatggcc tgtgacgagg  120
ctggtgttcc ttacaaggat gccatcaagg ccgttctcga aagagcccc ctcgtcgcct   180
ccgtctctga cgtcggtgtc aacgatgcct ccgataagac cgcctacccc cacccgccg   240
tcgagggtgc tcaacagatc aaggccggta aggctgaccg tggcctcttc atctgcggta  300
ctggtctagg tgtcgctatc gccgccaaca aggttcccgg tattcgtgcc gttactgccc  360
acgacccttt ctccgtcgag cgttccattc tgagcaacga tgctcaggtc ctctgcatgg  420
gtcaacgtgt cattggcgtc gaacttgcga agaagcttgc cctcgattgg ctcaactacc  480
gtttcgatcc taagagtgcc tctgccgcga aggtccaggc tatctccgac tacgagacca  540
agttcgctgg ctcttcttaa atgcattatc ttgcatgaat gacggtcttc gtacatactt  600
tgccacatat gggttctaat tgcactgcgt ctgcagtctc gatatgaaac cattggattg  660
cgatggatgt ccctttttcca tttgcaactt tttatatact ttcttttcta ccaagcgctt  720
catgatacca cgattcgatt accgagttct gctgtttgct ttggtcggta gatctagata  780
cacaatgcag tatattcgag tttc                                        804
```

SEQ ID NO: 100            moltype = DNA    length = 782
FEATURE                   Location/Qualifiers
source                    1..782
                          mol_type = genomic DNA
                          organism = unidentified
SEQUENCE: 100
```
acttctcctt ttctgttagc tttgactcta ctatcctgct cctcctctaa atccgtggaa   60
tccaattttt tcacaataac ttcgctacca taatgtccgt cactaccact tcctccgccg  120
ccgcagcctc ctgcactccc tcttggcaga ttcctgtcga cgatgttgcc tgtgccggtc  180
agatcagcgg taatatcacc aaggttttcg atacctgctg taagggaaac agccctgtca  240
agtacaacga cgactgcaac atctactgtc ttgcccaagg acaaaccaag caagagttga  300
ccgactgttt gaccgagaag agcggaaaca accagatctt ctgtggtcat ggcaagcaga  360
atgccactgc tacagctgaa gccaccacca ccaaggagac tggcacatcg accggcactt  420
caacctcttc cactggcact tctaccgaga ccaacgctgc cgtgctcaac caacccatct  480
ccaagaccgg tcttggactc gtcgcatgc tcttctgctc tgccctcgtt ggtgttgtcg  540
cctaagttat gactccaaaa cgaacacatt actgcggtat ggatacggca attatgacaa  600
ccagaggacc gcagggacgg agaatggtaa ttgatgaacc cggaaaagat acgtggtgca  660
tggacataaa tgtttgattt actcttactg tctgcttcaa cttccgaga ggaatattgt   720
ttcttctgta ccaatagcga tagcattaac agcatcttaa ttctaatttt gcatatcact  780
tc                                                                782
```

SEQ ID NO: 101            moltype = DNA    length = 693
FEATURE                   Location/Qualifiers
source                    1..693
                          mol_type = genomic DNA
                          organism = unidentified
SEQUENCE: 101
```
gccggggtcg atcgaggtgt catcaccaag gacgagaagg acagcagtat caatagacta   60
ctcgtcactg gttacggtct ggccgaggtc atgggtacag atggtgtgaa cggcatcaag  120
acgcgaacca atcacgtcat ggagacgtgc gaggttctgg gcatcgaagc cgctcgacag  180
accatctaca acgagattca gcataccatg acatgtcaat cgatgtcaat cgatcctcga  240
cacgttatgc tgctcggaga cgtcatgact tacaagggcg aggtgctcgg tatcactcga  300
ttcggtgtgc aaaagatgaa ggactcggtt ctcatgttgg ccagtttcga gaagaccact  360
gatcatctgt tcgatgcctc gctgttttcg aaaaaggatg aaatccaagg cgtctccgag  420
tgtatcatta tgggcacacc cgcgccaggt tgtggcacct cacttgcatc gatcgtcaca  480
cctgccctc tcctcccacg caaaaagcct ttgctgtttg aaacagcgtt caaagctggt  540
caggatcgat tgagctatca cgaaaacaat ggcggcatgg aggtggacat gtgaacccgg  600
tccctcatac atcttcttct gattgtctgt accatacata catcgcattg cttcttttca  660
catacgacac gacatgcatc tgacatctac gac                              693
```

SEQ ID NO: 102            moltype = DNA    length = 776
FEATURE                   Location/Qualifiers
source                    1..776
                          mol_type = genomic DNA
                          organism = unidentified
SEQUENCE: 102
```
gcaggatcag gaggagcata ttccttctct ctgaccacct tctcgccttc tggaaagctt   60
gtccagatcg aacatgcatt ggcagcagta gcgggtggaa caacatcact gggtatcaaa  120
gctaccaacg tgttgtcct tgcgactgag aagaagtcac cgtcactcct gctcgatacg  180
tctgttctcg aaaaggtagc tcctatatgt cccaacattg gtttcgtcta ctcgggtatg  240
ggacccgatt tccgagtcct ggtcgccaaa gctaggaaga tcgcccaagc gtactataaa  300
```

```
gtgtatggcg agtacccacc tacaaaggtt ctagtgcagg aggtggcggg cgtgatgcaa    360
aaggctacgc aatctggtgg tgtgcgacca tatggtatct ccctcttgat cgctggttgg    420
gattcgcacc gaggtcagag cctgtaccaa gtggatccgt caggtagcta ctgggcgtgg    480
aaggcaagcc cgatcggcaa gaacatggtc aacggaaaga cattccttga gaagcgatac    540
aatgacgacc tgtcactcga agatgccatt cacacgcgcc ttctcacgct gaaagaaggt    600
ttcgagggac agatgactga gaacacgatc gagatcggtg tagtgacggt accgacggcc    660
gagcagatgc aggagaagcc aggagagagg ctacctccca cgttcaggaa gttgacggag    720
caggaagtga gggactatct cgccttgtag acgatgcaga cagaacatga ccatcc        776
```

```
SEQ ID NO: 103          moltype = DNA   length = 1191
FEATURE                 Location/Qualifiers
source                  1..1191
                        mol_type = genomic DNA
                        organism = unidentified
SEQUENCE: 103
aagtctacga ctcctccagc caatttactt tgatccaaaa tgttgaccag cgccttttct    60
acatctgctt ccaagatgct cggcaagaga gcagtctcgt cttccagcgc cttgaacgga    120
aaggttgccg tcctcggtgc tgctggcggt attggccagc ccctctcctt gctggtcaag    180
cagaaccctg ctgtctccag cctctccctt tacgatgttc gcggctcccc tggtgttgct    240
gctgacatta gccacatcaa caccctgct gtcaccgagg gcttcctccc cgacaacgat    300
ggcctcaagc aagccctcga gggtgctgag gtggtcctca ttcctgctgg tgttcctcgc    360
aagccggca tgacccgtga cgacctttc aacaccaacg cttccatcgt caagatgctt    420
gctgaggctt ctgccaagta ctgccccaag gctatgatgc tcatcattgc caaccccgtc    480
aactccaccg tgccgatcgt cgctgagacc ttcaagcgtg ctggtgtcta cgaccctgcc    540
cgtctcttcg tgtcaccac cctcgacgtt gtccgctctt ccactttcgt ctctggcatc    600
accggtgcca agccctccga caccgtggtc caggtcatcg gtggtcactc tggcgccaac    660
atcgtgcccc tgctctccca gatccctcag ggcgacaaga ttgtcaaggc tggcggccag    720
cagtacgctg acctcgtcaa gcgcatccag tttggcggtg acgaagtcgt caaggccaag    780
gacggcactg gctccgctac cctctccatg gcttacgccg ctgccgtctt caacgacgct    840
ctcctcaagg ctatgcaacg ccaaaagggt tccgttcaac tctacgt cgagagcgcc       900
cacttcgcca aggagggtgc taagtacttc gcctccaacg tcgagctcgg ccccaacggt    960
gttgagaaga tcctcgacat cggcaacatg tcctctgagg agcaggagct ccttaaggag    1020
tgccttcccc agctcgccaa gaacattgct gctggtgaga gttcgtcgc tgacaactag    1080
aggatatccc acgacgttgc tccctataat aatgagagca agcgagaaca agagaaataa    1140
agacatagca aattgaatag ggcttccaac tgcaccaaaa agcagtgatg c            1191
```

```
SEQ ID NO: 104          moltype = DNA   length = 1191
FEATURE                 Location/Qualifiers
source                  1..1191
                        mol_type = genomic DNA
                        organism = unidentified
SEQUENCE: 104
gcatcactgc ttttggtgc agttggaagc cctattcaat ttgctatgtc tttatttctc     60
ttgttctcgc ttgctctcat tattataggg agcaacgtcg tgggatatcc tctagttgtc   120
agcgacgaac ttctcaccag cagcaatgtt cttggcgagc tggggaaggc actccttaag   180
gagctcctgc tcctcagagg acatgttgcc gatgtcgagg atcttctcaa caccgttggg   240
gccgagctcg acgttggagg cgaagtactt agcacctcc ttggcgaagt ggggggctctc    300
gacgtaagcg ggttgaacga dacccttttg gccgtccata gccttgagga gagcgtcgtt   360
gaagacggca gcggcgtaag cctggagag ggtagcggag ccagtgccgt ccttggcctt    420
gacgacttcg tcaccgccaa actggatgcg cttgacgagg tcagcgtact gctggccgcc   480
agccttgaca atcttgtcgc cctgagggat ctgggagagc aggggcacga tgtcgtccaa   540
agagtgacca ccgatgacct ggaccacggt gtcggagggc ttggcaccgg tgatgccaga   600
gacgaaagtg gaagagcgga caacgtcgag ggtggtgaca ccgaagagac gggcagggtc   660
gtagacacca gcacgcttga aggtctcagc gacgatcggc acggtggagt tgacggggtt   720
ggcaatgatg agcatcatag ccttggggca gtacttgcga gaagcctcag caagcatctt   780
gacgatggaa gcgttggtgt tgaaaaggtc gtcacgggtc atgccgggct tgcgaggaac   840
accagcagga atgaggacca cctcagcacc ctcgagggct tgcttgaggc catcgttgtc   900
ggggaggaag ccctcggtga cagcaggggt gttgatgtgg ctaatgtcag cagcaacacc   960
aggggagccg cgaacacgt aaaggagag gctggagaca gcagggtct gcttgaccag    1020
caaggagagg ggctggccaa taccgccagc agcaccgagg acggcaacct ttccgttcaa    1080
ggcgctggaa gacgagactg ctctcttgcc gagcatcttg gaagcagatg tagaaaaggc   1140
gctggtcaac attttggatc aaagtaaatt ggctggagga gtcgtagact t            1191
```

```
SEQ ID NO: 105          moltype = DNA   length = 1505
FEATURE                 Location/Qualifiers
source                  1..1505
                        mol_type = genomic DNA
                        organism = unidentified
SEQUENCE: 105
ggggcaagcg tgctgcttcc ggcactgcat ttcgacgagc gggagcaacg acctggacgt     60
acgtcttcga ctgcaagtct gctgcagcgt cacgatcgca atgaaccttt atcgctcaac   120
tcgcactcgc cgacatctgt ggaccacact cccactactg cgcatttcac tggtgctgaa   180
gagttgctcg cctccgacgt cggaccgacc gcgacagctg ggctacccgg tgatgcgag    240
cttgagagca agctcaagct gcttgaagag tcaaacgtg cacgggaatc ggtacatagc    300
tcgctcgaga ggatcagagc cggcacgcct accccgtcta tcagccaggg aatgccagc    360
ccgacaccct ctggtgcccc tggttacgct agaactccgt cgtctgtcgg cctgtcggac    420
gacgtgcgct cgagacgagg ctcaacgacc agctccaagg ttcttgacgc tatcgacaag    480
cctcgagtcg ctacccaatc cgaatgggac gagtacgttc gcaaccggca tgtcatctca    540
cctccacccca ctcagtttgc cgtattgccc acatctgctg cgatggtcga tcgtggtacc   600
```

```
agtcgacaca gccagtatgc ccttgtttcc gacggcgttg ccaaagcgct tgacaggcgg   660
gagcgaacta tttcaatgat ggagccgcaa gttgccgagg actgggggacc aagagagacg   720
ctcgacagca ctccggctca tgtctcgatg ggccgtcgag ccatgtcatt ccatgagata   780
cctctggcat cgcctgtcgc tgcctctcga cctcaggacc gctcctccta ctctgccgga   840
ccacgtcagg tcatagggtc agctgctggc cacacgcagg gacccgggtat cagtcaatcg   900
agatcagccc acggccggac tatgacatac gacgagctga cggagagaca tcgtcagcgc   960
ttgtcggcat tgcaagcgcc agtcagcgcc aaaatcaggg agccgatgga catcgcgtcc  1020
gccaaagcca gctgggacaa gcaaaagcgg gtcgagcggg acgaaatgaa gaggcgagaa  1080
gccgagaagc tcgctcaggc tcacgcaaga gagcgacgag ggccgcgctgt cgacaagaag  1140
gaagttctca agtcgaccga cgaatggagg cgaagcgtcc acgcgggtct cgacggtttc  1200
gccgttccgc acctaccggc ccacgctcga ggttccacgc agcctggtgg atccggcgcc  1260
aagcgatctt cactctctca aaggcccagc aactacttcg ccaactaggc ataatcgaat  1320
cgcggacagt catctgtaca tagaaccgta cctgtattac caaccctgca cttccgctca  1380
cacctgttgc ctataccttcg tctaccaacg ctcattccaa tatcatagct acattccttt  1440
gcaaggacac tatcacaccg cagtcatgac tccgtatgga tattcaatgc ataccctctt  1500
cagag                                                              1505

SEQ ID NO: 106          moltype = DNA   length = 1391
FEATURE                 Location/Qualifiers
source                  1..1391
                        mol_type = genomic DNA
                        organism = unidentified
SEQUENCE: 106
aacctcggcc gagaggacaa gattatcaag aatgggatct cctgcgcctc accaccgcca    60
tcaatcctca cttgaaggag tcattgactt ttctactggt agaggcatc cattgaatcc    120
ctatcaacgc gacaaggccg agagcgtttt tactggcatt atcaaccgct tcgaggactc   180
gtcgaccgta gagaaaccat acaaccgtgc caagctggtt cgcctgacgt atgagtatgc   240
tcgctcggaa gattctcgat gcaatttctt gcaagcattc ttcggatcag taaacgttac   300
gatggatgac tctattgatt tcgacgatga agcggtagaa gaggggattc gctcgagcct   360
gaattcctc gcagatttct tggtggagaa cttcttcctt ccactcaagg cttccgccag    420
caggacgccc ccagcccccc agcccaagtt ccgagcagca gtcctgctgt ggggtctgtg    480
gaaagagtgg cctcgctcag acgcgactgc ctcatccgcg atcgacatcg ttgcgtaatc    540
tctcgcaact tcgacatgaa agaagctgag cgacgtcttg acgatagcgg atatgaccat    600
gcctcggacg atgaaggaca tttactgaaa gatcaggagc atgggtcatt cgcggaacta    660
gaagttgcgc atatacttcc tcactcattg atgactacga tcgcgaactc cgagctgaac    720
aagtccaaag aaacggcatt gacaatactt aatatgttcg acagtggcat tgtccatcta    780
atcgacggtc cagacattga tcgccctcga aatgctctta ccttaagcat tgacctccat    840
cgacagtttg gcaacttcaa ggttttttt gagcctatgc ctgagcccca tacctaccgg    900
attgattcaa ccctccgcca gccatttaga aacccgatct tcctgtaac ccgtgcactc    960
tacctcacccc ctgagcgaac tattgatccc ccgtccggtc gacttcttgc cgttcatcgc   1020
gcaatttgcc acatttttaca tctcagtgct gctgggaatt acatcgacag catacttcgc   1080
gacatggatg acgggactgt acaagccaac ggctcgactc gcctggctag catagttcgt   1140
ctgaaactgg ggggttggtg ggatgggcact gttgttgaat agtcaaccac ttcgacccctc  1200
tccatacacc acaacggcaa ctcgagctga tgcataccg atctacctac gccattcgcg    1260
tggaggattg tcgcatatca ccactaggtt cgtgcgactg gatatgaaac gcggcccgta   1320
ctttggggtc gtgtatccgg tttcacatcc agcttgtcgc atcaaggatt ccaatcctaa   1380
cgacatgagc c                                                        1391

SEQ ID NO: 107          moltype = DNA   length = 665
FEATURE                 Location/Qualifiers
source                  1..665
                        mol_type = genomic DNA
                        organism = unidentified
SEQUENCE: 107
ggacgaccga aataccgtca aaatggtcaa catcccgaag acgcgcagga cctactgcaa    60
gggcaaggaa tgcaagaagc acacccagca caaggtcacc cagtacaagg ctggcaaggc   120
ctccctcttc gcgcagggta agcgtcgtta cgaccgtaag cagtccggtt acggtggtca   180
gaccaagccc gtcttccaca agaaggccaa gaccaccaag aaggtcgtcc tcagattaga   240
atgcacttcg tgcaagacca aggcgcagct cgctctcaaa cgctgcaagc acttcgagct   300
tggtggtgac aagaagacca agggtgccgc tcttgtcttc tagatgggtg cataacggtt   360
atggcgctag ggatgatgat ggagcggtct gtgcatgtag cctccttgag tacatgatcc   420
tcgagggctc ggaatcaaag cttcgtttct cctacgatcg tcccactcgc aaagacatgt   480
ctcgtcatat catggcttgc gcacaacatt cttcgagggt ccatcagaga tgcccgaccc   540
tgccgctacg ctgcgtggga tgtgactcca gcacaaccgc cttccagtat catctcttcg   600
cgtgcagaag tgaggacgat tttacgacag tccatataac aaatcgaaa tgccaacaag    660
atcaa                                                               665

SEQ ID NO: 108          moltype = DNA   length = 1327
FEATURE                 Location/Qualifiers
source                  1..1327
                        mol_type = genomic DNA
                        organism = unidentified
SEQUENCE: 108
ggcccctctt gaactttgga cttttttagca tctattttct ctacttctct ctccctcctc    60
ctatctacct tctctatcat ctccttcagc tccctacaac atgaagctca cctttaagga   120
cctgaagcag gagaagttcg taatcgaggt cgagccctcc gagactgttc gcgaagtcaa   180
gcaaaaaatt gctcaagaaa aaggcgaata tgaggcggaa cgaatgaaag ttatctactc   240
gggcaagatc cttcaggatg acaagaccgt cgaatcatac aacatccagg agaaggattt   300
cctagtctgt ctgccttcaa agggtcctaa gcccgctgcc tcgtcgtctg cctcccaggc   360
```

```
accegecact cegecceccta gagetectgt tgctactect getectectg ccccegetge  420
tcctgcacct gctagttcta cgcctgctgt ccctgcgact ccctcgcctg ctggcgccca  480
gaccggtccc tctttcggtg acccatctgc attgaccatg ggttctgcgg ctgagggtgc  540
cgtcactcag atgaagcaa tgggatttgc agaagcgat attgaccggg ccatgcgggc   600
tgcattcttc aatcctgacc gcgctgtcga ttacctcttg aacggtattc cgccgatgt   660
tcaacaggaa caacagcagc ggcaacaaga gcaacaagcg gaccgtgctg cagaacaagc  720
tcctgtgccc agcgctgagg atgctgctgc tgccgccgct ctgggtggcg atgagggttt  780
taacatgttc gaggctgccg ctcaggctgg tgatggtcgt ggtggtggtg ctcggtctgg  840
aggtagcgag gcccttgcga acctggactt tctccgcagt aacccccatt tccagcaact  900
gagacagttg gtccagcagc agccgcacat gctcgaaccc atcctgcaac aggttgctgc  960
cggaaaccca cagatttccc agatcattgg ccaaaactct gaacagtttc tccaactgct 1020
aagtgaggag ggtgatgagg aagatgcggc cctgcctcct ggtacacaag ctatctccgt 1080
tacagaggag gagcgggacg ccattgagcg gttgtgccgc ctgggtttcc ccgggattcc 1140
cgtcatccag gcctacttcg cctgcgacaa gaacgaagaa ctcgcagcaa acttcctctt 1200
cgaccagccg gacgatgatg aggagtaaat ctgatccacg atgctgtggt tcacttcttt 1260
actccatgtc ttatcccctt ccccttttgc ttctttacgt tctgatgaat accaagcatg 1320
cctgttg                                                           1327

SEQ ID NO: 109          moltype = DNA   length = 1326
FEATURE                 Location/Qualifiers
source                  1..1326
                        mol_type = genomic DNA
                        organism = unidentified
SEQUENCE: 109
ggccctctt gaactttgga ctttttagca tctattttct ctacttctct ctccctcctc  60
ctatctacct tctctatcat ctcctteage tccctacaac atgaagctca cctttaagga 120
cctgaagcag gagaagttcg taatcgaggt cgagccctcc gagactgttc gcgaagtcaa 180
gcaaaaattg ctcaagaaaa aggcgaatat gaggcggaac gaatgaaagt tatctactcg 240
ggcaagatcc ttcaggatga caagaccgtc gaatcataca acatccagga gaaggatttc 300
ctagtctgtc tgccttcaaa gggtcctaag ccccgctgcct cgtcgtctgc tcccaggca  360
cccgccactc cggcccctag agctcctgtt gctactcctg ctgctcctgc ccccgctgct 420
cctgcacctg ctagttctac gcctgctgtc cctgcgactc cctcgcctgc tggcgcccag 480
accggtccct ctttcggtga cccatctgca ttgaccatgg ggttctgcgg ctgagggtgcc 540
gtcactcaga tggaagcaat gggatttgcc agaagcgata ttgaccgggc catgcgggct 600
gcattcttca atcctgaccg cgctgtcgat tacctcttga acggtattcc cgccgatgtt 660
caacaggaac aacagcagcg gcaacaagag caacaagcgg accgtgctgc agaacaagct 720
cctgtgccca gcgctgagga tgctgctgct gccgccgctc tgggtggcga tgagggtttt 780
aacatgttcg aggctgccgc tcaggctggt gatggtcgtg gtggtggtgc tcggtctgga 840
ggtagcgagg cccttgcgaa cctggacttt ctccgcagta accccccattt ccagcaactg 900
agacagttgg tccagcagca gccgcacatg ctcgaaccca tcctgcaaca ggttgctgcc 960
ggaaacccac agatttccca gatcattggc caaaactctg aacagtttct ccaactgcta 1020
agtgaggagg gtgatgagga agatgcggcc ctgcctcctg gtacacaagc tatctccgtt 1080
acagaggagg agcgggacgc cattgagcgg ttgtgccgcc tgggtttccc cgggattcc  1140
gtcatccagg cctacttcgc ctgcgacaag aacgaagaac tcgcagcaaa cttcctcttc 1200
gaccagccgg acgatgatga ggagtaaatc tgatccacga tgctgtggtt cacttcttta 1260
ctccatgtct tatcccctto ccctttgot tctttacgtt ctgatgaata ccaagcatgc 1320
ctgttg                                                           1326

SEQ ID NO: 110          moltype = DNA   length = 1162
FEATURE                 Location/Qualifiers
source                  1..1162
                        mol_type = genomic DNA
                        organism = unidentified
SEQUENCE: 110
gcgccggggg acatggagac tgccgacgcc aagaacaggg ctatgcgagc cgctggcttc  60
atcgttcccg acaccttcga agacctgccc gaggtcctca agaccaccta cactggtctg 120
gttcaaaagg gtgtcatcgt tcccaaggcc gagatcgacc cacccaacat ccccatggac 180
taccagtggg cttccaagtt gggtcttatc cgaaagcccg ccgccttcat ctcgaccatc 240
tcggacgagc gaggtcagga gttgatgtac gccggtatgc gaatcctcga cgttttcaag 300
gaggagatcg gtatcggtgg tgtcatctcc ctcctgtggt tcaagcgacg attgccacct 360
ttcgcctgca aattcatcga gatggttctg caattgactg ccgaccacgg acccgccgtt 420
tcgggtgcca tgaacaccat catcaccgct cgagcaggca aggacctgat ctcgtccctg 480
gccgctggtc tcttgaccat cggtgaccga ttcggtggcg ctctcgatgg tgccgccgcc 540
gagttctctc gaggtctcaa ctctggtcga acccacgag aatttgtcga ctcgatgcga 600
aaggccaacc gattgattcc cggtatcgga cacaagatca agtcaaagac caaccccgat 660
ctccgagtcg ttctcgttgt cgattacgtc aagaagcact tccgtctca caagacgctc 720
gactttgcct tggccgtcga ggacgtcacg acgcaaaagt ccaacacgct catcttgaac 780
gttgatggtg ctattgccgc ttccttctgt gatttgctta gcggttgcgg tgctttcact 840
gaggatgagg ctgccgatta cctcaagaac ggtactctta acggtctttt cgttcttggt 900
cgatcgatcg gtttcatcgg tcactacctc gaccaaaggc tcctcaagca gcctctctac 960
cgacaccccg ccgacgacat tttcatcaac atgaagagcg agttgtctt ccagcctggg 1020
tccaactaag aggcgaccgc gactacgggt ctcggcaatt tctcccttgg gtttcctcc 1080
ttcaattaaa actactgtac ataccaccca catcattat ctcttctttc atgactatag 1140
acgcatgcac gggatcgctc gg                                         1162

SEQ ID NO: 111          moltype = DNA   length = 965
FEATURE                 Location/Qualifiers
source                  1..965
                        mol_type = genomic DNA
```

```
                     organism = unidentified
SEQUENCE: 111
ggggcataca aggagggcaa gttcaccagc gaaagcatcc aaaagtcaaa gctcagattc    60
caggacatct tcgttgagct gccctcagg gttcacaact cccaccttct caccagcttc   120
ctgcaccagg tcccgcaggc gccgccggca aagaaccccc tcgacttccc ttcatccctt   180
gcagagcttt cgcgcgactc cgatgtcagc tccaacccct tcgcaccccaa ccttgacacc   240
ctggacctca gcatcgaccc cttccagtac tggcagcgcg ccctcggccg cgagcagcag   300
aagatcaccg catggcaaca gaagcgcaag gctgagaatg ctgcacgcgc cgcgagcaag   360
cagccgcccc ttgacgagaa tgagtggcag aagctgttca agctgcccac ggagcccagc   420
aggctcgagg ctctgcttgt cggcaggcag gtcgagcagt acgcccgcca ggtcgacgga   480
ttctccgcca ccgtttccgc caagatgttt ggcgtcaggg gcaacctcct ccctaacgag   540
atcgagtaga ggacgaatat tacgagacg ggaccggcgt ttatgcatag cgaggcgttc   600
tcggctgggt ggggtagagt acatgcggca tggctacaaa aaaaaggatg atgtggttcc   660
gccatcgacg agttcagggc aacgctgcat agaatcccaa aagaagaaag gattttaacg   720
ttttgaatt tggaacttct tcgcattgga cgattgcttt cttgacgact ccgtcagttg   780
cgcgctttt ccatgcccca taccctcttt atctctaatg agggtgcgcc accgcagacc   840
caccagctac tcgaagaaaa gtcgctattt ttatttggga gttattagcg agtacaaacg   900
gaggcatgtc tagaggctga ggagtgtggt agtaagatta tagatgtctt tatgctcgat   960
atgag                                                              965

SEQ ID NO: 112         moltype = DNA  length = 965
FEATURE                Location/Qualifiers
source                 1..965
                       mol_type = genomic DNA
                       organism = unidentified
SEQUENCE: 112
ctcatatcga gcataaagac atctataatc ttactaccac actcctcagc ctctagacat    60
gcctccgttt gtactcgcta ataactccaa ataaaaaata gcgacttttc ttcgagtagc   120
tggtgggtct gcggtggcgc accctcatta gagataaaga gggtatgggc catggaaaaa   180
gcgcgcaact gacggagtcg tcaagaaagc aatcgtccaa tgcgaagaag ttccaaattc   240
aaaaacgtta aaatcctttc ttcttttggg attctatgca gcgttgccct gaactcgtcg   300
atggcggaac cacatcatcc ttttttttgt agccatgccg catgtactct accccaccca   360
gccgagaacg cctcgctatg cataaacgcc ggtcccgtct ccgtaatatt cgtcctctac   420
tcgatctcgt tagggaggag gttgcccctg acgccaaaca tcttggcgga aacggtggcg   480
gagaatccgt cgacctggcg ggcgtactgc tcgacctgcc tgccgacaag cagagcctcg   540
agcctgctgg gctccgtggg cagcttgaac agcttctgcc actcattctc gtcaagggc   600
ggctgcttgc tcgcggcgcg tgcagcattc tcagccttgc gcttctgttg ccatgcggtg   660
atcttctgct gctcgcggcc gagggcgcgc tgccagtact ggaaggggtc gatgctgagg   720
tccaggtgt caaggttggg tgcgaagggg ttggagctga catcgagtc gcgcgaaagc   780
tctgcaaggg atgaagggaa gtcgagggg ttctttgccg gcggcgcctg cgggacctgg   840
tgcaggaagc tggtgagaag gtgggagttg tgaaccctga ggggcagctc aacgaggatg   900
tcctggaatc tgagctttga cttttggatg ctttcgctgg tgaacttgcc ctccttgtat   960
gcccc                                                              965

SEQ ID NO: 113         moltype = DNA  length = 1160
FEATURE                Location/Qualifiers
source                 1..1160
                       mol_type = genomic DNA
                       organism = unidentified
SEQUENCE: 113
gacttcggcg aaggcgatga gcaactcttt cataaggcac cttccttcga ctcttcgtgc    60
gtttcgttca tctactgcat tctctcttac acgttcattc tcttccacca tggcatccaa   120
cgggacatcc acaaatggcg ttcagcatga cgctcgcaag gtcttcttct tcgacatcga   180
caactgtctt taccccgaaat cgtatcaaat acacgacaag atggccgtgc tgatcgacaa   240
ctactttcaa aaccatctgt cgctgtccca agaagatgcg accactcttc atcagcggta   300
ctataaggac tacggcctcg ccatcgaggg gcttgttcgc caccacaaag tcgaccccact   360
tgagtacaac gagaaggtcg acgatgcgtt gcctctggat gatatcatca aacccgatcc   420
gaaacttcga aaattgctgc aagacataga caccgacaag gtgaagctgt ggctattcac   480
caacgcctac gtgaaccacg ccaaaagggt gactcgcctg cttggtgtag acgatttgtt   540
cgaaggcatg actttttgcg actacgccgc ggaacgcctc tctgcaagc ccacgacgga   600
gatgtacaac aaggctatgc aagaggcgaa cgccaccgat atcgatcagt gctactttgt   660
tgatgattca gcgctgaatg cggctgctgc tatgaaatac ggttgaaaa ctgcgcatct   720
ggtcgagcct accgcgaagc ctccgcccca gcccgtctca caacaccaga tcagcaacct   780
tgaagagctg cgcaaggtct tccctgaagt atttaagact tcatgatgcc atggaaattt   840
taacgaagac acgagtgtat tttacgaaaa ctactcagga ttcccttgcc ttgtaagatg   900
cgaccatcgc tactgggttg ggattggaga tggtgcccag caacgctttt gcgacactat   960
caggtctaag gactctattg taaaacccgg tcgatttgc atatggttaa ttcgaatctt  1020
ccatgaacac agcatttcgt gaaccaaaga gcacacacgt cgaagtgttg ggatgtcttt  1080
gagcagccag cttggatttc ttgagaggtc ggaagcaatt ctataggata gacagcataa  1140
atgcaataaa gccactattg                                             1160

SEQ ID NO: 114         moltype = DNA  length = 982
FEATURE                Location/Qualifiers
source                 1..982
                       mol_type = genomic DNA
                       organism = unidentified
SEQUENCE: 114
atacaagact taccatcaac acaatggctc gcatctttat cactggcagc accgacggcc    60
tcggtcttct ttctgcgaag cttctctcgg aacaaggcca cagcgtcttc ctccatgccc   120
```

```
gcaatgccga acgagcatcc caggccaaag cagcagtgcc caaagcccaa ggtgtcatca    180
tcggcgatct ttcaaacgtc tcagacgtga agcagctcgc cgccgatgcc aacaaggctg    240
gaccttttga cgccgttgtt cacaatgctg gcctcggact caccaccaat ggccagaaga    300
ctgctgaggg cgtagcccag attttgccg ttaacagcat ggcaccttac attctgaccg     360
ctctcatgga caagccgaag aggctctttgt acgtcagctc cgactgcac ttcggtggcg    420
accccagcct cgaggacgtc acttgggcca caagggagtt ccgaccatcg gatgcataca    480
acgatacaaa gatgcaaaac gtcatgctct cgaaagcagt cgccaaacgc tggcctgatg    540
tgcagagcgc ctctcttgac ccaggctggg tgaagactaa gctcggcggg tcggccgcgc    600
ctggcaccac cgacgctcca gcagagatga ttgctgagta cgctgccggc aaatcttgcg    660
caggcgatca aacaggtgcc tacttgactc cgcgtggcgt ggaagagccg catgatgcga    720
ctaagctggc cgagaagcag gatcgtctga tgcagattta caaggaggta tcgggtgttt    780
cgttcccca gtaaacacag cttcatggct ttgcctcgcg gagacctcac attttcaatt     840
agatctccct gccgattgca gcagaccagt actcactagg ctgtgcaggg gcatgttga    900
tcaagaacga gccataacga catgccatgt caacggacaa tgagtgggcg aagtaacaca    960
tgaaattcat tatctaagcg cc                                             982

SEQ ID NO: 115       moltype = DNA    length = 982
FEATURE              Location/Qualifiers
source               1..982
                     mol_type = genomic DNA
                     organism = unidentified
SEQUENCE: 115
ggcgcttaga taatgaattt catgtgttac ttcgcccact cattgtccgt tgacatggca     60
tgtcgttatg gctcgttctt gatcaacatg cccctgcac agcctagtga gtactggtct    120
gctgcaatcg gcagggagat ctaattgaaa atgtgaggtc ccgcgaggc aaagccatga    180
agctgtgttt actggggaa cgaaacaccc gatacctcct tgtaaatctg catcagacga    240
tcctgcttct cggccagctt agtcgcatca tgcggctctt ccacgccacg cggagtcaag    300
taggcacctg tttgatcgcc tgcgcaagat ttgccggcag cgtactcagc aatcatctct    360
gctggagcgt cggtggtgcc aggcgcggcc gacccgccga gcttagtctt cacccagcct    420
gggtcaagag agccgctctg cacatcaggc cagcgtttgg cgactgcttt cgagagcatg    480
acgttttgca tctttgtatc gttgtatgca tccgatggtc ggaactccct tgtggcccaa    540
gtgacgtcct cgaggctggg gtcgccaccg aagtgcagtc cggagctgac gtacaagagc    600
ctcttcggct tgtccatgag agcggtcaga atgtaaggtg ccatgctgtt aacggcaaaa    660
atctgggcta cgccctcagc agtcttctgg ccattggtgg tgagtccgag gccagcattg    720
tgaacaacga cgtcaaaagg tccagccttg ttggcatcga cggcgagctg cttcacgtct    780
gagacgtttg aaagatcgcc gatgatgaca ccttgggctt tgggcactgc tgctttggcc    840
tgggatgctc gttcggcatt gcgggcatgg aggaagacgc tgtggccttg ttccgagaga    900
agcttcgcag aaagaagacc gaggccgtcg gtgctgccag tgataaagat gcgagccatt    960
gtgttgatgg taagtcttgt at                                             982

SEQ ID NO: 116       moltype = DNA    length = 821
FEATURE              Location/Qualifiers
source               1..821
                     mol_type = genomic DNA
                     organism = unidentified
SEQUENCE: 116
agcgactccg acaacaacga ccaccgggac gactcatatc cttcacaatg gccattggac     60
aatcctcgca gcagcaggcc gacgccagaa atgtcgtcac ccagggcaac tctgacaagg    120
ccgccaaccc catgcgcgag ctgcgcatcc agaagctcgt cctcaacatc tccgtcggcg    180
agtctggtga cagacttact cgtgccgcca aggtgctcga gcagctgagc ggtcagaccc    240
ccgtctacag caaggcccgc tacaccgtcc gtaccttcgg tatccgccgt aacgagaaga    300
tctccgtcca cgttaccgtc cgtggcgcca aggccgagga gatcctcgag cgtggcctca    360
aggtcaagga gtacgagctc cgcaagcgca acttctctgc caccggtaat ttcggtttcg    420
gtatctccga gcacatcgac ctgggtatca agtacgaccc tgcgatcggt atctacggca    480
tggacttcta cgtcgtcatg tcccgtcccg gtgagcgtgt cgactgcttc cgtcgcgcga    540
agacccgcgt tggtgcttct cacaaggtca acgctcccga ggtcatcaag tggtacaaga    600
accgcttcga gggcatcgtc aggtaaaaag cttgaaaggt ggtctgggat gatgaaaaat    660
tcaacttgtg gttttggcaa cggcgcaaaa gagcgaggct attttccgt agcttgagga     720
tatatccggc ctatcggagc tttacttta cgcttgagca agatcgcaaa aatggaggcc    780
tcgtatacca agcgagcgtg ccgcataacc attgatcgct c                        821

SEQ ID NO: 117       moltype = DNA    length = 674
FEATURE              Location/Qualifiers
source               1..674
                     mol_type = genomic DNA
                     organism = unidentified
SEQUENCE: 117
ggacacaccg gtgacgtctt gagcgtctcg ttctcggccg acaaccgaca aatcgtttct     60
gcttcccgag accgaactat caagctctgg aacactctcg gagagtgcaa gttcaacatt    120
gttgacgatg gtcactcgga gtgggtctct tgcgttcgat tctctcctaa ccccgtcatt    180
cccgtcatcg tctctgctgg ttgggacaag gtcgtcaagg tctgggaatt gtccaagtgc    240
aagctcaaga ccaaccacca cggtcacact ggttacatca acaccctcgc cgtttcgccc    300
gacggatcgc tcgccgcatc cggtggaaag gatggcatca ccatgctttg ggatttgaac    360
gatggcaaac acctctactc tctagaggct ggagacattg tcaactcgct cgtcttctct    420
cctaaccgat actggctctg tgccgccact gcttcgtcaa tcaagatctt cgacttggag    480
tccaagtcaa tcgttgacga cctcaagcca gacttctccg ccgagtactc tgacaaggct    540
caaaagccac aatgtacttc cctcgcctgg tctgccgatg tcagaccct ctttgccggt     600
ttctccgaca acctcgtccg agtctgggtt gtcactgctt agagtcgtga ggattgtatg    660
catggataac gtgg                                                      674
```

```
SEQ ID NO: 118         moltype = DNA  length = 1183
FEATURE                Location/Qualifiers
source                 1..1183
                       mol_type = genomic DNA
                       organism = unidentified
SEQUENCE: 118
gaagtaccgt tttctgtgca gttttttta  aacccagaac ttgcaattga gatcacgcgt   60
cgcaatggca ccctctaccc agaagcaatg gaccgttaaa aacggggagc aggactttga  120
cggcctcgtt tacggcgacg cgccagttcc gactgcgggg gactcggaag tcgttgtcaa  180
gctccatggt gcctcgctca actaccgtga cctgattatc cccaagggaa agtacccctt  240
cccgctctcg ttcccggtcg tccccggctc tgacggtgcc ggtgaagtcg tcaggtcgg   300
atccaaggtc aagcaattca agaagggcga caaggttgtt accctcttca accagctcca  360
tcagtacggt cccgttgacg ctgctgcggc atcgtcgggc ctcggtggtg cggttgacgg  420
aaccctgcgc cagtacggtg tcttcaatga aacggcgtc  gtcagggccc cgaccaacct  480
gaacttcctt gagtcgagca cactaacctg tgcgggacta caagctggaa tgcgctgta   540
tgggctgaag ccgcttcttc ctggccagac cgtcctggtg cagggcactg gcggtgtgag  600
tatctttgct ttgcagttcg caaaagcagc gggcgcaact gtgatcgcaa caacctcatc  660
cgaagagaaa ggcaagcgcc ttaaggacct cggtgccgat cacgtcatta actacaagac  720
ccaaaccaac tggggcgaga tcgcgcgcgg tttgacgcgc gacaacatcg ggggttgacca  780
catcattgag gttggaggcg ccggcaccct ggagcagagc ttcaagtgca tcaagttcga  840
gggagtcatt agtattattg gcttcttggg cggaatgaac cccagcacca taccccaatgt  900
tctgcagacc ctgagcaaca tctgcactgt gcgcggtgtg tatgttggca gcaaggcgct  960
gatgaacgac atgatcaacg ccatcgaggc gaacaatatc cacccgttg tggatggaac  1020
tgtgttcacc cttgagaaga cacgagaggc ctatgagtac atgtgggcgc agaagcactt  1080
cggaaagctg accatccaga tcgcttaatc acttgatgaa tataatgagg gatatatcgg  1140
actaggaatt atgcgctaat gaatataata accatgcaat tag                    1183

SEQ ID NO: 119         moltype = DNA  length = 1563
FEATURE                Location/Qualifiers
source                 1..1563
                       mol_type = genomic DNA
                       organism = unidentified
SEQUENCE: 119
ggggccatgc tcgagcagca gtaccagatg cgaaaggagc agcaagtgca atttacacct   60
atggcatcgc cgtccagcac tccttaccac atgcatcaag atttcactgt tccgggcgac  120
ttttttctccc cctcacatc  gcctgcgctc cacgctcaga atcagccaca atcgcgacag  180
caattcacgg ctcatcaaca gggctactac acgaatccca gcaccgctgc gagctcggcg  240
gctccgagtc caatcgacgc gaacggagat gtggaaatgg gtgagcgacgg tgttgcgctg  300
ccagagtcag cgagccaacc gaagaagcct tcccgaagga agcctgcgac accgaggact  360
ttcgccatga acaaggtcaa gcaaagtccc atacaaaac cgcaaaaag  gaagtctgtg   420
gcgttggcac acaaggatgc agatgctgtg gtgcaggacg cccaacggtc tggccatatc  480
gcgcccaaat ccgcaggtct ccaaatgccg cctccgtttg agagctcgga aaacgacagt  540
gtttcgccgg aagcgctgaa cgacctgcct atgggccccc cgcctagacc tggatccgtt  600
tcgcagtcgc ccgccatcgc tcctcagaat cagagcgttt ctggaccggc cgcgactccc  660
aaatctctcc tttctatgaa gggcgctcaa gatatgaatg cacctgccag tactggtatt  720
tctggccaaa tgggacaggc atccttagaa gatctcgaac ttccgaagc tgccgaaaat  780
ccaggatcga ctgcgacaca ctcgcaagtc ttgaactcgc aagagccgac acctcgcctc  840
atgccctccc gtaaaacgcc aaaactcggc cctcttagca cgccttcatc gggcaagcct  900
acttctgctt ccaacagtcc cgctcatgcg ttgtctccca tgacagcgag taccctgct   960
ggtctgctga aggacaagaa ggacaacaaa ggcggacgtg caaccagcaa gaagcgtgat 1020
agtgtcagta ccaccaattc agcaatggtc tctccggcac tccgaccgaa ggtcagcccg 1080
agtatcaagc ctctgctacc gaaggcacc  agcctcaact ccccgaccca tgccctcctc 1140
ctcgcctcca aatccaatta ccagaacctc ctggaaggca accacctccc cggcatctcc 1200
tacccggact ccctctcaac cggcctcacc agcaaacgca cctcgcacaa agtcgccgag 1260
caaggccgcc gcaaccgcat caacgacgcc ctcaaagaaa tgcaagccct catcccccgc 1320
tcgtccggcg cccgcgccga agagctcatg accgccgacg ccggcgacga cgacagccag 1380
gaaaccaagg agaaggaccg cgacgccgct gtcaagagca atagctccaa agccgcgacc 1440
gtcgagagtg cgaatcggta tattcgcgtg ttgaaggaga gcgacgcggc gcagaaggat 1500
gcgatcgcgc ggccgaattc cccgggctcg agaagcttgg atccaccgga tctagataac 1560
tga                                                                1563

SEQ ID NO: 120         moltype = DNA  length = 939
FEATURE                Location/Qualifiers
source                 1..939
                       mol_type = genomic DNA
                       organism = unidentified
SEQUENCE: 120
gacgacacaa tgagaaacat cctcctagta ttggcgtctg cagcgcttgc tgttgtggca   60
caaaagccag atctcgacgt gaaaggcacg tttggagacg cgaacccctt ctccaaggtc  120
gtcaacggcc aaagcaacaa gctctacctc acgctggaca accacagccc tgagtctctg  180
gtggtcaagt ctatcagcgg gtcatggtct gagaagacgt ccgcttcatc cggtcaagag  240
aagtttctta agaactctac cacccaagag aagctcactg tccccatccc tcccaagtcc  300
gagggcgcat tccagcctcc tacagtcttg acctaccagt tctgagcga attcaagcct  360
agagagttgc tcttgaccgt tttgggttga ctatgttgat gctaccggtc actcgtacag  420
agaaacagcc tacgaaggcc aagtgactgt cgttgaggcc ccgggatctt tctttgaccc  480
cgccttgctc tttgcctacg ccatggtgct ggctctcgtc ggcggcgccg gctaccttgc  540
ctacaacatc tactttccac ctgccgcaa  gcccagaaga agcgccaaca ccgcacctac  600
agatgctcct gctgctccgg ctgaccctga cgaatggatt cctgtccacc acaagagggc  660
```

```
caaaaagacg tctggcgcg gggccaccag tggtgaagag agcgaagcca ctgaaggcta     720
tgcaagcgag aagtctgcca gtggagccaa gaagagaggc aaaggtggca gaaaataaat    780
actgacatgt gcctcgagct gcagacgacg ctcgtcaaaa gtgtagcaag ttgaagaagc    840
ccagcacgaa gtcccccagct tgactgctgc cgtttggctt aatggcacag aaagcgagtg    900
tacgtcgtac acggcttata gtctcgaatg caacaaagg                            939

SEQ ID NO: 121          moltype = DNA  length = 896
FEATURE                 Location/Qualifiers
source                  1..896
                        mol_type = genomic DNA
                        organism = unidentified
SEQUENCE: 121
gccaaccacg acattgatcc ctttcacgac ttgctttcgc catgtcagat aacaacgatg     60
gaaatcacgg gggaggcgta ggcgcgtctt actactatgg cggcatcgcg attgcgctgt    120
gtcttgtgat tgtgttgacg cttgtatcaa gaatattata tcgacgacgt gtaaggaaca    180
gactcctgcg agccaacaga caagagcgca ttacttgcg agaccgggga gaagcgcag     240
gcctgccaac ctatcgggag tctcgcaatc agccctcatt accgcgatac acggccgagg    300
cagactacgc acctccaccc ggcccgcctc cttccaacag cccggacaac gaaggccacc    360
acttccactt ccatttcccc tctttacatg tgcctcaggc actgcacttg cggcctaggc    420
aggcagacga tcctgctgac cagatcccca ccgtgccccc tccgtcctac gagccgccca    480
agtatgagcc gcccagtgga gcgcctccag agcagcaaca agagcctgtg gctagcggga    540
gtagcgagca tcatcaccag cagtctgctt tgggcgaaca taccgcggcg gcaacagccg    600
ctgccacaac tccggcagag cacagtggcg agtcgacaga gcttaggagt gcgtcgcctt    660
ctcagccaca atctcaatcc aacctcaag caccagcaca accacaagag caggattacg    720
gctacgacga tgccgacttt atccatcctg aagagcgacg caggatcgag gctgcgcagc    780
gcaatgatcc gcagacatga ttcaaacatg tgttgtaaag tgtactacta tgaactcgtt    840
gaccagtata atcgaagcgt atataacggc acaaatgcaa agctgccatc atcccg       896

SEQ ID NO: 122          moltype = DNA  length = 697
FEATURE                 Location/Qualifiers
source                  1..697
                        mol_type = genomic DNA
                        organism = unidentified
SEQUENCE: 122
cattacggcc gggaagcttt cagaagctaa tcgagttctt cctatccctt tcaactttac     60
acaccatgtc tagaattggc gatccaacga acaaccctgc tacccagcaa ctgtactctg    120
ataggccctt gcatctccct ggccccggcc tcaagccatc caggcagctc actatcagct    180
cggctgttgc gttccgcgag gattcgggcc aaacacgctt caacctcatc agctctgacc    240
accgcgaggt gttgcacatt agtattcgtg caagggacaa cgttctcgtg ctcaacacca    300
aggcccccga tggcgattgg ggcaaagaag agcgacatga tctcaaaccc cttttcgata    360
ccccactgct gccttacatc accgtaatgg caacgaagaa cagctatatc cttttctgttc    420
ctggtaaacg ggagatcatc ttcaataaga ggaaagggtt catggagcct gctgtgagga    480
ttgagtatga ctatgatgag atgtctgcgt tctccgaccc ctgctacatt acagtcccat    540
cttcatctta aagcttccct agttggcttg gagttggcgg atatggtcac attggttttt    600
tcacacggca aacggtaaag aattacggct tctctctcct gtcatgttca gcggacgatg    660
tatgatgtag tgttctgttc aattgatctg gttgttg                             697

SEQ ID NO: 123          moltype = DNA  length = 329
FEATURE                 Location/Qualifiers
source                  1..329
                        mol_type = genomic DNA
                        organism = unidentified
SEQUENCE: 123
ggaacgacca cgagcagttt ttaaaatgcc acaagaaatc aaggacatca agaacttact     60
cgaaatgct cgtcgtaagg acgctcgttc cgcccgcaca aagaagacca agaccgttgg    120
tgctaagggc gagccagctc aacttaccaa gttcaagatt cgttgctctc gctacctcta    180
cactctcgtc gtctctgacg gtgagaaggc agagaagctt aagcaatcac tcccaccaac    240
cctcaacgtc gaggagattg gtaaggtttc aaagaagtag attagtgatg taatttgctg    300
ccttgattga ttgtccttgt tggtattt                                        329

SEQ ID NO: 124          moltype = DNA  length = 747
FEATURE                 Location/Qualifiers
source                  1..747
                        mol_type = genomic DNA
                        organism = unidentified
SEQUENCE: 124
gtacacataa ctcttcattc ctcatcatgt ctcacacttt ctacgatggc accatcgtgg     60
tgcttcaagg cattcttgaa acttttttctc atatccttca caaagccgaa gaaagcccaa    120
actctagcgc ttttcccgca gctcgtctgc acgaggacat gtatccattg accgaccaaa    180
ttcgcctagc aactcaattt tctgagtata ttctggctaa agtgaccggc cgcgagccaa    240
ggaagttcga aggcaatcca ttgaccttcg ctgaattcta tgagcgtatc gataccatgc    300
tgaagtcact caaagaagca gataaggatg tcgtcaatgc aaatgccgac aaggaggagc    360
ttactcaagt tggacctacc gcaaaaattg aattgagtaa tgctatatac gcccatcgca    420
tgccttgcc caacatttac ttccatctca acattgctta cggcattttg cggaaggagg    480
gcgtgcctct tggcaagctt gactattttg cgggctttt cccaccgagc atggctcaag    540
gcaagtaaag aagtgatgtt ggtatgtttt ccggatggag agggtgctga tctatgaaa    600
tgagttccga gtagaccatg atggtctaga gtggacttg agctttcatt tgccaaattc    660
ttgtggaaag atagcaatga cggaacaagc gatttgtatg tacatttaat gaagtctatc    720
tatagaatta atctccgatc tatcgcg                                         747
```

```
SEQ ID NO: 125          moltype = DNA  length = 693
FEATURE                 Location/Qualifiers
source                  1..693
                        mol_type = genomic DNA
                        organism = unidentified
SEQUENCE: 125
aagctcttca aagctaatta tcgagttctc ctatctcttg cacttataca caccatgtct   60
agaattggcg attttgcgaa caacaaccag gctacccagc agctgttctc tgatagaccc  120
atgcagctcc ctggcccggg ccttaagccg tccaggcagc tcacggtcag ctcagctatg  180
gcgttccgct gggactctgg ccaaacccgc ttcaacctca tcagctctga ccgtcgtgaa  240
gtgctgcaca tcagcatccg cgcaaaagac gacgtccttg tgcttaacac taaggctcct  300
gatggcaatt ggggcaagga agagcgacac gagctcaaac cccttttcga caccccgatg  360
ctgccttata tcaccgtaac ggcgactaag actagctata tcctgtccgt tcctggtaat  420
caggagatca tcttcaataa gaggaaaggg ttcatggagc ctgctgtcaa gattgagtat  480
gactatgacg agaaccctgc gttctctgat ccgtgctacg tcacagttcc gcatttatct  540
taaggtctta ttggcttgga gttggcggat agtcacaccg ttttttttca cacggcaaaa  600
ggcaaagtat tacggctttt ctctcctgtc ctgtttagcg gatgtacgat gtatgttgta  660
gtagtgttct ggaatttgtg ttcaagttgt tgg                               693

SEQ ID NO: 126          moltype = DNA  length = 1030
FEATURE                 Location/Qualifiers
source                  1..1030
                        mol_type = genomic DNA
                        organism = unidentified
SEQUENCE: 126
gagcgacttc atcaaaaatg tcagagcaac ttcactacaa gggttcattg gccggccacg    60
gcaactgggt tactgccatc gctacctctg cagagaaccc agacatgatc ctcactgctt   120
cccgtgacaa gtctgtcatc gtctggcaac tcacccgtga cgacgctcag tacggttacc   180
caaagagaat cctcaagggc cacaaccact tcgtctctga cgtctccatc tcatacgacg   240
gtcaattcgc tttgtcctcc tcatgggaca agaccctccg tctctgggac ctcaacactg   300
gtcttaccac cagacgtttc gttggccacg aagcagacgt tctctccgtc tccttctccg   360
ccgacaacac acaaatcgtc tctggctccc gcgaccgcac catcaagctc tggaacaccc   420
ttggtgaatg caagttcgac atcaaggatg aaggccatcc cgaatgggtt tcatgcgttc   480
gtttctctcc aaaccccaatg aacccagtca tcgtctcagc tggttgggac aaggttgtca   540
aggtttggga actctcaaac tgcaagctca agaccaacca ctacggtcac actggctaca   600
tcaacaccgt ctctgtctcc ccagacggat cccttgctgc ctccggcggt aaggacggca   660
tcaccatgct ttgggacctc aacgagggca agcacctcta ctccctcgag gctggtgaca   720
ttgtcaacgc actcgtcttc tcaccaaacc gttactggtt gtgcgctgct actgcctcat   780
gcatcaagat cttcgacctc gagtccaagt ccatcgtcga cgagctcaag ccagactttg   840
tcgacgtcgg caagaactcc cgcgagcag aagctgtctc cctctcctgg tccgctgatg   900
gtcaaaccct cttcgctggt ttcaccgaca acgccgtccg tgtctggacc gtcgcataaa   960
actaagctgt atctaataga cagggtattg ggttttgtaa cactattgcg aggaactcat  1020
gattttaccg                                                         1030

SEQ ID NO: 127          moltype = DNA  length = 668
FEATURE                 Location/Qualifiers
source                  1..668
                        mol_type = genomic DNA
                        organism = unidentified
SEQUENCE: 127
ggggaaggtg gtggtatcca cggaaccacc ttcaactcca tcatgaagtg tgatgttgac   60
gtccgtaagg atctctatgg caacattgtc atgtctggtg gtactactat gtaccctggt  120
attgccgacc gtatgcagaa ggaaatcacc gctcttgctc cttcgtcgat gaaggtcaag  180
atcattgctc ctcctgagcg taaatactct gtgtggattg gtggttccat cctggcttct  240
ctgtccacct tccagcagat gtggatctcg aagcaggagt acgacgagag cggcccttcg  300
atcgtccacc gcaagtgctt ctaagcttaa gcgcatggtt gatttgcttg tttgtacttc  360
ttttctggcg tatcaaaagg caggacagtg tggcatgcgg acctttttctg acctgatgac  420
gagagggatc gcctaagaaa aaggaacttt atttttagttg tggaatagag acggtttatt  480
tgacgctagt tctcgtccag agcatcctcg agacgatagt ctgggttcgt cttaagcgat  540
ggatggtggt gattctcttc gtattgttcc tgtacctgta ctacatattg cctacaccat  600
gtcctgttca tttcttctct gtttgcgttg cgttagacct tataaattta aatgtcgtat  660
tgctcccc                                                           668

SEQ ID NO: 128          moltype = DNA  length = 668
FEATURE                 Location/Qualifiers
source                  1..668
                        mol_type = genomic DNA
                        organism = unidentified
SEQUENCE: 128
ggggagcaat acgacattta aatttataag gtcaacgca acgcaaacag agaagaaatg    60
aacaggacat ggtgtaggca atatgtagta caggtacagg aacaatacga agagaatcac  120
caccatccat cgcttaagac gaacccgac tatcgtctcg aggatgctct ggacgagaac  180
tagcgtcaaa taaaccgtct ctattccaca actaaaataa agttccttttt tcttaggcga  240
tccctctcgt catcaggtca gaaaaggtcc gcatgccaca ctgtcctgcc ttttgatacg  300
ccagaaaaga agtacaaaca agcaaatcaa ccatgcgctt aagcttagaa gcacttgcgg  360
tggacgatca aagggccgct ctcgtcgtac tcctgcttcg agatccacat ctgctggaag  420
gtggacagag aagccaggat ggaaccacca atccacacag agtatttacg ctcaggagga  480
gcaatgatct tgaccttcat cgacgaagga gcaagagcgg tgatttcctt ctgcatacgg  540
```

```
tcggcaatac cagggtacat agtagtacca ccagacatga caatgttgcc atagagatcc   600
ttacggacgt caacatcaca cttcatgatg gagttgaagg tggttccgtg gataccacca   660
ccttcccc                                                            668

SEQ ID NO: 129         moltype = DNA   length = 1018
FEATURE                Location/Qualifiers
source                 1..1018
                       mol_type = genomic DNA
                       organism = unidentified
SEQUENCE: 129
gactttctca tttcagaatt attttctata ctctgacaag agcaagcaat accaaacatc    60
ttccacatcg aagctttaac cattttgccc ttaacatttg aacaagacga aatgccttc    120
ttcccacact acaccactaa tctgtcgcct ctgctctact tgttggacga cgactatgct   180
gtctaccgct caacttgtcc aaagtccaac taccaccaca agcaaccaca cagccgccgt   240
cagccttcgc cagttcgtta ctttagtccg aatttttgata tgcgagaggg gaatgactcc   300
tactaccttg acggagagct ccctggtgtc aaccagaatg atgtcgatat tgaattctct   360
gaccctcaga cactggtgat caagggtcga gtggagcgga attacaacaa tctcgacggc   420
atgaacgagg aaaaccagca agatgaagaa caattctctg aaactctctc tagcaagtcg   480
taccaaccca ctgtcgagga cgaggacgag gcgaaccatt caccaccgt ggcgacacca    540
acctactctg agaagtctgt tactgagaaa actcagaagc ctgcgtacaa ataccgaaat   600
tctgaacgtg ctattggcga attccaccga gccttcaatc tccctacaag agtcgatcaa   660
gatgcggtca gggctacatt gaggaatgga atcctctcgc tggagctccc gaaggagccg   720
gcaccgaaga tgaagaagat tcggattgaa tagaggattt cgaataaaat ttttgatttg   780
atgagtagtt ggtgtttatt gttatgtcta attatatggg gctatgtcat gattgggaaa   840
tgggacaccg catttgtttc cttttccccc attttcttcag acgccatcta tattgcatgt   900
atgttgcatg aactatggtt tttgctagga gcggttgctt ctgctttgca ttttcatgaa   960
ctatttcttt tttattaaat taataactag catatcaatt aatgatctgt catatggc    1018

SEQ ID NO: 130         moltype = DNA   length = 686
FEATURE                Location/Qualifiers
source                 1..686
                       mol_type = genomic DNA
                       organism = unidentified
SEQUENCE: 130
aagctttcag aagctaatcg agttcttcct atcctttca actttacaca ccatgtctag     60
aattggcgat ccaacgaaca accctgctac ccagcaactg tactctgata ggcccttgca   120
tctccctggc cccggcctca agccatccag gcagctcact atcagctcgg ctgttgcgtt   180
ccgcgaggat tcgggccaaa cacgcttcaa cctcatcagc tctgaccacc gcgaggtgtt   240
gcacattagt attcgtgcaa gggacaacgt tctcgtcgta aacaccaagg ccccgatgg    300
cgattgggc aaagaagagc gacatgatct caaaccccct ttcgatccc cactgctgcc    360
ttacatcacc gtaatggcaa cgaagaacag ctatatcctt tctgttcctg gtaaacggga   420
gatcatcttc aataagagga aagggttcat ggagcctgct gtgaggattg agtatgacta   480
tgatgagatg tctgcgttct ccgacccctg ctacattaca gtcccatctt catcttaaag   540
ctttcctagt tggcttggag ttggcggata tggtcacatt ggttttttca cacggcaaac   600
ggtaaagaat tacggcttct ctctcctgtc atgttcagcg gacgatgtat gatgtagtgt   660
tctgttcaat tgatctggtt gttgac                                        686

SEQ ID NO: 131         moltype = DNA   length = 698
FEATURE                Location/Qualifiers
source                 1..698
                       mol_type = genomic DNA
                       organism = unidentified
SEQUENCE: 131
gggcatataa ccacaggtca ttcgcatccg tcgcagaact tcttacatct gagctttcct     60
gtccgttaga tataggcaaa atgaaggcct actggtacga taaccaaccg ggcgaccagc   120
gcttgcctca cgactccggc cgccccgtca ccgagtccta cctcgagtcc atcggcgtct   180
tctaccgcca ctgcccaaca attgaccttg tcgactccct ggccgccgag cgcggctaca   240
agaaccgcga cgaggtctgc gtctcgccgc agactatggg cgatgtctac gaggagaagg   300
tgaagacgtt ctttagtgaa catttgcacg aggacgagga gattcggtac attcgagatg   360
gggaggggta ctttgatgtg cgtggggcagg aggatgagtg ggtacggatt cggttgagta   420
aggatgatct gatcattctt ccggctggga tctaccatcg gttacgaca gatgataaga    480
actacgtcaa ggctatgcgt ctcttccagg aggagcccaa gtggacgccc ttgaaccgtg   540
gccctgaggt tgatgtcaac cctcaccgga agacataccct ggaaaccgtc cccagccctg   600
ctgtggctgc gaactaagtg agcatcgaat gctcttgttg aacaatctat ttgcatctc    660
ttagccttta tacacctcaa tgcatcaatg gatttagg                           698

SEQ ID NO: 132         moltype = DNA   length = 884
FEATURE                Location/Qualifiers
source                 1..884
                       mol_type = genomic DNA
                       organism = unidentified
SEQUENCE: 132
gtggctgccg gctacacccc cgaggccctc gagatcctct ccaagaagaa gggcggcaag     60
tacctcgtcc tcgagatgga cgagacctac aaccccccg ccgaggagac acgtactctc   120
tacggtgtcc agctcaccca ggcccgcaac gatgctgtca tctcccccca gaagaccttc   180
aataccatca ttaccccccaa gaacaccgag tccctcccg agtccgccct ccgcgacctc   240
accgtcgcca ccctcgccct gaaatacaca cagtccaact ccgtctgcta cgcgctcaac   300
ggacaggtcg tcggcctcgg tgccggccag caaagtcgta tccactgcac tcgtcttgcc   360
ggcgacaaga ccgacaactg gtggatgcgc ttccacgagc gcgtgctcaa catcaagtgg   420
```

```
aagcagggca ccaagcgtgc tgacaagagc aacgccatcg acctgctctg ctcgggccag    480
acgccccgca atgacgctga gaaggtcgag tacgagcgtg tgttcgcgga ggttcctgct    540
ccgttcaccc aggaggagcg tgatgcttgg ctctcgcagt tgaccaacgt tgctatttct    600
tcggatgctt tcgtatgtct ctcccctctg ttagagcatt ctaagttcta agatcatgct    660
aattggtgaa atagttcccc ttcatcgaca acgtcttccg agccgcccgc tccggcgtca    720
agtacatcgc tgcacccagc ggttcgcaga acgacgggcc tgtcttcgag actgccgaga    780
agcttggtat ctcgttcgtt gagcagggta ctcgtctgtt ccaccactaa cttgcttttc    840
cggtggcgtg gtattatggt ataaaaagaa aaagggtttg gggg                     884
```

SEQ ID NO: 133         moltype = DNA   length = 822
FEATURE                Location/Qualifiers
source                 1..822
                       mol_type = genomic DNA
                       organism = unidentified
SEQUENCE: 133

```
gtggctgccg gctacacccc cgaggccctc gagatcctct ccaagaagaa gggcggcaag     60
tacctcgtcc tcgagatgga cgagacctac aaccccccg ccgaggagac acgtactctc    120
tacggtgtcc agctcaccca ggcccgcaac gatgctgtca tctcccccca gaagacctc    180
aataccatca ttaccccaa gaacaccgag tccctccccg agtccgccct ccgcgacctc    240
accgtcgcca ccctcgccct gaaatacaca cagtccaact ccgtctgcta cgcgctcaac    300
ggacaggtcg tcggcctcgg tgccggccag caaagtcgta tccactgcac tcgtcttgcc    360
ggcgcaaaga ccgacaactg gtggatgcgc ttccacgagg gtgctcaa catcaagtgg    420
aagcagggca ccaagcgtgc tgacaagagc aacgccatcg acctgctctg ctcgggccag    480
acgccccgca atgacgctga gaaggtcgag tacgagcgtg tgttcgcgga ggttcctgct    540
ccgttcaccc aggaggagcg tgatgcttgg ctctcgcagt tgaccaacgt tgctatttct    600
tcggatgctt tcttcccctt catcgacaac gtcttccgag ccgcccgctc cggcgtcaag    660
tacatcgctg cacccagcgg ttcgcagaac gacggccctg tcttcgagac tgccgagaag    720
cttggtatct cgttcgttga gcagggtact cgtctgttcc accactaact tgcttttccg    780
gtggcgtggt attatggtat aaaaagaaaa agggtttggg gg                       822
```

SEQ ID NO: 134         moltype = DNA   length = 996
FEATURE                Location/Qualifiers
source                 1..996
                       mol_type = genomic DNA
                       organism = unidentified
SEQUENCE: 134

```
tgaagcagtg gtatcaacgc aagcagtggt atcaacgcag aatgtgcgat cgctctagaa     60
tcggtcccaa gggttgggaa gcagtggtat caacgcaagc agtggtatca acgcaagcag    120
tggtatcaac gcaagcagtg gtatcaacgc aagcagtggt atcaacgcag tcagcagttg    180
caacgcagag tgcgcagccc ggtgctatct ctgctcctgt ggcagctggt aaggacgttg    240
agctgcagtg gaccgaatgg ccggaaaagtc atcatggccc tgtcattact tacctggcca    300
actgcaacgg tgactgctct gaggtcgaca atcctctct ggagttttc aagatcgatc    360
agaagggtct catcgatgac agcaatgtcc ctggcacatg ggctaccgac aaactaatct    420
ccaacaacaa cagctacacc gtcaccatcc ccagcgacat tgctgccggt aactacgtcc    480
tccgccatga aatcattgct ctgcactccg ctggcaacga ggatggtgcc cagaactacc    540
cccagtgtct caacctcaag gttactggtg gtggcaacgc ttctccctca ggtactcttg    600
gtaccaagct ctacaacgag gacgactcgg tgatcccttg cagtatctac cagcagcttg    660
actcctacga catccccggc cctgctctgt actctggcgc ttcctcgtcc tccaactctg    720
gttcttcttc cagcgttgct tcggccactg ctttctgccac ttctgccgct gcttcctctc    780
cctcgtcctc tcaggcttcc ggtacccccg cttccaggt caaggctcag accgctagct    840
ctactcctag cgcttcgtcc ggtgccactt ccggcagtct gtccgactac ttcagctctc    900
tgagcgctga ggagttcctc aacgttatca gcgagactct gtcttggttg gtcactgaca    960
agattcacgc tcgtgacttg tcgtaccgcat aaatgg                             996
```

SEQ ID NO: 135         moltype = DNA   length = 823
FEATURE                Location/Qualifiers
source                 1..823
                       mol_type = genomic DNA
                       organism = unidentified
SEQUENCE: 135

```
gtggtatcaa cgcagagtgc gcagcccggt gctatctctg ctcctgtggc agctggtaag     60
gacgttgagc tgcagtggac cgaatggccg aaaagtcatc atggccctgt cattacttac    120
ctggccaact gcaacggtga ctgctctgag tcgacaaat cctctctgga ttttttcaag    180
atcgatcaga agggtctcat cgatgacagc aatgtccctg gcacatgggc taccgacaaa    240
ctaatctcca acaacaacag ctacaccgtc accatcccca gcgacattgc tgccggtaac    300
tacgtcctcc gccatgaaat cattgctctg cactccgctg gcaacgagga tggtgcccag    360
aactaccccc agtgtctcaa cctcaaggtt actggtggtg gcaacgcttc tccctcaggt    420
actcttggta ccaagctcta caacgaggac gactcggta tccttgtcag tatctaccag    480
cagcttgact cctacgacat ccccggccct gctctgtact ctggcgcttc ctcgtcctcc    540
aactctggtt cttcttccag cgttgcttcg gccactgctt ctgccacttc tgccgctgct    600
tcctctccct cgtcctctca ggcttccggt accccgcttc caggtcaa ggctcagacc    660
gctagctcta ctcctagcgc ttcgtccggt gccacttccg gcagtctgtc cgactacttc    720
agctctctga gcgctgagga gttcctcaac gttatcagcg agactctgtc ttggttggtc    780
actgacaaga ttcacgctcg tgacttgtcg accgcataaa tgg                      823
```

SEQ ID NO: 136         moltype = DNA   length = 1000
FEATURE                Location/Qualifiers
source                 1..1000
                       mol_type = genomic DNA

```
                        organism = unidentified
SEQUENCE: 136
gacggtgaag ttggaataga ataaaatgtt gagcatgttt accagagtgg ccagaggaca   60
ggccaaggtg tttacccgca acgcatccac agcatcatcc aaaccaacga atcaatcatc  120
caacaaggct gccactatcg cagcttcaat ttcaggtgtt accgccgagc tatacgccca  180
ccaatacggc ctcattgaca gcgtcttcgc tagtggctta gaagagggtt tgcacgctcc  240
tcatttccct tggtcacaca atggctggtt ggacagcttt gaccacaact ccattagacg  300
cggttaccaa gtttaccgtg aggtgtgcag ctcgtgtcac tctttggaca gaatagcgtg  360
gagaaacctt gtcgctgtgt cacacacttc agatgaagcc agacgatgg ctgaagagca  420
agagtacact gatggtccaa atgaccaagg agagtctttc caaagacctg gtaaattggc  480
tgattacatg ccagctcctt atccaaatga ggaagcttcg agggccgcca atggtggtgc  540
tcttcctcct gatcttttctc tcatcgttaa agcaagacac ggaggagctg attacattat  600
ggctctgctc actggttacc aggatcctcc tgctggtatt caagttcaag agggcatgaa  660
cttcaaccca tatttcccag gtggtggtat tgccatgggt agagttttgt tcgatggtcg  720
ggtagaatac gacgatggca ctcctgctac tactacacaa atggctaagg atgtcgctac  780
tttcctcagc tgggctagtg agccagaaca cgacgacaga aagaagatgg gcttccaagc  840
tgtcattatc ctctcagcta tgaccgccat ctcactctac gtcaagagac tcaagtggtc  900
gcctatcaag acgaggaaac tgacttacaa cccaccaaag tgatctgaat gtagagaaaa  960
gtttgacccg tataaaaaat ttcatcctct ccttttttccg                       1000

SEQ ID NO: 137          moltype = DNA    length = 544
FEATURE                 Location/Qualifiers
source                  1..544
                        mol_type = genomic DNA
                        organism = unidentified
SEQUENCE: 137
ggaggtagtc cagccaaaaa gagtttgata ggcgcgatgg aggcacaaaa tctcaagact   60
ttcccaaagc aacctatctt ccaaaactca aagacccgtg gtaacaagaa ggtcaccaag  120
gaccgtcgtt ggtacaagga cgtcggtctc ggtttcaaga ctcctcaaga agccatcacc  180
ggtacttaca tcgacaagaa gtgcccatgg accggtacga tttccatcga aggccgtatc  240
ttgtccggca aggtggtctc taccaagatg accgtacga tcgtcatcag aagagagtac  300
cttcactacg tgccaaagta caacagatac gagaagcgtc acaagaacct cccagtgcac  360
gcatcacctg cattccgtat cgagaatggt gaccaagtcg tcgttggcca atgccgtcca  420
cttttcaaaga ctgtgagatt caacgtcctc cgtgtcatca gaacaaggc tgctgctaag  480
gctttcgcaa agttctaaac ttgttattaa tgtagttggt ccattcacag aattttgaaa  540
gtcc                                                              544

SEQ ID NO: 138          moltype = DNA    length = 938
FEATURE                 Location/Qualifiers
source                  1..938
                        mol_type = genomic DNA
                        organism = unidentified
SEQUENCE: 138
acgttcaatt gacttttcca ttcttttgtt cgttctgaag agttttcttt tttctttcat   60
tgtcgcctcc tttctttcgc ctttcccgttg tttccgatca tcgggtgttg ccagagtata  120
tatagagttg gggctccctt ttatctatct caccgcaacc gtcctcctga tcctctctcc  180
tgatcctcct ccttcattcc ttgactcctc ttcacgctcc tctgaccag ccaagtctta  240
catccctctc tacaactact actcttcaaa taatcctctc ctctcggtgg gcttgaatcc  300
cttatcttcc gcctctcccc acgaaccgga ccggatcgtc ttatcgcctc cgcaccagct  360
ggcgcttact acctcatcca cctctttccc gtctcgccac cgaaaccagt ctacaatgcc  420
tcctcgcaag cccagatgct cctttaagga gtgcaaggaa cccagcagc gcattgtcgg  480
agactgcagc ttctgcagcg gtcacttctg ctccaagcat cgcatgctcg aagccactc  540
ctgctccggt ctggaagact gcaagaagga gtcccacgcc cgcaatgctg ataagttgaa  600
cagcgagcgc acacaggtta tcaagggtgt atgacgggat cacatctaca ctactacaac  660
aatctcggcg catttcgatt gcatttactt gccattttta tccgacgttg agttagcgcg  720
gtgttattta caattccttc tttttcttat tttgcctacg atgtctcccc ctatcggtat  780
ggtggtgtct cgtttcggga gcgacatggt ttacaatgat tttggttttgg ggtggtctct  840
cggtatttgt ctattatcca cttatttttcc ggggtattat gcgcatggcg ttactatatg  900
gagtttgata ttctatctcg aatcgatact tttacaac                          938

SEQ ID NO: 139          moltype = DNA    length = 687
FEATURE                 Location/Qualifiers
source                  1..687
                        mol_type = genomic DNA
                        organism = unidentified
SEQUENCE: 139
aagctctccc aagctaatcg agttttttact gtcacttgca tttatacata ccatgtctag   60
gaacttcggc gattttttcga ctaaccaggc tactcagcag ctgtactccg atagaccctc  120
gcatctccct ggaaatggcc ttaagccggc tagacagctc acgatcagtt cagctgtcct  180
attccgctgg gactctgacc aaacccgctt caacctgatc agctctgacc gtcgcgaagt  240
gttgcacatc agcattcgcg caaaagacaa cgttctcgtc ctcaacacca aggcgcccga  300
tggtgactgg ggcagggaag agcgacacga gctcaagaaa cttttcgata cccctatgct  360
gccttacatc accgtgacgg cgacgaagat gacctataac atcactgtcc ctagtggtca  420
agaaatcatc ttcaacaaga ggaaaggatt catggaacct gctgtgaaga ttgagtatga  480
ctatgatgag cactctgcgt tctccgaccc atgctacatt acggttccat cttcttaaag  540
gctcgtcggc ttagagttgg cggatagtca cactggtttt tcatacggca aacggcaatg  600
tattacggct tttctctcct gtcctgttca gcgtagatg tacgatgtat ttgtagtgt   660
ttcaaatttg agttcaagtt gttggcc                                      687
```

| SEQ ID NO: 140 | moltype = DNA length = 601 |
| --- | --- |
| FEATURE | Location/Qualifiers |
| source | 1..601 |
| | mol_type = genomic DNA |
| | organism = unidentified |

SEQUENCE: 140
```
gtctgcttgc ttcaacgagc gctgaatttc ttgttggccg gtgttgattc cccggattcc   60
ctgttatcgc ctgctgtgtt cgccttggta gcaggtgttt gaattggtcc tgcaatttcg  120
ctgattgctg gcctcgaact cccgatcgaa cgaactctcc tctcctccgt caacgcacct  180
tcacatatcg caaagcacaa tggtttccaa gattctcttc tggagtggct tcggcatcgc  240
cgtccgtctc tggcaactcg gtatcgaaat gcgtcccatt cttgccaagc agggtctctg  300
ggcctacccc gtcttcgcag gtgtcggtgg aagcttcggt tactggctcc agggtgtcga  360
ggaccgtcag ctgaagattc ttgcgcagcg ccgcgaagcc atcctcgaca gcgccggag   420
acgggacgag cgtgagggtc tgagcaacat tgagaaggag ggtactttgg ctgcgaccgc  480
atgatttgtt gcgttggctg ttgtttattt tcactgcctt cggagaaaga ccggcaattg  540
cattgctggg catgtatcat accaaaacag aggaaggtta atggtcaatt gtttaatgac  600
c                                                                  601
```

| SEQ ID NO: 141 | moltype = DNA length = 601 |
| --- | --- |
| FEATURE | Location/Qualifiers |
| source | 1..601 |
| | mol_type = genomic DNA |
| | organism = unidentified |

SEQUENCE: 141
```
ggtcattaaa caattgacca ttaaccttcc tctgttttgg tatgatacat gcccagcaat   60
gcaattgccg gtctttctcc gaaggcagtg aaaataaaca acagccaacg caacaaatca  120
tggggtcgca gccaaagtac cctccttctc aatgttgctc agaccctcac gctcgtcccg  180
tctccggcgc ttgtcgagga tggcttcgcg gcgctgcgca agaatcttca gctgacggtc  240
ctcgacaccc tggagccagt aaccgaagct tccaccgaca cctgcgaaga cggggtaggc  300
ccagaggccc tgcttggcaa gaatgggacg catttcgata ccgagttgcc agagacggac  360
ggcgatgccg aagccactcc agaagagaat cttggaaacc attgtgcttt gcgtatgtg   420
aaggtgcgtt gacggaggag aggagagttc gttcgatcgg gagttcgagg ccagcaatca  480
gcgaaattgc aggaccaatt caaacacctg ctaccaaggc gaacacagca ggcgataaca  540
gggaatccgg ggaatcaaca ccggccaaca agaaattcag cgctcgttga agcaagcaga  600
c                                                                  601
```

| SEQ ID NO: 142 | moltype = DNA length = 380 |
| --- | --- |
| FEATURE | Location/Qualifiers |
| source | 1..380 |
| | mol_type = genomic DNA |
| | organism = unidentified |

SEQUENCE: 142
```
gggggcgaca tggcttcgac gccggtgaca atccctgagg tgcatgccga gagcgtaacg   60
tatctcgtaa atccaacgtt acgataaaat agtcgcaaac gacgacaact acgctcaggg  120
cgcgctggca gcgtaacaac tgctagcttc tagtccggcc cggaggtgat gtgcccattc  180
atcaccgaag ggatacgagc tcagactgat gggatcgcgg ctggctttgt cctcgcgtca  240
gccgctaaaa cttagaggaa tcgcgtcgct ggatcctgcc cgtcggagcc agaggcgcta  300
aatcaaaaga cggaccctaag catgtagagc cgatgggtga gtgccggcgg acggggttc   360
aattccccccc gcctccacca                                             380
```

| SEQ ID NO: 143 | moltype = DNA length = 977 |
| --- | --- |
| FEATURE | Location/Qualifiers |
| source | 1..977 |
| | mol_type = genomic DNA |
| | organism = unidentified |

SEQUENCE: 143
```
gggaccagaa cagcttcagc tacaatgcca ttcatcaagg aagccaagag caacagctac   60
ttctctcgct accaagtcaa gtaccgcaga cgtcgtgaag gcaagactga cttctacgca  120
cgtaagcgct tggtaacgca agctaagaac aagtacaacg caccaaagta ccgtctcgta  180
gttagattca cgaacaagga catcatctgt caaatcgtgt catcaaagct tcaaggtgac  240
gttgttctca ctcacgctcg cgcccgcgaa cttccacgtt acggcatcaa gcacggtctc  300
acgtcatggt catccgctta cgcggttggt ctcctcgtcg caagaagagc gctcaccaag  360
ctcggtcttg ctgacaagta cgagggtgac gttgaagcta ctggtgaata caaccctacc  420
gagccacttg gcgatgatga accacgtcct ttcaaggtct tcttgacgt tggtcttaag   480
cgtacctcta ctggttctag agtcttcggt gctcttaagg gcgcctcaga cggtggtctc  540
tacatccctc actctgagaa ccgtttccca ggttacgata tcgagagcaa ggaactcgac  600
gctgaaaatc tgaacaagta catcttgggt ggtcacattg ctgagtacat ggaggctctt  660
gaggaggaag atgaggagag attcaaggct caattctcta cctatcttga agacggtatt  720
ggatctgagg acattgaaga aatcttctcg ggcgcacacg aggctatccg tgctgaccca  780
accttcaagc caagtgaggc tgccaagggc accgactgga agtccgagtc aaagaagcac  840
cgcgctgtca gactcaccaa gcaacaacgc gaggacgcta ccaacagcg tatcaagtac  900
taccagcaag ctggcgacct cgagtaaacg gtaattgtag cggtctacat agacaatcaa  960
tgtctgttgt tccttag                                                 977
```

| SEQ ID NO: 144 | moltype = DNA length = 73 |
| --- | --- |
| FEATURE | Location/Qualifiers |
| source | 1..73 |
| | mol_type = genomic DNA |
| | organism = unidentified |

```
SEQUENCE: 144
gattacccgc tgaacttaag catatcaata agcggaggaa agaaactaa caaggattcc    60
cctagtaacg gcg                                                      73

SEQ ID NO: 145         moltype = DNA  length = 823
FEATURE                Location/Qualifiers
source                 1..823
                       mol_type = genomic DNA
                       organism = unidentified
SEQUENCE: 145
gggtctcttc catttgaatt tttcaaccca cagcatggcc ttcatgaatc tcccatggcc    60
cactgaatgc ctacatgccg ctctcaagaa cggatcctta cctttctggg gatttgtaat   120
ctatcgaacg acctacaccg ctcagtcaga tgccgcctgg ccgcagatta tcgagcttat   180
tgcctcctat atgaaagcct tactctacca cgagtataac gacaagaaaa aagatggaga   240
tgagcctaca gtctacgacg aaatctgggc aaggcatcag ttgacgatta tggatgatag   300
acaattcaac ggagcgtctg tgtttgatat ccaacttcac ttcgaaaagt gggttgaggc   360
gcagggaaag cgagatgaat ctactatgta tcgcatgtgt atggtcattg atgatgaatc   420
aatccagacg ttattggagg cgccacccgg ggaaaatagg aaactcggac gacgtatagg   480
gggccctgta cgctttgtca aagtcgtgga ggctttcccc gagctagaca gccttgacga   540
attccaggga tggatgaaat gtgagatcaa cgcgttatgg ccgctgtgga agatgatgtc   600
tgacggagat gaaatgagga tgtcatatga tgagatgaag gggaatggaa agcaggtcta   660
tggcgcaatt taatcggttt ttcttcatgt tatcctgatg gaaaaaatgg cagaacatat   720
gtctgtacat gcagaaaata aggtgattgg aaaatacttg aatgctatga agttagatag   780
tagctgttct agcggccaga taaagccgcg catgtgaatt tcg                     823

SEQ ID NO: 146         moltype = DNA  length = 181
FEATURE                Location/Qualifiers
source                 1..181
                       mol_type = genomic DNA
                       organism = unidentified
SEQUENCE: 146
gtactaacca ctcgtcaggc gctgaaagaa gaagatgcag taagtttgat gttttctgtg    60
tatgattata cataaagttg ttgtataact acgcagaaaa gttttcgtat gcaaaacttt   120
gattggtgtt aagtcgaaat aaggttcgtg taatggaaat tgcacgggga gtataaaatg   180
t                                                                   181

SEQ ID NO: 147         moltype = DNA  length = 734
FEATURE                Location/Qualifiers
source                 1..734
                       mol_type = genomic DNA
                       organism = unidentified
SEQUENCE: 147
atgacagaga aactttacac cgagcaagtg aatgcgttcg gaaacgaatt acctcctcta    60
tcatacaaag acctggacaa actcccctta caccaaaacg tcatcaaaga aactcttcga   120
atccacaact caattcatac actcatgcgt aaagtgaaaa atcccctccc agtcccagga   180
acaagattgc ttataccaac cagtcacacc ctcctcgcgt ccccgggcgt aacaacccgc   240
gacgattcac acttccgaaa cgcaatgacc tgggatccac ccgttgggaa aacacgaagt   300
gaggtcgaag atgatggtga gacaatcgat tatggatatg gggttgtttc aaaggggacg   360
aagagtcctt atttgccctt tggagcgggt cgacatcgat gtattgggga gaaattcgca   420
tacttgaatc ttactgttat tgttgctact cttgtgagga attttcggtt ttctgaacct   480
gatgatagag agggtgttcc tgaaacggat tattcgttac tcttttctag acctatgcgt   540
ccggcgactg ctcggtggga acgacgtggg gagtactaga ggtgggatta ttggggattt   600
gattgctttt tggaattggg atggaagagt cttgggata tattcttgtt cttcgaggct   660
ttcccaggtg attttcaca gggcttggta ttatcgtatt taatcaatca attcactaca   720
cttttcgagc ttgc                                                     734

SEQ ID NO: 148         moltype = DNA  length = 801
FEATURE                Location/Qualifiers
source                 1..801
                       mol_type = genomic DNA
                       organism = unidentified
SEQUENCE: 148
gacatcattg catccaatat cagatcacat tccatagcct catttactgc ccaagaaggc    60
ttatggccca ttggagagag gagtacctaa ctgcactggc agtgcgagat cagagggaga   120
aggccaatct cagtatttac gatgcctata cccgactcgc agatagcacg gccaaacttc   180
cagctacaat agatacaagt ggcagcccct caggtgataa agggccatct ggtacctacg   240
agtccgaaaa gacggcattt tctcaatcaa ggacagccaa gaagcagcag acagaagtgg   300
agccttcagt tacggagctt ctaaatacta cacgtgcaga actagccgaa gcacagcgct   360
ctcgggcaga attgcgagat cgtctagagc gagctactaa cgaagcggag aaattgcgga   420
aacagattgg caaagatggt cgacgaatac atggactgga aaatgaagtt gctcaacagc   480
aaaagcgccg caaagatgtt gaagaagagt tgagaggaaa ggctaagcta ctcaatgaat   540
tccaagacga aattgcagct ctgactctcc aggtgaacat ggccgagaga aaagctaaga   600
agcttggaga ggagaacgat gatcttgtta atcgttggat gaagagaatg ggccaggaag   660
ctgatgcaat gaatgatgcc tccaagtttt cgtgactgcc gaatcagaat agaatcaaat   720
ggcccagata ggccttcgca ttgttatgac atgatcgaat tccgaggcaa attcgcctat   780
catggtaatg aacggataaa g                                             801

SEQ ID NO: 149         moltype = AA  length = 213
FEATURE                Location/Qualifiers
```

```
source                  1..213
                        mol_type = protein
                        organism = unidentified
SEQUENCE: 149
MAFFPHYTTN LSPLLYLLDD DYAVYRSTCP KSNYHHKQHH SRRQPSPVRY FSPNFDMREG    60
NDSYYLDGEL PGVNQNDVDI EFSDPQTLVI KGRVERNYNN LDGMNEENQQ DEEQFSETLS   120
SKSYQPTVED EDEANHSPPV ATPTYSEKSV TEKTQKPAYK YRNSERAIGE FHRAFNLPTR   180
VDQDAVRATL RNGILSLELP KEPAPKMKKI RIE                               213

SEQ ID NO: 150          moltype = AA  length = 164
FEATURE                 Location/Qualifiers
source                  1..164
                        mol_type = protein
                        organism = unidentified
SEQUENCE: 150
MQLLSTLTPL ALLVTVASAT GKAVNNAVGN AVVTNHCKDP IYLWSVGSSV SPKHTIPSGS    60
NYTEPFRHDD ASGGIALKIT RNDNGLYDGS AQLVYSYALD GEQVWYDLSS VFGDAFAGEA   120
VAVKPENEGC GSICWPKGTT PGGSQVKVCD AEGDVGLVVC AKGC                   164

SEQ ID NO: 151          moltype = AA  length = 149
FEATURE                 Location/Qualifiers
source                  1..149
                        mol_type = protein
                        organism = unidentified
SEQUENCE: 151
LLAEAIRRGL LGWRRAEAKW QRCCCWLSTG HSARKCTREH SLVLHERLSR NRARHWQGVV    60
ALCLRCQQPL CFRTVSFALT VLLECIINRQ RLVHQVLAIH SRDCLVRAVK VVVLDESISF   120
QKKKKKKKKK TGGQVLKLPE GISPHGQKF                                    149

SEQ ID NO: 152          moltype = AA  length = 119
FEATURE                 Location/Qualifiers
source                  1..119
                        mol_type = protein
                        organism = unidentified
SEQUENCE: 152
LKGYGFIQYN DFDSSDQAIT AMNGQYLMNK PLTVDYAFKK DGKGERHGTE AERLLAAEAK    60
RNNALPMPGA IPGQPFMQYQ GMFAGALSGA MPGAQPAATP LPFGFSPAPP QQSTPYGFS   119

SEQ ID NO: 153          moltype = AA  length = 188
FEATURE                 Location/Qualifiers
source                  1..188
                        mol_type = protein
                        organism = unidentified
SEQUENCE: 153
MFGFNFNTTK LLKTILVVCY LQATVLADPY TRVSWEAYMN HVNGSDDYRT QGDDTRATRF    60
PETKPPKQGK DFLWSSKPVP SSDLFLEFFM YEGEPDEFSR TTESYQSLPS NALTARQNAL   120
TCQDIESCSY PPQVNNFQAL FDDLGPSTCN LIKDETRDWI LQQWPGLAVG AVISFAVAVA   180
GSSCDILY                                                           188

SEQ ID NO: 154          moltype = AA  length = 187
FEATURE                 Location/Qualifiers
source                  1..187
                        mol_type = protein
                        organism = unidentified
SEQUENCE: 154
MVRYAHNAEN PEKTAKARGQ HLRTHFKNTR EVAAALTGLK LSKAYKYLGD VQEHKDVIPF    60
RRFNGGVGRA AQAKNHGTTQ GRWPVKSIGF LLRLLKNAEA NADAKSLDTE DLLIKHIVVQ   120
QAPKTRRRTY RAHGRINPYQ GHPCHIEITL AVPDEQVARN KDVEVNQPKK IQGNKRQVAA   180
QRRLTSA                                                            187

SEQ ID NO: 155          moltype = AA  length = 103
FEATURE                 Location/Qualifiers
source                  1..103
                        mol_type = protein
                        organism = unidentified
SEQUENCE: 155
MTGRGKGGKG LGKGGAKRHR KILRDNIQGI TKPAIRRLAR GGVKRISAM IYEETRGVLK     60
TFLEGVIRDA VTYTEHAKRK TVTSLDVVYA LKRQGRTLYG FGG                    103

SEQ ID NO: 156          moltype = AA  length = 307
FEATURE                 Location/Qualifiers
source                  1..307
                        mol_type = protein
                        organism = unidentified
SEQUENCE: 156
MSLDVGDVDA WIDTLSQCKQ LSESDVKLLC DKAREILIEE SNVQPVRCPV TVCGDIHGQF    60
HDLIELFRIG GNSPSTNYLF MGDYVDRGYY SVETVTLLVA LKLRYRERIT ILRGNHESRQ   120
ITQVYGFYDE CLRKYGNANV WKFFTDLFDY LPLTALIDNQ IFCLHGGLSP SIDTLDHIRS   180
IDRIQEVPHE GPMCDLLWSD PDDRCGWGIS PRGAGYTFGQ DISEAFNHSN GLTLVARAHQ   240
```

```
LVMEGYNWSQ DRNVVTLFSA PNYCYRCGNQ AAIMEIDENL KYTFLQFDPA PRAGEPMVSR    300
RVPDYFL                                                              307

SEQ ID NO: 157          moltype = AA  length = 103
FEATURE                 Location/Qualifiers
source                  1..103
                        mol_type = protein
                        organism = unidentified
SEQUENCE: 157
MTGRGKGGKG LGKGGAKRHR KILRDNIQGI TKPAIRRLAR RGGVKRISAM IYEETRGVLK    60
TFLEGVIRDA VTYTEHAKRK TVTSLDVVYA LKRQGRTLYG FGG                      103

SEQ ID NO: 158          moltype = AA  length = 151
FEATURE                 Location/Qualifiers
source                  1..151
                        mol_type = protein
                        organism = unidentified
SEQUENCE: 158
GATTTSILHH FQLSTSSNNS FYHYYLNNLH QNDWTRQGRQ GSRKGRRQAS PQDLARQHPG    60
HHQARHPPSG ASWRCQAYLR HDLRGDPRCP QDLPRGCHPR RRHLHRARQA QDRHLPRRRL    120
RPQEARPHPL RFRWLSSSLF SLRLLCFLQT Q                                   151

SEQ ID NO: 159          moltype = AA  length = 146
FEATURE                 Location/Qualifiers
source                  1..146
                        mol_type = protein
                        organism = unidentified
SEQUENCE: 159
MFSKLIAIAS LALAANAAVI DPSDHTVQYE AAPGKVVTEH YEVLSHAEAS RIIEANPHIS    60
DYRYRCNYQC NDSSGNYMRN LQQGVPNQAC IFSSCYDCDW KFQNCSYCRL STGHNYRDIG    120
GLESWCYNNG GTTVTHNCGY TDGDQC                                         146

SEQ ID NO: 160          moltype = AA  length = 142
FEATURE                 Location/Qualifiers
source                  1..142
                        mol_type = protein
                        organism = unidentified
SEQUENCE: 160
MHFKSLFIAG ALFMVGASAV DCATPEIHCE TSDGSPWYDD AVQATEYWKE IQDAGKDSCG    60
DAGCAQPHGS GCHSDGGSYG TAEIVLCQDD SSSSTPQCAD CRCVYSYLKP LLDQCKGANN    120
KIGGYAHVDM GGNYINYEFV KK                                             142

SEQ ID NO: 161          moltype = AA  length = 100
FEATURE                 Location/Qualifiers
source                  1..100
                        mol_type = protein
                        organism = unidentified
SEQUENCE: 161
LLAPSSWSVP VPLIVPLLRF TARLVMAAPG TTMPSKPLNT GKKSRTPAKT AAVMLVAHSP    60
MALDATATVV AMVPPRSFSA RMTRPLQLPN VPTAGVSTAT                          100

SEQ ID NO: 162          moltype = AA  length = 185
FEATURE                 Location/Qualifiers
source                  1..185
                        mol_type = protein
                        organism = unidentified
SEQUENCE: 162
RAGGNWTMID DLTTGSEDSF SNSWISWFLS TKGNEYFCEV DEEYILDRFN LTGLNNDVQN    60
YSQALELITD SLDDEDLDDE QRDAIENSAR YLYGLIHARY IITSRGLAKM LFLVYPQQLP    120
SKTTNSVPST KPATSADAAV GVDRYLPKIF GFPVHEMSKH ARWQEAQRDL QISRLQQSAS    180
DPSYV                                                                185

SEQ ID NO: 163          moltype = AA  length = 415
FEATURE                 Location/Qualifiers
source                  1..415
                        mol_type = protein
                        organism = unidentified
SEQUENCE: 163
MSLTPEQTEI IKATVPVVKE HGKTITTVFY KNMLEAHPEL NAIFNTTNQV NGHQPNALAG    60
ALFAYASNID NLGALGPAVE LICNKHASLY IQPEHYGIVG KFLLEAMGQV LGDALTPQIL    120
DAWAAAYWQL ANLFIGRESA IYKQSEGWTQ WREFRVAQKV PESAEITSFY LKPVDEKPLP    180
RFRPGQYISV QVHVPQLECP QARQYSLSDK PRDDYYRISV KKETGLNTAK PEAKVNPGYV    240
SNILHENVNE GDVIKVSHPC GDFFLTEQEP SHPVVLIAAG VGLTPLTSML NTLDSTPADS    300
QRKIHFIHGA RTTSVRAFKD QIKSRAERLP NLQATFFTSS PSADEKQGVD YDVQGRIDVS    360
KMDASKDLFL DNAQTEFYIC GPTSFMNDIA NSLKARGATS ERIHMELFGT GGVPV         415

SEQ ID NO: 164          moltype = AA  length = 212
FEATURE                 Location/Qualifiers
source                  1..212
```

```
                        mol_type = protein
                        organism = unidentified
SEQUENCE: 164
MAFMNLPWPT ECLHAALKNG SLPFWGFVIY RTTYTAQSDA AWPQIIELIA SYMKALLYHE   60
YNDKKKDGDE PTVYDEIWAR HQLTIMDDRQ FNGASVFDIQ LHFEKWVEAQ GKRDESTMYR  120
MCMVIDDESI QTLLEAPPGE NRKLGRRIGG PVRFVKVVEA FPELDSLDEF QGWMKCEINA  180
LWPLWKMMSD GDEMRMSYDE MKGNGKQVYG AI                                212

SEQ ID NO: 165          moltype = AA   length = 222
FEATURE                 Location/Qualifiers
source                  1..222
                        mol_type = protein
                        organism = unidentified
SEQUENCE: 165
MARRPARCYR YCKNKPYPKS RFNRGVPDPK IRIFDLGRKK ASVDDFPLCV HMVSNEYEQL   60
SSEALEAARI CANKYLVKIA GKEGFHLRVR AHPFHVVRIN KMLSCAGADR LQTGMRGAFG  120
KPNGVVARVN IGQILLSIRT RDSNRAAAVE AMRRSTYKFP GRQKIIISKN WGFTPVRREE  180
YVKLRQEGKL KQDGAYVQFL RGHGLVEENM KRFPQAYEGV AQ                     222

SEQ ID NO: 166          moltype = AA   length = 252
FEATURE                 Location/Qualifiers
source                  1..252
                        mol_type = protein
                        organism = unidentified
SEQUENCE: 166
MSFYQSRPDT IKGPDPLTDN WTYDSAIDLF SWNPMMPDPF TFDLPDDLMK FESKDMSAGM   60
VAPSDISGFA IGNHLGEDAA SISDPESDDH PWSPSAHAAF PELSPITSTE QVHQETARYS  120
TTPDATSPQE QPSSPPTRST RRRSSADGPV RNAAKRAAHN VIEKRYRTNM NAKFVALEKA  180
MNGGNGVQTS SRGGGSASLK KSEILSNAIA YMHGLQEENR YLQKELAIVK QNLVPAGIWR  240
GAPSCKRETS YR                                                      252

SEQ ID NO: 167          moltype = AA   length = 254
FEATURE                 Location/Qualifiers
source                  1..254
                        mol_type = protein
                        organism = unidentified
SEQUENCE: 167
MGRVIRNQRK GRGSIFTAHT RLNKAPAQFR TLDFAERHGY TRGVVKEIIH DAGRGAPLAK   60
VQFRHPYKFK MVTETFIANE GMYTGQFIYA GKNAQLTVGN VLPLASMPEG TVISNVEEKS  120
GDRGALGRTS GNYVTVIGHN PEDGKTRVKL PSGAKKVIKN TARGMVGIVA GGGRTDKPLL  180
KASRAKHKFA VKRNSWPKTR GVAMNPVDHP HGGGNHQHIG KASTISRYAA QGQKAGLIAA  240
RRTGLLRGTQ KTKD                                                    254

SEQ ID NO: 168          moltype = AA   length = 249
FEATURE                 Location/Qualifiers
source                  1..249
                        mol_type = protein
                        organism = unidentified
SEQUENCE: 168
GAEAYYSPVS SLIGMSTGLR FSTLPAASNP QSSSLIPSPS APISTFPYTL TLTLTPLTGS   60
LSTSYSLRAS PNLSFSSRFG FNVYSWESEM VAGFELWRQS KKPKLAAGSD GDDLEWARRK  120
VRVWDPSAFP LAPPEPEIPQ PNHEDESQES VLKLRVDQSW NVRLLWEGRV KELLVSAGVG  180
LGPSSFSPSS YANPPGTAGA QGSGGGSPAS YWRGVGGFGI IFFMRDFFGS MYLNEHCLDV  240
YSLSDFMRQ                                                          249

SEQ ID NO: 169          moltype = AA   length = 211
FEATURE                 Location/Qualifiers
source                  1..211
                        mol_type = protein
                        organism = unidentified
SEQUENCE: 169
GPGVLSGFQP PDLPLITSIE LDLDVVLPPP ACRTMFLRTV SRAVPRSTAA IRAAPTASVN   60
ALQTRAASDH AIPNPTLANI EKRWEVMPPQ EQAELWMQLR DRMKVDWHQM TLQEKKAAYY  120
IAFGAHGPRA QPPKGEGMRV FAKVLQLTAA SVAVFYAIHA FAGKQPATMS KEWQEASNEY  180
ALKEKINPIH GISKEGYEGK GFVQSPPAEK S                                 211

SEQ ID NO: 170          moltype = AA   length = 153
FEATURE                 Location/Qualifiers
source                  1..153
                        mol_type = protein
                        organism = unidentified
SEQUENCE: 170
VARRGIYLD GNNDLVTMKG NYIYHTSGRS PKVQGNTLLH AVNNYWHDNS GHAFEIGEGG    60
YVLAEGNVFQ DVTTPVEDPV DGQLFTSPDP STNAQCSSYL GRACEINGFG NSGTFNQADT  120
SLLSKFKGQN IASADAYSKV ASSVASNAGQ GHL                                153

SEQ ID NO: 171          moltype = AA   length = 120
FEATURE                 Location/Qualifiers
source                  1..120
```

```
                              mol_type = protein
                              organism = unidentified
SEQUENCE: 171
VRVVTFWPRV TSSRMLLPPL RTPLTASSSL PLTPAPTLSA RHTLAGPAKS TASVTLVPST   60
RLTLACCLNL RVRTLLLLML TLRLPRALPA TPVRDTCKME RGGSELNLLM SDDIALAACW  120

SEQ ID NO: 172        moltype = AA   length = 80
FEATURE               Location/Qualifiers
source                1..80
                      mol_type = protein
                      organism = unidentified
SEQUENCE: 172
MPSKTEAARL QNDFGADYWV RNTQERRHST AGRGLFAGLQ DVKHYNVDHG WARRKSSDNP   60
GLLASFFSRF TGGSYHPPSE                                                80

SEQ ID NO: 173        moltype = AA   length = 137
FEATURE               Location/Qualifiers
source                1..137
                      mol_type = protein
                      organism = unidentified
SEQUENCE: 173
VARRDSHHQI KSRLILLDIT TIQHKVPSYF KQISTIESKC HPKPKQPVYK TTSAQTTGLE   60
IPKNAATQPL AADYSPVSRM SSTITSTMAG PVASLAITPD SLLLSSVDSP GDHTIRPRNR  120
IPFLNVRYWE ECDLNWE                                                 137

SEQ ID NO: 174        moltype = AA   length = 181
FEATURE               Location/Qualifiers
source                1..181
                      mol_type = protein
                      organism = unidentified
SEQUENCE: 174
VVSTQSDEPT IPGGAAVTIH SRNEKKARKA IGKLGLKHVP GITRVTLRRP KNILFVVNQP   60
DVYKSPSSNT WIIFGEAKIE DLNSQAQASA AQQLAAAEAA AGGEHAGHDH EHDILGKGKA  120
PETEGKKEEE EDDGEEVDEA GLEAKDIDLV MAQANVSRKK AVKALRENDN DIVNSIMALS  180
I                                                                  181

SEQ ID NO: 175        moltype = AA   length = 191
FEATURE               Location/Qualifiers
source                1..191
                      mol_type = protein
                      organism = unidentified
SEQUENCE: 175
MFLQRTVSTL ARRTPVRGLA AARPFSSSVS RFNKYEVKEA KLRSLDEIQT EEDLIPPGAK   60
PGTVPSDIEH ATGLERLELV GKMQGIDIFD LRPLDASRKG TLENPIVVNG AGDEQYAGCT  120
GYPVDSHQVN WLTVSRERPI ERCNECGNVV KLNYVGPEED PHAHDHGHGH HPAPEEPKTF  180
ADYVKPEYWY R                                                       191

SEQ ID NO: 176        moltype = AA   length = 261
FEATURE               Location/Qualifiers
source                1..261
                      mol_type = protein
                      organism = unidentified
SEQUENCE: 176
MNPYIVDPML KYVAFDIPAL ARLDPSLCLF LILFFENSRV VLLGYLPVPV LGLDVVGEGL   60
GLLGGRVVAV AVVVSVRVLL RSDIVQLDNV TAFVAALDGA LTRDSQPVNL VRVDGVTSAT  120
SVLLVTSTVD NNGVFEGSLA GSIQRPQVED VNSLHFTDEF ETLETSGVFD IARDGTGLST  180
RGDEVFFSLD LVKRTELGLL NLVLVESANG RRKRARGSKA PHGGAPREGR YRTLKEHSPC  240
CNRTGRSNGR GEGGGGVDVG S                                            261

SEQ ID NO: 177        moltype = AA   length = 221
FEATURE               Location/Qualifiers
source                1..221
                      mol_type = protein
                      organism = unidentified
SEQUENCE: 177
MADITAVGEE NPSPTQDELQ QAAAGNGAPD NRTPKRRMSD DEEDEEKQGR ERRKIEIKFI   60
QDKSRRHITF SKRKAGIMKK AYELSVLTGT QVLLLVVSET GLVYTFTTPK LQPLVTKAEG  120
KNLIQACLNA PDPTTSENGV DAPEVPAETP EDVNHANVNA AAAQQTNIPR PTGMHPGYMT  180
NEQQQQMAYY QNHLQQQQQA GGQYPGMSVG GRMPTQHQPT A                      221

SEQ ID NO: 178        moltype = AA   length = 176
FEATURE               Location/Qualifiers
source                1..176
                      mol_type = protein
                      organism = unidentified
SEQUENCE: 178
MSFAADPPPN NHGTLTHLFR APEDLVYPIP ENFSLEETVL VEPLSVAIHG ARVAGITPGH   60
TVLVQASGTI GLFCAATATA FGAKQVIISD INQTKLDFAR DYLGCPIFLP NISSSHPEEE  120
ASRMKEYIES QRRCRYSSVV YGSGILVAKS GPGGVVVPNW TRFNRVQSNG TYHQYV      176
```

```
SEQ ID NO: 179              moltype = AA   length = 86
FEATURE                     Location/Qualifiers
source                      1..86
                            mol_type = protein
                            organism = unidentified
SEQUENCE: 179
MPRGAEYANG PLQSDNAIEA GENKAHGTSG NTGLNRVNKV AEFPEGARGT GTAANPLSGQ    60
GSAGHQDGKG GHDPKTLGEN KGLGTQ                                        86

SEQ ID NO: 180              moltype = AA   length = 78
FEATURE                     Location/Qualifiers
source                      1..78
                            mol_type = protein
                            organism = unidentified
SEQUENCE: 180
MPSKLAKIRP TEPPVTPAST ASTRSPNSPK APEEPVPLLT RSVARVAPAI RMERVAMTRR    60
PLERTRDWVL NDLMIQKT                                                 78

SEQ ID NO: 181              moltype = AA   length = 166
FEATURE                     Location/Qualifiers
source                      1..166
                            mol_type = protein
                            organism = unidentified
SEQUENCE: 181
MTTITEFPPF YTQQPNASAL TQQLGLWQKH ILSTCKQRRQ FKLSVSDDIW ANERIKRAAS    60
REFISVIISS LVTEGLASYT DATKEAVWVY WRSLSDWAQA AYAYAESTAQ LNTPLTYYEL    120
VQGEYSHLSE LHEMPVELLK LAVSLLVKQN KAVIIKTSQG EGVKFV                  166

SEQ ID NO: 182              moltype = AA   length = 130
FEATURE                     Location/Qualifiers
source                      1..130
                            mol_type = protein
                            organism = unidentified
SEQUENCE: 182
MSIPKAAAHT DKAPQPFKDL YSQAVIAGGV VYCSGIVAID PETGSLIEGD VKAHTERILQ    60
SLSSTLQAAG TSLDRAVKIN VYLANMEDFT SMNSVYEKYF VDGVKPCRTC VAVKSLPFGT    120
DVEMECIAVL                                                          130

SEQ ID NO: 183              moltype = AA   length = 113
FEATURE                     Location/Qualifiers
source                      1..113
                            mol_type = protein
                            organism = unidentified
SEQUENCE: 183
MLRSQFGVIS NAAKTAAFLK PVQTRLYASG ALSKGDIQTR IFDVLKSFDK VKADNLTESA    60
SFTNDLGLDS LDAVEVVMAI EEEFAIEIPD AEADAIQNVN QAIEYIAKTP EAH           113

SEQ ID NO: 184              moltype = AA   length = 200
FEATURE                     Location/Qualifiers
source                      1..200
                            mol_type = protein
                            organism = unidentified
SEQUENCE: 184
VVSTQSGAPG TKKVSSTYLS KICKEQHKSI FFYLIDLHSS ASLRSVTTLP ARMERIRLSE    60
QAATICNQIR EMIPETATLP NQPGKDQAEL MHEDENGNKI YGGKLLTERA ARLKEHMKID    120
QVSARFISQY FTNGIQDWTE RLVYWTKPTK LLNQRKQGYI IPLSKDIVLQ PGGPLEANNG    180
FRVTNERILS SGAALFIMPQ                                               200

SEQ ID NO: 185              moltype = AA   length = 524
FEATURE                     Location/Qualifiers
source                      1..524
                            mol_type = protein
                            organism = unidentified
SEQUENCE: 185
MLARSLQQIR RSSRLSLQLR AYASSPDRSA SFSKLSEQDL PSLASIFSSP DTSLLTTLGD    60
KPTATSDDLE PFNVDWMGKY KGHSSIIVKP KTTQEVSKVL QWCNERNVAV VPQGGNTGLV    120
GGSVPLHDEV VLSLSSMNSI RHFDPLSGYV SVDSGIVLEN LDNYLAQQGH IVPLDLGAKG    180
SCQIGGNVAT NAGGLRMLRY GSLHGNVLGL EVVLPDGRVI NGMKGLKKDN TGIDLKQLFI    240
GSEGVLGVIT GVTLATPVRP SATNVAVFAL PDYESVQTAF SSARRDLGEI LSAFEFFDAA    300
SYKLVRSHGH AAERKTFEDG EDAPFFCLVE TSGSNKDHDD EKLGAFLEQL MESGIVNDGV    360
LAQDETQIGQ LWSLREGIPE AAGKAGRVYK YDLSLPVEKM YSLVPELRQK LAEKGLLAAE    420
SEGGNGDGPV KTVFGFGHLG DGNLHINIVA DAYRKEVEEV VEPYIYELVA KYNGSISAEH    480
GLGLMKAPYV AYSQDAPSLD LMRTLKKTLD PKGILNPYKC VTAE                     524

SEQ ID NO: 186              moltype = AA   length = 185
FEATURE                     Location/Qualifiers
source                      1..185
                            mol_type = protein
```

```
                        organism   = unidentified
SEQUENCE: 186
MALYYGIVFG ILTFEIILFF LFLLPIPTRW QKPVFRWLAT SPTIAHAQYI MKIVFVFIFV    60
LFLDSVNTLR AFYEVVNTED ENGGIPAAGN SDFRAQVGQA AKKFYAQRNL YLTGFTILLL   120
LILNKIKNMA MDYIRLEDQF IELEGSVSKD PAIRKASKEI DTTPIEDHVT RLEPVEQEQE   180
NKKDI                                                              185

SEQ ID NO: 187          moltype = AA   length = 138
FEATURE                 Location/Qualifiers
source                  1..138
                        mol_type = protein
                        organism = unidentified
SEQUENCE: 187
VARREAPNGH ELPPRGYDPG ENTYQAPPDE RSQVDVAIDP KSNRLQLLKP FQKWDGKDIT    60
NVPILIKVQG KCTTDHISMA GPWLKYRGHL DNISNNFLIG AKSSEGKVNS IKNAFTGEYK   120
GVQKQLVITR RKVFVGSW                                                138

SEQ ID NO: 188          moltype = AA   length = 144
FEATURE                 Location/Qualifiers
source                  1..144
                        mol_type = protein
                        organism = unidentified
SEQUENCE: 188
GCPETARDYK KEGVRWVVVG DENYGEGSSR EHAALEPRFL NGAAIITKSF ARIHETNLKK    60
QGMLPLTFAD PKDYDKVDAS DKVDILGLTD FQEGKPLTLR LHKKDGSTVD VPLNHTFNGQ   120
QIEWFKHGSA LNLMKENTAK NGSL                                         144

SEQ ID NO: 189          moltype = AA   length = 264
FEATURE                 Location/Qualifiers
source                  1..264
                        mol_type = protein
                        organism = unidentified
SEQUENCE: 189
VARREAPNGH ELPPRGYDPG ENTYQAPPDE RSQVDVAIDP KSNRLQLLKP FQKWDGKDIT    60
NVPILIKVQG KCTTDHISMA GPWLKYRGHL DNISNNFLIG AKSSEGKVNS IKNAFTGEYK   120
GVPETARDYK KEGVRWVVVG DENYGEGSSR EHAALEPRFL NGAAIITKSF ARIHETNLKK   180
QGMLPLTFAD PKDYDKVDAS DKVDILGLTD FQEGKPLTLR LHKKDGSTVD VPLNHTFNGQ   240
QIEWFKHGSA LNLMKENTAK NGSL                                         264

SEQ ID NO: 190          moltype = AA   length = 195
FEATURE                 Location/Qualifiers
source                  1..195
                        mol_type = protein
                        organism = unidentified
SEQUENCE: 190
GAPLTQEHGF PVRVIVPGVA GARAVKWLDH ITVQREMSSN HYMHFDYKVL PPEAVDAERA    60
RTFWHKVPPV IDMPANSAIT SPRNEDTVEV DAEGFITVDG YALPGGEDGP VKRVEVSIDK   120
ERWVDAELFT HPMESKWTWK IWKAKVQVEP GERRCLYSRT TDEAGNSQPQ RSQWNLRGVC   180
YNGYGEVRNL KVVKG                                                   195

SEQ ID NO: 191          moltype = AA   length = 50
FEATURE                 Location/Qualifiers
source                  1..50
                        mol_type = protein
                        organism = unidentified
SEQUENCE: 191
MPANTMSATL RSLHVPGKPV IFANVWDTVS AKSIAPLDSC KALATASYAI               50

SEQ ID NO: 192          moltype = AA   length = 373
FEATURE                 Location/Qualifiers
source                  1..373
                        mol_type = protein
                        organism = unidentified
SEQUENCE: 192
ALPMLLINPP RNLIGQSQSG TGKTAAFTLN MLSRVDPNIM TPQAICLAPS RELARQIQEV    60
VDKIGQFTQI KSFLAVPGSW SRNVKIDKHI LVGTPGTLVD MLSRGGRIFD PKQIRVFVLD   120
EADEMIALQG LGDQTKRIKR MLPPGVQNVL FSATFPDNVR DFAGDFAPEA NQIFLKKEEI   180
TVDAIKQLYL ECDGEEQKYN ALSALYDIMS IGQSIVFCKS KTDADRIAAR LTDEGHSVAS   240
LHGDKQTRDR DDILDAFRDG KTKVLITTNV VARGIDIQQV NMVVNYDVPD LGPEGDWKPD   300
IETYIHRIGR TGRFGRKGCS VIFAHDQRSM QDVQFIADTL GKKMSRINAT RQTDLDQLEA   360
ALKAAIKGNQ PKE                                                     373

SEQ ID NO: 193          moltype = AA   length = 274
FEATURE                 Location/Qualifiers
source                  1..274
                        mol_type = protein
                        organism = unidentified
SEQUENCE: 193
MATFSTRINL VPTSRTLASG VPFAPRIALV HPPASHGHGT SGPRSDVPPR WAGVQGGFAS    60
```

| | | | | | |
|---|---|---|---|---|---|
| NSRVNVLPTG | NFQQRFMSTT | PARKIEAQPH | VRGVPDWSAY | QSSGKGENTR | SLSYFMVGSL | 120 |
| GVLAASGAKS | TVSDILSNMA | ASADVLALAK | IEVEMGAIPE | GKNLIVKWRG | KPVFIRHRTE | 180 |
| DEINEARAVD | IKSLRDPESD | EDRTQRGEWL | VMLGVCTHLG | CVPIGEAGDY | GGWFCPCHGS | 240 |
| HYDISGRIRR | GPAPLNLEVP | EYAFNDDEEK | LVIG | | | 274 |

```
SEQ ID NO: 194          moltype = AA   length = 472
FEATURE                 Location/Qualifiers
source                  1..472
                        mol_type = protein
                        organism = unidentified
SEQUENCE: 194
GEHHHSDRDC SSVKRVFALG RLDVTLAVEC GSVRTMSLRD LACYTLTLKP STENTLLTEL   60
TALEGPSEEP RFARVREKVE GEVYSSAIYD ALTGAKLASV GFASEKQKNR RLQLHNPDES  120
VPFDNTSKLG FEWTFIFEGN KYRWTRELYG KDYICSLDRK PDPRVEICLA RDADSKAPGR  180
LQILHYNIER FPPNEIKDLRG LETLLIATLM CFVDAAEDRS NSGPTRTSPL PAKPVANAAA  240
GQSGTSASGS SDTRAKVAPV TVPVITAEDF EDDCDPNEIL VGTETDVGEH IARAIALLED  300
PTMLFIVIRT RTAAASSRAL EVSLGVTRFR HREGMSELHQ YVVEEDPVRK PKPIMPAQGL  360
KLINLDDRPA AQSPTKPEWS APPNIAVYLS SIELPDLTPK PKPVQGHTRP PTQAPHARPP  420
PPSQLPQKPQ PRPRPPPSDG SGSSQTTLAS TRPPQDDGKD SRKSSFGRLF GR          472

SEQ ID NO: 195          moltype = AA   length = 82
FEATURE                 Location/Qualifiers
source                  1..82
                        mol_type = protein
                        organism = unidentified
SEQUENCE: 195
MASQLMPLEL IDRCIGSRMR VIMKGDKEFS GTLLGFDDFV NMVLEDVTEY DYTGATTKLP   60
KILLNGNNIC MLIPGGMPEG ES                                            82

SEQ ID NO: 196          moltype = AA   length = 116
FEATURE                 Location/Qualifiers
source                  1..116
                        mol_type = protein
                        organism = unidentified
SEQUENCE: 196
GDDNKKTIPH LNIFNNGVPI DAPGADRSLH RIKNACDHER RQRVQRHTSR IRRLRQYGAR   60
GCHRVRLHRR NDQASQDPSE RQQHLHAHPR WHARGRVMNH GHMISLLTSL EMAKRV      116

SEQ ID NO: 197          moltype = AA   length = 108
FEATURE                 Location/Qualifiers
source                  1..108
                        mol_type = protein
                        organism = unidentified
SEQUENCE: 197
AKELSPDVKP EPTWSCGEVV NVVDEHGNVI KPSDLWVKMG MQQQDNVDNL LIDDLCDQMR   60
AKAKCTENGA QLNVDDLNHM MSYDKSYKQK RVDDLKDKYG WGAVFGPK               108

SEQ ID NO: 198          moltype = AA   length = 38
FEATURE                 Location/Qualifiers
source                  1..38
                        mol_type = protein
                        organism = unidentified
SEQUENCE: 198
GSLTRRAWFI QSTCATTGDG LYEGLEWLAD TLRKTNRD                           38

SEQ ID NO: 199          moltype = AA   length = 311
FEATURE                 Location/Qualifiers
source                  1..311
                        mol_type = protein
                        organism = unidentified
SEQUENCE: 199
MENLLRQMQG GGGRMGARPG PGGETILADN GETVHISSLA LLKMLKHGRA GVPMEVMGLM   60
LGEFVDDYTI SCVDVFAMPQ SGTTVTVESV DHVFQTKMLD MLKQTGRPEM VVGWYHSHPG  120
FGCWLSSVDV NTQQSFEQLH PRAVAVVIDP IQSVRGKVVI DAFRSINPQS LVAGQESRQT  180
TSNIGHLNKP SIQALIHGLN RHYYSLAIDY RKTEGEQGML LNLHKRGWTE GLKMRDHSEM  240
KEGNEKAIKE MLSLASAYTK SVQEETTMTA EQLKTRHVGK LDPKRHLGEA AEKAMGDQVT  300
QSLAMGVLAE L                                                       311

SEQ ID NO: 200          moltype = AA   length = 213
FEATURE                 Location/Qualifiers
source                  1..213
                        mol_type = protein
                        organism = unidentified
SEQUENCE: 200
GHTGDVLSVS FSADNRQIVS ASRDRTTKLW NTLGECKFNI VDDGHSEWVS CVRFSPNPVI   60
PVIVSAGWDK VVKVWELSKC KLKTNHHGHT GYINTLAVSP DGSLAASGGK YGITMLWDLN  120
DGKHLYSLEA GDIVNSLVFS PNRYWLCAAT ASSIKILDLE SKSIVDDLKP DFSAEYPDKA  180
QKPQCTSLAW SADGQTLFAG FSDNLVRVWV VTA                               213
```

```
SEQ ID NO: 201          moltype = AA   length = 76
FEATURE                 Location/Qualifiers
source                  1..76
                        mol_type = protein
                        organism = unidentified
SEQUENCE: 201
MVTRSGSLAF DSLLTPSFPS SSLLVGTRSS RSGNCPSASS RPTTTVTLVT STPSPFRPTD    60
RSPHPVESMA SPCFGI                                                   76

SEQ ID NO: 202          moltype = AA   length = 99
FEATURE                 Location/Qualifiers
source                  1..99
                        mol_type = protein
                        organism = unidentified
SEQUENCE: 202
MLWDLNDGKH LYSLEAGDIV NSLVFSPNRY WLCAATASSI KILDLESKSI VDDLKPDFSA    60
EYPDKAQKPQ CTSLAWSADG QTLFAGFSDN LVRVWVVTA                           99

SEQ ID NO: 203          moltype = AA   length = 124
FEATURE                 Location/Qualifiers
source                  1..124
                        mol_type = protein
                        organism = unidentified
SEQUENCE: 203
VPAIVQIPKH GDAILSTGCG ERSVGRNGEG VDVTSVTVVV GLELALGQFP DLDDLVPTSR    60
DDDGNDGVRR ESNARDPLRV TIVNNVELAL SESVPELGSS VSGSRNDLSV VGRERDAQDV   120
TGVS                                                                124

SEQ ID NO: 204          moltype = AA   length = 38
FEATURE                 Location/Qualifiers
source                  1..38
                        mol_type = protein
                        organism = unidentified
SEQUENCE: 204
GSLTRRAWFI QSTCATTGDG LYEGLEWLAD TLRKTNRD                            38

SEQ ID NO: 205          moltype = AA   length = 393
FEATURE                 Location/Qualifiers
source                  1..393
                        mol_type = protein
                        organism = unidentified
SEQUENCE: 205
GRYDFKQPQR IRDASVTATP EWNLLEEIEF GRLGKLNLSV EEPEDLESHG TLQGYDKTFD    60
RINTRTERPL EIIDRAWYNQ TTSDDPVIAQ LAQTQSAQIF ATDAILAVLM CTTRSVNSWD   120
IILERRGNQL FLDKRDSGPF DYVTVHENAA DPPADSDDPN NVNSASSLSL EATYITRNFS   180
SQVIDAKSKP YSPSPNPFYS EDEPSPVASC LYRYRKFDLS VGEEDTLDLI VRTEVDAYQG   240
KKDSLVTVKA LNEFDPRASG GKALDWRKY LDTQKGAIVA SEMKNNSAKL ARWAIQSVLA    300
GAEVMKMGYI SRASPRDTTH HVIVGVQNYK PKDFAAQMNV SLNNGWGIVR TIADLVLKQP   360
EGKYVLVKDP NAGIIRLYSV PENAFEAEEE EEQ                                393

SEQ ID NO: 206          moltype = AA   length = 106
FEATURE                 Location/Qualifiers
source                  1..106
                        mol_type = protein
                        organism = unidentified
SEQUENCE: 206
MTSSSLSEFE TLLSRPRQNG TCLKRSSLAD WASSTFPSKS PKTSNRTVPS KVTTRRLTAS    60
TLVPKDLSRS LIEHGTIKPL LTIPLLLSSL KRSLPKSSRQ MPFLRF                  106

SEQ ID NO: 207          moltype = AA   length = 245
FEATURE                 Location/Qualifiers
source                  1..245
                        mol_type = protein
                        organism = unidentified
SEQUENCE: 207
ERSRSLAPEA DQGVATQCHE VRSSGSYDTF EIGHHQPDSD TSGVADLRTS SRMDTCDAHL    60
LRRVKSCPLF SYREDEVSET VQLPTGEWTT IRDITPSAPK IGFEVRDSLS AFPTAKPVEA   120
KHESASSISN DLPSQPSSRP LIECPTLVAD SRTTTGSNSV RSFDAQTERL SGLSDVHHRY   180
MQDKPSQRSD SWTDVKSSAP SSQSMAVPNK AAYLAPIPAG PNDSKTSSSG RAPSDAATEH   240
ECSLQ                                                               245

SEQ ID NO: 208          moltype = AA   length = 148
FEATURE                 Location/Qualifiers
source                  1..148
                        mol_type = protein
                        organism = unidentified
SEQUENCE: 208
MAPKSTDKPA STAGKAPSAG GKAPASKTVG AKKTAAKKSA KSTGEGGEKK KRVKSRKETY    60
STYIYKVLKQ VHPDTGISNK AMLILNSFVN DIFERIAGEA SKLATYNKKS TISSREIQTA   120
```

```
VRLILPGELS KHAISEGTKG VTKYSSSK                                          148

SEQ ID NO: 209           moltype = AA  length = 369
FEATURE                  Location/Qualifiers
source                   1..369
                         mol_type = protein
                         organism = unidentified
SEQUENCE: 209
DVKRFTKDLL FNSEGNLTFK PHLWNDIRHT LLPTFIRQIG YVPIPRAEFS SPDIDLVIEN        60
LVLSGPNLFP NVVSLESHNS FKFSPYQQLN KGMDTHHHKF RLGMSQIQAD IRDVRFSFRR       120
KTGWPKLKDH GLADVILAGK GMSIDVELES VEGRRDSVVR VNHVHTTIDT LTFSIRDSKH       180
DLLYKFVKSV ATGTIKKAIQ AAVDNAIRTA VGHLDDQLVQ VRNTVDDAKK SDETTRTQAL       240
KDLYSKKADT AQKKQAESKE QPGTFRIVAN RDSVLNPDMG GGKGAMTNKM WKTEDLAHSG       300
KEWHSPAFDL LDSKHPARTG QTHPEAKEGA GHGNSLSSKA QPGANAADQL KATHGQSEAE       360
AIAGQKRQQ                                                              369

SEQ ID NO: 210           moltype = AA  length = 173
FEATURE                  Location/Qualifiers
source                   1..173
                         mol_type = protein
                         organism = unidentified
SEQUENCE: 210
MSDSRSDERL DGPSSRTTVS PMSSLPVRVC RSTSSSSLSR DDETLLCEST TSTPPSTPSP        60
SPSETPSTTC STSSSSRWPR VRSRRQSRPP STMPSVRLSV TSTTSSSRSE TPSMTPRSLT       120
RPPERKPSRT CTRRRRTRHR RSRPSPRSSL VLSESSPTET LFSTPTWAVA RAP              173

SEQ ID NO: 211           moltype = AA  length = 248
FEATURE                  Location/Qualifiers
source                   1..248
                         mol_type = protein
                         organism = unidentified
SEQUENCE: 211
MYTSAVTLLS LVLLLATSVI AQEQAGRPGT QRGGVFFGCY ADRPTGNANQ PITRVANSDT        60
FFECMENCAA ITSPSLLGYY QPSSGQCFCG NLLFNPQAQL NGNGCQGSDW SFGRTSTTFR       120
RFGDACRPFG GVGFSANQYT TVTGPVACHV QCASNRFAYV WSDTGSNSWV CACSNNVRVQ       180
EDFQYTCQGG GVFVFEHSVQ AQASSLNRKR TVEEQWAVPK DALCPFGMSA CKVSGVDNAY       240
EVCFFSDR                                                               248

SEQ ID NO: 212           moltype = AA  length = 116
FEATURE                  Location/Qualifiers
source                   1..116
                         mol_type = protein
                         organism = unidentified
SEQUENCE: 212
MFNAHQTDSP MSGPILEATH GNVLAATMSV FRRTSSTLVK VAVYLCLNIQ YKLRLLRLTG        60
SGRWRNNGLF RKTPSVHSEC QRARYQVSIM LTRYASFQTA RPLVPWPRGL KHAIDL          116

SEQ ID NO: 213           moltype = AA  length = 271
FEATURE                  Location/Qualifiers
source                   1..271
                         mol_type = protein
                         organism = unidentified
SEQUENCE: 213
GGGTVVSNAL LENAKLCKTQ GKESSLRVIV CGRNRLENGS APHWAEAFAT HGKLVEVRMP        60
QNGIRMEGIK AIADGLAKCP TLEVLDLQDN TATKTGTRSI VRHLSTWPKL RILNLSDCLL       120
GSVGGIALAT ALSTGSNKHL EQLKLQYGEF DKRTVEILST AISQHLPKLT TLELNGNRFD       180
AEDECVETLK KALELHGNED ALDELDDMEE VDEDEEDDDD EDEEDEDEDK DTSADDGIDA       240
GAAGEDALPP VTKKDEDVLA DLLSKVHVQP S                                     271

SEQ ID NO: 214           moltype = AA  length = 222
FEATURE                  Location/Qualifiers
source                   1..222
                         mol_type = protein
                         organism = unidentified
SEQUENCE: 214
LDRRSASTSS SFFVTGGRAS SPAAPASIPS SALVSLSSSS SSSSSSSSSS SSSSTSSISS        60
SSSKASSFPC SSSAFFRVST HSSSASKRFP FSSSVVNFGK CWLIAVDSIS TVLLSNSPYC       120
SLSCSRCLFE PVDNAVARAI PPTEPKRQSE RLSIRSLGQV ERCRTILRVP VLVAVLSCKS       180
STSNVGHLAS PSAIALMPSM RMPFCGILTS TNLPCVANAS AQ                         222

SEQ ID NO: 215           moltype = AA  length = 176
FEATURE                  Location/Qualifiers
source                   1..176
                         mol_type = protein
                         organism = unidentified
SEQUENCE: 215
MVKLSNSLVR RLKWQHVRSL GVVALTAQLR GPQPQSAEDE DSEAAGKKLK LAGDQATSAV        60
IPKSADKPDT FPLLDTLPAT MAAGTRSMTR PLHVGDLRLA DLRKIMQAAG HTAEFRGEGT       120
LLIDKSVAVR KSGTGQIEIE ASAQAAANQA TPGRGASSFL AVKRKIYEGL AVVTGS          176
```

```
SEQ ID NO: 216          moltype = AA   length = 139
FEATURE                 Location/Qualifiers
source                  1..139
                        mol_type = protein
                        organism = unidentified
SEQUENCE: 216
KMKIDVEKLN KDISLFPQVH PITEDMKITH KGVSRLVMLD RYSFKDTEKI TLSEGDFVVL   60
TIKEDPKFPA RGLGYIKEID WENKKAKVQV EEEFRHTLEK PEERETGIIV RSLDVIEKPL  120
EIFYEQIAKR NATGLAAVE                                               139

SEQ ID NO: 217          moltype = AA   length = 282
FEATURE                 Location/Qualifiers
source                  1..282
                        mol_type = protein
                        organism = unidentified
SEQUENCE: 217
GDATVTQLRE IMDDPAGYFL PNLKHGADNM FYVGPRGLAQ ELEELFTFPS TILRKRQDTS   60
QHDERQAKKA RTQEDEAAGD ALEEPETGRR DSVLPTERAA FGLEGDDSGF FLGDQTMGDD  120
MLPMDDMGAM DTGVDQRRMR TPSVAPSVTE SIARQIQNDR SAGTHPLAIF EKEARDDTQS  180
QSQATPNKSV ASESISKTSS GQSKNTGMAM GLLRREIEAI EEEDKMVGFD HLADKASKRA  240
ASAFFFELLV LGTKHAVKLE QAQAFGDIHI RGKDKLFAEV VA                     282

SEQ ID NO: 218          moltype = AA   length = 261
FEATURE                 Location/Qualifiers
source                  1..261
                        mol_type = protein
                        organism = unidentified
SEQUENCE: 218
MAPITCSTSV HADLHKSSRS FLPSQAQSSE SARIPVSMTK GRQRRRARKR TKRLVTRWRS   60
PRLGDATVCF RLNGPLLVSR VMTRAFSLAT RRWETTCCLW TTWEPWTPEW TSDACEHHQS  120
HRRSPNRSHV RFRMTEALAH THWLYSRRRQ GTTRSRNRRL RPTNRWPPSL SARLLLANQR  180
ILAWPWVCCE GRLRRSRRKT RWSGLITWQT RRPSEQRLHS SSSCWCLVPN MRSSLNKLRL  240
SATSTYAAKT SCLQRLLHRQ T                                            261

SEQ ID NO: 219          moltype = AA   length = 108
FEATURE                 Location/Qualifiers
source                  1..108
                        mol_type = protein
                        organism = unidentified
SEQUENCE: 219
MGDHATTNDP SNATFEEKGK GKDVQDQIAE DSSDEESDQE PEMVDEEEDD NNLEPISQDN   60
IISGGRRTRG KIIDYAAEAE KNKDEMEDSE DDEDYQGAND DEDDQMRD                108

SEQ ID NO: 220          moltype = AA   length = 78
FEATURE                 Location/Qualifiers
source                  1..78
                        mol_type = protein
                        organism = unidentified
SEQUENCE: 220
ELKYFKAVAL YNLSRYLDAR KAINDLIQSY PDFRQAEALK SAIDDKVVRD GLIGVSVAGA   60
VVAGVVGLAV ALARGNRG                                                 78

SEQ ID NO: 221          moltype = AA   length = 27
FEATURE                 Location/Qualifiers
source                  1..27
                        mol_type = protein
                        organism = unidentified
SEQUENCE: 221
MGHVESRVNQ RGPPRKAKYS WVTDSEK                                       27

SEQ ID NO: 222          moltype = AA   length = 27
FEATURE                 Location/Qualifiers
source                  1..27
                        mol_type = protein
                        organism = unidentified
SEQUENCE: 222
MLKAPFFHRP CGGKGVQLKW ATPDSAV                                       27

SEQ ID NO: 223          moltype = AA   length = 177
FEATURE                 Location/Qualifiers
source                  1..177
                        mol_type = protein
                        organism = unidentified
SEQUENCE: 223
MPVRPYLEEM ADMPVPLFAY DAPPTLADHP HAREHQHTTF MQYLARKQPD PKNYPNYPDV   60
DIRDAINHYL IELECPGIKD AADIHCQWTS SRHLTVTGDI ARPEESQIEA QIESRPVYLV  120
LGERRIGSFR RNFTFPVEVE QENMTAKLEA GLLKIVLPKH KHHTPKGTGK VDIDVIE     177
```

```
SEQ ID NO: 224            moltype = AA  length = 163
FEATURE                   Location/Qualifiers
source                    1..163
                          mol_type = protein
                          organism = unidentified
SEQUENCE: 224
MVLVLGQDNL QQSGLQLGSH IFLLDLHREG KVATERANAS LSQNQVDGPA LDLRFDLAFL    60
RTGDVAGDGQ VPRARPLAVD VGCVFDPRAF ELDQVVIDGV ADVHVRVVGV VLWVRLLARK   120
VLHEGRVLVL AGVRVVGQGG RCVVREQGHG HVGHFFQVGS YGH                     163

SEQ ID NO: 225            moltype = AA  length = 118
FEATURE                   Location/Qualifiers
source                    1..118
                          mol_type = protein
                          organism = unidentified
SEQUENCE: 225
MFGFNFNTTK LLKTILVVCY LQATVLADPY TRVSWEAYMN HVNGSDDYRT QGDDTRATRF    60
PETKPPKQGK DFLWSSKPVP SSDLFLEFFM YEGEPDEFSR TTESYQSLPS NALTARQK     118

SEQ ID NO: 226            moltype = AA  length = 349
FEATURE                   Location/Qualifiers
source                    1..349
                          mol_type = protein
                          organism = unidentified
SEQUENCE: 226
MSPTPTSPHN KLSLPARASS HDSTDGIRKR VCKACDRCRL KKSKCDGSSP CSRCKADNAI    60
CVFGERKRSH DKHYPKGYVE MLEQQQGQLV SGLKEMYHRL QKASAWDGPV LDESTGQPLT   120
HDILSALDLL EPKHDDSNEP EVFEENCEKL QSKLLADGAG FAHRRGSISS DSEHSHHDRP   180
KTSSRHDTPV QPKPSIFKEN LSFASAASSP LTQSPIPRSK PLNVMPYQTL QPSSRPSPLQ   240
MPSAYNDPQL YAPEWAQALA DMSGDPNYRQ RFSMQQQQQN DFDNLLWDPS AQAPMESPFS   300
QPAFFNQAQL IGSGNVFGLS DINDLGPNPA DGGMDFDFSK FVQQTEVMT               349

SEQ ID NO: 227            moltype = AA  length = 149
FEATURE                   Location/Qualifiers
source                    1..149
                          mol_type = protein
                          organism = unidentified
SEQUENCE: 227
MSSFRVAAPK MASMAAQSSV KVARPAFQAA QLQKFTRAYS AVPKNTVFNT MKRTQMMARQ    60
ASPIAKRAYS SEMANALVQV SQNIGMGSAA IGLAGAGVGI GLVFAALIQA VARNPSLRGQ   120
LFSYAILGFA FVEAIGLFDL MVAMMAKFL                                     149

SEQ ID NO: 228            moltype = AA  length = 165
FEATURE                   Location/Qualifiers
source                    1..165
                          mol_type = protein
                          organism = unidentified
SEQUENCE: 228
MECTFLQELG HHGNHEVEET DGLDESETKN GVREKLATEG GVAGDGLDEG GEDETDTDTS    60
TGKTDGGGTH TDVLGDLDEG VGHLRGVGTL GDGGGLAGHH LGALHGVEDG VLGDRGVGAG   120
ELLELSSLEG RAGDLHGGLS GHGGHLGGGD AEGRHCDDGE VVRWS                   165

SEQ ID NO: 229            moltype = AA  length = 425
FEATURE                   Location/Qualifiers
source                    1..425
                          mol_type = protein
                          organism = unidentified
SEQUENCE: 229
GGFSVKFRTA EGNWDFVANN TPVFFLRDPA KFPHFIHTQK RDPATHLSGD DDSTMFWDYL    60
SQNPESIHQV MILMGDRGIP KGWRFMHGYY GHTLKIVNDK GEWVYAQFHL ISDQGTQNFT   120
GDEAAQQSND YGQKDLYEAI EKGDFPSWTM KVQIMTEKQA EEAWEQKRIN VFDLTHVWPH   180
GDYPLRTVGK FTLNENAKNY FAEVEQVAFN PSHMIPGVEP SNDPVLQSRL FSYPDAHRHR   240
IGANYQQLPV NQNVCPFALG NFQRDGQMAF YNQGSRPNYL SSIEPISFKE RAYDLNKVHG   300
KFVGEAVAFL SEIRPEDFNA PRALWQKVFS EESKQRFVDT VSGHMSTVRD KAITARMMTI   360
FREVSPDLGD RLEKATGVKG ESTIAGMKFN GTHNGFDKAN KIPANGMKKG GEVIFDNGAP   420
ATAAR                                                               425

SEQ ID NO: 230            moltype = AA  length = 239
FEATURE                   Location/Qualifiers
source                    1..239
                          mol_type = protein
                          organism = unidentified
SEQUENCE: 230
VSVSIGVREQ SRLQHWVVGR LDTGNHVRRV ECDLFHLGEV VLGILVKGEF TDCSKWVITM    60
RPDVGQIKDV DPLLLPCLLG LLLGHDLNLH RPRGEVSLLD GFVQILLSVI VGLLSSLVTR   120
EVLGALIRDE VELGVDPFAL VIDNLEGVAV VAMHESPALG DTSITHEDHD LVDRLGVLRQ   180
VVPEHGRVIV TRQVGGGISL LGVDEVGELG RVSEEEDGGV VGHKVPISFC GPELDRESS    239

SEQ ID NO: 231            moltype = AA  length = 368
```

| FEATURE | Location/Qualifiers |
|---|---|
| source | 1..368<br>mol_type = protein<br>organism = unidentified |

SEQUENCE: 231

```
DTIDAEVLDS LGVTQENFQF ALGVSNPSAL REVAVVEVPN VRWEDIGGLE EVKRELIESV    60
QYPVDHPEKF LKFGMSPSKG VLFYGPPGTG KTLLAKAVAN ECAANFISVK GPELLSMWFG   120
ESESNIRDIF DKARAAAPCV VFLDELDSIA KSRGGSQGDA GGASDRVVNQ LLTEMDGMTS   180
KKNVFVIGAT NRPEQLDNAL CRPGRLDTLV YVPLPDQEGR ESILKAQLRK TPIADDIDLS   240
YMASKTHGFS GADLGFITQR AVKLAIKQSI DLAIQNQKAR EAEGDTAMDE DIEEDDPVPE   300
LTKAHFEEAM SMARRSVTDT EIRRYEAFAQ SMKSSGGGSA FFRFPESGAD GNAAEQQQNG   360
AGEEDLYD                                                            368
```

| SEQ ID NO: 232 | moltype = AA length = 317 |
|---|---|
| FEATURE | Location/Qualifiers |
| source | 1..317<br>mol_type = protein<br>organism = unidentified |

SEQUENCE: 232

```
MHDCSLHLEY YSDNSKGLGR EVRETNLVVE VLLASTILLL LGCVAIGTAL REAEESAAAT    60
GALHALGESL VAPDLGVGDG ATSHAHSLLK VSLGQLGHGV VLLDVLVHGG VTLGLSSLLV   120
LDGQVNRLLD GQLDGTLGDE AKIGTRETVS LGGHVGKVGN VGDRSLAELG LENALTALLV   180
RQGNVDESVE TTRTAESVVE LLRPVGGTDD ENVLLAGHTV HLSEKLVDHT VGSTASIALR   240
TATRLGDGVQ LVEEDNARRG STSLVEDVTN VALRLTEPHG EKLGTLDGNK VGRALVGDSL   300
GQKSLTSTRG TVEKHTL                                                  317
```

| SEQ ID NO: 233 | moltype = AA length = 166 |
|---|---|
| FEATURE | Location/Qualifiers |
| source | 1..166<br>mol_type = protein<br>organism = unidentified |

SEQUENCE: 233

```
VSPKRTSSLP LASATPLPFA RSQWSRFPTS DGRTLVVSRR SRGSSSRACN TPSTTPRSSS    60
SLACPHQRVC FSTVPLVLVR LFWPRLSPTS ARPTLFPSRV PSFSPCGSVS LRATFVTSST   120
RLVLPRLALS SSTSWTPSPS LVAVLRAMLA VLPTVWSTSF SLRWTV                  166
```

| SEQ ID NO: 234 | moltype = AA length = 160 |
|---|---|
| FEATURE | Location/Qualifiers |
| source | 1..160<br>mol_type = protein<br>organism = unidentified |

SEQUENCE: 234

```
MGHSAGLRKG TRYAFSRDFK KRGMIPLSTY LKQYKVGDIV HVVCNGAVQK GMPHKDFHGK    60
TGVVYNVTKS AVGVILYKQV GNRYIEKRVN LRIEHVRLSR SREEFIVRVK TNAEKKRKAK   120
EEGTTVFLKR QADKPREART ISAKDNKPES IAPIAYDTHI                         160
```

| SEQ ID NO: 235 | moltype = AA length = 526 |
|---|---|
| FEATURE | Location/Qualifiers |
| source | 1..526<br>mol_type = protein<br>organism = unidentified |

SEQUENCE: 235

```
DMGIGGLDTE FSAIFRRAFA SRIFPPGLVE KLGIQHVKGI LLFGPPGTGK TLMARQIGTM    60
LNAREPKVVN GPEILNKFVG QSEENIRKLF ADAEKEQKEK GDESGLHIII FDELDAICKQ   120
RGSTNSGTGV GDSVVNQLLS KMDGVDQLNN VLIIGMTNRM DMIDEALLRP GRLEVHIEIS   180
LPDEAGRFQI LNIHTNKMRT NGVMDSDVDL GELAALTKNF SGAEIGGLVK SATSFAFNRH   240
VKVGSVAAFD DIDNMKISRA DFLHALDEVT PAFGVSEEEL QQVVQNGIIH YSQHVNDTLN   300
DGSLLVEQVR KSDRTPLVSA LLHGPSGAGK TALAATIAMA SEFPFIKLIS PETMVGFSEP   360
QKIAQLNKVF TDSYKSPMSI IVVDSLERLL DWNPIGPRFS NGVLQALVVL FGKRPPKGRR   420
LLILATTSNR NILTDMDVLS AFDTDIPINP ISSIDAVVHV LDEVKLFPNS KEKQRATQML   480
REARLGEGGR PDLLVGVKKL LSMAEMARQD PDPTMKIVTS ILREAS                  526
```

| SEQ ID NO: 236 | moltype = AA length = 425 |
|---|---|
| FEATURE | Location/Qualifiers |
| source | 1..425<br>mol_type = protein<br>organism = unidentified |

SEQUENCE: 236

```
GGFSVKFRTA EGNWDFVANN TPVFFLRDPA KFPHFIHTQK RDPATHLSGD DDSTMFWDYL    60
SQNPESIHQV MILMGDRGIP KGWRFMHGYY GHTLKIVNDK GEWVYAQFHL ISDQGTQNFT   120
GDEAAQQSND YGQKDLYEAI EKGDFPSWTM KVQIMTEKQA EEAWEQKRIN VFDLTHVWPH   180
GDYPLRTVGK FTLNENAKNY FAEVEQVAFN PSHMIPGVEP SNDPVLQSRL FSYPDAHRHR   240
IGANYQQLPV NQNVCPFALG NFQRDGQMAF YNQGSRPNYL SSIEPISFKE RAYDLNKVHG   300
KFVGEAVAFL SEIRPEDFNA PRALWQKVFS EESKQRFVDT VSGHMSTVRD KAITARMMTI   360
FREVSPDLGD RLEKATGVKG ESTIAGMKFN GTHNGFDKAN KIPANGMKKG GEVIFDNGAP   420
ATAAR                                                               425
```

| SEQ ID NO: 237 | moltype = AA length = 122 |
|---|---|
| FEATURE | Location/Qualifiers |

| | | |
|---|---|---|
| source | 1..122 | |
| | mol_type = protein | |
| | organism = unidentified | |

SEQUENCE: 237
```
MLTDTESEPT ISNCPLTRMC APSPWATSSE TARWHSTIKV VDPTTFLRLS QSHSRRGRMI    60
STRSTANSSE KPSPSCLKSG QRTSMPQGHC GRKSLARKAS SDSSTPSLVT CRQSETKPSP   120
LE                                                                122
```

| | | |
|---|---|---|
| SEQ ID NO: 238 | moltype = AA   length = 309 | |
| FEATURE | Location/Qualifiers | |
| source | 1..309 | |
| | mol_type = protein | |
| | organism = unidentified | |

SEQUENCE: 238
```
MPPRQPATRL FALPPRFLCP SLPTTQTRTI RSIDKPAPKP SRFNASLNLP VLGSSSTAAF    60
ARKEHSLPLR TGALAIKKGM TALFDPVTAK RTPCTVLQLD RCQVVSHKRR DIHGYWAVQV   120
GAGAKEARNV TRPERGHFAA YNVPLSRHLA EFRVKNAEGL PPVGSAITAD LFIEGQFIDA   180
KADRRGMGFE GGMKRWNFGG QPASHGNSLA HRLMGSSGGG QGSGSRVLPG KKMPGRMGGE   240
QATVANLRVM QVDKENGIVV VSGAVPGPKN CMVKLQDALK KPWPDATWPP SIEGATEVLR   300
EATEKAPAA                                                          309
```

| | | |
|---|---|---|
| SEQ ID NO: 239 | moltype = AA   length = 130 | |
| FEATURE | Location/Qualifiers | |
| source | 1..130 | |
| | mol_type = protein | |
| | organism = unidentified | |

SEQUENCE: 239
```
MGIWDAFTDI VEAVTPWSVV EAEAPAEEPQ EENESKTESK DEPEEEEEDE EEEEDEDDEE    60
ELVDPKETLE EECKNSPQCA PAKHHFDECV ERVQQQESEG GAKEDCVEEF FHLAHCATAC   120
AAPKLWSQLK                                                         130
```

| | | |
|---|---|---|
| SEQ ID NO: 240 | moltype = AA   length = 136 | |
| FEATURE | Location/Qualifiers | |
| source | 1..136 | |
| | mol_type = protein | |
| | organism = unidentified | |

SEQUENCE: 240
```
MRKKRRMRMM RRSSSTPRRL SRKSARTLLN VPPPSTTSTS VLSAFSSRRA RVVLRRTVSR    60
SSSTLPTVRP LAPLPSFGLS SSKLTTLGYR LLRRRNGYIH VEKMPGAGTR QCCPLRKAVP   120
LYECSSAGYQ VGQRLL                                                  136
```

| | | |
|---|---|---|
| SEQ ID NO: 241 | moltype = AA   length = 194 | |
| FEATURE | Location/Qualifiers | |
| source | 1..194 | |
| | mol_type = protein | |
| | organism = unidentified | |

SEQUENCE: 241
```
GRYYRAPEIM LTWQKYDVAV DIWSTGCIFA EMLEGKPLFP GKDHVNQFSI ITELLGTPPD    60
DVIQTIASEN TLRFVQSLPK REKVPFTTKF ANADPLSLDL LEKMLVFDPR TRISASEGLS   120
HEYLAPYHDP TDEPVAAEVF DWSFNDADLP VDTWKVMMYS EILDFHNLGD IQQDQAAEGP   180
VTGDLAPPSA TTSA                                                    194
```

| | | |
|---|---|---|
| SEQ ID NO: 242 | moltype = AA   length = 134 | |
| FEATURE | Location/Qualifiers | |
| source | 1..134 | |
| | mol_type = protein | |
| | organism = unidentified | |

SEQUENCE: 242
```
MSPSTFGAQD VSSPRCSRES PCSRARTTLI SSRSSQNCSA HLLTMSSRPS HLRTPSDSSS    60
RCPSVRRSHS LRNSPMPTRF RLTCWRRCLS SIHVPVSRHQ KGCRTSTLRH TMTRRMSPSL   120
PRCLTGVSTM RIYQ                                                    134
```

| | | |
|---|---|---|
| SEQ ID NO: 243 | moltype = AA   length = 111 | |
| FEATURE | Location/Qualifiers | |
| source | 1..111 | |
| | mol_type = protein | |
| | organism = unidentified | |

SEQUENCE: 243
```
GYPLNLSISI SGGKETNRDC PSNGERSGKS SNLKAGPLGV RIVICRGCFG NGPHLSALER    60
AVIEGENPVW DGVAAPVSSS FDESSCLGMQ LKLGGKFHLK LNIGRRPIAH K            111
```

| | | |
|---|---|---|
| SEQ ID NO: 244 | moltype = AA   length = 41 | |
| FEATURE | Location/Qualifiers | |
| source | 1..41 | |
| | mol_type = protein | |
| | organism = unidentified | |

SEQUENCE: 244
```
GLVAIARRPH PFPCQTRKLS VSAPKVVGGS PPVRIGRCQA K                       41
```

```
SEQ ID NO: 245            moltype = AA  length = 218
FEATURE                   Location/Qualifiers
source                    1..218
                          mol_type = protein
                          organism = unidentified
SEQUENCE: 245
MEPDQEESEE EEEEEDDEMD EDEDEGQQQD ASGMQTPSGL ATPSGYASTT STMPGGMETP        60
DFMDLRKQRQ TRDETADQED QGAPRDLYTV VPERRATASG FLGSDRAYDL SNAPQSSNMP       120
VLGQEDSRKK KGGRSGADDV DLALDPAELE GMSEQELRQK YDSHRRSSSS QGAGGQQDKE       180
DFSDFVAQEV AKKRQRAQQR GGSGRDRESS RSKEKFKF                              218

SEQ ID NO: 246            moltype = AA  length = 210
FEATURE                   Location/Qualifiers
source                    1..210
                          mol_type = protein
                          organism = unidentified
SEQUENCE: 246
MTRWMKMRMR ASSRTPVACR HPLGSPRPQA MPLLHQCLV AWRRLTLWTC ASSDRRATRP         60
LIKRTRVHRE TSIRSCPSAE PPLLASSVLT APMTCPMRHS LPTCLCWVKK TRARRKAADL       120
VQTTSTWPWI QLSSRACLSK SLGRSTTRTG APRPVKAPAD SRTKKISQIS SRKRSQRRGR       180
GLSSAAAVDA TAKALGARKS SSFRVYVCIV                                       210

SEQ ID NO: 247            moltype = AA  length = 164
FEATURE                   Location/Qualifiers
source                    1..164
                          mol_type = protein
                          organism = unidentified
SEQUENCE: 247
GVIQVDEPAL REGLPLRTGA ARDAYVKWAV NAFKLSTAGV TDSTQVHSHF CYSEFQDFFH        60
AIAALDTDVL SIENSKSDAK LLQVFVDQSF PAHIGPGVYD IHSPRVPSVD EIKERIEQML       120
QYLKPEQLWI NPDCGLKTRT TEQTIGQLTS LVEAAKFYRQ KYTQ                        164

SEQ ID NO: 248            moltype = AA  length = 125
FEATURE                   Location/Qualifiers
source                    1..125
                          mol_type = protein
                          organism = unidentified
SEQUENCE: 248
VRVFLCVLAL PVMLMLSGLS MLSSCLLLVS PTAPRSTPTS ATVNSRTSST LLLPLIPMFC        60
PSRTASPMPS SSRSSLIRVS PPTLDLVSTI STLLVFPPWM RSRSVSSRCS STSSLSSSGS       120
TLTAV                                                                  125

SEQ ID NO: 249            moltype = AA  length = 171
FEATURE                   Location/Qualifiers
source                    1..171
                          mol_type = protein
                          organism = unidentified
SEQUENCE: 249
MLMRTELLSV LLAVELSSLD QRGQLADSLL SGTGLQTAVR VDPELLRLEV LEHLLDTLLD        60
LIHGGNTRRV DIVDTRSNVG GETLINEDLE ELGIGLAVLD GQNIGIKGSN SVEEVLEFTV       120
AEVGVDLGAV GDTSSRQLES IDSPLNISIT GSASTQRKTL TQGRLVDLDD P                171

SEQ ID NO: 250            moltype = AA  length = 66
FEATURE                   Location/Qualifiers
source                    1..66
                          mol_type = protein
                          organism = unidentified
SEQUENCE: 250
LKSGVFGVRV VICRGCFWAA TDLSSLEQDV IEGENPVCGR KGTLHVAPST SRVVWECSSK        60
WEVNFF                                                                  66

SEQ ID NO: 251            moltype = AA  length = 189
FEATURE                   Location/Qualifiers
source                    1..189
                          mol_type = protein
                          organism = unidentified
SEQUENCE: 251
MKLSNSAHYS LFLLSSILGF SSASANSHLS DDSPCVARSP TSGLYYDLNA ISLAPPEWKN        60
GKKVDQEARD ESWHAKGHDY PANFTINVCA PVLENVTNVV GVDASRWANV SAFYEQAGKI       120
YSMGEQASEP FFRGRKLVLN YTDGSPCPGD SNTASGNSSI RTKSTLMSFL CDRAAEFPGL       180
EKLGSTGSR                                                              189

SEQ ID NO: 252            moltype = AA  length = 393
FEATURE                   Location/Qualifiers
source                    1..393
                          mol_type = protein
                          organism = unidentified
SEQUENCE: 252
MNGFNEKGLD GDAFGEKSNL SGLKTFDAFP KTKTSYTTPT RRGGQWTVLI LAVCTLFSLH        60
```

```
ELRTWWRGTE AHHFSVEKGV SHDLQLNLDM VVHMPCDTLR INIQDASGDR VLAGELLTRE    120
DTNWDLWMKK RNFESHGEHE YQTLNHEAAD RLSAQDEDAH VHHVLGEVRR NPRRKFSKGP    180
RLRWGDNKDS CRIYGSLEGN KVQGDFHITA RGHGYMELAP HLDHEVFNFS HMITELSFGP    240
HYPSLLNPLD KTIAESETHY QKFQYFLSVV PTLYSKGHNA LDLVTTNKDN SVRYGRNTIF    300
TNQYAATSQS TALPEIPTLI PGIFFKYNIE PILLLVSEER TGFLALVIRV INTVSGVLVT    360
GGWIYQISGW IVEILGKRKR QSEGVLTGKH YSD                                 393

SEQ ID NO: 253          moltype = AA   length = 292
FEATURE                 Location/Qualifiers
source                  1..292
                        mol_type = protein
                        organism = unidentified
SEQUENCE: 253
MFTRTLRPAV AVARTQAVQQ QQAGMATLKE IDQRLKSVKN IGKITKSMKV VASTKLTRAE    60
KAMREAKKYG AANNVLFEQT KAGEEEPKER KILYLAMTSD GGLCGGIHSN ITRYMKKAVA    120
KEPGMLAVVG DKPKAQLSRA MPKALTMSFN GVGKDVPTFV EASAIADEIM KSAGDFDEIR    180
IVSNKYLSAI AYEPHTNAVI SAEALRQAAG FQQYEMEEDV SKDLAEFALA NAIYTALVEG    240
HAAEISARRQ AMENASNNAN DMINSLQLQY NRGRQAVITT ELIDIITGAS AL            292

SEQ ID NO: 254          moltype = AA   length = 317
FEATURE                 Location/Qualifiers
source                  1..317
                        mol_type = protein
                        organism = unidentified
SEQUENCE: 254
MSFAACHFCC FVHLVYTRLQ SRGTGNDIDQ LGGNDSLSTT VVLQLERVDH VVGVVGSVLH    60
SLPPCRDLGG VSLDQGSVDG VGKSELGQVL GDILLHLVLL ETGGLSECLS GDDGVGVRFV    120
GDSGKVLVRD DSDLVKVTGR FHNLIGDSAG LDESGDILAD AVERHGQSLG HRSRELSLGL    180
VTDNSQHSGF LGHSLLHVSR NVGVDTTAQT TVGCHGEVED LALLGLLLTS LGLLEQNVVG    240
GTVLLGFTHG LLSSRQLGRG NDLHRLGDLP NVLDGFQTLV DFLQCGHTGL LLLDSLSPGD    300
RHGRSESTRE HGVERGE                                                   317

SEQ ID NO: 255          moltype = AA   length = 311
FEATURE                 Location/Qualifiers
source                  1..311
                        mol_type = protein
                        organism = unidentified
SEQUENCE: 255
MENLLRQMQG GGGRMGARPG PGGETILADN GETVHISSLA LLKMLKHGRA GVPMEVMGLM    60
LGEFVDDYTI SCVDVFAMPQ SGTTVTVESV DHVFQTKMLD MLKQTGRPEM VVGWYHSHPG    120
FGCWLSSVDV NTQQSFEQLH PRAVAVVIDP IQSVRGKVVI DAFRSINPQS LVAGQESRQT    180
TSNIGHLNKP SIQALIHGLN RHYYSLAIDY RKTEGEQGML LNLHKRGWTE GLKMRDHSEM    240
KEGNEKAIKE MLSLASAYTK SVQEETTMTA EQLKTRHVGK LDPKRHLGEA AEKAMGDQVT    300
QSLAMGVLAE L                                                         311

SEQ ID NO: 256          moltype = AA   length = 93
FEATURE                 Location/Qualifiers
source                  1..93
                        mol_type = protein
                        organism = unidentified
SEQUENCE: 256
MGAIPEYDPE EPLETKPFKF VTAGYDARFP QQNQTKHCWQ NYVDYYKCVE AKGEDFRPCK    60
QFYHAFRSLC PKAWTDRWDT QREGGNFPAI LNK                                 93

SEQ ID NO: 257          moltype = AA   length = 252
FEATURE                 Location/Qualifiers
source                  1..252
                        mol_type = protein
                        organism = unidentified
SEQUENCE: 257
GPLLEELDVE AYAKKYRYLR FMCQETLDHL AFLKDKVKDV EGFWASTLLK HRDLRGYITS    60
RSDKDALKYL THIELVQDPK DPRPFALKFY FKENPYFSDL VLEKKYDMSE GSEPAPADGS    120
ITEGMRNFKE DELVTKATTI NWKSDDKNLV AKQPRSKIPD NDDDEDFDGD VGSFFNYFTD    180
DTDIFQIGAL LQSELLPDAI DYFVGRGEQV DSEGEELDEL EEDDEDDDED DEGSIDLEDE    240
EEQPSKKKPK RA                                                        252

SEQ ID NO: 258          moltype = AA   length = 165
FEATURE                 Location/Qualifiers
source                  1..165
                        mol_type = protein
                        organism = unidentified
SEQUENCE: 258
GSFLTPQHTH TPFGRAMHNA LTVSRLNDKF QEPLVVLVEL LRARVLHDRN FSNRQFSGGP    60
SFGTDNQKRS MLLIFRTLSI IPLQFKAEHW SGPLSRELLV FNSFHKTLSR SLRTLVESIT    120
MNAFLKNNAR RARDDYLDIA LSLPFQNDTN TGFGIFFKVG GLAGV                    165

SEQ ID NO: 259          moltype = AA   length = 94
FEATURE                 Location/Qualifiers
source                  1..94
```

```
                              mol_type = protein
                              organism = unidentified
SEQUENCE: 259
QIYLDALTTF  AEGNITEENK  DSESVKEAKQ  SAMEILGDAI  PNVKDPEAEL  LRGFRFWDAV   60
LVCVRTLKAD  RAIDLKLAES  FEAANSYLNM  MRPN                                 94

SEQ ID NO: 260           moltype = AA  length = 251
FEATURE                  Location/Qualifiers
source                   1..251
                         mol_type = protein
                         organism = unidentified
SEQUENCE: 260
GSFLTPQHTH  TPFGRAMHNA  LTVSRLNDKF  QEPLVVLVEL  LRARVLHDRN  FSNRQFSGGP   60
SFGTDNQKRS  MLLIFRTLSI  IPLQFKAEHW  SGPLSRELLV  FNSFHKTLSR  SLRTLVESIT  120
MNAFLKNNAR  RARDDYLDIA  LSLPFQNDTN  TGFGIFFKIY  LDALTTFAEG  NITEENKDSE  180
SVKEAKQSAM  EILGDAIPNV  KDPEAELLRG  FRFWDAVLVC  VRTLKADRAI  DLKLAESFEA  240
ANSYLNMMRP  N                                                           251

SEQ ID NO: 261           moltype = AA  length = 148
FEATURE                  Location/Qualifiers
source                   1..148
                         mol_type = protein
                         organism = unidentified
SEQUENCE: 261
GIYLDGNNDL  VTMKGNYIYH  TSGRSPKVQG  NTLLHAVNNY  WHDNSGHAFE  IGEGGYVLAE   60
GNVFQDVTTP  VEDPVDGQLL  TSPDPSTNAQ  CSSYLGRACE  INGFGNSGTF  NQADTSLLSK  120
FKGQNIASAD  AYSKVASSVA  SNAGQGHL                                        148

SEQ ID NO: 262           moltype = AA  length = 120
FEATURE                  Location/Qualifiers
source                   1..120
                         mol_type = protein
                         organism = unidentified
SEQUENCE: 262
VRVVTFWPRV  TSSRMLLPPL  RTPLTASSSL  PLTPAPTLSA  RHTLAGPAKS  TASVTLVPST   60
RLTLACCLNL  RVRTLLLLML  TLRLPRALPA  TPVRDTCKME  RGGSELNLLM  SDDIALAACW  120

SEQ ID NO: 263           moltype = AA  length = 160
FEATURE                  Location/Qualifiers
source                   1..160
                         mol_type = protein
                         organism = unidentified
SEQUENCE: 263
MSAQPLRIVM  ACDEAGVPYK  DAIKAVLEKS  PLVASVSDVG  VNDASDKTAY  PHPAVEGAQQ   60
IKAGKADRGL  FICGTGLGVA  IAANKVPGIR  AVTAHDPFSV  ERSILSNDAQ  VLCMGQRVIG  120
VELAKKLALD  WLNYRFDPKS  ASAAKVQAIS  DYETKFAGSS                          160

SEQ ID NO: 264           moltype = AA  length = 150
FEATURE                  Location/Qualifiers
source                   1..150
                         mol_type = protein
                         organism = unidentified
SEQUENCE: 264
MSVTTTSSAA  AASCTPSWQI  PVDDVACAGQ  ISGNITKVFD  TCCKGNSPVK  YNDDCNIYCL   60
AQGQTKQELT  DCLTEKSGNN  QIFCGHGKQN  ATATAEATTT  KETGTSTGTS  TSSTGTSTET  120
NAAVLNQPIS  KTGLGLVAML  FCSALVGVVA                                      150

SEQ ID NO: 265           moltype = AA  length = 197
FEATURE                  Location/Qualifiers
source                   1..197
                         mol_type = protein
                         organism = unidentified
SEQUENCE: 265
AGVDRGVITK  DEKDSSINRL  LVTGYGLAEV  MGTDGVNGIK  TRTNHVMETC  EVLGIEAARQ   60
TIYNEIQHTM  TSHGMSIDPR  HVMLLGDVMT  YKGEVLGITR  FGVQKMKDSV  LMLASFEKTT  120
DHLFDASLFS  KKDEIQGVSE  CIIMGTPAPG  CGTSLASIVT  PAPLLPRKKP  LLFETAFKAG  180
QDRLSYHENN  GGMEVDM                                                     197

SEQ ID NO: 266           moltype = AA  length = 249
FEATURE                  Location/Qualifiers
source                   1..249
                         mol_type = protein
                         organism = unidentified
SEQUENCE: 266
AGSGGAYSFS  LTTFSPSGKL  VQIEHALAAV  AGGTTSLGIK  ATNGVVLATE  KKSPSLLLDT   60
SVLEKVAPIC  PNIGFVYSGM  GPDFRVLVAK  ARKIAQAYYK  VYGEYPPTKV  LVQEVAGVMQ  120
KATQSGGVRP  YGISLLIAGW  DSHRGQSLYQ  VDPSGSYWAW  KASAIGKNMV  NGKTFLEKRY  180
NDDLSLEDAI  HTALLTLKEG  FEGQMTENTI  EIGVVTVPTA  EQMQEKPGER  LPPTFRKLTE  240
QEVRDYLAL                                                               249
```

```
SEQ ID NO: 267          moltype = AA  length = 346
FEATURE                 Location/Qualifiers
source                  1..346
                        mol_type = protein
                        organism = unidentified
SEQUENCE: 267
MLTSAFSTSA SKMLGKRAVS SSSALNGKVA VLGAAGGIGQ PLSLLVKQNP AVSSLSLYDV    60
RGSPGVAADI SHINTPAVTE GFLPDNDGLK QALEGAEVVL IPAGVPRKPG MTRDDLFNTN   120
ASIVKMLAEA SAKYCPKAMM LIIANPVNST VPIVAETFKR AGVYDPARLF GVTTLDVVRS   180
STFVSGITGA KPSDTVVQVI GGHSGATIVP LLSQIPQGDK IVKAGGQQYA DLVKRIQFGG   240
DEVVKAKDGT GSATLSMAYA AAVFNDALLK AMDGQKGLVQ PAYVESPHFA KEGAKYFASN   300
VELGPNGVEK ILDIGNMSSE EQELLKECLP QLAKNIAAGE KFVADN                  346

SEQ ID NO: 268          moltype = AA  length = 373
FEATURE                 Location/Qualifiers
source                  1..373
                        mol_type = protein
                        organism = unidentified
SEQUENCE: 268
MSLFLLFSLA LIIIGSNVVG YPLVVSDELL TSSNVLGELG KALLKELLLL RGHVADVEDL    60
LNTVGAELDV GGEVLSTLLG EVGALDVSGL NETLLAVHSL EESVVEDGSG VSHGEGSGAS   120
AVLGLDDFVT AKLDALDEVS VLLAASLDNL VALRDLGEQG HDGGARVTTD DLDHGVGGLG   180
TGDARDESGR ADNVEGGDTE ETGRVVDTST LEGLSDDRHG GVDGVGNDEH HSLGAVLGRS   240
LSKHLDDGSV GVEKVVTGHA GLARNTSRNE DHLSTLEGLL EAIVVGEEAL GDSRGVDVAN   300
VSSNTRGAAN IVKGEAGDSR VLLDQQGEGL ANTASSTEDG NLSVQGAGRR DCSLAEHLGS   360
RCRKGAGQHF GSK                                                     373

SEQ ID NO: 269          moltype = AA  length = 435
FEATURE                 Location/Qualifiers
source                  1..435
                        mol_type = protein
                        organism = unidentified
SEQUENCE: 269
GASVLLPALH FDEREQRPGR TSSTASLLQR HDRNEPLSLN SHSPTSVDHT PTTAHFTGAE    60
ELLASDVGPT ATAGLPGDAE LESKLKLLEE VKRARESVHS SLERIRAGTP TPSISQGMPS   120
PTPSGAPGYA RTPSSVGLSD DVRSRRGSTT SSKVLDAIDK PRVATQSEWD EYVRNRHVIS   180
PPPTQFAVLP TSAAMVDRGT SRHSQYALVS DGVAKALDRR ERTISMMEPQ VAEDWGPRET   240
LDSTPAHVSM GRRAMSFHEI PLASPVAASR PQDRSSYSAG PRQVIGSAAG HTQRPGISQS   300
RSAHGRTMTY DELTERHRQR LSALQAPVSA KIREPMDIAS AKASWDKQKR VERDEMKRRE   360
AEKLAQAHAR ERRGPAVDKK EVLKSTDEWR RSVHGGLDGF AVPHLPAHAR GSTQPGGSGA   420
KRSSLSQRPS NYFAN                                                   435

SEQ ID NO: 270          moltype = AA  length = 225
FEATURE                 Location/Qualifiers
source                  1..225
                        mol_type = protein
                        organism = unidentified
SEQUENCE: 270
GQACCFRHCI STSGSNDLDV RLRLQVCCSV TIAMNLYRST RTRRHLWTTL PLLRISLVLK    60
SCSPPTSDRP RQLGYPVMRS LRASSSCLKR SNVHGNRYIA RSRGSEPARL PRLSARECPA   120
RHPLVPLVTL ELRRLSACRT TCARDEAQRP APRFLTLSTS LESLPNPNGT STFATGMSSH   180
LHPLSLPYCP HLLRWSIVVP VDTASMPLFP TALPKRLTGG SELFQ                   225

SEQ ID NO: 271          moltype = AA  length = 168
FEATURE                 Location/Qualifiers
source                  1..168
                        mol_type = protein
                        organism = unidentified
SEQUENCE: 271
MGSPAPHHRH QSSLEGVIDF STGRGHPLNP YQRDKAESVF TGIINRFEDS STVEKPYNRA    60
KLVRLTYEYA RSEDSRCNFL QAFFGSVNVT MDDSIDFDDE AVEEGIRSSL NSFADFLVEN   120
FFLPLKASAS RTPPAPQPKF RADVLLWGLW KEWPRSDATA SSAIDIVA                168

SEQ ID NO: 272          moltype = AA  length = 253
FEATURE                 Location/Qualifiers
source                  1..253
                        mol_type = protein
                        organism = unidentified
SEQUENCE: 272
QDAPSPPAQV PSRRPAVGSV ERVASLRRDC LIRDRHRCVI SRNFDMKEAE RRLDDSGYDH    60
ASDDEGHLLK DQEHGSFAEL EVAHILPHSL MTTTANSELN KSKETALTIL NMFDSGIVHL   120
IDGPDIDRPR NALTLSIDLH RQFGNFKVFF EPMPEPHTYR IDSTLRQPFR NPIFPVTRAL   180
YLTPERTIDP PSGRLLAVHR AICHILHLSA AGNYIDSILR DMDDGTVQAN GSTRLASIVR   240
LKLGGWWDGT VVG                                                     253

SEQ ID NO: 273          moltype = AA  length = 106
FEATURE                 Location/Qualifiers
source                  1..106
```

-continued

```
                                mol_type = protein
                                organism = unidentified
SEQUENCE: 273
MVNIPKTRRT  YCKGKECKKH  TQHKVTQYKA  GKASLFAQGK  RRYDRKQSGY  GGQTKPVFHK   60
KAKTTKKVVL  RLECTSCKTK  AQLALKRCKH  FELGGDKKTK  GAALVF                  106

SEQ ID NO: 274              moltype = AA  length = 84
FEATURE                     Location/Qualifiers
source                      1..84
                            mol_type = protein
                            organism = unidentified
SEQUENCE: 274
MILEGSESKL  RFSYDRPTRK  DMSRHIMACA  QHSSRVHQRC  PTLPLRCVGC  DSSTTAFQYH   60
LFACRSEDDF  TTVHITNRKC  QQDQ                                             84

SEQ ID NO: 275              moltype = AA  length = 41
FEATURE                     Location/Qualifiers
source                      1..41
                            mol_type = protein
                            organism = unidentified
SEQUENCE: 275
MKLTFKDLKQ  EKFVIEVEPS  ETVREVKQKL  LKKKANMRRN  E                        41

SEQ ID NO: 276              moltype = AA  length = 369
FEATURE                     Location/Qualifiers
source                      1..369
                            mol_type = protein
                            organism = unidentified
SEQUENCE: 276
GPEAGEVRNR  GRALRDCSRS  QAKIAQEKGE  YEAERMKVIY  SGKILQDDKT  VESYNIQEKD   60
FLVCLPSKGP  KPAASSSASQ  APATPAPRAP  VATPAAPAPA  APAPASSTPA  VPATPSPAGA  120
QTGPSFGDPS  ALTMGSAAEG  AVTQMEAMGF  ARSDIDRAMR  AAFFNPDRAV  DYLLNGIPAD  180
VQQEQQQRQQ  EQQADRAAEQ  APVPSAEDAA  AAALGGDEG   FNMFEAAAQA  GDGRGGGARS  240
GGSEALANLD  FLRSNPHFQQ  LRQLVQQQPH  MLEPILQQVA  AGNPQISQII  GQNSEQFLQL  300
LSEEGDEEDA  ALPPGTQAIS  VTEEERDAIE  RLCRLGFPRD  SVIQAYFACD  KNEELAANFL  360
FDQPDDDEE                                                               369

SEQ ID NO: 277              moltype = AA  length = 375
FEATURE                     Location/Qualifiers
source                      1..375
                            mol_type = protein
                            organism = unidentified
SEQUENCE: 277
MKLTFKDLKQ  EKFVIEVEPS  ETVREVKQKI  AQEKGEYEAE  RMKVIYSGKI  LQDDKTVESY   60
NIQEKDFLVC  LPSKGPKPAA  SSSASQAPAT  PAPRAPVATP  AAPAPAAPAP  ASSTPAVPAT  120
PSPAGAQTGP  SFGDPSALTM  GSAAEGAVTQ  MEAMGFARSD  IDRAMRAAFF  NPDRAVDYLL  180
NGIPADVQQE  QQQRQQEQQA  DRAAEQAPVP  SAEDAAAAAA  LGGDEGFNMF  EAAAQAGDGR  240
GGGARSGGSE  ALANLDFLRS  NPHFQQLRQL  VQQQPHMLEP  ILQQVAAGNP  QISQIIGQNS  300
EQFLQLLSEE  GDEEDAALPP  GTQAISVTEE  ERDAIERLCR  LGFPRDSVIQ  AYFACDKNEE  360
LAANFLFDQP  DDDEE                                                       375

SEQ ID NO: 278              moltype = AA  length = 342
FEATURE                     Location/Qualifiers
source                      1..342
                            mol_type = protein
                            organism = unidentified
SEQUENCE: 278
APGDMETADA  KNRAMRAAGF  IVPDTFEDLP  EVLKTTYTGL  VQKGVIVPKA  EIDPPNIPMD   60
YQWASKLGLI  RKPAAFISTI  SDERGQELMY  AGMRISDVFK  EEIGIGGVIS  LLWFKRRLPP  120
FACKFIEMVL  QLTADHGPAV  SGAMNTIITA  RAGKDLISSL  AAGLLTIGDR  FGGALDGAAA  180
EFSRGLNSGA  TPREFVDSMR  KANRLIPIG   HKIKSKTNPD  LRVVLVVDYV  KKHFPSHKTL  240
DFALAVEDVT  TQKSNTLILN  VDGAIAASFC  DLLSGCGAFT  EDEAADYLKN  GTLNGLFVLG  300
RSIGFIGHYL  DQRLLKQPLY  RHPADDIFIN  MQERVVFQPG  SN                      342

SEQ ID NO: 279              moltype = AA  length = 182
FEATURE                     Location/Qualifiers
source                      1..182
                            mol_type = protein
                            organism = unidentified
SEQUENCE: 279
GAYKEGKFTS  ESIQKSKLRF  QDILVELPLR  VHNSHLLTSF  LHQVPQAPPA  KNPLDFPSSL   60
AELSRDSDVS  SNPFAPNLDT  LDLSIDPFQY  WQRALGREQQ  KITAWQQKRK  AENAARAASK  120
QPPLDENEWQ  KLFKLPTEPS  RLEALLVGRQ  VEQYARQVDG  FSATVSAKMF  GVRGNLLPNE  180
IE                                                                      182

SEQ ID NO: 280              moltype = AA  length = 171
FEATURE                     Location/Qualifiers
source                      1..171
                            mol_type = protein
```

```
                              organism = unidentified
SEQUENCE: 280
MSAPTPSHPT LTPWTSASTP SSTGSAPSAA SSRRSPHGNR SARLRMLHAP RASSRPLTRM    60
SGRSCSSCPR SPAGSRLCLS AGRSSSTPAR STDSPPPFPP RCLASGATSS LTRSSRGRIL   120
RRRDRRLCIA RRSRLGGVEY MRHGYKKKDD VVPPSTSSGQ RCIESQKKKG F            171

SEQ ID NO: 281             moltype = AA  length = 217
FEATURE                    Location/Qualifiers
source                     1..217
                           mol_type = protein
                           organism = unidentified
SEQUENCE: 281
MRRSSKFKNV KILSSFGILC SVALNSSMAE PHHPFFCSHA ACTLPHPAEN ASLCINAGPV    60
SVIFVLYSIS LGRRLPLTPN ILAETVAENP STWRAYCSTC LPTSRASSLL GSVGSLNSFC   120
HSFSSRGGCL LAARAAFSAL RFCCHAVIFC CSRPRARCQY WKGSMLRSRV SRLGAKGLEL   180
TSESRESSAR DEGKSRGFFA GGACGTWCRK LVRRWEL                            217

SEQ ID NO: 282             moltype = AA  length = 150
FEATURE                    Location/Qualifiers
source                     1..150
                           mol_type = protein
                           organism = unidentified
SEQUENCE: 282
MYSTPPSRER LAMHKRRSRL RNIRPLLDLV REEVAPDAKH LGGNGGGESV DLAGVLLDLP    60
ADKQSLEPAG LRGQLEQLLP LILVKGRLLA RGACSILSLA LLLPCGDLLL LAAEGALPVL   120
EGVDAEVQGV KVGCEGVGAD IGVARKLCKG                                    150

SEQ ID NO: 283             moltype = AA  length = 269
FEATURE                    Location/Qualifiers
source                     1..269
                           mol_type = protein
                           organism = unidentified
SEQUENCE: 283
MSNSFIRHLP STLRAFRSST AFSLTRSFSS TMASNGTSTN GVQHDARKVF FFDIDNCLYP    60
KSYQIHDKMA VLIDNYFQNH LSLSQEDATT LHQRYYKDYG LAIEGLVRHH KVDPLEYNEK   120
VDDALPLDDI IKPDPKLRKL LQDIDTDKVK LWLFTNAYVN HAKRVTRLLG VDDLFEGMTF   180
CDYAAERLLC KPTTEMYNKA MQEANATDID QCYFVDDSAL NAAAAMKYGW KTAHLVEPTA   240
KPPPQPVSQH QISNLEELRK VFPEVFKTS                                     269

SEQ ID NO: 284             moltype = AA  length = 256
FEATURE                    Location/Qualifiers
source                     1..256
                           mol_type = protein
                           organism = unidentified
SEQUENCE: 284
MARIFITGST DGLGLLSAKL LSEQGHSVFL HARNAERASQ AKAAVPKAQG VIIGDLSNVS    60
DVKQLAADAN KAGPFDAVVH NAGLGLTTNG QKTAEGVAQI FAVNSMAPYI LTALMDKPKR   120
LLYVSSGLHF GGDPSLEDVT WATREFRPSD AYNDTKMQNV MLSKAVAKRW PDVQSGSLDP   180
GWVKTKLGGS AAPGTTDAPA EMIAEYAAGK SCAGDQTGAY LTPRGVEEPH DATKLAEKQD   240
RLMQIYKEVS GVSFPQ                                                   256

SEQ ID NO: 285             moltype = AA  length = 201
FEATURE                    Location/Qualifiers
source                     1..201
                           mol_type = protein
                           organism = unidentified
SEQUENCE: 285
MKLCLLGERN TRYLLVNLHQ TILLLGQLSR IMRLFHATRS QVGTCLIACA RFAGSVLSNH    60
LCWSVGGARR GRPAELSLHP AWVKRAALHI RPAFGDCFRE HDVLHLCIVV CIRWSELPCG   120
PSDVLEAGVA TEVQSGADVQ EPLRLVHESG QNVRCHAVNG KNLGYALSSL LAIGGESEAS   180
IVNNGVKRSS LVGIGGELLH V                                             201

SEQ ID NO: 286             moltype = AA  length = 192
FEATURE                    Location/Qualifiers
source                     1..192
                           mol_type = protein
                           organism = unidentified
SEQUENCE: 286
MAIGQSSQQQ ADGQNVVTQG NSDKAANPMR ELRIQKLVLN ISVGESGDRL TRAAKVLEQL    60
SGQTPVYSKA RYTVRTFGIR RNEKISVHVT VRGAKAEEIL ERGLKVKEYE LRKRNFSATG   120
NFGFGISEHI DLGIKYDPAI GIYGMDFYVV MSRPGERVAR RRRAKTRVGA SHKVNAPEVI   180
KWYKNRFEGI VR                                                       192

SEQ ID NO: 287             moltype = AA  length = 213
FEATURE                    Location/Qualifiers
source                     1..213
                           mol_type = protein
                           organism = unidentified
SEQUENCE: 287
```

```
GHTGDVLSVS FSADNRQIVS ASRDRTIKLW NTLGECKFNI VDDGHSEWVS CVRFSPNPVI    60
PVIVSAGWDK VVKVWELSKC KLKTNHHGHT GYINTLAVSP DGSLAASGGK DGITMLWDLN   120
DGKHLYSLEA GDIVNSLVFS PNRYWLCAAT ASSIKIFDLE SKSIVDDLKP DFSAEYSDKA   180
QKPQCTSLAW SADGQTLFAG FSDNLVRVWV VTA                               213

SEQ ID NO: 288              moltype = AA   length = 347
FEATURE                     Location/Qualifiers
source                      1..347
                            mol_type = protein
                            organism = unidentified
SEQUENCE: 288
MAPSTQKQWT VKNGEQDFDG LVYGDAPVPT AGDSEVVVKL HGASLNYRDL IIPKGKYPFP    60
LSFPVVPGSD GAGEVVEVGS KVKQFKKGDK VVTLFNQLHQ YGPVDAAAAS SGLGGAVDGT   120
LRQYGVFNEN GVVRAPTNLN FLESSTLTCA GLTSWNALYG LKPLLPGQTV LVQGTGGVSI   180
FALQFAKAAG ATVIATTSSE EKGKRLKDLG ADHVINYKTQ TNWGEIARGL TRDNIGVDHI   240
IEVGGAGTLE QSFKCIKFEG VISIIGFLGG MNPSTIPNVL QTLSNICTVR GVYVGSKALM   300
NDMINAIEAN NIHPVVDGTV FTLEKTREAY EYMWAQKHFG KLTIQIA                 347

SEQ ID NO: 289              moltype = AA   length = 518
FEATURE                     Location/Qualifiers
source                      1..518
                            mol_type = protein
                            organism = unidentified
SEQUENCE: 289
MLEQQYQMRK EQQVQFTPMA SPSSTPYHMH QDFTVPGDFF SPLTSPALHA QNQPQSRQQF    60
TAHQQGYYTN PSTAASSAAP SPIDANGDVE MGGDGDVALPE SASQPKKPSR RKPATPRTFA   120
MNKVKQSPIQ KPQKRKSVAL AHKDADAVVQ DAQRSGHIAP KSAGLQMPPP FESSENDSVS   180
PEALNDLPMG PPPRPGSVSQ SPAIAPQNQS VSGPAATPKS LLSMKGAQDM NAPASTGISG   240
QMGQASLEDL ELPEAAENPG STATHSQVLN SQEPTPRLMP SRKTPKLGPL STPSSGKPTS   300
ASNSPAHALS PMTASTPAGL LKDKKDNKGG RATSKKRGSV STTNSAMVSP ALRPKVSPSI   360
KPLLPEGTSL NSPTHALLLA SKSNYQNLLE GNHLPGISYP DSLSTGLTSK RTSHKVAEQG   420
RRNRINDALK EMQALIPASS GARAEELMTA DAGDDDSQET KEKDRDAAVK SNSSKAATVE   480
SANRYIRVLK ESDAAQKDAI ARPNSPGSRS LDPPDLDN                          518

SEQ ID NO: 290              moltype = AA   length = 126
FEATURE                     Location/Qualifiers
source                      1..126
                            mol_type = protein
                            organism = unidentified
SEQUENCE: 290
MRNILLVLAS AALAVVAQKP DLDVKGTFGD ANPFSKVVNG QSNKLYLTLD NHSPESLVVK    60
SISGSWSEKT SASSGQEKFL KNSTTQEKLT VPIPPKSEGA FQPPTVLTYQ FWSEFKPREL   120
LLTVLG                                                             126

SEQ ID NO: 291              moltype = AA   length = 91
FEATURE                     Location/Qualifiers
source                      1..91
                            mol_type = protein
                            organism = unidentified
SEQUENCE: 291
MVLALVGGAG YLAYNIYFPP ARKPRRSANT APTDAPAAPA DPDEWIPVHH KRAKKTSGGG    60
ATSGEESEAT EGYASEKSAS GAKKRGKGGR K                                  91

SEQ ID NO: 292              moltype = AA   length = 252
FEATURE                     Location/Qualifiers
source                      1..252
                            mol_type = protein
                            organism = unidentified
SEQUENCE: 292
MSDNNDGNHG GGVGASYYYG GIAIALCLVI VLTLVSRILY RRRVRNRLLR ANRQERITLR    60
DRGEAPGLPT YRESRNQPSL PRYTAEADYA PPPGPPPSNS PDNEGHHFHF HPSLHVPQA   120
LHLRPRQADD PADQIPTVPP PSYEPPKYEP PSGAPPEQQQ EPVASGSSEH HHQQSALGEH   180
TAAATAAATT PAEHSGESTE LRSASPSQPQ SQSQPQAPAQ PQEQDYGYDD ADFIHPEERR   240
RIEAAQRNDP QT                                                     252

SEQ ID NO: 293              moltype = AA   length = 161
FEATURE                     Location/Qualifiers
source                      1..161
                            mol_type = protein
                            organism = unidentified
SEQUENCE: 293
MSRIGDPTNN PATQQLYSDR PLHLPGPGLK PSRQLTISSA VAFREDSGQT RFNLISSDHR    60
EVLHISIRAR DNVLVLNTKA PDGDWGKEER HDLKPLFDTP LLPYITVMAT KNSYILSVPG   120
KREIIFNKRK GFMEPAVRIE YDYDEMSAFS DPCYITVPSS S                      161

SEQ ID NO: 294              moltype = AA   length = 84
FEATURE                     Location/Qualifiers
source                      1..84
                            mol_type = protein
```

```
                         organism = unidentified
SEQUENCE: 294
MPQEIKDIKN LLEIARRKDA RSARIKKTKT VGAKGEPAQL TKFKIRCSRY LYTLVVSDGE    60
KAEKLKQSLP PTLNVEEIGK VSKK                                          84

SEQ ID NO: 295           moltype = AA   length = 173
FEATURE                  Location/Qualifiers
source                   1..173
                         mol_type = protein
                         organism = unidentified
SEQUENCE: 295
MSHTFYDGTI VVLQGILETF SHILHKAEES PNSSAFPAAR LHEDMYPLTD QIRLATQFSE    60
YILAKVTGRE PRKFEGNPLT FAEFYERIDT MLKSLKEADK DVVNANADKE ELTQVGPTAK   120
IELSNAIYAH RIALPNIYFH LNIAYGILRK EGVPLGKLDY FAGFFPPSMA QGK          173

SEQ ID NO: 296           moltype = AA   length = 162
FEATURE                  Location/Qualifiers
source                   1..162
                         mol_type = protein
                         organism = unidentified
SEQUENCE: 296
MSRIGDFANN NQATQQLFSD RPMQLPGPGL KPSRQLTVSS AMAFRWDSGQ TRFNLISSDR    60
REVLHISIRA KDDVLVLNTK APDGNWGKEE RHELKPLFDT PMLPYITVTA TKTSYILSVP   120
GNQEIIFNKR KGFMEPAVKI EYDYDENPAF SDPCYVTVPH LS                     162

SEQ ID NO: 297           moltype = AA   length = 313
FEATURE                  Location/Qualifiers
source                   1..313
                         mol_type = protein
                         organism = unidentified
SEQUENCE: 297
MSEQLHYKGS LAGHGNWVTA IATSAENPDM ILTASRDKSV IVWQLTRDDA QYGYPKRILK    60
GHNHFVSDVS ISYDGQFALS SSWDKTLRLW DLNTGLTTRR FVGHEADVLS VSFSADNRQI   120
VSGSRDRTIK LWNTLGECKF DIKDEGHSEW VSCVRFSPNW MNPVIVSAGW DKVVKVWELS   180
NCKLKTNHYG HTGYINTVSV SPDGSLAASG GKDITMLWD LNEGKHLYSL EAGDIVNALV    240
FSPNRYWLCA ATASCIKIFD LESKSIVDEL KPDFVDVGKN SREPEAVSLS WSADGQTLFA   300
GFTDNAVRVW TVA                                                     313

SEQ ID NO: 298           moltype = AA   length = 107
FEATURE                  Location/Qualifiers
source                   1..107
                         mol_type = protein
                         organism = unidentified
SEQUENCE: 298
GEGGGIHGTT FNSIMKCDVD VRKDLYGNIV MSGGTTMYPG IADRMQKEIT ALAPSSMKVK    60
IIAAPPERKYS VWIGGSILAS LSTFQQMWIS KQEYDESGPS IVHRKCF                107

SEQ ID NO: 299           moltype = AA   length = 111
FEATURE                  Location/Qualifiers
source                   1..111
                         mol_type = protein
                         organism = unidentified
SEQUENCE: 299
MRLSLEALAV DDRRAALVVL LLRDPHLLEG GQRSQDGTTN PHRVFTLRRS NDLDLHRRRS    60
KSGDFLLHTV GNTRVHSSTT RHDNVAIEIL TDVNITLHDG VEGGSVDTTT F           111

SEQ ID NO: 300           moltype = AA   length = 213
FEATURE                  Location/Qualifiers
source                   1..213
                         mol_type = protein
                         organism = unidentified
SEQUENCE: 300
MAFFPHYTTN LSPLLYLLDD DYAVYRSTCP KSNYHHKQHH SRRQPSPVRY FSPNFDMREG    60
NDSYYLDGEL PGVNQNDVDI EFSDPQTLVI KGRVERNYNN LDGMNEENQQ DEEQFSETLS   120
SKSYQPTVED EDEAHSPPV ATPTYSEKSV TEKTQKPAYK YRNSERAIGE FHRAFNLPTR    180
VDQDAVRATL RNGILSLELP KEPAPKMKKI RIE                               213

SEQ ID NO: 301           moltype = AA   length = 161
FEATURE                  Location/Qualifiers
source                   1..161
                         mol_type = protein
                         organism = unidentified
SEQUENCE: 301
MSRIGDPTNN PATQQLYSDR PLHLPGPGLK PSRQLTISSA VAFREDSGQT RFNLISSDHR    60
EVLHISIRAR DNVLVLNTKA PDGDWGKEER HDLKPLFDTP LLPYITVMAT KNSYILSVPG   120
KREIIFNKRK GFMEPAVRIE YDYDEMSAFS DPCYITVPSS S                      161

SEQ ID NO: 302           moltype = AA   length = 178
FEATURE                  Location/Qualifiers
```

```
source                  1..178
                        mol_type = protein
                        organism = unidentified
SEQUENCE: 302
MKAYWYDNQP GDQRLPHDSG RPVTESYLES IGVFYRHCPT IDLVDSLAAE RGYKNRDEVC    60
VSPQTMGDVY EEKVKTFFSE HLHEDEEIRY IRDGEGYFDV RGQEDEWVRI RLSKDDLIIL   120
PAGIYHRFTT DDKNYVKAMR LFQEEPKWTP LNRGPEVDVN PHRKTYLETV PSPAVAAN     178

SEQ ID NO: 303          moltype = AA  length = 216
FEATURE                 Location/Qualifiers
source                  1..216
                        mol_type = protein
                        organism = unidentified
SEQUENCE: 303
VAAGYTPEAL EILSKKKGGK YLVLEMDETY NPPAEETRTL YGVQLTQARN DAVISPQKTF    60
NTIITPKNTE SLPESALRDL TVATLALKYT QSNSVCYALN GQVVGLGAGQ QSRIHCTRLA   120
GDKTDNWWMR FHERVLNIKW KQGTKRADKS NAIDLLCSGQ TPRNDAEKVE YERVFAEVPA   180
PFTQEERDAW LSQLTNVAIS SDAFVCLSPL LEHSKF                             216

SEQ ID NO: 304          moltype = AA  length = 51
FEATURE                 Location/Qualifiers
source                  1..51
                        mol_type = protein
                        organism = unidentified
SEQUENCE: 304
FPFIDNVFRA ARSGVKYIAA PSGSQNDGPV FETAEKLGIS FVEQGTRLFH H             51

SEQ ID NO: 305          moltype = AA  length = 255
FEATURE                 Location/Qualifiers
source                  1..255
                        mol_type = protein
                        organism = unidentified
SEQUENCE: 305
VAAGYTPEAL EILSKKKGGK YLVLEMDETY NPPAEETRTL YGVQLTQARN DAVISPQKTF    60
NTIITPKNTE SLPESALRDL TVATLALKYT QSNSVCYALN GQVVGLGAGQ QSRIHCTRLA   120
GDKTDNWWMR FHERVLNIKW KQGTKRADKS NAIDLLCSGQ TPRNDAEKVE YERVFAEVPA   180
PFTQEERDAW LSQLTNVAIS SDAFFPFIDN VFRAARSGVK YIAAPSGSQN DGPVFETAEK   240
LGISFVEQGT RLFHH                                                    255

SEQ ID NO: 306          moltype = AA  length = 316
FEATURE                 Location/Qualifiers
source                  1..316
                        mol_type = protein
                        organism = unidentified
SEQUENCE: 306
MCDRSRIGPK GWEAVVSTQA VVSTQAVVST QAVVSTQAVV STQAVVSTQS AQPGAISAPV    60
AAGKDVELQW TEWPESHHGP VITYLANCNG DCSEVDKSSL EFFKIDQKGL IDDSNVPGTW   120
ATDKLISNNN SYTVTIPSDI AAGNYVLRHE IIALHSAGNE DGAQNYPQCL NLKVTGGGNA   180
SPSGTLGTKL YNEDDSGILV SIYQQLDSYD IPGPALYSGA SSSSNSGSSS SVASATASAT   240
SAAASSPSSS QASGTPASQV KAQTASSTPS ASSGATSGSL SDYFSSLSAE EFLNVISETL   300
SWLVTDKIHA RDLSTA                                                   316

SEQ ID NO: 307          moltype = AA  length = 138
FEATURE                 Location/Qualifiers
source                  1..138
                        mol_type = protein
                        organism = unidentified
SEQUENCE: 307
MKSLLCTPLA TRMVPRTTPS VSTSRLLVVA TLLPQVLLVP SSTTRTTRVS LSVSTSSLTP    60
TTSPALLCTL ALPRPPTLVL LPALLRPLLL PLLPLLPLPR PLRLPVPPLP RSRLRPLALL   120
LALRPVPLPA VCPTTSAL                                                 138

SEQ ID NO: 308          moltype = AA  length = 272
FEATURE                 Location/Qualifiers
source                  1..272
                        mol_type = protein
                        organism = unidentified
SEQUENCE: 308
VVSTQSAQPG AISAPVAAGK DVELQWTEWP ESHHGPVITY LANCNGDCSE VDKSSLEFFK    60
IDQKGLIDDS NVPGTWATDK LISNNNSYTV TIPSDIAAGN YVLRHEIIAL HSAGNEDGAQ   120
NYPQCLNLKV TGGGNASPSG TLGTKLYNED DSGILVSIYQ QLDSYDIPGP ALYSGASSSS   180
NSGSSSSVAS ATASATSAAA SSPSSSQASG TPASQVKAQT ASSTPSASSG ATSGSLSDYF   240
SSLSAEEFLN VISETLSWLV TDKIHARDLS TA                                 272

SEQ ID NO: 309          moltype = AA  length = 138
FEATURE                 Location/Qualifiers
source                  1..138
                        mol_type = protein
                        organism = unidentified
```

```
                                    -continued

SEQUENCE: 309
MKSLLCTPLA  TRMVPRTTPS  VSTSRLLVVA  TLLPQVLLVP  SSTTRTTRVS  LSVSTSSLTP   60
TTSPALLCTL  ALPRPPTLVL  LPALLRPLLL  PLLPLLPLPR  PLRLPVPPLP  RSRLRPLALL  120
LALRPVPLPA  VCPTTSAL                                                    138

SEQ ID NO: 310          moltype = AA  length = 305
FEATURE                 Location/Qualifiers
source                  1..305
                        mol_type = protein
                        organism = unidentified
SEQUENCE: 310
MLSMFTRVAR  GQAKVFTRNA  STASSKPTNQ  SSNKAATIAA  SISGVTAALY  AHQYGLIDSV   60
FASGLEEGLH  APHFPWSHNG  WLDSPDHNSI  RRGYQVYREV  CSSCHSLDRI  AWRNLVAVSH  120
TSDEARAMAE  EQEYTDGPND  QGESFQRPGK  LADYMPAPYP  NEEASRAANG  GALPPDLSLI  180
VKARHGGADY  IMALLTGYQD  PPAGIQVQEG  MNFNPYFPGG  GIAMGRVLFD  GLVEYDDGTP  240
ATTTQMAKDV  ATFLSWASEP  EHDDRKKMGF  QAVIILSAMT  AISLYVKRLK  WSPIKTRKLT  300
YNPPK                                                                   305

SEQ ID NO: 311          moltype = AA  length = 165
FEATURE                 Location/Qualifiers
source                  1..165
                        mol_type = protein
                        organism = unidentified
SEQUENCE: 311
GGSPAKKSLI  GAMEAQNLKT  FPKQPIFQNS  KTRGNKKVTK  DRRWYKDVGL  GFKTPQEAIT   60
GTYIDKKCPW  TGEVSIRGRI  LSGKVVSTKM  TRTIVIRREY  LHYVPKYNRY  EKRHKNLPVH  120
ASPAFRIENG  DQVVVGQCRP  LSKTVRFNVL  RVIKNKAAAK  AFAKF                   165

SEQ ID NO: 312          moltype = AA  length = 72
FEATURE                 Location/Qualifiers
source                  1..72
                        mol_type = protein
                        organism = unidentified
SEQUENCE: 312
MPPRKPRCSF  KECKEQAQRI  VGDCSFCSGH  FCSKHRMLEA  HSCSGLEDCK  KESHARNADK   60
LNSERTQVIK  GV                                                           72

SEQ ID NO: 313          moltype = AA  length = 161
FEATURE                 Location/Qualifiers
source                  1..161
                        mol_type = protein
                        organism = unidentified
SEQUENCE: 313
MSRNFGDFST  NQATQQLYSD  RPLHLPGNGL  KPARQLTISS  AVAFRWDSDQ  TRFNLISSDR   60
REVLHISIRA  KDNVLVLNTK  APDGDWGREE  RHELKKLFDT  PMLPYITVTA  TKMTYNITVP  120
SGQEIIFNKR  KGFMEPAVKI  EYDYDEHSAF  SDPCYITVPS  S                       161

SEQ ID NO: 314          moltype = AA  length = 119
FEATURE                 Location/Qualifiers
source                  1..119
                        mol_type = protein
                        organism = unidentified
SEQUENCE: 314
LLASNSRSNE  LSSPPSTHLH  ISQSTMVSKI  LFWSGFGIAV  RLWQLGIEMR  PILAKQGLWA   60
YPVFAGVGGS  FGYWLQGVED  RQLKILAQRR  EAILDKRRRR  DEREGLSNIE  KEGTLAATP   119

SEQ ID NO: 315          moltype = AA  length = 91
FEATURE                 Location/Qualifiers
source                  1..91
                        mol_type = protein
                        organism = unidentified
SEQUENCE: 315
LNWSCNFADC  WPRTPDRTNS  PLLRQRTFTY  RKAQWFPRFS  SGVASASPSV  SGNSVSKCVP   60
FLPSRVSGPT  PSSQVSVEAS  VTGSRVSRTV  S                                    91

SEQ ID NO: 316          moltype = AA  length = 182
FEATURE                 Location/Qualifiers
source                  1..182
                        mol_type = protein
                        organism = unidentified
SEQUENCE: 316
MIHAQQCNCR  SFSEGSENKQ  QPTQQIMGSQ  PKYPPSQCCS  DPHARPVSGA  CRGWLRGAAQ   60
ESSADGPRHP  GASNRSFHRH  LRRRGRPRDP  AWQEWDAFRY  RVARDGRRCR  SHSRRESWKP  120
LCFAICEGAL  TEERRVRSIG  SSRPAISEIA  GPIQTPATKA  NTAGDNRESG  ESTPANKKFS  180
AR                                                                      182

SEQ ID NO: 317          moltype = AA  length = 127
FEATURE                 Location/Qualifiers
source                  1..127
```

```
                        mol_type = protein
                        organism = unidentified
SEQUENCE: 317
MPSNAIAGLS PKAVKINNSQ RNKSWGRSQS TLLLNVAQTL TLVPSPALVE DGFAALRKNL     60
QLTVLDTLEP VTEASTDTCE DGVGPETLLG KNGTHFDTEL PETDGDAEAT PEENLGNHCA    120
LRYVKVR                                                              127

SEQ ID NO: 318          moltype = AA  length = 300
FEATURE                 Location/Qualifiers
source                  1..300
                        mol_type = protein
                        organism = unidentified
SEQUENCE: 318
MPFIKEAKSN SYFSRYQVKY RRRREGKTDF YARKRLVTQA KNKYNAPKYR LVVRFTNKDI     60
ICQIVSSKLQ GDVVLTHARA RELPRYGIKH GLTSWSSAYA VGLLVARRAL TKLGLADKYE    120
GDVEATGEYN LTEPLGDDEP RPFKVFLDVG LKRTSTGSRV FGALKGASDG GLYIPHSENR    180
FPGYDIESKE LDAEILNKYI LGGHIAEYME ALEEEDEERF KAQFSTYLED GIGSEDIEEI    240
FSGAHEAIRA DPTFKPSEAA KGTDWKSESK KHRAVRLTKQ QREDAIQQRI KYYQQAGDLE    300

SEQ ID NO: 319          moltype = AA  length = 212
FEATURE                 Location/Qualifiers
source                  1..212
                        mol_type = protein
                        organism = unidentified
SEQUENCE: 319
MAFMNLPWPT ECLHAALKNG SLPFWGFVIY RTTYTAQSDA AWPQIIELIA SYMKALLYHE     60
YNDKKKDGDE PTVYDEIWAR HQLTIMDDRQ FNGASVFDIQ LHFEKWVEAQ GKRDESTMYR    120
MCMVIDDESI QTLLEAPPGE NRKLGRRIGG PVRFVKVVEA FPELDSLDEF QGWMKCEINA    180
LWPLWKMMSD GDEMRMSYDE MKGNGKQVYG AI                                  212

SEQ ID NO: 320          moltype = AA  length = 192
FEATURE                 Location/Qualifiers
source                  1..192
                        mol_type = protein
                        organism = unidentified
SEQUENCE: 320
MTEKLYTEQV NAFGNELPPL SYKDLDKLPL HQNVIKETLR IHNSIHTLMR KVKNPLPVPG     60
TRFVIPTSHT LLASPGVTTR DDSHFRNAMT WDPHRWETRS EVEDDGETID YGYGVVSKGT    120
KSPYLPFGAG RHRCIGEKFA YLNLTVIVAT LVRNFRFSEP DDREGVPETD YSSLFSRPMR    180
PATARWERRG EY                                                        192

SEQ ID NO: 321          moltype = AA  length = 210
FEATURE                 Location/Qualifiers
source                  1..210
                        mol_type = protein
                        organism = unidentified
SEQUENCE: 321
MAHWREEYLT ALAVRDQREK ANLSIYDAYT RLADSTAKLP ATIDTSGSPS GDKGPSGTYE     60
SEKTAFSQSR TAKKQQTEVE PSVTELLNTT RAELAEAQRS RAELRDRLER ATNEAEKLRK    120
QIGKDGRRIH GLENEVAQQQ KRRKDVEEEL RGKAKLLNEF QDEIAALTLQ VNMAERKAKK    180
LGEENDDLVN RWMKRMGQEA DAMNDASKFS                                     210

SEQ ID NO: 322          moltype = DNA  length = 53
FEATURE                 Location/Qualifiers
misc_feature            1..53
                        note = poly-A mRNA primer
misc_feature            52..53
misc_feature            52
                        note = a,c or g
misc_feature            53
                        note = n is a, c, g, or t
source                  1..53
                        mol_type = other DNA
                        organism = synthetic construct
SEQUENCE: 322
attctagagc gatcgcacat gttttttttt tttttttttt tttttttttt tvn            53

SEQ ID NO: 323          moltype = DNA  length = 34
FEATURE                 Location/Qualifiers
misc_feature            1..34
                        note = poly-A mRNA primer
misc_feature            32..33
                        note = Ribonucleotide Guanosine
source                  1..34
                        mol_type = other DNA
                        organism = synthetic construct
misc_RNA                34
                        note = Locked Nucleic Acid (LNA)
SEQUENCE: 323
```

```
aagcagtggt atcaacgcag agtggcgcgc cggg                            34

SEQ ID NO: 324         moltype = DNA  length = 34
FEATURE                Location/Qualifiers
misc_feature           1..32
                       note = oligo-capping rapid amplification of cDNA ends
                        primers
misc_feature           1
                       note = 5' Inverted Dideoxy-T
misc_feature           2..32
                       note = Ribonucleotide
source                 1..34
                       mol_type = other DNA
                       organism = synthetic construct
SEQUENCE: 324
aagcagtggt atcaacgcag agtggcgcgc cggg                            34

SEQ ID NO: 325         moltype = DNA  length = 33
FEATURE                Location/Qualifiers
misc_feature           1..33
                       note = primer for amplification of prokaryote cDNA library
misc_feature           1
                       note = 5' Inverted Dideoxy-T
misc_feature           2..33
                       note = Ribonucleotide
source                 1..33
                       mol_type = other DNA
                       organism = synthetic construct
SEQUENCE: 325
taagcagtgg tatcaacgca gagtggcgcg ccg                             33

SEQ ID NO: 326         moltype = DNA  length = 20
FEATURE                Location/Qualifiers
misc_feature           1..20
                       note = primer for CaMV 35S promoter
source                 1..20
                       mol_type = other DNA
                       organism = synthetic construct
SEQUENCE: 326
ccactgacgt aagggatgac                                            20

SEQ ID NO: 327         moltype = DNA  length = 20
FEATURE                Location/Qualifiers
misc_feature           1..20
                       note = primer for CBF3 promoter
source                 1..20
                       mol_type = other DNA
                       organism = synthetic construct
SEQUENCE: 327
cagcatgctc tcactccaac                                            20

SEQ ID NO: 328         moltype = DNA  length = 20
FEATURE                Location/Qualifiers
misc_feature           1..20
                       note = primer for Erd10 promoter
source                 1..20
                       mol_type = other DNA
                       organism = synthetic construct
SEQUENCE: 328
cgtgagaatg acacaaccac                                            20

SEQ ID NO: 329         moltype = DNA  length = 18
FEATURE                Location/Qualifiers
misc_feature           1..18
                       note = primer for Kin1 promoter
source                 1..18
                       mol_type = other DNA
                       organism = synthetic construct
SEQUENCE: 329
ctcgtggcac cacactcc                                              18

SEQ ID NO: 330         moltype = DNA  length = 19
FEATURE                Location/Qualifiers
misc_feature           1..19
                       note = primer for NOS/HSP terminator
source                 1..19
                       mol_type = other DNA
                       organism = synthetic construct
SEQUENCE: 330
```

```
ggaaattcgc tcgagatc                                                       19

SEQ ID NO: 331          moltype = DNA  length = 1391
FEATURE                 Location/Qualifiers
source                  1..1391
                        mol_type = genomic DNA
                        organism = Arabidopsis thaliana
SEQUENCE: 331
ataccggagc tcagagaatc atatgactaa ggacgtggtg gttgaaggaa atgagagaat    60
acatgaagaa gagaaacttc tttgagtgag aaggaagtgc gctggctgga gagaaaagag   120
agaaaagagt ttcgagtgag agagagggcg ttgagattgt gatcaactta atgtaatatg   180
ttcttttatt acatttcctt tttgtcatat actcaaacct tttactattt tgtctcataa   240
atctaacaca ccccaccatt tgttaatgca tgatggtaga aaatattaaa tataattaac   300
tactttttatg tgatcaaaat taggtttcag actcgtttcg cgatccgatc tacaattaca   360
actgcatgct tctaattgat ctaaattcta aatttttat acatattaaa aaaacaactt   420
tttgttaaat tctcaatcat catttttgtg attaacaatt ttttataact ctaaaccaat   480
aatatttgat tatttatttt atatgtataa tgatgattga gaatttttaat tagcagtcta   540
tttagggttt tcctaaagtt acaatatgtt gttacccttc tagttaaatt ttccaaaata   600
ccatatttca taacttttca aactgtttat taattcaacc gtaaaaagca ctaaaatgtt   660
acatttgatc attcacccaa attaaattca aagttttttc cgccaaaact acttggtgac   720
ttacgtgctt atatacggac gactattatt atgttctata cttttttata ctttgttgca   780
caaatatcta ctctcccaat tcatattcta gaaggatgtg ctataagaat gggagaaatt   840
acacaagaag agcatcttta aatatcctct cacaatcttt atgtctaata cacgggtgaa   900
caattaacga caatttcttt attcaggaat ataataatga ataacggtta ccctacacct   960
agtacactaa atccttaaca gccacacatt catacgcaaa gagtttataa aactcataaa  1020
ggtataataa taacgagtga ataagtcaaa aaaagtcttc tctggacaca tggcagatct  1080
taatgagtga atccttaaac tactcatttt acaattgctt cgctgtgtat agtttacgtg  1140
gcattaccag agacacaaac tccgtcttcg cctttctttt tgcctctaaa atatcttccg  1200
ccattataaa acagcatgct ctcactccaa cttttattta tctacaaaca ttaaatccac  1260
ctgaactaga acagaaagag agagaaaacta ttatttcagc aaaccatacc aacaaaaaag  1320
acagagatct tttagttacc ttatccagtt tcttgaaaca gagtactctt ctgatcaggc  1380
gcgccgccat a                                                       1391

SEQ ID NO: 332          moltype = DNA  length = 1215
FEATURE                 Location/Qualifiers
source                  1..1215
                        mol_type = genomic DNA
                        organism = Arabidopsis thaliana
SEQUENCE: 332
ataccggagc tcgactaggt ggacaaaata atttgttaat taaataaaaa ttagttcaat    60
atagaaatga aaacgattgc tttgtttggt atgtgtcggt acagtgacca tcctaatgcc   120
taatatataaa gattcgatcg gtatgttaca agttgcgtgt atatgaaaac gtcacatttt   180
attaagtggc acgtcgttgt gatgaatctt tcaaccgaac acgattcata atctataagc   240
aaaatccgaa aatggtgcct tctcaatgcc ccctatctgt tcaatctttt ttttttttt   300
ttttttttgta tatctgttca atcttattta aatgtaatga caaattaaat gaagtttacg   360
ttagtaatat aagctgacaa acaacaccac attacataca taaaattaaa ttcttttaag   420
tatttcaata acgttttcttt atcttaaaaa ttaaatttac ttcgagagct tcctacttcg   480
tcaaaaataa aattttacttt tgctgcatgt ttttactttc ttttttgtaac gtcttaaaaa   540
ggtgattaac gtcaacttaa ttcaccgaaa gtctctgcaa ttgatatttt ctgccgacgt   600
ggcataagaa gtccgattgg cccacatgac cgacatccac gcttaaacca atcaaaaccg   660
gccattcagt tccatctgtg ggctcctgaa acgttctgtt gacacgtgtt taccatatat   720
tggcttaatc catccatagt cttttctattt actgacaggt agtatttttc ctatcaatta   780
tttattttca cgtggcatga tggctatgcc tagttgaacc tgtgaataac ttggtcatat   840
ctactctcta tttatttaga tgattcatttt tcttgaagga cttgcaattt tatcccctta   900
cttttatttc tttgagagat aacctaaaat tctcaaaatg agttggaaaac atcccttga   960
agttcctcta caggctttct atgtgcataa gaatctgctt aacattggaa ataatatatg  1020
cattcttctc caattctcct agttggatac atatatgaag tctataaaatt acacatattt  1080
cccacaaaaa ttattgtaag agtttatatt tcaacatata gtatgcaaac ttaaatcgtg  1140
agaatgacac aaaccactaat tcaaaccact acattatata ttctaatcca ttcaaattca  1200
tggcgcgccg ccata                                                   1215

SEQ ID NO: 333          moltype = DNA  length = 960
FEATURE                 Location/Qualifiers
source                  1..960
                        mol_type = genomic DNA
                        organism = Arabidopsis thaliana
SEQUENCE: 333
ataccggagc tcggtaactt gaattcaacc atgaactgtt tggattggca aacataaact    60
caaataaaat atctaggtat aattgtggtt catacaagaa ttacttcata ctgttgggcc   120
aaaggacgta tccttccccg cacctccaaa ccatgggctt actactgatc cgacatcaaa   180
accgtgttag ttgcaaccaa cgaatgataa gtcaataaga ttcaacttgt caacaaatat   240
acagcttata tgacatgtct ggctccaaac tgaattttag tagaaagtta ctaattcata   300
aaattaatttt atatacaatt tttcaatttt tatttataa attaaagaaa aaaactgaa   360
aaatacggga ggttcggcaa acacaacatt taactgcca acgtatcat ctaacttcc   420
caccttatac aaggaaccat ttttttcaata ataaagtttt ttttttttg tcttcgcaaa   480
taagagcacg aaatgtttgc caaacgcata tgcaacaaac ccacgttaca taattctgtt   540
tacagccata gagcaagcta tattgttaaa gacctaaaaa aaactttact ataacatata   600
gaggcttcga gatatttcga aagactcaac ttatatataa ataaactcaa aagaaaaca   660
cggaggcgag aggatcatac tctcacacag aaagagtcac attattatat cctctaaaaa   720
```

-continued

```
accaaactaa aacgacacgt gaagtcttga tcagccgata aatagctacc gacataaggc 780
aaaactgatc gtaccatcaa atgtaatcca cgtggtttta gattactcgt ggcaccacac 840
tccctttagc ctataaatat aaaccattaa gcccacatct cttctcatca tcactaacca 900
aaacacactt caaaaacgat tttacaagaa ataaatatct gaaaaaggcg cgccgccata 960
```